US007241862B2

(12) United States Patent
Eaton et al.

(10) Patent No.: US 7,241,862 B2
(45) Date of Patent: Jul. 10, 2007

(54) POLYPEPTIDES THAT INDUCE CELL PROLIFERATION OR INDUCE FETAL HEMOGLOBIN

(75) Inventors: Dan L. Eaton, San Rafael, CA (US); Audrey Goddard, San Francisco, CA (US); Paul J. Godowski, Hillsborough, CA (US); Austin L. Gurney, Belmont, CA (US); James Pan, Belmont, CA (US); Colin K. Watanabe, Moraga, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 755 days.

(21) Appl. No.: 10/035,958

(22) Filed: Dec. 26, 2001

(65) Prior Publication Data

US 2003/0049733 A1 Mar. 13, 2003

Related U.S. Application Data

(63) Continuation of application No. 09/931,836, filed on Aug. 16, 2001, which is a continuation of application No. PCT/US00/05601, filed on Mar. 1, 2000.

(60) Provisional application No. 60/131,270, filed on Apr. 27, 1999.

(51) Int. Cl.
*C07K 14/435* (2006.01)
*C07K 19/00* (2006.01)

(52) U.S. Cl. .................................... 530/350; 530/387.3
(58) Field of Classification Search ................ 530/350; 514/12
See application file for complete search history.

(56) References Cited

U.S. PATENT DOCUMENTS

| 5,538,637 | A | | 7/1996 | Jacobs |
| 5,888,742 | A | * | 3/1999 | Lal et al. ..................... 435/6 |
| 6,063,767 | A | * | 5/2000 | Lal et al. ..................... 514/12 |
| 2003/0232054 | A1 | * | 12/2003 | Tang et al. |

FOREIGN PATENT DOCUMENTS

| EP | 1033401 A2 | | 9/2000 |
| WO | WO 96/14331 | | 5/1996 |
| WO | WO 97/25424 | | 7/1997 |
| WO | WO 99/06550 | | 2/1999 |
| WO | WO 99/06551 | | 2/1999 |
| WO | WO 99/31236 | * | 6/1999 |
| WO | WO 99/53051 | * | 10/1999 |
| WO | WO 00/35937 | | 6/2000 |
| WO | WO 00/56889 | | 9/2000 |
| WO | WO 00/58473 | | 10/2000 |
| WO | WO 00/78802 | | 12/2000 |
| WO | WO01/12660 | | 2/2001 |
| WO | WO 01/55437 | * | 8/2001 |

OTHER PUBLICATIONS

Vukicevic et al., 1996. Induction of nephrogenic mesenchyme by osteogenic protein 1 (bone morphogenetic protein 7) PNAS USA 93:9021-9026.*
Alberts et al. 1994. Molecular biology of the Cell. New York:Garland Publishing, Inc. p. 582.*
Liu, L-R. et al. 2005. Journal of Biological Chemistry 280:7452-7459.*
Miller, JL. 2002. Hemoglobin switching and modulation: genes, cells, and signals. Current Opinion in Hematology 9:87-92.*
Lo et al. 1998. Protein Engineering 11:495-500.*
Alberts et al. 1994. Molecular Biology of the Cell, p. 582.*
Klein et al., *Selection for genes encoding secreted proteins and receptors*, Proc. Natl. Acad. Sci. USA. vol. 93, pp. 7108-7113 (Jul. 1996).
Database search, Locus list: hum (349, 801 seqs, 66, 964, 548 aa), Mon Jan. 7 16:13:07 2002 [BLASTP 2.2.1 [Jul. 12, 2001], NCBI].
Database search, Locus list: hum—est (1, 803, 435 seqs, 6, 559, 376, 613 bp), Tue Jan. 8 09:19:05 2002 [BLASTN 2.2.1 [Jul. 12, 2001], NCBI].
Duby, et al. "Using Synthetic Oligonucleotides as Probes." *Current Protocols in Molecular Biology.* 6.4.1-6.4.10 (1993).
Rovin BH et al. "15-Deoxy-$\Delta^{12,14}$-prostaglandin $J_2$ regulates mesangial cell proliferation and death." *Kidney International.* 61: 1293-1302 (2002).
Wang, et al. "A Novel Human Phosphatidylethanolamine-binding Protein Resists Tumor Necrosis Factor α-induced Apoptosis by Inhibiting Mitogen-activated Protein Kinase Pathway Activation and Phosphatidylethanolamine Externalization." 279(44): 48555-45864 (2004).
Partial European Search Report for European Application No. EP 06005614 dated Jul. 6, 2006.
Tashiro, et al. "Signal Sequence Trap: A Cloning Strategy for Secreted Proteins and Type I Membrane Proteins." Science. 261: 600-603 (1993).

* cited by examiner

*Primary Examiner*—Robert C. Hayes
*Assistant Examiner*—Daniel E. Kolker
(74) *Attorney, Agent, or Firm*—Elizabeth M. Barnes; Mark T Kresnak; Knobbe Martens Olson & Bear LLP

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

12 Claims, 46 Drawing Sheets

FIGURE 1

GGCATCTGCCCGAGGAGACCACGCTCCTGGAGCTCTGCTGTCTTCTCAGGGAGACTCTGAGG
CTCTGTTGAGAATCATGCTTTGGAGGCAGCTCATCTATTGGCAACTGCTGGCTTTGTTTTTC
CTCCCTTTTTGCCTGTGTCAAGATGAATACATGGAGTCTCCACAAACCGGAGGACTACCCCC
AGACTGCAGTAAGTGTTGTCATGGAGACTACAGCTTTCGAGGCTACCAAGGCCCCCCTGGGC
CACCGGGCCCTCCTGGCATTCCAGGAAACCATGGAAACAATGGCAACAATGGAGCCACTGGT
CATGAAGGAGCCAAAGGTGAGAAGGGCGACAAAGGTGACCTGGGGCCTCGAGGGGAGCGGGG
GCAGCATGGCCCCAAAGGAGAGAAGGGCTACCCGGGGATTCCACCAGAACTTCAGATTGCAT
TCATGGCTTCTCTGGCAACCCACTTCAGCAATCAGAACAGTGGGATTATCTTCAGCAGTGTT
GAGACCAACATTGGAAACTTCTTTGATGTCATGACTGGTAGATTTGGGGCCCCAGTATCAGG
TGTGTATTTCTTCACCTTCAGCATGATGAAGCATGAGGATGTTGAGGAAGTGTATGTGTACC
TTATGCACAATGGCAACACAGTCTTCAGCATGTACAGCTATGAAATGAAGGGCAAATCAGAT
ACATCCAGCAATCATGCTGTGCTGAAGCTAGCCAAAGGGGATGAGGTTTGGCTGCGAATGGG
CAATGGCGCTCTCCATGGGGACCACCAACGCTTCTCCACCTTTGCAGGATTCCTGCTCTTTG
AAACTAAGTAAATATATGACTAGAATAGCTCCACTTTGGGGAAGACTTGTAGCTGAGCTGAT
TTGTTACGATCTGAGGAACATTAAAGTTGAGGGTTTTACATTGCTGTATTCAAAAAATTATT
GGTTGCAATGTTGTTCACGCTACAGGTACACCAATAATGTTGGACAATTCAGGGGCTCAGAA
GAATCAACCACAAAATAGTCTTCTCAGATGACCTTGACTAATATACTCAGCATCTTTATCAC
TCTTTCCTTGGCACCTAAAAGATAATTCTCCTCTGACGCAGGTTGGAAATATTTTTTTCTAT
CACAGAAGTCATTTGCAAAGAATTTTGACTACTCTGCTTTTAATTTAATACCAGTTTTCAGG
AACCCCTGAAGTTTTAAGTTCATTATTCTTTATAACATTTGAGAGAATCGGATGTAGTGATA
TGACAGGGCTGGGGCAAGAACAGGGGCACTAGCTGCCTTATTAGCTAATTTAGTGCCCTCCG
TGTTCAGCTTAGCCTTTGACCCTTTCCTTTTGATCCACAAAATACATTAAAACTCTGAATTC
ACATACAATGCTATTTTAAAGTCAATAGATTTTAGCTATAAAGTGCTTGACCAGTAATGTGG
TTGTAATTTTGTGTATGTTCCCCCACATCGCCCCCAACTTCGGATGTGGGGTCAGGAGGTTG
AGGTTCACTATTAACAAATGTCATAAATATCTCATAGAGGTACAGTGCCAATAGATATTCAA
ATGTTGCATGTTGACCAGAGGGATTTTATATCTGAAGAACATACACTATTAATAAATACCTT
AGAGAAAGATTTTGACCTGGCTTTAGATAAAACTGTGGCAAGAAAATGTAATGAGCAATAT
ATGGAAATAAACACACCTTTGTTAAAGATAAAAAAAAA

FIGURE 2

></usr/seqdb2/sst/DNA/Dnaseqs.min/ss.DNA44686
><subunit 1 of 1, 246 aa, 1 stop
><MW: 26994, pI: 6.43, NX(S/T): 0
MLWRQLIYWQLLALFFLPFCLCQDEYMESPQTGGLPPDCSKCCHGDYSFRGYQGPPGPPGPP
GIPGNHGNNGNNGATGHEGAKGEKGDKGDLGPRGERGQHGPKGEKGYPGIPPELQIAFMASL
ATHFSNQNSGIIFSSVETNIGNFFDVMTGRFGAPVSGVYFFTFSMMKHEDVEEVYVYLMHNG
NTVFSMYSYEMKGKSDTSSNHAVLKLAKGDEVWLRMGNGALHGDHQRFSTFAGFLLFETK

Important features of the protein:
Signal peptide:
amino acids 1-22

Motif name: C1q domain signature.
amino acids 137-167

C1q domain proteins.
amino acids 135-169, 202-221, 235-244, 57-91, 60-94, 54-88, 81-114, 78-111, 63-96, 51-84, 45-78, 48-81, 33-66, 66-99 and 42-75

FIGURE 3

GAGAGAATAGCTACAGATTCTCCATCCTCAGTCTTTGCAAGGCGACAGCTGTGCCAGCCGGG
CTCTGGCAGGCTCCTGGCAGCATGGCAGTGAAGCTTGGGACCCTCCTGCTGGCCCTTGCCCT
GGGCCTGGCCCAGCCAGCCTCTGCCCGCCGGAAGCTGCTGGTGTTTCTGCTGGATGGTTTTC
GCTCAGACTACATCAGTGATGAGGCGCTGGAGTCATTGCCTGGTTTCAAAGAGATTGTGAGC
AGGGGAGTAAAAGTGGATTACTTGACTCCAGACTTCCCTAGTCTCTCGTATCCCAATTATTA
TACCCTAATGACTGGCCGCCATTGTGAAGTCCATCAGATGATCGGGAACTACATGTGGGACC
CCACCACCAACAAGTCCTTTGACATTGGCGTCAACAAAGACAGCCTAATGCCTCTCTGGTGG
AATGGATCAGAACCTCTGTGGGTCACTCTGACCAAGGCCAAAAGGAAGGTCTACATGTACTA
CTGGCCAGGCTGTGAGGTTGAGATTCTGGGTGTCAGACCCACCTACTGCCTAGAATATAAAA
ATGTCCCAACGGATATCAATTTTGCCAATGCAGTCAGCGATGCTCTTGACTCCTTCAAGAGT
GGCCGGGCCGACCTGGCAGCCATATACCATGAGCGCATTGACGTGGAAGGCCACCACTACGG
GCCTGCATCTCCGCAGAGGAAAGATGCCCTCAAGGCTGTAGACACTGTCCTGAAGTACATGA
CCAAGTGGATCCAGGAGCGGGGCCTGCAGGACCGCCTGAACGTCATTATTTTCTCGGATCAC
GGAATGACCGACATTTTCTGGATGGACAAAGTGATTGAGCTGAATAAGTACATCAGCCTGAA
TGACCTGCAGCAAGTGAAGGACCGCGGGCCTGTTGTGAGCCTTTGGCCGGCCCCTGGGAAAC
ACTCTGAGATATATAACAAACTGAGCACAGTGGAACACATGACTGTCTACGAGAAAGAAGCC
ATCCCAAGCAGGTTCTATTACAAGAAAGGAAAGTTTGTCTCTCCTTTGACTTTAGTGGCTGA
TGAAGGCTGGTTCATAACTGAGAATCGAGAGATGCTTCCGTTTTGGATGAACAGCACCGGCA
GGCGGGAAGGTTGGCAGCGTGGATGGCACGGCTACGACAACGAGCTCATGGACATGCGGGGC
ATCTTCCTGGCCTTCGGACCTGATTTCAAATCCAACTTCAGAGCTGCTCCTATCAGGTCGGT
GGACGTCTACAATGTCATGTGCAATGTGGTGGGCATCACCCCGCTGCCCAACAACGGATCCT
GGTCCAGGGTGATGTGCATGCTGAAGGGCCGCGCCGGCACTGCCCCGCCTGTCTGGCCCAGC
CACTGTGCCCTGGCACTGATTCTTCTCTTCCTGCTTGCATAACTGATCATATTGCTTGTCTC
AGAAAAAAACACCATCAGCAAAGTGGGCCTCCAAAGCCAGATGATTTTCATTTTATGTGTGA
ATAATAGCTTCATTAACACAATCAAGACCATGCACATTGTAAATACATTATTCTTGGATAAT
TCTATACATAAAAGTTCCTACTTGTTAAA

FIGURE 4

MAVKLGTLLLALALGLAQPASARRKLLVFLLDGFRSDYISDEALESLPGFKEIVSRGVKVDY
LTPDFPSLSYPNYYTLMTGRHCEVHQMIGNYMWDPTTNKSFDIGVNKDSLMPLWWNGSEPLW
VTLTKAKRKVYMYYWPGCEVEILGVRPTYCLEYKNVPTDINFANAVSDALDSFKSGRADLAA
IYHERIDVEGHHYGPASPQRKDALKAVDTVLKYMTKWIQERGLQDRLNVIIFSDHGMTDIFW
MDKVIELNKYISLNDLQQVKDRGPVVSLWPAPGKHSEIYNKLSTVEHMTVYEKEAIPSRFYY
KKGKFVSPLTLVADEGWFITENREMLPFWMNSTGRREGWQRGWHGYDNELMDMRGIFLAFGP
DFKSNFRAAPIRSVDVYNVMCNVVGITPLPNNGSWSRVMCMLKGRAGTAPPVWPSHCALALI
LLFLLA

Important features of the protein:

Signal peptide:

amino acids 1-22

N-glycosylation sites.

amino acids 100-104, 118-122, 341-345, 404-408

N-myristoylation sites.

amino acids 148-154, 365-371

Amidation site.

amino acids 343-347

FIGURE 5

GCCAGGTGTGCAGGCCGCTCCAAGCCCAGCCTGCCCCGCTGCCGCCACCATGACGCTCCTCC
CCGGCCTCCTGTTTCTGACCTGGCTGCACACATGCCTGGCCCACCATGACCCCTCCCTCAGG
GGGCACCCCCACAGTCACGGTACCCCACACTGCTACTCGGCTGAGGAACTGCCCCTCGGCCA
GGCCCCCCACACCTGCTGGCTCGAGGTGCCAAGTGGGGCAGGCTTTGCCTGTAGCCCTGG
TGTCCAGCCTGGAGGCAGCAAGCCACAGGGGGAGGCACGAGAGGCCCTCAGCTACGACCCAG
TGCCCGGTGCTGCGGCCGGAGGAGGTGTTGGAGGCAGACACCCACCAGCGCTCCATCTCACC
CTGGAGATACCGTGTGGACACGGATGAGGACCGCTATCCACAGAAGCTGGCCTTCGCCGAGT
GCCTGTGCAGAGGCTGTATCGATGCACGGACGGGCCGCGAGACAGCTGCGCTCAACTCCGTG
CGGCTGCTCCAGAGCCTGCTGGTGCTGCGCCGCCGGCCCTGCTCCCGCGACGGCTCGGGGCT
CCCCACACCTGGGGCCTTTGCCTTCCACACCGAGTTCATCCACGTCCCCGTCGGCTGCACCT
GCGTGCTGCCCCGTTCAGTGTGACCGCCGAGGCCGTGGGGCCCCTAGACTGGACACGTGTGC
TCCCCAGAGGGCACCCCCTATTTATGTGTATTTATTGTTATTTATATGCCTCCCCCAACACT
ACCCTTGGGGTCTGGGCATTCCCCGTGTCTGGAGGACAGCCCCCCACTGTTCTCCTCATCTC
CAGCCTCAGTAGTTGGGGGTAGAAGGAGCTCAGCACCTCTTCCAGCCCTTAAAGCTGCAGAA
AAGGTGTCACACGGCTGCCTGTACCTTGGCTCCCTGTCCTGCTCCCGGCTTCCCTTACCCTA
TCACTGGCCTCAGGCCCCGCAGGCTGCCTCTTCCCAACCTCCTTGGAAGTACCCCTGTTTCT
TAAACAATTATTTAAGTGTACGTGTATTATTAAACTGATGAACACATCCCCAAAA

FIGURE 6

MTLLPGLLFLTWLHTCLAHHDPSLRGHPHSHGTPHCYSAEELPLGQAPPHLLARGAKWGQAL
PVALVSSLEAASHRGRHERPSATTQCPVLRPEEVLEADTHQRSISPWRYRVDTDEDRYPQKL
AFAECLCRGCIDARTGRETAALNSVRLLQSLLVLRRRPCSRDGSGLPTPGAFAFHTEFIHVP
VGCTCVLPRSV

Important features:

Signal peptide:

amino acids 1-18

Tyrosine kinase phosphorylation site.

amino acids 112-121

N-myristoylation sites.

amino acids 32-38, 55-61, 133-139

Leucine zipper pattern.

amino acids 3-25

Homologous region to IL-17.

amino acids 99-195

FIGURE 7

CGGCCAGGGCGCCGACAGCCCGACCTCACCAGGAGAACATGCAGCTCGGCACTGGGCTCCTG
CTGGCCGCCGTCCTGAGCCTGCAGCTGGCTGCAGCCGAAGCCATATGGTGTCACCAGTGCAC
GGGCTTCGGAGGGTGCTCCCATGGATCCAGATGCCTGAGGGACTCCACCCACTGTGTCACCA
CTGCCACCCGGGTCCTCAGCAACACCGAGGATTTGCCTCTGGTCACCAAGATGTGCCACATA
GGCTGCCCCGATATCCCCAGCCTGGGCCTGGGCCCCTACGTATCCATCGCTTGCTGCCAGAC
CAGCCTCTGCAACCATGACTGACGGCTGCCCTCCTCCAGGCCCCGGACGCTCAGCCCCCAC
AGCCCCCACAGCCTGGCGCCAGGGCTCACGGCCGCCCCTCCCTCGAGACTGGCCAGCCCACC
TCTCCCGGCCTCTGCAGCCACCGTCCAGCACCGCTTGTCCTAGGGAAGTCCTGCGTGGAGTC
TTGCCTCAATCTGCTGCCGTCCAAGCCTGGGGCCCATCGTGCCTGCCGCCCCTTCAGGTCCC
GACCTCCCCACAATAAAATGTGATTGGATCGTGTGGTACAAAAAAAAAAAAAAAAAAAAAA
AAAAAAAAAAAAAAAAAAAAAAAAAAAAAAAAAAAAAA

FIGURE 8

></usr/seqdb2/sst/DNA/Dnaseqs.min/ss.DNA77623
><subunit 1 of 1, 97 aa, 1 stop
><MW: 10160, pI: 6.56, NX(S/T): 0
MQLGTGLLLAAVLSLQLAAAEAIWCHQCTGFGGCSHGSRCLRDSTHCVTTATRVLSNTEDLP
LVTKMCHIGCPDIPSLGLGPYVSIACCQTSLCNHD

Important features of the protein:

Signal peptide:

amino acids 1-20

N-myristoylation sites.

amino acids 6-11 and 33-38

Prokaryotic membrane lipoprotein lipid attachment sites.

amino acids 24-34 and 78-88

FIGURE 9

CCAGGACCAGGGCGCACCGGCTCAGCCTCTCACTTGTCAGAGGCCGGGGAAGAGAAGCAAAG
CGCAACGGTGTGGTCCAAGCCGGGGCTTCTGCTTCGCCTCTAGGACATACACGGGACCCCCT
AACTTCAGTCCCCCAAACGCGCACCCTCGAAGTCTTGAACTCCAGCCCCGCACATCCACGCG
CGGCACAGGCGCGGCAGGCGGCAGGTCCCGGCCGAAGGCGATGCGCGCAGGGGGTCGGGCAG
CTGGGCTCGGGCGGCGGGAGTAGGGCCCGGCAGGGAGGCAGGGAGGCTGCATATTCAGAGTC
GCGGGCTGCGCCCTGGGCAGAGGCCGCCCTCGCTCCACGCAACACCTGCTGCTGCCACCGCG
CCGCGATGAGCCGCGTGGTCTCGCTGCTGCTGGGCGCCGCGCTGCTCTGCGGCCACGGAGCC
TTCTGCCGCCGCGTGGTCAGCGGCCAAAAGGTGTGTTTTGCTGACTTCAAGCATCCCTGCTA
CAAAATGGCCTACTTCCATGAACTGTCCAGCCGAGTGAGCTTTCAGGAGGCACGCCTGGCTT
GTGAGAGTGAGGGAGGAGTCCTCCTCAGCCTTGAGAATGAAGCAGAACAGAAGTTAATAGAG
AGCATGTTGCAAAACCTGACAAAACCCGGGACAGGGATTTCTGATGGTGATTTCTGGATAGG
GCTTTGGAGGAATGGAGATGGGCAAACATCTGGTGCCTGCCCAGATCTCTACCAGTGGTCTG
ATGGAAGCAATTCCCAGTACCGAAACTGGTACACAGATGAACCTTCCTGCGGAAGTGAAAAG
TGTGTTGTGATGTATCACCAACCAACTGCCAATCCTGGCCTTGGGGGTCCCTACCTTTACCA
GTGGAATGATGACAGGTGTAACATGAAGCACAATTATATTTGCAAGTATGAACCAGAGATTA
ATCCAACAGCCCCTGTAGAAAAGCCTTATCTTACAAATCAACCAGGAGACACCCATCAGAAT
GTGGTTGTTACTGAAGCAGGTATAATTCCCAATCTAATTTATGTTGTTATACCAACAATACC
CCTGCTCTTACTGATACTGGTTGCTTTTGGAACCTGTTGTTTCCAGATGCTGCATAAAAGTA
AAGGAAGAACAAAAACTAGTCCAAACCAGTCTACACTGTGGATTTCAAAGAGTACCAGAAAA
GAAAGTGGCATGGAAGTATAATAACTCATTGACTTGGTTCCAGAATTTTGTAATTCTGGATC
TGTATAAGGAATGGCATCAGAACAATAGCTTGGAATGGCTTGAAATCACAAAGGATCTGCAA
GATGAACTGTAAGCTCCCCCTTGAGGCAAATATTAAAGTAATTTTATATGTCTATTATTTC
ATTTAAAGAATATGCTGTGCTAATAATGGAGTGAGACATGCTTATTTTGCTAAAGGATGCAC
CCAAACTTCAAACTTCAAGCAAATGAAATGGACAATGCAGATAAAGTTGTTATCAACACGTC
GGGAGTATGTGTGTTAGAAGCAATTCCTTTTATTTCTTTCACCTTTCATAAGTTGTTATCTA
GTCAATGTAATGTATATTGTATTGAAATTTACAGTGTGCAAAAGTATTTACCTTTGCATAA
GTGTTTGATAAAAATGAACTGTTCTAATATTTATTTTATGGCATCTCATTTTTCAATACAT
GCTCTTTTGATTAAAGAAACTTATTACTGTTGTCAACTGAATTCACACACACACAAATATAG
TACCATAGAAAAGTTTGTTTTCTCGAAATAATTCATCTTTCAGCTTCTCTGCTTTTGGTCA
ATGTCTAGGAAATCTCTTCAGAAATAAGAAGCTATTTCATTAAGTGTGATATAAACCTCCTC
AAACATTTTACTTAGAGGCAAGGATTGTCTAATTTCAATTGTGCAAGACATGTGCCTTATAA
TTATTTTTAGCTTAAAATTAAACAGATTTTGTAATAATGTAACTTTGTTAATAGGTGCATAA
ACACTAATGCAGTCAATTTGAACAAAAGAAGTGACATACACAATATAAATCATATGTCTTCA
CACGTTGCCTATATAATGAGAAGCAGCTCTCTGAGGGTTCTGAAATCAATGTGGTCCCTCTC
TTGCCCACTAAACAAAGATGGTTGTTCGGGGTTTGGGATTGACACTGGAGGCAGATAGTTGC
AAAGTTAGTCTAAGGTTTCCCTAGCTGTATTTAGCCTCTGACTATATTAGTATACAAAGAGG
TCATGTGGTTGAGACCAGGTGAATAGTCACTATCAGTGTGGAGACAAGCACAGCACACAGAC
ATTTTAGGAAGGAAAGGAACTACGAAATCGTGTGAAAATGGGTTGGAACCCATCAGTGATCG
CATATTCATTGATGAGGGTTTGCTTGAGATAGAAATGGTGGCTCCTTTCTGTCTTATCTCC
TAGTTTCTTCAATGCTTACGCCTTGTTCTTCTCAAGAGAAAGTTGTAACTCTCTGGTCTTCA
TATGTCCCTGTGCTCCTTTTAACCAAATAAGAGTTCTTGTTTCTGGGGGAAAAAAAAAAA
AAAAAAAAAAAAAAAAAAAAAAAAAAA

FIGURE 10

></usr/seqdb2/sst/DNA/Dnaseqs.min/ss.DNA79230
><subunit 1 of 1, 273 aa, 1 stop
><MW: 30431, pI: 6.79, NX(S/T): 3
MSRVVSLLLGAALLCGHGAFCRRVVSGQKVCFADFKHPCYKMAYFHELSSRVSFQEARLACE
SEGGVLLSLENEAEQKLIESMLQNLTKPGTGISDGDFWIGLWRNGDGQTSGACPDLYQWSDG
SNSQYRNWYTDEPSCGSEKCVVMYHQPTANPGLGGPYLYQWNDDRCNMKHNYICKYEPEINP
TAPVEKPYLTNQPGDTHQNVVVTEAGIIPNLIYVVIPTIPLLLLILVAFGTCCFQMLHKSKG
RTKTSPNQSTLWISKSTRKESGMEV

Important features of the protein:

Signal peptide:

amino acids 1-21

Transmembrane domain:

amino acids 214-235

N-glycosylation sites.

amino acids 86-89 and 255-258 cAMP- and cGMP-dependent protein kinase phosphorylation site.

amino acids 266-269

N-myristoylation sites.

amino acids 27-32, 66-71, 91-96, 93-98, 102-107, 109-114, 140-145 and 212-217

FIGURE 11

```
GGAGAATGGAGAGAGCAGTGAGAGTGGAGTCCGGGGTCCTGGTCGGGGTGGTCTGTCTGCTCCTGGCATGCCCTG
CCACAGCCACTGGGCCCGAAGTTGCTCAGCCTGAAGTAGACACCACCCTGGGTCGTGTGCGAGGCCGGCAGGTGG
GCGTGAAGGGCACAGACCGCCTTGTGAATGTCTTTCTGGGCATTCCATTTGCCCAGCCGCCACTGGGCCCTGACC
GGTTCTCAGCCCCACACCCAGCACAGCCCTGGGAGGGTGTGCGGATGCCAGCACTGCGCCCCAATGTGCCTAC
AAGACGTGGAGAGCATGAACAGCAGCAGATTTGTCCTCAACGGAAAACAGCAGATCTTCTCCGTTTCAGAGGACT
GCCTGGTCCTCAACGTCTATAGCCCAGCTGAGGTCCCCGCAGGGTCCGGTAGGCCGGTCATGGTATGGGTCCATG
GAGGCGCTCTGATAACTGGCGCTGCCACCTCCTACGATGGATCAGCTCTGGCTGCCTATGGGGATGTGGTCGTGG
TTACAGTCCAGTACCGCCTTGGGGTCCTTGGCTTCTTCAGCACTGGAGATGAGCATGCACCTGGCAACCAGGGCT
TCCTAGATGTGGTAGCTGCTTTGCGCTGGGTGCAAGAAAACATCGCCCCCTTCGGGGGTGACCTCAACTGTGTCA
CTGTCTTTGGTGGATCTGCCGGTGGGAGCATCATCTCTGGCCTGGTCCTGTCCCAGTGGCTGCAGGGCTGTTCC
ACAGAGCCATCACACAGAGTGGGGTCATCACCACCCCAGGGATCATCGACTCTCACCCTTGGCCCCTAGCTCAGA
AAATCGCAAACACCTTGGCCTGCAGCTCCAGCTCCCCGGCTGAGATGGTGCAGTGCCTTCAGCAGAAAGAAGGAG
AAGAGCTGGTCCTTAGCAAGAAGCTGAAAAATACTATCTATCCTCTCACCGTTGATGGCACTGTCTTCCCCAAAA
GCCCCAAGGAACTCCTGAAGGAGAAGCCCTTCCACTCTGTGCCCTTCCTCATGGGTGTCAACAACCATGAGTTCA
GCTGGCTCATCCCCAGGGGCTGGGTCTCCTGGATACAATGGAGCAGATGAGCCGGGAGGACATGCTGGCCATCT
CAACACCCGTCTTGACCAGTCTGGATGTGCCCCCTGAGATGATGCCCACCGTCATAGATGAATACCTAGGAAGCA
ACTCGGACGCACAAGCCAAATGCCAGGCGTTCCAGGAATTCATGGGTGACGTATTCATCAATGTTCCCACCGTCA
GTTTTTCAAGATACCTTCGAGATTCTGGAAGCCCTGTCTTTTTCTATGAGTTCCAGCATCGACCCAGTTCTTTTG
CGAAGATCAAACCTGCCTGGGTGAAGGCTGATCATGGGGCCGAGGGTGCTTTTGTGTTCGGAGGTCCCTTCCTCA
TGGACGAGAGCTCCCGCCTGGCCTTTCCAGAGGCCACAGAGGAGGAGAAGCAGCTAAGCCTCACCATGATGGCCC
AGTGGACCCACTTTGCCCGGACAGGGGACCCCAATAGCAAGGCTCTGCCTCCTTGGCCCCAATTCAACCAGGCGG
AACAATATCTGGAGATCAACCCAGTGCCACGGGCCGGACAGAAGTTCAGGGAGGCCTGGATGCAGTTCTGGTCAG
AGACGCTCCCCAGCAAGATACAACAGTGGCACCAGAAGCAGAAGAACAGGAAGGCCCAGGAGGACCTCTGAGGCC
AGGCCTGAACCTTCTTGGCTGGGGCAAACCACTCTTCAAGTGGTGGCAGAGTCCCAGCACGGCAGCCCGCCTCTC
CCCCTGCTGAGACTTTAATCTCCACCAGCCCTTAAAGTGTCGGCCGCTCTGTGACTGGAGTTATGCTCTTTTGAA
ATGTCACAAGGCCGCCTCCCACCTCTGGGGCATTGTACAAGTTCTTCCCTCTCCCTGAAGTGCCTTTCCTGCTTT
CTTCGTGGTAGGTTCTAGCACATTCCTCTAGCTTCCTGGAGGACTCACTCCCCAGGAAGCCTTCCCTGCCTTCTC
TGGGCTGTGCGGCCCCGAGTCTGCGTCCATTAGAGCACAGTCCACCCGAGGCTAGCACCGTGTCTGTGTCTGTCT
CCCCCTCAGAGGAGCTCTCTCAAAATGGGGATTAGCCTAACCCCACTCTGTCACCCACACCAGGATCGGGTGGGA
CCTGGAGCTAGGGGGTGTTTGCTGAGTGAGTGAGTGAAACACAGAATATGGGAATGGCAGCTGCTGAACTTGAAC
CCAGAGCCTTCAGGTGCCAAAGCCATACTCAGGCCCCCACCGACATTGTCCACCCTGGCCAGAAGGGTGCATGCC
AATGGCAGAGACCTGGGATGGGAGAAGTCCTGGGGCGCCAGGGGATCCAGCCTAGAGCAGACCTTAGCCCCTGAC
TAAGGCCTCAGACTAGGGCGGGAGGGGTCTCCTCCTCTCTGCTGCCCAGTCCTGGCCCCTGCACAAGACAACAGA
ATCCATCAGGGCCATGAGTGTCACCCAGACCTGACCCTCACCAATTCCAGCCCCTGACCCTCAGGACGCTGGATG
CCAGCTCCCAGCCCCAGTGCCGGGTCCTCCCTCCCTTCCTGGCTTGGGGAGACCAGTTTCTGGGGACCTTCCAAG
AGCACCCACCAAGACACAGCAGGACAGGCCAGGGGAGGGCATCTGGACCAGGGCATCCGTCGGGCTATTGTCACA
GAGAAAAGAAGAGACCCACCCACTCGGGCTGCAAAAGGTGAAAAGCACCAAGAGGTTTTCAGATGGAAGTGAGAG
GTGACAGTGTGCTGGCAGCCCTCACAGCCCTCGCTTGCTCTCCCTGCCGCCTCTGCCTGGGCTCCCACTTTGGCA
GCACTTGAGGAGCCCTTCAACCCGCCGCTGCACTGTAGGAGCCCCTTTCTGGGCTGGCCAAGGCCGGAGCCAGCT
CCCTCAGCTTGCGGGGAGGTGCGGAGGGAGAGGGCGGGCAGGAACCGGGGCTGCGCGCACCGCTTGCGGGCCAG
AGTGAGTTCCGGGTGGGCGTGGGCTCGGCGGGGCCCACTCAGAGCAGCTGGCCGGCCCCAGGCAGTGAGGGCCT
TAGCACCTGGGCCAGCAGCTGCTGTGCTCGATTTCTCGCTGGGCCTTAGCTGCCTCCCCGCGGGCAGGGCTCGG
GACCTGCAGCCCTCCATGCCTGACCCTCCCCCCACCCCCGTGGGCTCCTGTGCGGCCGGAGCCTCCCCAAGGAG
CGCCGCCCCTGCTCCACAGCGCCCAGTCCCATCGACCACCCAAGGGCTGAGGAGTGCGGGTGCACAGCGCGGGA
CTGGCAGGCAGCTCCACCTGCTGCCCCAGTGCTGGATCCACTGGGTGAAGCCAGCTGGGCTCCTGAGTCTGGTGG
GGACTTGGAGAACCCTTTATGTCTAGCTAAGGGATTGTAAATACACCGATGGGCACTCTGTATCTAGCTCAAGGTT
TGTAAACACACCAATCAGCACCCTGTGTCTAGCTCAGTGTTTGTGAATGCACCAATCCACACTCTGTATCTGGCT
ACTCTGGTGGGGACTTGGAGAACCTTTGTGTCCACACTCTGTATCTAGCTAATCTAGTGGGGATGTGGAGAACCT
TTGTGTCTAGCTCAGGGATCGTAAACGCACCAATCAGCACCCTGTCAAAACAGACCACTTGACTCTCTGTAAAAT
GGACCAATCAGCAGGATGTGGGTGGGGCGAGACAAGAGAATAAAAGCAGGCTGCCTGAGCCAGCAGTGACAACCC
CCCTCGGGTCCCCTCCCACGCCGTGGAAGCTTTGTTCTTTCGCTCTTTGCAATAAATCTTGCTACTGCCCAAAA
```

FIGURE 12

```
></usr/seqdb2/sst/DNA/Dnaseqs.min/ss.DNA79862
><subunit 1 of 1, 571 aa, 1 stop
><MW: 62282, pI: 5.56, NX(S/T): 1
MERAVRVESGVLVGVVCLLLACPATATGPEVAQPEVDTTLGRVRGRQVGVKGTDRLVNVFLG
IPFAQPPLGPDRFSAPHPAQPWEGVRDASTAPPMCLQDVESMNSSRFVLNGKQQIFSVSEDC
LVLNVYSPAEVPAGSRPVMVWVHGGALITGAATSYDGSALAAYGDVVVVTVQYRLGVLGFF
STGDEHAPGNQGFLDVVAALRWVQENIAPFGGDLNCVTVFGGSAGGSIISGLVLSPVAAGLF
HRAITQSGVITTPGIIDSHPWPLAQKIANTLACSSSSPAEMVQCLQQKEGEELVLSKKLKNT
IYPLTVDGTVFPKSPKELLKEKPFHSVPFLMGVNNHEFSWLIPRGWGLLDTMEQMSREDMLA
ISTPVLTSLDVPPEMMPTVIDEYLGSNSDAQAKCQAFQEFMGDVFINVPTVSFSRYLRDSGS
PVFFYEFQHRPSSFAKIKPAWVKADHGAEGAFVFGGPFLMDESSRLAFPEATEEEKQLSLTM
MAQWTHFARTGDPNSKALPPWPQFNQAEQYLEINPVPRAGQKFREAWMQFWSETLPSKIQQW
HQKQKNRKAQEDL
```

Important features of the protein:

Signal peptide:

amino acids 1-27

Transmembrane domain:

amino acids 226-245

N-glycosylation site.

amino acids 105-109

N-myristoylation sites.

amino acids 10-16, 49-55, 62-68, 86-92, 150-156, 155-161, 162-168, 217-223, 227-233, 228-234, 232-238, 262-268, 357-363, 461-467

Prokaryotic membrane lipoprotein lipid attachment site.

amino acids 12-23

Carboxylesterases type-B serine active site.

amino acids 216-232

FIGURE 13

CATGGAGCCTCTTGCAGCTTACCCGCTAAAATGTTCCGGGCCCAGAGCAAAGGTATTTGCAG
TTTTGCTGTCTATAGTTCTATGCACAGTAACGCTATTTCTTCTACAACTAAAATTCCTCAAA
CCTAAAATCAACAGCTTTTATGCCTTTGAAGTGAAGGATGCAAAAGGAAGAACTGTTTCTCT
GGAAAAGTATAAAGGCAAAGTTTCACTAGTTGTAAACGTGGCCAGTGACTGCCAACTCACAG
ACAGAAATTACTTAGGGCTGAAGGAACTGCACAAAGAGTTTGGACCATCCCACTTCAGCGTG
TTGGCTTTTCCCTGCAATCAGTTTGGAGAATCGGAGCCCCGCCCAAGCAAGGAAGTAGAATC
TTTTGCAAGAAAAAACTACGGAGTAACTTTCCCCATCTTCCACAAGATTAAGATTCTAGGAT
CTGAAGGAGAACCTGCATTTAGATTTCTTGTTGATTCTTCAAAGAAGGAACCAAGGTGGAAT
TTTTGGAAGTATCTTGTCAACCCTGAGGGTCAAGTTGTGAAGTTCTGGAGGCCAGAGGAGCC
CATTGAAGTCATCAGGCCTGACATAGCAGCTCTGGTTAGACAAGTGATCATAAAAAAGAAAG
AGGATCTATGAGAATGCCATTGCGTTTCTAATAGAACAGAGAAATGTCTCCATGAGGGTTTG
GTCTCATTTTAAACATTTTTTTTTGGAGACAGTGTCTCACTCTGTCACCCAGGCTGGAGTG
CAGTAGTGCGTTCTCAGCTCATTGCAACCTCTGCCTTTTTAAACATGCTATTAAATGTGGCA
ATGAAGGATTTTTTTTAATGTTATCTTGCTATTAAGTGGTAATGAATGTTCCCAGGATGAG
GATGTTACCCAAAGCAAAAATCAAGAGTAGCCAAAGAATCAACATGAAATATATTAACTACT
TCCTCTGACCATACTAAAGAATTCAGAATACACAGTGACCAATGTGCCTCAATATCTTATTG
TTCAACTTGACATTTTCTAGGACTGTACTTGATGAAAATGCCAACACACTAGACCACTCTTT
GGATTCAAGAGCACTGTGTATGACTGAAATTTCTGGAATAACTGTAAATGGTTATGTTAATG
GAATAAAACACAAATGTTGAAAATGTAAATATATATACATAGATTCAAATCCTTATATAT
GTATGCTTGTTTTGTGTACAGGATTTTGTTTTTTCTTTTTAAGTACAGGTTCCTAGTGTTTT
ACTATAACTGTCACTATGTATGTAACTGACATATATAAATAGTCATTTATAAATGACCGTAT
TATAACATTTGAAAAGTCTTCATCAAAAAAAAAAAAAAA

FIGURE 14

></usr/seqdb2/sst/DNA/Dnaseqs.min/ss.DNA80136
><subunit 1 of 1, 209 aa, 1 stop
><MW: 23909, pI: 9.68, NX(S/T): 0
MEPLAAYPLKCSGPRAKVFAVLLSIVLCTVTLFLLQLKFLKPKINSFYAFEVKDAKGRTVSL
EKYKGKVSLVVNVASDCQLTDRNYLGLKELHKEFGPSHFSVLAFPCNQFGESEPRPSKEVES
FARKNYGVTFPIFHKIKILGSEGEPAFRFLVDSSKKEPRWNFWKYLVNPEGQVVKFWRPEEP
IEVIRPDIAALVRQVIIKKKEDL

Important features of the protein:

Signal peptide:

amino acids 1-31

Glutathione peroxidases signature 2.

amino acids 104-112

Glutathione peroxidases.

amino acids 57-82

FIGURE 15

```
TGTCGCCTGGCCCTCGCCATGCAGACCCCGCGAGCGTCCCCTCCCCGCCCGGCCCTCCTGCTTCTGCTGCTGCTA
CTGGGGGGCGCCCACGGCCTCTTTCCTGAGGAGCCGCCGCCGCTTAGCGTGGCCCCCAGGGACTACCTGAACCAC
TATCCCGTGTTTGTGGGCAGCGGGCCCGGACGCCTGACCCCCGCAGAAGGTGCTGACGACCTCAACATCCAGCGA
GTCCTGCGGGTCAACAGGACGCTGTTCATTGGGGACAGGGACAACCTCTACCGCGTAGAGCTGGAGCCCCCCACG
TCCACGGAGCTGCGGTACCAGAGGAAGCTGACCTGGAGATCTAACCCCAGCGACATAAACGTGTGTCGGATGAAG
GGCAAACAGGAGGGCGAGTGTCGAAACTTCGTAAAGGTGCTGCTCCTTCGGGACGAGTCCACGCTCTTTGTGTGC
GGTTCCAACGCCTTCAACCCGGTGTGCGCCAACTACAGCATAGACACCCTGCAGCCCGTCGGAGACAACATCAGC
GGTATGGCCCGCTGCCCGTACGACCCCAAGCACGCCAATGTTGCCCTCTTCTCTGACGGGATGCTCTTCACAGCT
ACTGTTACCGACTTCCTAGCCATTGATGCTGTCATCTACCGCAGCCTCGGGGACAGGCCCACCCTGCGCACCGTG
AAACATGACTCCAAGTGGTTCAAAGAGCCTTACTTTGTCCATGCGGTGGAGTGGGGCAGCCATGTCTACTTCTTC
TTCCGGGAGATTGCGATGGAGTTTAACTACCTGGAGAAGGTGGTGGTGTCCCGCGTGGCCCGAGTGTGCAAGAAC
GACGTGGGAGGCTCCCCCCGCGTGCTGGAGAAGCAGTGGACGTCCTTCCTGAAGGCGCGGCTCAACTGCTCTGTA
CCCGGAGACTCCCATTTCTACTTCAACGTGCTGCAGGCTGTCACGGGCGTGGTCAGCCTCGGGGGCCGGCCCGTG
GTCCTGGCCGTTTTTTCCACGCCCAGCAACAGCATCCCTGGCTCGGCTGTCTGCGCCTTTGACCTGACACAGGTG
GCAGCTGTGTTTGAAGGCCGCTTCCGAGAGCAGAAGTCCCCCGAGTCCATCTGGACGCCGGTGCCGGAGGATCAG
GTGCCTCGACCCCGGCCCGGGTGCTGCGCAGCCCCCGGGATGCAGTACAATGCCTCCAGCGCCTTGCCGGATGAC
ATCCTCAACTTTGTCAAGACCCACCCTCTGATGGACGAGGCGGTGCCCTCGCTGGGCCATGCGCCCTGGATCCTG
CGGACCCTGATGAGGCACCAGCTGACTCGAGTGGCTGTGGACGTGGGAGCCGGCCCCTGGGCAACCAGACCGTT
GTCTTCCTGGGTTCTGAGGCGGGGACGGTCCTCAAGTTCCTCGTCCGGCCCAATGCCAGCACCTCAGGGACGTCT
GGGCTCAGTGTCTTCCTGGAGGAGTTTGAGACCTACCGGCGGACAGGTGTGGACGGCCCGGCGGTGGCGAGACA
GGGCAGCGGCTGCTGAGCTTGGAGCTGGACGCAGCTTCGGGGGGCCTGCTGGCTGCCTTCCCCCGCTGCGTGGTC
CGAGTGCCTGTGGCTCGCTGCCAGCAGTACTCGGGGTGTATGAAGAACTGTATCGGCAGTCAGGACCCCTACTGC
GGGTGGGCCCCCGACGGCTCCTGCATCTTCCTCAGCCCGGGCACCAGAGCCGCCTTTGAGCAGGACGTGTCCGGG
GCCAGCACCTCAGGCTTAGGGGACTGCACAGGACTCCTGCGGGCCAGCCTCTCCGAGGACCGCGCGGGGCTGGTG
TCGGTGAACCTGCTGGTAACGTCGTCGGTGGCGGCCTTCGTGGTGGGAGCCGTGGTGTCCGGCTTCAGCGTGGGC
TGGTTCGTGGGCCTCCGTGAGCGGCGGGAGCTGGCCCGGCGCAAGGACAAGGAGGCCATCCTGGCGCACGGGGCG
GGCGAGGCGGTGCTGAGCGTCAGCCGCCTGGGCGAGCGCAGGGCGCAGGGTCCCGGGGGCCGGGGCGGAGGCGGT
GGCGGTGGCGCCGGGGTTCCCCCGGAGGCCCTGCTGGCGCCCTGATGCAGAACGGCTGGGCCAAGGCCACGCTG
CTGCAGGGCGGGCCCCACGACCTGGACTCGGGGCTGCTGCCCACGCCCGAGCAGACGCCGCTGCCGCAGAAGCGC
CTGCCCACTCCGCACCCGCACCCCCACGCCCTGGGCCCCGCGCCTGGGACCACGGCCACCCCCTGCTCCCGGCC
TCCGCTTCATCCTCCCTCCTGCTGCTGGCGCCCGCCCGGGCCCCGAGCAGCCCCCGCGCCTGGGGAGCCGACC
CCCGACGGCCGCCTCTATGCTGCCCCGGCCGCGCCTCCCACGGCGACTTCCCGCTCACCCCCCACGCCAGC
CCGGACCGCCGGCGGGTGGTGTCCGCGCCCACGGGCCCCTTGGACCCAGCCTCAGCCGCCGATGGCCTCCCGCGG
CCCTGGAGCCCGCCCCGACGGGCAGCCTGAGGAGGCCACTGGGCCCCACGCCCCTCCGGCCGCCACCCTGCGC
CGCACCCACACGTTCAACAGCGGCGAGGCCCGGCCTGGGGACCGCCACCGCGGCTGCCACGCCCGGCCGGGCACA
GACTTGGCCCACCTCCTCCCCTATGGGGGGCGGACAGGACTGCGCCCCCCGTGCCCTAGGCCGGGGGCCCCCG
ATGCCTTGGCAGTGCCAGCCACGGGAACCAGGAGCGAGAGACGGTGCCAGAACGCCGGGGCCCGGGGCAACTCCG
AGTGGGTGCTCAAGTCCCCCCGCGACCCACCCGCGGAGTGGGGGGCCCCTCCGCCACAAGGAAGCACAACCAG
CTCGCCCTCCCCCTACCCGGGGCCGCAGGACGCTGAGACGGTTTGGGGGTGGGTGGGCGGGAGGACTTTGCTATG
GATTTGAGGTTGACCTTATGCGCGTAGGTTTTGGTTTTTTTTGCAGTTTTGGTTTCTTTTGCGGTTTTCTAACC
AATTGCACAACTCCGTTCTCGGGGTGGCGGCAGGCAGGGGAGGCTTGGACGCCGGTGGGGAATGGGGGCCACAG
CTGCAGACCTAAGCCCTCCCCCACCCCTGGAAAGGTCCCTCCCCAACCCAGGCCCCTGGCGTGTGTGGGTGTGCG
TGCGTGTGCGTGCCGTGTTCGTGTGCAAGGGGCCGGGGAGGTGGGCGTGTGTGCGTGCCAGCGAAGGCTGCTG
TGGGCGTGTGTGTCAAGTGGGCCACGCGTGCAGGGTGTGTCCACGAGCGACGATCGTGGTGGCCCCAGCGGCC
TGGGCGTTGGCTGAGCCGACGCTGGGCTTCCAGAAGGCCCGGGGTCTCCGAGGTGCCGGTTAGGAGTTTGAAC
CCCCCCACTCTGCAGAGGGAAGCGGGACAATGCCGGGGTTTCAGGCAGGAGACACGAGGAGGGCCTGCCCGGA
AGTCACATCGGCAGCAGCTGTCTAAAGGGCTTGGGGCCTGGGGGCGGCGAAGGTGGGTGGGCCCCTCTGTAA
ATACGGCCCCAGGGTGGTGAGAGAGTCCCATGCCACCCGTCCCCTTGTGACCTCCCCCCTATGACCTCCAGCTGA
CCATGCATGCCACGTGGCTGGCTGGGTCCTCTGCCCTCTTTGGAGTTTGCCTCCCCCAGCCCCCTCCCCATCAAT
AAAACTCTGTTTACAACCAAAAAAAAAAAAAAAAAAAAAAAAAAAA
```

FIGURE 16

></usr/seqdb2/sst/DNA/Dnaseqs.min/ss.DNA80145

><subunit 1 of 1, 888 aa, 1 stop

><MW: 95285, pI: 8.89, NX(S/T): 8

MQTPRASPPRPALLLLLLLLGGAHGLFPEEPPPLSVAPRDYLNHYPVFVGSGPGRLTPAEGA
DDLNIQRVLRVNRTLFIGDRDNLYRVELEPPTSTELRYQRKLTWRSNPSDINVCRMKGKQEG
ECRNFVKVLLLRDESTLFVCGSNAFNPVCANYSIDTLQPVGDNISGMARCPYDPKHANVALF
SDGMLFTATVTDFLAIDAVIYRSLGDRPTLRTVKHDSKWFKEPYFVHAVEWGSHVYFFFREI
AMEFNYLEKVVVSRVARVCKNDVGGSPRVLEKQWTSFLKARLNCSVPGDSHFYFNVLQAVTG
VVSLGGRPVVLAVFSTPSNSIPGSAVCAFDLTQVAAVFEGRFREQKSPESIWTPVPEDQVPR
PRPGCCAAPGMQYNASSALPDDILNFVKTHPLMDEAVPSLGHAPWILRTLMRHQLTRVAVDV
GAGPWGNQTVVFLGSEAGTVLKFLVRPNASTSGTSGLSVFLEEFETYRPDRCGRPGGGETGQ
RLLSLELDAASGGLLAAFPRCVVRVPVARCQQYSGCMKNCIGSQDPYCGWAPDGSCIFLSPG
TRAAFEQDVSGASTSGLGDCTGLLRASLSEDRAGLVSVNLLVTSSVAAFVVGAVVSGFSVGW
FVGLRERRELARRKDKEAILAHGAGEAVLSVSRLGERRAQGPGGRGGGGGGAGVPPEALLA
PLMQNGWAKATLLQGGPHDLDSGLLPTPEQTPLPQKRLPTPHPHPHALGPRAWDHGHPLLPA
SASSSLLLLAPARAPEQPPAPGEPTPDGRLYAARPGRASHGDFPLTPHASPDRRRVVSAPTG
PLDPASAADGLPRPWSPPPTGSLRRPLGPHAPPAATLRRTHTFNSGEARPGDRHRGCHARPG
TDLAHLLPYGGADRTAPPVP

Important features of the protein:

Signal peptide:

amino acids 1-25

Transmembrane domains:

amino acids 318-339, 598-617

N-glycosylation sites.

amino acids 74-78, 155-159, 167-171, 291-295, 386-390, 441-445, 462-466

Glycosaminoglycan attachment sites.

amino acids 51-55, 573-577 cAMP- and cGMP-dependent protein kinase phosphorylation site.

amino acids 102-106

N-myristoylation sites.

amino acids 21-27, 50-56, 189-195, 333-339, 382-388, 448-454, 490-496, 491-497, 508-514, 509-515, 531-537, 558-564, 569-575, 574-580, 580-586, 610-616, 643-649, 663-669, 666-672, 667-673, 668-674, 669-675, 670-676, 868-874, 879-885

FIGURE 17

AGCAACTCAAGTTCATCATTGTCCTGAGAGAGAGGAGCAGCGCGGTTCTCGGCCGGGACAGC
AGAACGCCAGGGGACCCTCACCTGGGCGCGCCGGGGCACGGGCTTTGATTGTCCTGGGGTCG
CGGAGACCCGCGCGCCTGCCCTGCACGCCGGGCGGCAACCTTTGCAGTCGCGTTGGCTGCTG
CGATCGGCCGGCGGGTCCCTGCCGAAGGCTCGGCTGCTTCTGTCCACCTCTTACACTTCTTC
ATTTATCGGTGGATCATTTCGAGAGTCCGTCTTGTAAATGTTTGGCACTTTGCTACTTTATT
GCTTCTTTCTGGCGACAGTTCCAGCACTCGCCGAGACCGGCGGAGAAAGGCAGCTGAGCCCG
GAGAAGAGCGAAATATGGGGACCCGGGCTAAAAGCAGACGTCGTCCTTCCCGCCCGCTATTT
CTATATTCAGGCAGTGGATACATCAGGGAATAAATTCACATCTTCTCCAGGCGAAAAGGTCT
TCCAGGTGAAAGTCTCAGCACCAGAGGAGCAATTCACTAGAGTTGGAGTCCAGGTTTTAGAC
CGAAAAGATGGGTCCTTCATAGTAAGATACAGAATGTATGCAAGCTACAAAAATCTGAAGGT
GGAAATTAAATTCCAAGGGCAACATGTGGCCAAATCCCCATATATTTTAAAAGGGCCGGTTT
ACCATGAGAACTGTGACTGTCCTCTGCAAGATAGTGCAGCCTGGCTACGGGAGATGAACTGC
CCTGAAACCATTGCTCAGATTCAGAGAGATCTGGCACATTTCCCTGCTGTGGATCCAGAAAA
GATTGCAGTAGAAATCCCAAAAAGATTTGGACAGAGGCAGAGCCTATGTCACTACACCTTAA
AGGATAACAAGGTTTATATCAAGACTCATGGTGAACATGTAGGTTTTAGAATTTTCATGGAT
GCCATACTACTTTCTTTGACTAGAAAGGTGAAGATGCCAGATGTGGAGCTCTTTGTTAATTT
GGGAGACTGGCCTTTGGAAAAAAGAAATCCAATTCAAACATCCATCCGATCTTTTCCTGGT
GTGGCTCCACAGATTCCAAGGATATCGTGATGCCTACGTACGATTTGACTGATTCTGTTCTG
GAAACCATGGGCCGGGTAAGTCTGGATATGATGTCCGTGCAAGCTAACACGGGTCCTCCCTG
GGAAAGCAAAAATTCCACTGCCGTCTGGAGAGGGCGAGACAGCCGCAAAGAGAGACTCGAGC
TGGTTAAACTCAGTAGAAAACACCCAGAACTCATAGACGCTGCTTTCACCAACTTTTCTTC
TTTAAACACGATGAAAACCTGTATGGTCCCATTGTGAAACATATTTCATTTTTTGATTTCTT
CAAGCATAAGTATCAAATAAATATCGATGGCACTGTAGCAGCTTATCGCCTGCCATATTTGC
TAGTTGGTGACAGTGTTGTGCTGAAGCAGGATTCCATCTACTATGAACATTTTTACAATGAG
CTGCAGCCCTGGAAACACTACATTCCAGTTAAGAGCAACCTGAGCGATCTGCTAGAAAAACT
TAAATGGGCGAAAGATCACGATGAAGAGGCCAAAAAGATAGCAAAGCAGGACAAGAATTTG
CAAGAAATAATCTCATGGGCGATGACATATTCTGTTATTATTTCAAACTTTTCCAGGAATAT
GCCAATTTACAAGTGAGTGAGCCCCAAATCCGAGAGGGCATGAAAAGGGTAGAACCACAGAC
TGAGGACGACCTCTTCCCTTGTACTTGCCATAGGAAAAAGACCAAAGATGAACTCTGATATG
CAAAATAACTTCTATTAGAATAATGGTGCTCTGAAGACTCTTCTTAACTAAAAAGAAGAATT
TTTTTAAGTATTAATTCCATGGACAATATAAAATCTGTGTGATTGTTTGCAGTATGAAGACA
CATTTCTACTTATGCAGTATTCTCATGACTGTACTTTAAAGTACATTTTTAGAATTTTATAA
TAAAACCACCTTTATTTTAAAGGAAAAAAA

FIGURE 18

></usr/seqdb2/sst/DNA/Dnaseqs.min/ss.DNA84917
><subunit 1 of 1, 502 aa, 1 stop
><MW: 58043, pI: 7.94, NX(S/T): 2

MFGTLLLYCFFLATVPALAETGGERQLSPEKSEIWGPGLKADVVLPARYFYIQAVDTSGNKF
TSSPGEKVFQVKVSAPEEQFTRVGVQVLDRKDGSFIVRYRMYASYKNLKVEIKFQGQHVAKS
PYILKGPVYHENCDCPLQDSAAWLREMNCPETIAQIQRDLAHFPAVDPEKIAVEIPKRFGQR
QSLCHYTLKDNKVYIKTHGEHVGFRIFMDAILLSLTRKVKMPDVELFVNLGDWPLEKKKSNS
NIHPIFSWCGSTDSKDIVMPTYDLTDSVLETMGRVSLDMMSVQANTGPPWESKNSTAVWRGR
DSRKERLELVKLSRKHPELIDAAFTNFFFFKHDENLYGPIVKHISFFDFFKHKYQINIDGTV
AAYRLPYLLVGDSVVLKQDSIYYEHFYNELQPWKHYIPVKSNLSDLLEKLKWAKDHDEEAKK
IAKAGQEFARNNLMGDDIFCYYFKLFQEYANLQVSEPQIREGMKRVEPQTEDDLFPCTCHRK
KTKDEL

Important features of the protein:

Signal peptide:

amino acids 1-17

N-glycosylation sites.

amino acids 302-306, 414-418 cAMP- and cGMP-dependent protein kinase phosphorylation sites.

amino acids 243-247, 495-499

Tyrosine kinase phosphorylation site.

amino acids 341-348

N-myristoylation sites.

amino acids 59-65, 118-124, 184-190, 258-264, 370-376, 439-445

Endoplasmic reticulum targeting sequence.

amino acids 499-504

FIGURE 19

```
CCTGGAGCCGGAAGCGCGGCTGCAGCAGGGCGAGGCTCCAGGTGGGGTCGGTTCCGCATCCA
GCCTAGCGTGTCCACGATGCGGCTGGGCTCCGGGACTTTCGCTACCTGTTGCGTAGCGATCG
AGGTGCTAGGGATCGCGGTCTTCCTTCGGGGATTCTTCCCGGCTCCCGTTCGTTCCTCTGCC
AGAGCGGAACACGGAGCGGAGCCCCCAGCGCCCGAACCCTCGGCTGGAGCCAGTTCTAACTG
GACCACGCTGCCACCACCTCTCTTCAGTAAAGTTGTTATTGTTCTGATAGATGCCTTGAGAG
ATGATTTTGTGTTTGGGTCAAAGGGTGTGAAATTTATGCCCTACACAACTTACCTTGTGGAA
AAAGGAGCATCTCACAGTTTTGTGGCTGAAGCAAAGCCACCTACAGTTACTATGCCTCGAAT
CAAGGCATTGATGACGGGGAGCCTTCCTGGCTTTGTCGACGTCATCAGGAACCTCAATTCTC
CTGCACTGCTGGAAGACAGTGTGATAAGACAAGCAAAAGCAGCTGGAAAAAGAATAGTCTTT
TATGGAGATGAAACCTGGGTTAAATTATTCCCAAAGCATTTTGTGGAATATGATGGAACAAC
CTCATTTTTCGTGTCAGATTACACAGAGGTGGATAATAATGTCACGAGGCATTTGGATAAAG
TATTAAAAAGAGGAGATTGGGACATATTAATCCTCCACTACCTGGGGCTGGACCACATTGGC
CACATTTCAGGGCCCAACAGCCCCCTGATTGGGCAGAAGCTGAGCGAGATGGACAGCGTGCT
GATGAAGATCCACACCTCACTGCAGTCGAAGGAGAGAGAGACGCCTTTACCCAATTTGCTGG
TTCTTTGTGGTGACCATGGCATGTCTGAAACAGGAAGTCACGGGGCCTCCTCCACCGAGGAG
GTGAATACACCTCTGATTTTAATCAGTTCTGCGTTTGAAAGGAAACCCGGTGATATCCGACA
TCCAAAGCACGTCCAATAGACGGATGTGGCTGCGACACTGGCGATAGCACTTGGCTTACCGA
TTCCAAAAGACAGTGTAGGGAGCCTCCTATTCCCAGTTGTGGAAGGAAGACCAATGAGAGAG
CAGTTGAGATTTTTACATTTGAATACAGTGCAGCTTAGTAAACTGTTGCAAGAGAATGTGCC
GTCATATGAAAAGATCCTGGGTTTGAGCAGTTTAAAATGTCAGAAAGATTGCATGGGAACT
GGATCAGACTGTACTTGGAGGAAAAGCATTCAGAAGTCCTATTCAACCTGGGCTCCAAGGTT
CTCAGGCAGTACCTGGATGCTCTGAAGACGCTGAGCTTGTCCCTGAGTGCACAAGTGGCCCA
GTTCTCACCCTGCTCCTGCTCAGCGTCCACAGGCACTGCACAGAAAGGCTGAGCTGGAAGT
CCCACTGTCATCTCCTGGGTTTTCTCTGCTCTTTTATTTGGTGATCCTGGTTCTTTCGGCCG
TTCACGTCATTGTGTGCACCTCAGCTGAAAGTTCGTGCTACTTCTGTGGCCTCTCGTGGCTG
GCGGCAGGCTGCCTTTCGTTTACCAGACTCTGGTTGAACACCTGGTGTGTGCCAAGTGCTGG
CAGTGCCCTGGACAGGGGGCCTCAGGGAAGGACGTGGAGCAGCCTTATCCCAGGCCTCTGGG
TGTCCCGACACAGGTGTTCACATCTGTGCTGTCAGGTCAGATGCCTCAGTTCTTGGAAAGCT
AGGTTCCTGCGACTGTTACCAAGGTGATTGTAAAGAGCTGGCGGTCACAGAGGAACAAGCCC
CCCAGCTGAGGGGGTGTGTGAATCGGACAGCCTCCCAGCAGAGGTGTGGGAGCTGCAGCTGA
GGGAAGAAGAGACAATCGGCCTGGACACTCAGGAGGGTCAAAAGGAGACTTGGTCGCACCAC
TCATCCTGCCACCCCCAGAATGCATCCTGCCTCATCAGGTCCAGATTTCTTTCCAAGGCGGA
CGTTTTCTGTTGGAATTCTTAGTCCTTGGCCTCGGACACCTTCATTCGTTAGCTGGGGAGTG
GTGGTGAGGCAGTGAAGAAGAGGCGGATGGTCACACTCAGATCCACAGAGCCCAGGATCAAG
GGACCCACTGCAGTGGCAGCAGGACTGTTGGGCCCCACCCCAACCCTGCACAGCCCTCATC
CCCTCTTGGCTTGAGCCGTCAGAGGCCCTGTGCTGAGTGTCTGACCGAGACACTCACAGCTT
TGTCATCAGGGCACAGGCTTCCTCGGAGCCAGGATGATCTGTGCCACGCTTGCACCTCGGGC
CCATCTGGGCTCATGCTCTCTCCTGCTATTGAATTAGTACCTAGCTGCACACAGTATGTA
GTTACCAAAAGAATAAACGGCAATAATTGAGAAAAAAA
```

FIGURE 20

></usr/seqdb2/sst/DNA/Dnaseqs.min/ss.DNA84920
><subunit 1 of 1, 310 aa, 1 stop
><MW: 33875, pI: 7.08, NX(S/T): 2
MRLGSGTFATCCVAIEVLGIAVFLRGFFPAPVRSSARAEHGAEPPAPEPSAGASSNWTTLPP
PLFSKVVIVLIDALRDDFVFGSKGVKFMPYTTYLVEKGASHSFVAEAKPPTVTMPRIKALMT
GSLPGFVDVIRNLNSPALLEDSVIRQAKAAGKRIVFYGDETWVKLFPKHFVEYDGTTSFFVS
DYTEVDNNVTRHLDKVLKRGDWDILILHYLGLDHIGHISGPNSPLIGQKLSEMDSVLMKIHT
SLQSKERETPLPNLLVLCGDHGMSETGSHGASSTEEVNTPLILISSAFERKPGDIRHPKHVQ

Important features of the protein:

Signal peptide:

amino acids 1-34

Transmembrane domain:

amino acids 58-76

N-glycosylation sites.

amino acids 56-60, 194-198

N-myristoylation sites.

amino acids 6-12, 52-58, 100-106, 125-131, 233-239, 270-276, 275-281, 278-284

Amidation site.

amino acids 154-158

Cell attachment sequence.

amino acids 205-208

FIGURE 21

AGCCAGGCAGCACATCACAGCGGGAGGAGCTGTCCCAGGTGGCCCAGCTCAGCAATGGCAAT
GGGGGTCCCCAGAGTCATTCTGCTCTGCCTCTTTGGGGCTGCGCTCTGCCTGACAGGGTCCC
AAGCCCTGCAGTGCTACAGCTTTGAGCACACCTACTTTGGCCCCTTTGACCTCAGGGCCATG
AAGCTGCCCAGCATCTCCTGTCCTCATGAGTGCTTTGAGGCTATCCTGTCTCTGGACACCGG
GTATCGCGCGCCGGTGACCCTGGTGCGGAAGGGCTGCTGGACCGGGCCTCCTGCGGGCCAGA
CGCAATCGAACCCGGACGCGCTGCCGCCAGACTACTCGGTGGTGCGCGGCTGCACAACTGAC
AAATGCAACGCCCACCTCATGACTCATGACGCCCTCCCCAACCTGAGCCAAGCACCCGACCC
GCCGACGCTCAGCGGCGCCGAGTGCTACGCCTGTATCGGGGTCCACCAGGATGACTGCGCTA
TCGGCAGGTCCCGACGAGTCCAGTGTCACCAGGACCAGACCGCCTGCTTCCAGGGCAGTGGC
AGAATGACAGTTGGCAATTTCTCAGTCCCTGTGTACATCAGAACCTGCCACCGGCCCTCCTG
CACCACCGAGGGCACCACCAGCCCCTGGACAGCCATCGACCTCCAGGGCTCCTGCTGTGAGG
GGTACCTCTGCAACAGGAAATCCATGACCCAGCCCTTCACCAGTGCTTCAGCCACCACCCCT
CCCCGAGCACTACAGGTCCTGGCCCTGCTCCTCCCAGTCCTCCTGCTGGTGGGGCTCTCAGC
ATAGACCGCCCCTCCAGGATGCTGGGGACAGGCTCACACACCTCATTCTTGCTGCTTCAGC
CCCTATCACATAGCTCACTGGAAAATGATGTTAAAGTAAGAATTGCAAAA

FIGURE 22

```
></usr/seqdb2/sst/DNA/Dnaseqs.min/ss.DNA86576
><subunit 1 of 1, 251 aa, 1 stop
><MW: 26935, pI: 7.42, NX(S/T): 2
MAMGVPRVILLCLFGAALCLTGSQALQCYSFEHTYFGPFDLRAMKLPSISCPHECFEAILSL
DTGYRAPVTLVRKGCWTGPPAGQTQSNPDALPPDYSVVRGCTTDKCNAHLMTHDALPNLSQA
PDPPTLSGAECYACIGVHQDDCAIGRSRRVQCHQDQTACFQGSGRMTVGNFSVPVYIRTCHR
PSCTTEGTTSPWTAIDLQGSCCEGYLCNRKSMTQPFTSASATTPPRALQVLALLLPVLLLVGLSA
```

Important features of the protein:

Signal peptide:

amino acids 1-19

Transmembrane domain:

amino acids 233-251

N-glycosylation sites.

amino acids 120-124, 174-178

N-myristoylation sites.

amino acids 15-21, 84-90

FIGURE 23

```
CCCACGCGTCCGGGACAGATGAACTTAAAAGAGAAGCTTTAGCTGCCAAAGATTGGGAAAGG
GAAAGGACAAAAAAGACCCCTGGGCTACACGGCGTAGGTGCAGGGTTTCCTACTGCTGTTCT
TTTATGCTGGGAGCTGTGGCTGTAACCAACTAGGAAATAACGTATGCAGCAGCATGGCTGT
CAGAGAGTTGTGCTTCCCAAGACAAAGGCAAGTCCTGTTTCTTTTTCTTTTTTGGGGAGTGT
CCTTGGCAGGTTCTGGGTTTGGACGTTATTCGGTGACTGAGGAAACAGAGAAAGGATCCTTT
GTGGTCAATCTGGCAAAGGATCTGGGACTAGCAGAGGGGGAGCTGGCTGCAAGGGGAACCAG
GGTGGTTTCCGATGATAACAAACAATACCTGCTCCTGGATTCACATACCGGGAATTTGCTCA
CAAATGAGAAACTGGACCGAGAGAAGCTGTGTGGCCCTAAAGAGCCCTGTATGCTGTATTTC
CAAATTTTAATGGATGATCCCTTTCAGATTTACCGGGCTGAGCTGAGAGTCAGGGATATAAA
TGATCACGCGCCAGTATTTCAGGACAAAGAAACAGTCTTAAAAATATCAGAAAATACAGCTG
AAGGGACAGCATTTAGACTAGAAAGAGCACAGGATCCAGATGGAGGACTTAACGGTATCCAA
AACTACACGATCAGCCCCAACTCTTTTTTCCATATTAACATTAGTGGCGGTGATGAAGGCAT
GATATATCCAGAGCTAGTGTTGGACAAAGCACTGGATCGGGAGGAGCAGGGAGAGCTCAGCT
TAACCCTCACAGCGCTGGATGGTGGGTCTCCATCCAGGTCTGGGACCTCTACTGTACGCATC
GTTGTCTTGGACGTCAATGACAATGCCCCACAGTTTGCCCAGGCTCTGTATGAGACCCAGGC
TCCAGAAAACAGCCCCATTGGGTTCCTTATTGTTAAGGTATGGGCAGAAGATGTAGACTCTG
GAGTCAACGCGGAAGTATCCTATTCATTTTTTGATGCCTCAGAAAATATTCGAACGACCTTT
CAAATCAATCCTTTTTCTGGGGAAATCTTTCTCAGAGAATTGCTTGATTATGAGTTAGTAAA
TTCTTACAAAATAAATATACAGGCAATGGACGGTGGAGGCCTTTCTGCAAGATGTAGGGTTT
TAGTGGAAGTATTGGACACCAATGACAATCCCCCTGAACTGATCGTATCATCATTTTCCAAC
TCTGTTGCTGAGAATTCTCCTGAGACGCCGCTGGCTGTTTTTAAGATTAATGACAGAGACTC
TGGAGAAAATGGAAAGATGGTTTGCTACATTCAAGAGAATCTGCCATTCCTACTAAAACCTT
CTGTGGAGAATTTTTACATCCTAATTACAGAAGGCGCGCTGGACAGAGAGATCAGAGCCGAG
TACAACATCACTATCACCGTCACTGACTTGGGGACACCCAGGCTGAAAACCGAGCACAACAT
AACGGTCCTGGTCTCCGACGTCAATGACAACGCCCCGCCTTCACCCAAACCTCCTACACCC
TGTTCGTCCGCGAGAACAACAGCCCCGCCCTGCACATCGGCAGCGTCAGCGCCACAGACAGA
GACTCGGGCACCAACGCCCAGGTCACCTACTCGCTGCTGCCGCCCCAAGACCCGCACCTGCC
CCTCGCCTCCCTGGTCTCCATCAACGCGGACAACGGCCACCTGTTCGCCCTCAGGTCGCTGG
ACTACGAGGCCCTGCAGGCTTTCGAGTTCCGCGTGGGCGCCACAGACCGCGGCTCCCCCGCG
CTGAGCAGAGAGGCGCTGGTGCGCGTGCTGGTGCTGGACGCCAACGACAACTCGCCCTTCGT
GCTGTACCCGCTGCAGAACGGCTCCGCGCCCTGCACCGAGCTGGTGCCCCGGGCGGCCGAGC
CGGGCTACCTGGTGACCAAGGTGGTGGCGGTGGACGGCGACTCGGGCCAGAACGCCTGGCTG
TCGTACCAGCTGCTCAAGGCCACGGAGCCCGGGCTGTTCGGTGTGTGGGCGCACAATGGGGA
GGTGCGCACCGCCAGGCTGCTGAGCGAGCGCGACGCAGCCAAGCACAGGCTCGTGGTGCTTG
TCAAGGACAATGGCGAGCCTCCTCGCTCGGCCACCGCCACGCTGCACTTGCTCCTGGTGGAC
GGCTTCTCCCAGCCCTACCTGCCTCTCCCGGAGGCGGCCCCGGCCCAGGCCCAGGCCGAGGC
CGACTTGCTCACCGTCTACCTGGTGGTGGCGTTGGCCTCGGTGTCTTCGCTCTTCCTCCTCT
CGGTGCTCCTGTTCGTGGCGGTGCGGCTGTGCAGGAGGAGCAGGGCGGCCTCGGTGGGTCGC
TGCTCGGTGCCCGAGGGTCCTTTTCCAGGGCATCTGGTGGACGTGAGGGGCGCTGAGACCCT
GTCCCAGAGCTACCAGTATGAGGTGTGTCTGACGGGAGGCCCCGGGACCAGTGAGTTCAAGT
TCTTGAAACCAGTTATTTCGGATATTCAGGCACAGGGCCCTGGGAGGAAGGGTGAAGAAAAT
TCCACCTTCCGAAATAGCTTTGGATTTAATATTCAGTAAAGTCTGTTTTAGTTTCATATAC
TTTTGGTGTGTTACATAGCCATGTTTCTATTAGTTTACTTTTAAATCTCAAATTTAAGTTAT
TATGCAACTTCAAGCATTATTTTCAAGTAGTATACCCCTGTGGTTTTACAATGTTTCATCAT
TTTTTTGCATTAATAACAACTGGGTTTAATTTAATGAGTATTTTTTCTAAATGATAGTGTT
AAGGTTTTAATTCTTTCCAACTGCCCAAGGAATTAATTACTATTATATCTCATTACAGAAAT
CTGAGGTTTTGATTCATTTCAGAGCTTGCATCTCATGATTCTAATCACTTCTGTCTATAGTG
TACTTGCTCTATTTAAGAAGGCATATCTACATTTCCAAACTCATTCTAACATTCTATATATT
CGTGTTTGAAAACCATGTCATTTATTTCTACATCATGTATTTAAAAGAAATATTTCTCTAC
TACTATGCTCATGACAAAATGAAACAAAGCATATTGTGAGCAATACTGAACATCAATAATAC
CCTTAGTTTATATACTTATTATTTTATCTTTAAGCATGCTACTTTTACTTGGCCAATATTTT
CTTATGTTAACTTTTGCTGATGTATAAAACAGACTATGCCTTATAATTGAAATAAAATTATA
ATCTGCCTGAAAATGAATAAAAATAAAACATTTTGAAATGTGAAAAAAAAAAAAAAAAAAAA
```

FIGURE 24

></usr/seqdb2/sst/DNA/Dnaseqs.min/ss.DNA87976

><subunit 1 of 1, 800 aa, 1 stop

><MW: 87621, pI: 4.77, NX(S/T): 7

```
MAVRELCFPRQRQVLFLFLFWGVSLAGSGFGRYSVTEETEKGSFVVNLAKDLGLAEGELAAR
GTRVVSDDNKQYLLLDSHTGNLLTNEKLDREKLCGPKEPCMLYFQILMDDPFQIYRAELRVR
DINDHAPVFQDKETVLKISENTAEGTAFRLERAQDPDGGLNGIQNYTISPNSFFHINISGGD
EGMIYPELVLDKALDREEQGELSLTLTALDGGSPSRSGTSTVRIVVLDVNDNAPQFAQALYE
TQAPENSPIGFLIVKVWAEDVDSGVNAEVSYSFFDASENIRTTFQINPFSGEIFLRELLDYE
LVNSYKINIQAMDGGGLSARCRVLVEVLDTNDNPPELIVSSFSNSVAENSPETPLAVFKIND
RDSGENGKMVCYIQENLPFLLKPSVENFYILITEGALDREIRAEYNITITVTDLGTPRLKTE
HNITVLVSDVNDNAPAFTQTSYTLFVRENNSPALHIGSVSATDRDSGTNAQVTYSLLPPQDP
HLPLASLVSINADNGHLFALRSLDYEALQAFEFRVGATDRGSPALSREALVRVLVLDANDNS
PFVLYPLQNGSAPCTELVPRAAEPGYLVTKVVAVDGDSGQNAWLSYQLLKATEPGLFGVWAH
NGEVRTARLLSERDAAKHRLVVLVKDNGEPPRSATATLHLLLVDGFSQPYLPLPEAAPAQAQ
AEADLLTVYLVVALASVSSLFLLSVLLFVAVRLCRRSRAASVGRCSVPEGPFPGHLVDVRGA
ETLSQSYQYEVCLTGGPGTSEFKFLKPVISDIQAQGPGRKGEENSTFRNSFGFNIQ
```

Important features of the protein:

Signal peptide:

amino acids 1-26

Transmembrane domain:

amino acids 687-711

N-glycosylation sites.

amino acids 169-173, 181-185, 418-422, 436-440, 567-571, 788-792

Glycosaminoglycan attachment site.

amino acids 28-32

Tyrosine kinase phosphorylation sites.

amino acids 394-402, 578-585

N-myristoylation sites.

amino acids 22-28, 27-33, 53-59, 82-88, 162-168, 184-190, 217-223, 324-330, 325-331, 471-477, 568-574, 759-765

Amidation site.

amino acids 781-785

Aminoacyl-transfer RNA synthetases class-II signature 1.

amino acids 117-138

Cadherins extracellular repeated domain signature.

amino acids 121-132, 230-241, 335-346, 439-450, 549-560

FIGURE 25

```
GAATGAATACCTCCGAAGCCGCTTTGTTCTCCAGATGTGAATAGCTCCACTATACCAGCCTC
GTCTTCCTTCCGGGGGACAACGTGGGTCAGGGCACAGAGAGATATTTAATGTCACCCTCTTG
GGGCTTTCATGGACTCCCTCTGCCACATTTTTGGAGGTTGGGAAAGTTGCTAGAGGCTTC
AGAACTCCAGCCTAATGGATCCCAAACTCGGGAGAATGGCTGCGTCCTGCTGGCTGTGCTG
CTGCTGCTGCTGGAGCGCGGCATGTTCTCCTCACCCTCCCCGCCCCGGCGCTGTTAGAGAA
AGTCTTCCAGTACATTGACCTCCATCAGGATGAATTTGTGCAGACGCTGAAGGAGTGGGTGG
CCATCGAGAGCGACTCTGTCCAGCCTGTGCCTCGCTTCAGACAAGAGCTCTTCAGAATGATG
GCCGTGGCTGCGGACACGCTGCAGCGCCTGGGGCCCGTGTGGCCTCGGTGGACATGGGTCC
TCAGCAGCTGCCCGATGGTCAGAGTCTTCCAATACCTCCCGTCATCCTGGCCGAACTGGGGA
GCGATCCCACGAAAGGCACCGTGTGCTTCTACGGCCACTTGGACGTGCAGCCTGCTGACCGG
GGCGATGGGTGGCTCACGGACCCCTATGTGCTGACGGAGGTAGACGGGAAACTTTATGGACG
AGGAGCGACCGACAACAAAGGCCCTGTCTTGGCTTGGATCAATGCTGTGAGCGCCTTCAGAG
CCCTGGAGCAAGATCTTCCTGTGAATATCAAATTCATCATTGAGGGGATGGAAGAGGCTGGC
TCTGTTGCCCTGGAGGAACTTGTGGAAAAGAAAAGGACCGATTCTTCTCTGGTGTGGACTA
CATTGTAATTTCAGATAACCTGTGGATCAGCCAAAGGAAGCCAGCAATCACTTATGGAACCC
GGGGGAACAGCTACTTCATGGTGGAGGTGAAATGCAGAGACCAGGATTTTCACTCAGGAACC
TTTGGTGGCATCCTTCATGAACCAATGGCTGATCTGGTTGCTCTTCTCGGTAGCCTGGTAGA
CTCGTCTGGTCATATCCTGGTCCCTGGAATCTATGATGAAGTGGTTCCTCTTACAGAAGAGG
AAATAAATACATACAAAGCCATCCATCTAGACCTAGAAGAATACCGGAATAGCAGCCGGGTT
GAGAAATTTCTGTTCGATACTAAGGAGGAGATTCTAATGCACCTCTGGAGGTACCCATCTCT
TTCTATTCATGGGATCGAGGGCGCGTTTGATGAGCCTGGAACTAAAACAGTCATACCTGGCC
GAGTTATAGGAAAATTTTCAATCCGTCTAGTCCCTCACATGAATGTGTCTGCGGTGGAAAAA
CAGGTGACACGACATCTTGAAGATGTGTTCTCCAAAAGAAATAGTTCCAACAAGATGGTTGT
TTCCATGACTCTAGGACTACACCCGTGGATTGCAAATATTGATGACACCCAGTATCTCGCAG
CAAAAAGAGCGATCAGAACAGTGTTTGGAACAGAACCAGATATGATCCGGGATGGATCCACC
ATTCCAATTGCCAAAATGTTCCAGGAGATCGTCCACAAGAGCGTGGTGCTAATTCCGCTGGG
AGCTGTTGATGATGGAGAACATTCGCAGAATGAGAAAATCAACAGGTGGAACTACATAGAGG
GAACCAAATTATTTGCTGCCTTTTTCTTAGAGATGGCCCAGCTCCATTAATCACAAGAACCT
TCTAGTCTGATCTGATCCACTGACAGATTCACCTCCCCACATCCCTAGACAGGGATGGAAT
GTAAATATCCAGAGAATTTGGGTCTAGTATAGTACATTTTCCCTTCCATTTAAAATGTCTTG
GGATATCTGGATCAGTAATAAAATATTTCAAAGGCACAGATGTTGGAAATGGTTTAAGGTCC
CCCACTGCACACCTTCCTCAAGTCATAGCTGCTTGCAGCAACTTGATTTCCCCAAGTCCTGT
GCAATAGCCCCAGGATTGGATTCCTTCCAACCTTTTAGCATATCTCCAACCTTGCAATTTGA
TTGGCATAATCACTCCGGTTTGCTTTCTAGGTCCTCAAGTGCTCGTGACACATAATCATTCC
ATCCAATGATCGCCTTTGCTTTACCACTCTTTCCTTTTATCTTATTAATAAAAATGTTGGTC
TCCACCACTGNCTCCCAAAAAAAAAAAAAAAAAAAAAAAAAAAAAAAAAAAAAAAAAAAAAA
AAAAAAAAA
```

FIGURE 26

```
></usr/seqdb2/sst/DNA/Dnaseqs.min/ss.DNA92234
><subunit 1 of 1, 507 aa, 1 stop
><MW: 56692, pI: 5.22, NX(S/T): 3
MDPKLGRMAASLLAVLLLLLERGMFSSPSPPPALLEKVFQYIDLHQDEFVQTLKEWVAIESD
SVQPVPRFRQELFRMMAVAADTLQRLGARVASVDMGPQQLPDGQSLPIPPVILAELGSDPTK
GTVCFYGHLDVQPADRGDGWLTDPYVLTEVDGKLYGRGATDNKGPVLAWINAVSAFRALEQD
LPVNIKFIIEGMEEAGSVALEELVEKEKDRFFSGVDYIVISDNLWISQRKPAITYGTRGNSY
FMVEVKCRDQDFHSGTFGGILHEPMADLVALLGSLVDSSGHILVPGIYDEVVPLTEEEINTY
KAIHLDLEEYRNSSRVEKFLFDTKEEILMHLWRYPSLSIHGIEGAFDEPGTKTVIPGRVIGK
FSIRLVPHMNVSAVEKQVTRHLEDVFSKRNSSNKMVVSMTLGLHPWIANIDDTQYLAAKRAI
RTVFGTEPDMIRDGSTIPIAKMFQEIVHKSVVLIPLGAVDDGEHSQNEKINRWNYIEGTKLF
AAFFLEMAQLH
```

Important features of the protein:

Signal peptide:

amino acids 1-26

Transmembrane domain:

273-292

N-glycosylation sites.

amino acids 322-326, 382-386, 402-406 cAMP- and cGMP-dependent protein kinase phosphorylation site.

amino acids 400-404

N-myristoylation sites.

amino acids 89-95, 119-125, 162-168, 197-203, 242-248, 263-269, 351-357

Cell attachment sequence.

amino acids 140-143

ArgE / dapE / ACY1 / CPG:

amino acids 156-167

FIGURE 27

CTCGGCTGGATTTAAGGTTGCCGCTAGCCGCCTGGGAATTTAAGGGACCCACACTACCTTCC
CGAAGTTGAAGGCAAGCGGTGATTGTTTGTAGACGGCGCTTTGTCATGGGACCTGTGCGGTT
GGGAATATTGCTTTTCCTTTTTTTGGCCGTGCACGAGGCTTGGGCTGGGATGTTGAAGGAGG
AGGACGATGACACAGAACGCTTGCCCAGCAAATGCGAAGTGTGTAAGCTGCTGAGCACAGAG
CTACAGGCGGAACTGAGTCGCACCGGTCGATCTCGAGAGGTGCTGGAGCTGGGGCAGGTGCT
GGATACAGGCAAGAGGAAGAGACACGTGCCTTACAGCGTTTCAGAGACAAGGCTGGAAGAGG
CCTTAGAGAATTTATGTGAGCGGATCCTGGACTATAGTGTTCACGCTGAGCGCAAGGGCTCA
CTGAGATATGCCAAGGGTCAGAGTCAGACCATGGCAACACTGAAAGGCCTAGTGCAGAAGGG
GGTGAAGGTGGATCTGGGGATCCCTCTGGAGCTTTGGGATGAGCCCAGCGTGGAGGTCACAT
ACCTCAAGAAGCAGTGTGAGACCATGTTGGAGGAGTTTGAAGACATTGTGGGAGACTGGTAC
TTCCACCATCAGGAGCAGCCCCTACAAAATTTTCTCTGTGAAGGTCATGTGCTCCCAGCTGC
TGAAACTGCATGTCTACAGGAAACTTGGACTGGAAAGGAGATCACAGATGGGGAAGAGAAAA
CAGAAGGGGAGGAAGAGCAGGAGGAGGAGGAGGAAGAGGAGGAAGAGGAAGGGGAGACAAG
ATGACCAAGACAGGAAGCCACCCCAAACTTGACCGAGAAGATCTTTGACCCTTGCCTTTGAG
CCCCCAGGAGGGGAAGGGATCATGGAGAGCCCTCTAAAGCCTGCACTCTCCCTGCTCCACAG
CTTTCAGGGTGTGTTTATGAGTGACTCCACCCAAGCTTGTAGCTGTTCTCTCCCATCTAACC
TCAGGCAAGATCCTGGTGAAACAGCATGACATGGCTTCTGGGGTGGAGGGTGGGGGTGGAGG
TCCTGCTCCTAGAGATGAACTCTATCCAGCCCCTTAATTGGCAGGTGTATGTGCTGACAGTA
CTGAAAGCTTTCCTCTTTAACTGATCCCACCCCCACCCAAAAGTCAGCAGTGGCACTGGAGC
TGTGGGCTTTGGGGAAGTCACTTAGCTCCTTAAGGTCTGTTTTTAGACCCTTCCAAGGAAGA
GGCCAGAACGGACATTCTCTGCGATCTATATACATTGCCTGTATCCAGGAGGCTACACACCA
GCAAACCGTGAAGGAGAATGGGACACTGGGTCATGGCCTGGAGTTGCTGATAATTTAGGTGG
GATAGATACTTGGTCTACTTAAGCTCAATGTAACCCAGAGCCCACCATATAGTTTTATAGGT
GCTCAACTTTCTATATCGCTATTAAACTTTTTTCTTTTTTCTA

FIGURE 28

```
></usr/seqdb2/sst/DNA/Dnaseqs.min/ss.DNA92256
><subunit 1 of 1, 248 aa, 1 stop
><MW: 28310, pI: 4.63, NX(S/T): 0
MGPVRLGILLFLFLAVHEAWAGMLKEEDDDTERLPSKCEVCKLLSTELQAELSRTGRSREVL
ELGQVLDTGKRKRHVPYSVSETRLEEALENLCERILDYSVHAERKGSLRYAKGQSQTMATLK
GLVQKGVKVDLGIPLELWDEPSVEVTYLKKQCETMLEEFEDIVGDWYFHHQEQPLQNFLCEG
HVLPAAETACLQETWTGKEITDGEEKTEGEEEQEEEEEEEEEGGDKMTKTGSHPKLDREDL
```

Important features of the protein:

Signal peptide:

amino acids 1-21 cAMP- and cGMP-dependent protein kinase phosphorylation site.

amino acids 106-110

N-myristoylation site.

amino acids 115-121

Amidation site.

amino acids 70-74

FIGURE 29

AAGTACTTGTGTCCGGGTGGTGGACTGGATTAGCTGCGGAGCCCTGGAAGCTGCCTGTCCTT
CTCCCTGTGCTTAACCAGAGGTGCCCATGGGTTGGACAATGAGGCTGGTCACAGCAGCACTG
TTACTGGGTCTCATGATGGTGGTCACTGGAGACGAGGATGAGAACAGCCCGTGTGCCCATGA
GGCCCTCTTGGACGAGGACACCCTCTTTTGCCAGGGCCTTGAAGTTTTCTACCCAGAGTTGG
GGAACATTGGCTGCAAGGTTGTTCCTGATTGTAACAACTACAGACAGAAGATCACCTCCTGG
ATGGAGCCGATAGTCAAGTTCCCGGGGCCGTGGACGGCGCAACCTATATCCTGGTGATGGT
GGATCCAGATGCCCCTAGCAGAGCAGAACCCAGACAGAGATTCTGGAGACATTGGCTGGTAA
CAGATATCAAGGGCGCCGACCTGAAGAAGGGAAGATTCAGGGCCAGGAGTTATCAGCCTAC
CAGGCTCCCTCCCCACCGGCACACAGTGGCTTCCATCGCTACCAGTTCTTTGTCTATCTTCA
GGAAGGAAAAGTCATCTCTCTCCTTCCCAAGGAAAACAAAACTCGAGGCTCTTGGAAAATGG
ACAGATTTCTGAACCGCTTCCACCTGGGCGAACCTGAAGCAAGCACCCAGTTCATGACCCAG
AACTACCAGGACTCACCAACCCTCCAGGCTCCCAGAGGAAGGGCCAGCGAGCCCAAGCACAA
AACCAGGCAGAGATAGCTGCCTGCTAGATAGCCGGCTTTGCCATCCGGGCATGTGGCCACAC
TGCTCACCACCGACGATGTGGGTATGGAACCCCTCTGGATACAGAACCCCTTCTTTTCCAA
ATTAAAAAAAAAAATCATCAAA

FIGURE 30

></usr/seqdb2/sst/DNA/Dnaseqs.min/ss.DNA92274
><subunit 1 of 1, 223 aa, 1 stop
><MW: 25402, pI: 8.14, NX(S/T): 1
MGWTMRLVTAALLLGLMMVVTGDEDENSPCAHEALLDEDTLFCQGLEVFYPELGNIGCKVVP
DCNNYRQKITSWMEPIVKFPGAVDGATYILVMVDPDAPSRAEPRQRFWRHWLVTDIKGADLK
KGKIQGQELSAYQAPSPPAHSGFHRYQFFVYLQEGKVISLLPKENKTRGSWKMDRFLNRFHL
GEPEASTQFMTQNYQDSPTLQAPRGRASEPKHKTRQR

Important features of the protein:
Signal peptide:
amino acids 1-22

N-glycosylation site.
amino acids 169-173

Tyrosine kinase phosphorylation site.
amino acids 59-68

N-myristoylation sites.
amino acids 54-60, 83-89, 130-136

Phosphatidylethanolamine signature.
amino acids 113-157

FIGURE 31

GTCGACCCACGCGTCCGAAGCTGCTGGAGCCACGATTCAGTCCCCTGGACTGTAGATAAAGA
CCCTTTCTTGCCAGGTGCTGAGACAACCACACTATGAGAGGCACTCCAGGAGACGCTGATGG
TGGAGGAAGGGCCGTCTATCAATCAATCACTGTTGCTGTTATCACATGCAAGTATCCAGAGG
CTCTTGAGCAAGGCAGAGGGGATCCCATTTATTTGGGAATCCAGAATCCAGAAATGTGTTTG
TATTGTGAGAAGGTTGGAGAACAGCCCACATTGCAGCTAAAAGAGCAGAAGATCATGGATCT
GTATGGCCAACCCGAGCCCGTGAAACCCTTCCTTTTCTACCGTGCCAAGACTGGTAGGACCT
CCACCCTTGAGTCTGTGGCCTTCCCGGACTGGTTCATTGCCTCCTCCAAGAGAGACCAGCCC
ATCATTCTGACTTCAGAACTTGGGAAGTCATACAACACTGCCTTTGAATTAAATATAAATGA
CTGAACTCAGCCTAGAGGTGGCAGCTTGGTCTTTGTCTTAAAGTTTCTGGTTCCCAATGTGT
TTTCGTCTACATTTTCTTAGTGTCATTTTCACGCTGGTGCTGAGACAGGAGCAAGGCTGCTG
TTATCATCTCATTTTATAATGAAGAAGAAGCAATTACTTCATAGCAACTGAAGAACAGGATG
TGGCCTCAGAAGCAGGAGAGCTGGGTGGTATAAGGCTGTCCTCTCAAGCTGGTGCTGTGTAG
GCCACAAGGCATCTGCATGAGTGACTTTAAGACTCAAAGACCAAACACTGAGCTTTCTTCTA
GGGGTGGGTATGAAGATGCTTCAGAGCTCATGCGCGTTACCCACGATGGCATGACTAGCACA
GAGCTGATCTCTGTTTCTGTTTTGCTTTATTCCCTCTTGGGATGATATCATCCAGTCTTTAT
ATGTTGCCAATATACCTCATTGTGTGTAATAGAACCTTCTTAGCATTAAGACCTTGTAAACA
AAAATAATTCTTGGGGTGGGTATGAAGATGCTTCAGAGCTCATGCGCGTTACCCACGATGGC
ATGACTAGCACAGAGCTGATCTCTGTTTCTGTTTTGCTTTATTCCCTCTTGGGATGATATCA
TCCAGTCTTTATATGTTGCCAATATACCTCATTGTGTGTAATAGAACCTTCTTAGCATTAAG
ACCTTGTAAACAAAATAATTCTTGTGTTAAGTTAAATCATTTTGTCCTAATTGTAATGTG
TAATCTTAAAGTTAAATAAACTTTGTGTATTTATATAATAATAAAGCTAAAACTGATATAAA
ATAAAGAAAGAGTAAACTG

FIGURE 32

MRGTPGDADGGGRAVYQSITVAVITCKYPEALEQGRGDPIYLGIQNPEMCLYCEKVGEQPTL
QLKEQKIMDLYGQPEPVKPFLFYRAKTGRTSTLESVAFPDWFIASSKRDQPIILTSELGKSY
NTAFELNIND

Signal sequence:

amino acids 1-17

N-myristoylation site.

amino acids 10-16

Cell attachment sequence.

amino acids 36-39

FIGURE 33

GCGAGGCTGCACCAGCGCCTGGCACCATGAGGACGCCTGGGCCTCTGCCCGTGCTGCTGCTG
CTCCTGGCGGGAGCCCCCGCCGCGCGGCCCACTCCCCCGACCTGCTACTCCCGCATGCGGGC
CCTGAGCCAGGAGATCACCCGCGACTTCAACCTCCTGCAGGTCTCGGAGCCCTCGGAGCCAT
GTGTGAGATACCTGCCCAGGCTGTACCTGGACATACACAATTACTGTGTGCTGGACAAGCTG
CGGGACTTTGTGGCCTCGCCCCGTGTTGGAAAGTGGCCCAGGTAGATTCCTTGAAGGACAA
AGCACGGAAGCTGTACACCATCATGAACTCGTTCTGCAGGAGAGATTTGGTATTCCTGTTGG
ATGACTGCAATGCCTTGGAATACCCAATCCCAGTGACTACGGTCCTGCCAGATCGTCAGCGC
TAAGGGAACTGAGACCAGAGAAAGAACCCAAGAGAACTAAAGTTATGTCAGCTACCCAGACT
TAATGGGCCAGAGCCATGACCCTCACAGGTCTTGTGTTAGTTGTATCTGAAACTGTTATGTA
TCTCTCTACCTTCTGGAAAACAGGGCTGGTATTCCTACCCAGGAACCTCCTTTGAGCATAGA
GTTAGCAACCATGCTTCTCATTCCCTTGACTCATGTCTTGCCAGGATGGTTAGATACACAGC
ATGTTGATTTGGTCACTAAAAAGAAGAAAAGGACTAACAAGCTTCACTTTTATGAACAACTA
TTTTGAGAACATGCACAATAGTATGTTTTTATTACTGGTTTAATGGAGTAATGGTACTTTTA
TTCTTTCTTGATAGAAACCTGCTTACATTTAACCAAGCTTCTATTATGCCTTTTTCTAACAC
AGACTTTCTTCACTGTCTTTCATTTAAAAGAAATTAATGCTCTTAAGATATATATTTTACG
TAGTGCTGACAGGACCCACTCTTTCATTGAAGGTGATGAAAATCAAATAAAGAATCTCTTC
ACATGGA

FIGURE 34

></usr/seqdb2/sst/DNA/Dnaseqs.min/ss.DNA93011
><subunit 1 of 1, 136 aa, 1 stop
><MW: 15577, pI: 8.88, NX(S/T): 0
MRTPGPLPVLLLLLAGAPAARPTPPTCYSRMRALSQEITRDFNLLQVSEPSEPCVRYLPRLY
LDIHNYCVLDKLRDFVASPPCWKVAQVDSLKDKARKLYTIMNSFCRRDLVFLLDDCNALEYP
IPVTTVLPDRQR

Important features of the protein:

Signal peptide:

amino acids 1-19

Tyrosine kinase phosphorylation site.

amino acids 60-69

N-myristoylation site.

amino acids 16-22

FIGURE 35

GTCTCCGCGTCACAGGAACTTCAGCACCCACAGGGCGGACAGCGCTCCCCTCTACCTGGAGA
CTTGACTCCCGCGCGCCCCAACCCTGCTTATCCCTTGACCGTCGAGTGTCAGAGATCCTGCA
GCCGCCCAGTCCCGGCCCCTCTCCCGCCCCACACCCACCCTCCTGGCTCTTCCTGTTTTTAC
TCCTCCTTTTCATTCATAACAAAAGCTACAGCTCCAGGAGCCCAGCGCCGGGCTGTGACCCA
AGCCGAGCGTGGAAGAATGGGGTTCCTCGGGACCGGCACTTGGATTCTGGTGTTAGTGCTCC
CGATTCAAGCTTTCCCCAAACCTGGAGGAAGCCAAGACAAATCTCTACATAATAGAGAATTA
AGTGCAGAAAGACCTTTGAATGAACAGATTGCTGAAGCAGAAGAAGACAAGATTAAAAAAAC
ATATCCTCCAGAAAACAAGCCAGGTCAGAGCAACTATTCTTTTGTTGATAACTTGAACCTGC
TAAAGGCAATAACAGAAAAGGAAAAAATTGAGAAAGAAAGACAATCTATAAGAAGCTCCCCA
CTTGATAATAAGTTGAATGTGGAAGATGTTGATTCAACCAAGAATCGAAAACTGATCGATGA
TTATGACTCTACTAAGAGTGGATTGGATCATAAATTTCAAGATGATCCAGATGGTCTTCATC
AACTAGACGGGACTCCTTTAACCGCTGAAGACATTGTCCATAAAATCGCTGCCAGGATTTAT
GAAGAAAATGACAGAGCCGTGTTTGACAAGATTGTTTCTAAACTACTTAATCTCGGCCTTAT
CACAGAAAGCCAAGCACATACACTGGAAGATGAAGTAGCAGAGGTTTTACAAAAATTAATCT
CAAAGGAAGCCAACAATTATGAGGAGGATCCCAATAAGCCCACAAGCTGGACTGAGAATCAG
GCTGGAAAAATACCAGAGAAAGTGACTCCAATGGCAGCAATTCAAGATGGTCTTGCTAAGGG
AGAAAACGATGAAACAGTATCTAACACATTAACCTTGACAAATGGCTTGGAAAGGAGAACTA
AAACCTACAGTGAAGACAACTTTGAGGAACTCCAATATTTCCCAAATTTCTATGCGCTACTG
AAAAGTATTGATTCAGAAAAGAAGCAAAAGAGAAAGAAACACTGATTACTATCATGAAAAC
ACTGATTGACTTTGTGAAGATGATGGTGAAATATGGAACAATATCTCCAGAAGAAGGTGTTT
CCTACCTTGAAAACTTGGATGAAATGATTGCTCTTCAGACCAAAAACAAGCTAGAAAAAAAT
GCTACTGACAATATAAGCAAGCTTTTCCCAGCACCATCAGAGAAGAGTCATGAAGAAACAGA
CAGTACCAAGGAAGAAGCAGCTAAGATGGAAAAGGAATATGGAAGCTTGAAGGATTCCACAA
AAGATGATAACTCCAACCCAGGAGGAAAGACAGATGAACCCAAAGGAAAAACAGAAGCCTAT
TTGGAAGCCATCAGAAAAAATATTGAATGGTTGAAGAAACATGACAAAAGGGAAATAAAGA
AGATTATGACCTTTCAAAGATGAGAGACTTCATCAATAAACAAGCTGATGCTTATGTGGAGA
AAGGCATCCTTGACAAGGAAGAAGCCGAGGCCATCAAGCGCATTTATAGCAGCCTGTAAAAA
TGGCAAAAGATCCAGGAGTCTTTCAACTGTTTCAGAAAACATAATATAGCTTAAACACTTC
TAATTCTGTGATTAAATTTTTTGACCCAAGGGTTATTAGAAAGTGCTGAATTTACAGTAGT
TAACCTTTTACAAGTGGTTAAAACATAGCTTTCTTCCCGTAAAAACTATCTGAAAGTAAAGT
TGTATGTAAGCTGAAAAAAAAAAAAAAAAAAA

FIGURE 36

MGFLGTGTWILVLVLPIQAFPKPGGSQDKSLHNRELSAERPLNEQIAEAEEDKIKKTYPPEN
KPGQSNYSFVDNLNLLKAITEKEKIEKERQSIRSSPLDNKLNVEDVDSTKNRKLIDDYDSTK
SGLDHKFQDDPDGLHQLDGTPLTAEDIVHKIAARIYEENDRAVFDKIVSKLLNLGLITESQA
HTLEDEVAEVLQKLISKEANNYEEDPNKPTSWTENQAGKIPEKVTPMAAIQDGLAKGENDET
VSNTLTLTNGLERRTKTYSEDNFEELQYFPNFYALLKSIDSEKEAKEKETLITIMKTLIDFV
KMMVKYGTISPEEGVSYLENLDEMIALQTKNKLEKNATDNISKLFPAPSEKSHEETDSTKEE
AAKMEKEYGSLKDSTKDDNSNPGGKTDEPKGKTEAYLEAIRKNIEWLKKHDKKGNKEDYDLS
KMRDFINKQADAYVEKGILDKEEAEAIKRIYSSL

N-glycosylation sites:
amino acids 68-71, 346-349, 350-353

Casein kinase II phosphorylation site:
amino acids 70-73, 82-85, 97-100, 125-128, 147-150, 188-191, 217-220, 265-268, 289-292, 305-308, 320-323, 326-329, 362-365, 368-341, 369-372, 382-385, 386-389, 387-390

N-myristoylation sites:
amino acids 143-148, 239-244

FIGURE 37

```
GTTGCTCCGGCGGCGCTCGGGGAGGGAGCCAGCAGCCTAGGGCCTAGGCCCGGGCCACCATG
GCGCTGCCTCCAGGCCCAGCCGCCCTCCGGCACACACTGCTGCTCCTGCCAGCCCTTCTGAG
CTCAGGTTGGGGGGAGTTGGAGCCACAAATAGATGGTCAGACCTGGGCTGAGCGGGCACTTC
GGGAGAATGAACGCCACGCCTTCACCTGCCGGGTGGCAGGGGGGCCTGGCACCCCCAGATTG
GCCTGGTATCTGGATGGACAGCTGCAGGAGGCCAGCACCTCAAGACTGCTGAGCGTGGGAGG
GGAGGCCTTCTCTGGAGGCACCAGCACCTTCACTGTCACTGCCCATCGGGCCCAGCATGAGC
TCAACTGCTCTCTGCAGGACCCCAGAAGTGGCCGATCAGCCAACGCCTCTGTCATCCTTAAT
GTGCAATTCAAGCCAGAGATTGCCCAAGTCGGCGCCAAGTACCAGGAAGCTCAGGGCCCAGG
CCTCCTGGTTGTCCTGTTTGCCCTGGTGCGTGCCAACCCGCCGGCCAATGTCACCTGGATCG
ACCAGGATGGGCCAGTGACTGTCAACACCTCTGACTTCCTGGTGCTGGATGCGCAGAACTAC
CCCTGGCTCACCAACCACACGGTGCAGCTGCAGCTCCGCAGCCTGGCACACAACCTCTCGGT
GGTGGCCACCAATGACGTGGGTGTCACCAGTGCGTCGCTTCCAGCCCCAGGCCCCTCCCGGC
ACCCATCTCTGATATCAAGTGACTCCAACAACCTAAAACTCAACAACGTGCGCCTGCCACGG
GAGAACATGTCCCTCCCGTCCAACCTTCAGCTCAATGACCTCACTCCAGATTCCAGAGCAGT
GAAACCAGCAGACCGGCAGATGGCTCAGAACAACAGCCGGCCAGAGCTTCTGGACCCGGAGC
CCGGCGGCCTCCTCACCAGCCAAGGTTTCATCCGCCTCCCAGTGCTGGGCTATATCTATCGA
GTGTCCAGCGTGAGCAGTGATGAGATCTGGCTCTGAGCCGAGGGCGAGACAGGAGTATTCTC
TTGGCCTCTGGACACCCTCCCATTCCTCCAAGGCATCCTCTACCTAGCTAGGTCACCAACGT
GAAGAAGTTATGCCACTGCCACTTTTGCTTGCCCTCCTGGCTGGGGTGCCCTCCATGTCATG
CACGTGATGCATTTCACTGGGCTGTAACCCGCAGGGGCACAGGTATCTTTGGCAAGGCTACC
AGTTGGACGTAAGCCCCTCATGCTGACTCAGGGTGGGCCCTGCATGTGATGACTGGGCCCTT
CCAGAGGGAGCTCTTTGGCCAGGGGTGTTCAGATGTCATCCAGCATCCAAGTGTGGCATGGC
CTGCTGTATACCCCACCCCAGTACTCCACAGCACCTTGTACAGTAGGCATGGGGCGTGCCT
GTGTGGGGGACAGGGAGGGCCCTGCATGGATTTTCCTCCTTCCTATGCTATGTAGCCTTGTT
CCCTCAGGTAAAATTTAGGACCCTGCTAGCTGTGCAGAACCCAATTGCCCTTTGCACAGAAA
CCAACCCCTGACCCAGCGGTACCGGCCAAGCACAAACGTCCTTTTGCTGCACACGTCTCTG
CCCTTCACTTCTTCTCTTCTGTCCCCACCTCCTCTTGGGAATTCTAGGTTACACGTTGGACC
TTCTCTACTACTTCACTGGGCACTAGACTTTTCTATTGGCCTGTGCCATCGCCCAGTATTAG
CACAAGTTAGGGAGGAAGAGGCAGGCGATGAGTCTAGTAGCACCCAGGACGGCTTGTAGCTA
TGCATCATTTTCCTACGGCGTTAGCACTTTAAGCACATCCCCTAGGGGAGGGGGTGAGTGAG
GGGCCCAGAGCCCTCTTTGTGGCTTCCCCACGTTTGGCCTTCTGGGATTCACTGTGAGTGTC
CTGAGCTCTCGGGGTTGATGGTTTTTCTCTCAGCATGTCTCCTCCACCACGGGACCCCAGCC
CTGACCAACCCATGGTTGCCTCATCAGCAGGAAGGTGCCCTTCCTGGAGGATGGTCGCCACA
GGCACATAATTCAACAGTGTGGAAGCTTTAGGGGAACATGGAGAAAGAAGGAGACCACATAC
CCCAAAGTGACCTAAGAACACTTTAAAAAGCAACATGTAAATGATTGGAAATTAATATAGTA
CAGAATATATTTTTCCCTTGTTGAGATCTTCTTTTGTAATGTTTTTCATGTTACTGCCTAGG
GCGGTGCTGAGCACACAGCAAGTTTAATAAACTTGACTGAATTCATTTAAAAAAAAAAAAA
AAAAAAAAAAAAAAAAAAAAAAAAAAAAAAAAAAAAAAAAAAAAAAAAAAAAAAAAAAAAAAA
AAAAAAAAAAAAAAAAAAAAA
```

FIGURE 38

MALPPGPAALRHTLLLLPALLSSGWGELEPQIDGQTWAERALRENERHAFTCRVAGGPGTPR
LAWYLDGQLQEASTSRLLSVGGEAFSGGTSTFTVTAHRAQHELNCSLQDPRSGRSANASVIL
NVQFKPEIAQVGAKYQEAQGPGLLVVLFALVRANPPANVTWIDQDGPVTVNTSDFLVLDAQN
YPWLTNHTVQLQLRSLAHNLSVVATNDVGVTSASLPAPGPSRHPSLISSDSNNLKLNNVRLP
RENMSLPSNLQLNDLTPDSRAVKPADRQMAQNNSRPELLDPEPGGLLTSQGFIRLPVLGYIY
RVSSVSSDEIWL

N-glycosylation sites:

amino acids 106-110, 119-123, 162-166, 175-179, 192-196, 205-209, 251-255, 280-284

Glycosaminoglycan attachment site:

amino acids 23-27

Casein kinase II phosphorylation sites:

amino acids 36-40, 108-112, 164-168, 282-286, 316-320

N-myristoylation sites:

amino acids 34-40, 89-95, 215-221, 292-298, 293-299

FIGURE 39

CGGGGACGGAAGCGGCCCCTGGGCCCGAGGGGCTGGAGCCGGGCCGGGGCGATGTGGAGCGC
GGGCCGCGGCGGGGCTGCCTGGCCGGTGCTGTTGGGGCTGCTGCTGGCGCTGTTAGTGCCGG
GCGGTGGTGCCGCCAAGACCGGTGCGGAGCTCGTGACCTGCGGGTCGGTGCTGAAGCTGCTC
AATACGCACCACCGCGTGCGGCTGCACTCGCACGACATCAAATACGGATCCGGCAGCGGCCA
GCAATCGGTGACCGGCGTAGAGGCGTCGGACGACGCCAATAGCTACTGGCGGATCCGCGGCG
GCTCGGAGGGCGGGTGCCCGCGCGGGTCCCGGTGCGCTGCGGGCAGGCGGTGAGGCTCACG
CATGTGCTTACGGGCAAGAACCTGCACACGCACCACTTCCCGTCGCCGCTGTCCAACAACCA
GGAGGTGAGTGCCTTTGGGGAAGACGGCGAGGGCGACGACCTGGACCTATGGACAGTGCGCT
GCTCTGGACAGCACTGGGAGCGTGAGGCTGCTGTGCGCTTCCAGCATGTGGGCACCTCTGTG
TTCCTGTCAGTCACGGGTGAGCAGTATGGAAGCCCCATCCGTGGGCAGCATGAGGTCCACGG
CATGCCCAGTGCCAACACGCACAATACGTGGAAGGCCATGGAAGGCATCTTCATCAAGCCTA
GTGTGGAGCCCTCTGCAGGTCACGATGAACTCTGAGTGTGTGGATGGATGGGTGGATGGAGG
GTGGCAGGTGGGGCGTCTGCAGGGCCACTCTTGGCAGAGACTTTGGGTTTGTAGGGGTCCTC
AAGTGCCTTTGTGATTAAAGAATGTTGGTCTATGAAA

FIGURE 40

></usr/seqdb2/sst/DNA/Dnaseqs.min/ss.DNA96857
><subunit 1 of 1, 221 aa, 1 stop
><MW: 23598, pI: 6.96, NX(S/T): 0

MWSAGRGGAAWPVLLGLLLALLVPGGGAAKTGAELVTCGSVLKLLNTHHRVRLHSHDIKYGS
GSGQQSVTGVEASDDANSYWRIRGGSEGGCPRGSPVRCGQAVRLTHVLTGKNLHTHHFPSPL
SNNQEVSAFGEDGEGDDLDLWTVRCSGQHWEREAAVRFQHVGTSVFLSVTGEQYGSPIRGQH
EVHGMPSANTHNTWKAMEGIFIKPSVEPSAGHDEL

Important features of the protein:

Signal peptide:

amino acids 1-28

Glycosaminoglycan attachment site.

amino acids 62-66

N-myristoylation sites.

amino acids 16-22, 25-31, 27-33, 61-67, 71-77, 86-92, 87-93, 91-97, 190-196

Endoplasmic reticulum targeting sequence.

amino acids 218-223

FIGURE 41

GTTGCTATGTTGCCCAGGCTGGTCTTGAAGTGCCTTGACCTCCTAAAGTGTTGGAACCACAG
ACGTGAGCCACTCCACCCAGCCTAAAACTTCATCTTCTTTGGATGAGATGAACACTTTTAAC
AAGAGAACAGGACTCTATATAAATCGCTGTGGGCTCACCACCTCTAAGGAGGAGCACTGACT
GAAGACAGAAAAATTGATGAACTGAAGAAGACATGGTCCATTATGCCTTACAAACTTACACA
GTGCTTTGGGAATTCCAAAGTACTCAGTGGAGAGAGGTGTTTCAGGAGCCGTAGAGCCAGAT
CGTCATCATGTCTGCATTGTGGCTGCTGCTGGGCCTCCTTGCCCTGATGGACTTGTCTGAAA
GCAGCAACTGGGGATGCTATGGAAACATCCAAAGCCTGGACACCCCTGGAGCATCTTGTGGG
ATTGGAAGACGTCACGGCCTGAACTACTGTGGAGTTCGTGCTTCTGAAAGGCTGGCTGAAAT
AGACATGCCATACCTCCTGAAATATCAACCCATGATGCAAACCATTGGCCAAAAGTACTGCA
TGGATCCTGCCGTGATCGCTGGTGTCTTGTCCAGGAAGTCTCCCGGTGACAAAATTCTGGTC
AACATGGGCGATAGGACTAGCATGGTGCAGGACCCTGGCTCTCAAGCTCCCACATCCTGGAT
TAGTGAGTCTCAGGTTTCCCAGACAACTGAAGTTCTGACTACTAGAATCAAAGAAATCCAGA
GGAGGTTTCCAACCTGGACCCCTGACCAGTACCTGAGAGGTGGACTCTGTGCCTACAGTGGG
GGTGCTGGCTATGTCCGAAGCAGCCAGGACCTGAGCTGTGACTTCTGCAATGATGTCCTTGC
ACGAGCCAAGTACCTCAAGAGACATGGCTTCTAACATCTCAGATGAAACCCAAGACCATGAT
CACATATGCAGCCTCAAATGTTACACAGATAAAACTAGCCAAGGGCACCTGTAACTGGGAAT
CTGAGTTTGACCTAAAAGTCATTAAATAACATGAATCCCATTAAAAAAAAAAAAAA

FIGURE 42

></usr/seqdb2/sst/DNA/Dnaseqs.min/ss.DNA96867
><subunit 1 of 1, 194 aa, 1 stop
><MW: 21431, pI: 8.57, NX(S/T): 0
MSALWLLLGLLALMDLSESSNWGCYGNIQSLDTPGASCGIGRRHGLNYCGVRASERLAEIDM
PYLLKYQPMMQTIGQKYCMDPAVIAGVLSRKSPGDKILVNMGDRTSMVQDPGSQAPTSWISE
SQVSQTTEVLTTRIKEIQRRFPTWTPDQYLRGGLCAYSGGAGYVRSSQDLSCDFCNDVLARA
KYLKRHGF

Important features of the protein:
Signal peptide:
amino acids 1-19

N-myristoylation sites.
amino acids 23-29, 26-32, 35-41, 45-51, 50-56, 76-82, 156-162

Amidation site.
amino acids 40-44

FIGURE 43

TTGAAAATCTACTCTATCAGCTGCTGTGGTTGCCACCATTCTCAGGACCCTCGCCATGAAAG
CCCTTATGCTGCTCACCCTGTCTGTTCTGCTCTGCTGGGTCTCAGCTGACATTCGCTGTCAC
TCCTGCTACAAGGTCCCTGTGCTGGGCTGTGTGGACCGGCAGTCCTGCCGCCTGGAGCCAGG
ACAGCAATGCCTGACAACACATGCATACCTTGGTAAGATGTGGGTTTTCTCCAATCTGCGCT
GTGGCACACCAGAAGAGCCCTGTCAGGAGGCCTTCAACCAAACCAACCGCAAGCTGGGTCTG
ACATATAACACCACCTGCTGCAACAAGGACAACTGCAACAGCGCAGGACCCCGGCCCACTCC
AGCCCTGGGCCTTGTCTTCCTTACCTCCTTGGCTGGCCTTGGCCTCTGGCTGCTGCACTGAG
ACTCATTCCATTGGCTGCCCCTCCTCCCACCTGCCTTGGCCTGAGCCTCTCTCCCTGTGTCT
CTGTATCCCCTGGCTTTACAGAATCGTCTCTCCCTAGCTCCCATTTCTTTAATTAAACACTG
TTCCGAGTGGTCTCCTCATCCATCCTTCCCACCTCACACCCTTCACTCTCCTTTTTCTGGGT
CCCTTCCCACTTCCTTCCAGGACCTCCATTGGCTCCTAGAAGGGCTCCCCACTTTGCTTCCT
ATACTCTGCTGTCCCCTACTTGAGGAGGGATTGGGATCTGGGCCTGAAATGGGGCTTCTGTG
TTGTCCCCAGTGAAGGCTCCCACAAGGACCTGATGACCTCACTGTACAGAGCTGACTCCCCA
AACCCAGGCTCCCATATGTACCCCATCCCCCATACTCACCTCTTTCCATTTTGAGTAATAAA
TGTCTGAGTCTGGAAAAAAAAAAAAAAAAA

FIGURE 44

></usr/seqdb2/sst/DNA/Dnaseqs.min/ss.DNA96878
><subunit 1 of 1, 125 aa, 1 stop
><MW: 13821, pI: 8.60, NX(S/T): 2
MKALMLLTLSVLLCWVSADIRCHSCYKVPVLGCVDRQSCRLEPGQQCLTTHAYLGKMWVFSN
LRCGTPEEPCQEAFNQTNRKLGLTYNTTCCNKDNCNSAGPRPTPALGLVFLTSLAGLGLWLLH

Important features of the protein:

Signal peptide:

amino acids 1-18

N-glycosylation sites.

amino acids 77-81, 88-92

N-myristoylation site.

amino acids 84-90

Ly-6 / u-PAR domain protein signature.

amino acids 85-98

FIGURE 45

ACGGGCCGCAGCGGCAGTGACGTAGGGTTGGCGCACGGATCCGTTGCGGCTGCAGCTCTGCA
GTCGGGCCGTTCCTTCGCCGCCGCCAGGGGTAGCGGTGTAGCTGCGCAGCGTCGCGCGCGCT
ACCGCACCCAGGTTCGGCCCGTAGGCGTCTGGCAGCCCGGCGCCATCTTCATCGAGCGCAT
GGCCGCAGCCTGCGGGCCGGGAGCGGCCGGGTACTGCTTGCTCCTCGGCTTGCATTTGTTTC
TGCTGACCGCGGGCCCTGCCCTGGGCTGGAACGACCCTGACAGAATGTTGCTGCGGGATGTA
AAAGCTCTTACCCTCCACTATGACCGCTATACCACCTCCCGCAGGCTGGATCCCATCCCACA
GTTGAAATGTGTTGGAGGCACAGCTGGTTGTGATTCTTATACCCCAAAAGTCATACAGTGTC
AGAACAAAGGCTGGGATGGGTATGATGTACAGTGGGAATGTAAGACGGACTTAGATATTGCA
TACAAATTTGGAAAAACTGTGGTGAGCTGTGAAGGCTATGAGTCCTCTGAAGACCAGTATGT
ACTAAGAGGTTCTTGTGGCTTGGAGTATAATTTAGATTATACAGAACTTGGCCTGCAGAAAC
TGAAGGAGTCTGGAAAGCAGCACGGCTTTGCCTCTTTCTCTGATTATTATTATAAGTGGTCC
TCGGCGGATTCCTGTAACATGAGTGGATTGATTACCATCGTGGTACTCCTTGGGATCGCCTT
TGTAGTCTATAAGCTGTTCCTGAGTGACGGGCAGTATTCTCCTCCACCGTACTCTGAGTATC
CTCCATTTTCCCACCGTTACCAGAGATTCACCAACTCAGCAGGACCTCCTCCCCAGGCTTT
AAGTCTGAGTTCACAGGACCACAGAATACTGGCCATGGTGCAACTTCTGGTTTTGGCAGTGC
TTTTACAGGACAACAAGGATATGAAAATTCAGGACCAGGGTTCTGGACAGGCTTGGGAACTG
GTGGAATACTAGGATATTTGTTTGGCAGCAATAGAGCGGCAACACCCTTCTCAGACTCGTGG
TACTACCCGTCCTATCCTCCCTCCTACCCTGGCACGTGGAATAGGGCTTACTCACCCCTTCA
TGGAGGCTCGGGCAGCTATTCGGTATGTTCAAACTCAGACACGAAAACCAGAACTGCATCAG
GATATGGTGGTACCAGGAGACGATAAAGTAGAAAGTTGGAGTCAAACACTGGATGCAGAAAT
TTTGGATTTTTCATCACTTTCTCTTTACAAAAAAGTACTACCTGTTAACAATTGGGAAAAG
GGGATATTCAAAAGTTCTGTGGTGTTATGTCCAGTGTAGCTTTTTGTATTCTATTATTTGAG
GCTAAAAGTTGATGTGTGACAAAATACTTATGTGTTGTATGTCAGTGTAACATGCAGATGTA
TATTGCAGTTTTTGAAAGTGATCATTACTGTGGAATGCTAAAAATACATTAATTTCTAAAAC
CTGTGATGCCCTAAGAAGCATTAAGAATGAAGGTGTTGTACTAATAGAAACTAAGTACAGAA
AATTTCAGTTTTAGGTGGTTGTAGCTGATGAGTTATTACCTCATAGAGACTATAATATTCTA
TTTGGTATTATATTATTTGATGTTTGCTGTTCTTCAAACATTTAAATCAAGCTTTGGACTAA
TTATGCTAATTTGTGAGTTCTGATCACTTTTGAGCTCTGAAGCTTTGAATCATTCAGTGGTG
GAGATGGCCTTCTGGTAACTGAATATTACCTTCTGTAGGAAAGGTGGAAAATAAGCATCTA
GAAGGTTGTTGTGAATGACTCTGTGCTGGCAAAATGCTTGAAACCTCTATATTTCTTTCGT
TCATAAGAGGTAAAGGTCAAATTTTTCAACAAAAGTCTTTTAATAACAAAAGCATGCAGTTC
TCTGTGAAATCTCAAATATTGTTGTAATAGTCTGTTTCAATCTTAAAAAGAATCA

FIGURE 46

></usr/seqdb2/sst/DNA/Dnaseqs.min/ss.DNA96889
><subunit 1 of 1, 339 aa, 1 stop
><MW: 36975, pI: 7.85, NX(S/T): 1
MAAACGPGAAGYCLLLGLHLFLLTAGPALGWNDPDRMLLRDVKALTLHYDRYTTSRRLDPIP
QLKCVGGTAGCDSYTPKVIQCQNKGWDGYDVQWECKTDLDIAYKFGKTVVSCEGYESSEDQY
VLRGSCGLEYNLDYTELGLQKLKESGKQHGFASFSDYYYKWSSADSCNMSGLITIVVLLGIA
FVVYKLFLSDGQYSPPPYSEYPPFSHRYQRFTNSAGPPPPGFKSEFTGPQNTGHGATSGFGS
AFTGQQGYENSGPGFWTGLGTGGILGYLFGSNRAATPFSDSWYYPSYPPSYPGTWNRAYSPL
HGGSGSYSVCSNSDTKTRTASGYGGTRRR

Signal peptide:

amino acids 1-30

Transmembrane domain:

amino acids 171-190

N-glycosylation site.

amino acids 172-176

Glycosaminoglycan attachment sites.

amino acids 244-248, 259-263, 331-335

Tyrosine kinase phosphorylation site.

amino acids 98-106

N-myristoylation sites.

amino acids 68-74, 69-75, 131-137, 241-247, 247-253, 266-272, 270-276, 278-284, 312-318

SEQUENCE LISTING

<160> NUMBER OF SEQ ID NOS: 80

<210> SEQ ID NO 1
<211> LENGTH: 1712
<212> TYPE: DNA
<213> ORGANISM: Homo Sapien

<400> SEQUENCE: 1

| | | | | | |
|---|---|---|---|---|---|
| ggcatctgcc | cgaggagacc | acgctcctgg | agctctgctg | tcttctcagg | 50 |
| gagactctga | ggctctgttg | agaatcatgc | tttggaggca | gctcatctat | 100 |
| tggcaactgc | tggctttgtt | tttcctccct | ttttgcctgt | gtcaagatga | 150 |
| atacatggag | tctccacaaa | ccggaggact | accccccagac | tgcagtaagt | 200 |
| gttgtcatgg | agactacagc | tttcgaggct | accaaggccc | cctgggcca | 250 |
| ccgggccctc | ctggcattcc | aggaaaccat | ggaaacaatg | caacaatgg | 300 |
| agccactggt | catgaaggag | ccaaaggtga | aagggcgac | aaaggtgacc | 350 |
| tggggcctcg | aggggagcgg | gggcagcatg | gccccaaagg | agagaagggc | 400 |
| tacccgggga | ttccaccaga | acttcagatt | gcattcatgg | cttctctggc | 450 |
| aacccacttc | agcaatcaga | acagtgggat | tatcttcagc | agtgttgaga | 500 |
| ccaacattgg | aaacttcttt | gatgtcatga | ctggtagatt | tggggcccca | 550 |
| gtatcaggtg | tgtatttctt | caccttcagc | atgatgaagc | atgaggatgt | 600 |
| tgaggaagtg | tatgtgtacc | ttatgcacaa | tggcaacaca | gtcttcagca | 650 |
| tgtacagcta | tgaaatgaag | ggcaaatcag | atacatccag | caatcatgct | 700 |
| gtgctgaagc | tagccaaagg | ggatgaggtt | tggctgcgaa | tgggcaatgg | 750 |
| cgctctccat | ggggaccacc | aacgcttctc | cacctttgca | ggattcctgc | 800 |
| tctttgaaac | taagtaaata | tatgactaga | atagctccac | tttggggaag | 850 |
| acttgtagct | gagctgattt | gttacgatct | gaggaacatt | aaagttgagg | 900 |
| gttttacatt | gctgtattca | aaaaattatt | ggttgcaatg | ttgttcacgc | 950 |
| tacaggtaca | ccaataatgt | tggacaattc | agggctcag | aagaatcaac | 1000 |
| cacaaaatag | tcttctcaga | tgaccttgac | taatatactc | agcatcttta | 1050 |
| tcactctttc | cttggcacct | aaaagataat | tctcctctga | cgcaggttgg | 1100 |
| aaatattttt | ttctatcaca | gaagtcattt | gcaaagaatt | ttgactactc | 1150 |
| tgcttttaat | ttaataccag | ttttcaggaa | ccctgaagt | tttaagttca | 1200 |
| ttattcttta | taacatttga | gagaatcgga | tgtagtgata | tgacagggct | 1250 |
| ggggcaagaa | cagggggcact | agctgcctta | ttagctaatt | tagtgccctc | 1300 |
| cgtgttcagc | ttagcctttg | acccttttcct | tttgatccac | aaaatacatt | 1350 |
| aaaactctga | attcacatac | aatgctattt | taaagtcaat | agattttagc | 1400 |
| tataaagtgc | ttgaccagta | atgtggttgt | aattttgtgt | atgttccccc | 1450 |
| acatcgcccc | caacttcgga | tgtggggtca | ggaggttgag | gttcactatt | 1500 |
| aacaaatgtc | ataatatct | catagaggta | cagtgccaat | agatattcaa | 1550 |
| atgttgcatg | ttgaccagag | ggattttata | tctgaagaac | atacactatt | 1600 |
| aataaatacc | ttagagaaag | attttgacct | ggctttagat | aaaactgtgg | 1650 |
| caagaaaaat | gtaatgagca | atatatggaa | ataaacacac | ctttgttaaa | 1700 | gataaaaaaa aa                                         1712

<210> SEQ ID NO 2
<211> LENGTH: 246
<212> TYPE: PRT
<213> ORGANISM: Homo Sapien

<400> SEQUENCE: 2

Met Leu Trp Arg Gln Leu Ile Tyr Trp Gln Leu Leu Ala Leu Phe
 1               5                  10                  15

Phe Leu Pro Phe Cys Leu Cys Gln Asp Glu Tyr Met Glu Ser Pro
                20                  25                  30

Gln Thr Gly Gly Leu Pro Pro Asp Cys Ser Lys Cys Cys His Gly
                35                  40                  45

Asp Tyr Ser Phe Arg Gly Tyr Gln Gly Pro Pro Gly Pro Pro Gly
                50                  55                  60

Pro Pro Gly Ile Pro Gly Asn His Gly Asn Asn Gly Asn Asn Gly
                65                  70                  75

Ala Thr Gly His Glu Gly Ala Lys Gly Glu Lys Gly Asp Lys Gly
                80                  85                  90

Asp Leu Gly Pro Arg Gly Glu Arg Gly Gln His Gly Pro Lys Gly
                95                  100                 105

Glu Lys Gly Tyr Pro Gly Ile Pro Pro Glu Leu Gln Ile Ala Phe
                110                 115                 120

Met Ala Ser Leu Ala Thr His Phe Ser Asn Gln Asn Ser Gly Ile
                125                 130                 135

Ile Phe Ser Ser Val Glu Thr Asn Ile Gly Asn Phe Phe Asp Val
                140                 145                 150

Met Thr Gly Arg Phe Gly Ala Pro Val Ser Gly Val Tyr Phe Phe
                155                 160                 165

Thr Phe Ser Met Met Lys His Glu Asp Val Glu Val Tyr Val Val
                170                 175                 180

Tyr Leu Met His Asn Gly Asn Thr Val Phe Ser Met Tyr Ser Tyr
                185                 190                 195

Glu Met Lys Gly Lys Ser Asp Thr Ser Ser Asn His Ala Val Leu
                200                 205                 210

Lys Leu Ala Lys Gly Asp Glu Val Trp Leu Arg Met Gly Asn Gly
                215                 220                 225

Ala Leu His Gly Asp His Gln Arg Phe Ser Thr Phe Ala Gly Phe
                230                 235                 240

Leu Leu Phe Glu Thr Lys
                245

<210> SEQ ID NO 3
<211> LENGTH: 43
<212> TYPE: DNA
<213> ORGANISM: Artificial Sequence
<220> FEATURE:
<223> OTHER INFORMATION: Synthetic oligonucleotide probe

<400> SEQUENCE: 3
tgtaaaacga cggccagtta aatagacctg caattattaa tct            43

<210> SEQ ID NO 4
<211> LENGTH: 41
<212> TYPE: DNA
<213> ORGANISM: Artificial Sequence -continued

```
<220> FEATURE:
<223> OTHER INFORMATION: Synthetic oligonucleotide probe

<400> SEQUENCE: 4
caggaaacag ctatgaccac ctgcacacct gcaaatccat t                           41

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 5
gcaacaatgg agccactggt catg                                              24

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 6
gcaaaggtgg agaagcgttg gtgg                                              24

<210> SEQ ID NO 7
<211> LENGTH: 52
<212> TYPE: DNA
<213> ORGANISM: Artificial Sequence
<220> FEATURE:
<223> OTHER INFORMATION: Synthetic oligonucleotide probe

<400> SEQUENCE: 7
cccacttcag caatcagaac agtgggatta tctttcagca gtgtttgaga                  50
cc                                                                      52

<210> SEQ ID NO 8
<211> LENGTH: 1579
<212> TYPE: DNA
<213> ORGANISM: Homo Sapien

<400> SEQUENCE: 8
gagagaatag ctacagattc tccatcctca gtctttgcaa ggcgacagct                  50
gtgccagccg ggctctggca ggctcctggc agcatggcag tgaagcttgg                 100
gaccctcctg ctggcccttg ccctgggcct ggcccagcca gcctctgccc                 150
gccggaagct gctggtgttt ctgctggatg gttttcgctc agactacatc                 200
agtgatgagg cgctggagtc attgcctggt ttcaaagaga ttgtgagcag                 250
gggagtaaaa gtggattact tgactccaga cttccctagt ctctcgtatc                 300
ccaattatta taccctaatg actggccgcc attgtgaagt ccatcagatg                 350
atcgggaact acatgtggga ccccaccacc aacaagtcct ttgacattgg                 400
cgtcaacaaa gacagcctaa tgcctctctg gtggaatgga tcagaacctc                 450
tgtgggtcac tctgaccaag gccaaaagga aggtctacat gtactactgg                 500
ccaggctgtg aggttgagat tctgggtgtc agacccacct actgcctaga                 550
atataaaaat gtcccaacgg atatcaattt tgccaatgca gtcagcgatg                 600
ctcttgactc cttcaagagt ggccgggccg acctggcagc catataccat                 650
```

-continued

| | |
|---|---|
| gagcgcattg acgtggaagg ccaccactac gggcctgcat ctccgcagag | 700 |
| gaaagatgcc ctcaaggctg tagacactgt cctgaagtac atgaccaagt | 750 |
| ggatccagga gcggggcctg caggaccgcc tgaacgtcat tattttctcg | 800 |
| gatcacggaa tgaccgacat tttctggatg gacaaagtga ttgagctgaa | 850 |
| taagtacatc agcctgaatg acctgcagca agtgaaggac cgcgggcctg | 900 |
| ttgtgagcct ttggccggcc cctgggaaac actctgagat atataacaaa | 950 |
| ctgagcacag tggaacacat gactgtctac gagaaagaag ccatcccaag | 1000 |
| caggttctat tacaagaaag gaaagtttgt ctctcctttg actttagtgg | 1050 |
| ctgatgaagg ctggttcata actgagaatc gagagatgct tccgttttgg | 1100 |
| atgaacagca ccggcaggcg ggaaggttgg cagcgtggag ggcacggcta | 1150 |
| cgacaacgag ctcatggaca tgcggggcat cttcctggcc ttcggacctg | 1200 |
| atttcaaatc caacttcaga gctgctccta tcaggtcggt ggacgtctac | 1250 |
| aatgtcatgt gcaatgtggt gggcatcacc ccgctgccca caacggatc | 1300 |
| ctggtccagg gtgatgtgca tgctgaaggg ccgcgccggc actgccccgc | 1350 |
| ctgtctggcc cagccactgt gccctggcac tgattcttct cttcctgctt | 1400 |
| gcataactga tcatattgct tgtctcagaa aaaaacacca tcagcaaagt | 1450 |
| gggcctccaa agccagatga ttttcatttt atgtgtgaat aatagcttca | 1500 |
| ttaacacaat caagaccatg cacattgtaa atacattatt cttggataat | 1550 |
| tctatacata aaagttccta cttgttaaa | 1579 |

<210> SEQ ID NO 9
<211> LENGTH: 440
<212> TYPE: PRT
<213> ORGANISM: Homo Sapien

<400> SEQUENCE: 9

Met Ala Val Lys Leu Gly Thr Leu Leu Ala Leu Ala Leu Gly
 1               5                   10                  15

Leu Ala Gln Pro Ala Ser Ala Arg Arg Lys Leu Leu Val Phe Leu
                20                  25                  30

Leu Asp Gly Phe Arg Ser Asp Tyr Ile Ser Asp Glu Ala Leu Glu
                35                  40                  45

Ser Leu Pro Gly Phe Lys Glu Ile Val Ser Arg Gly Val Lys Val
                50                  55                  60

Asp Tyr Leu Thr Pro Asp Phe Pro Ser Leu Ser Tyr Pro Asn Tyr
                65                  70                  75

Tyr Thr Leu Met Thr Gly Arg His Cys Glu Val His Gln Met Ile
                80                  85                  90

Gly Asn Tyr Met Trp Asp Pro Thr Thr Asn Lys Ser Phe Asp Ile
                95                  100                 105

Gly Val Asn Lys Asp Ser Leu Met Pro Leu Trp Trp Asn Gly Ser
                110                 115                 120

Glu Pro Leu Trp Val Thr Leu Thr Lys Ala Lys Arg Lys Val Tyr
                125                 130                 135

Met Tyr Tyr Trp Pro Gly Cys Glu Val Glu Ile Leu Gly Val Arg
                140                 145                 150

Pro Thr Tyr Cys Leu Glu Tyr Lys Asn Val Pro Thr Asp Ile Asn
                155                 160                 165

-continued

```
Phe Ala Asn Ala Val Ser Asp Ala Leu Asp Ser Phe Lys Ser Gly
                170                 175                 180
Arg Ala Asp Leu Ala Ala Ile Tyr His Glu Arg Ile Asp Val Glu
                185                 190                 195
Gly His His Tyr Gly Pro Ala Ser Pro Gln Arg Lys Asp Ala Leu
                200                 205                 210
Lys Ala Val Asp Thr Val Leu Lys Tyr Met Thr Lys Trp Ile Gln
                215                 220                 225
Glu Arg Gly Leu Gln Asp Arg Leu Asn Val Ile Ile Phe Ser Asp
                230                 235                 240
His Gly Met Thr Asp Ile Phe Trp Met Asp Lys Val Ile Glu Leu
                245                 250                 255
Asn Lys Tyr Ile Ser Leu Asn Asp Leu Gln Gln Val Lys Asp Arg
                260                 265                 270
Gly Pro Val Val Ser Leu Trp Pro Ala Pro Gly Lys His Ser Glu
                275                 280                 285
Ile Tyr Asn Lys Leu Ser Thr Val Glu His Met Thr Val Tyr Glu
                290                 295                 300
Lys Glu Ala Ile Pro Ser Arg Phe Tyr Tyr Lys Gly Lys Phe
                305                 310                 315
Val Ser Pro Leu Thr Leu Val Ala Asp Glu Gly Trp Phe Ile Thr
                320                 325                 330
Glu Asn Arg Glu Met Leu Pro Phe Trp Met Asn Ser Thr Gly Arg
                335                 340                 345
Arg Glu Gly Trp Gln Arg Gly Trp His Gly Tyr Asp Asn Glu Leu
                350                 355                 360
Met Asp Met Arg Gly Ile Phe Leu Ala Phe Gly Pro Asp Phe Lys
                365                 370                 375
Ser Asn Phe Arg Ala Ala Pro Ile Arg Ser Val Asp Val Tyr Asn
                380                 385                 390
Val Met Cys Asn Val Val Gly Ile Thr Pro Leu Pro Asn Asn Gly
                395                 400                 405
Ser Trp Ser Arg Val Met Cys Met Leu Lys Gly Arg Ala Gly Thr
                410                 415                 420
Ala Pro Pro Val Trp Pro Ser His Cys Ala Leu Ala Leu Ile Leu
                425                 430                 435
Leu Phe Leu Leu Ala
                440
```

<210> SEQ ID NO 10
<211> LENGTH: 1047
<212> TYPE: DNA
<213> ORGANISM: Homo Sapien

<400> SEQUENCE: 10

| | |
|---|---|
| gccaggtgtg caggccgctc aagcccagc ctgccccgct gccgccacca | 50 |
| tgacgctcct ccccggcctc ctgtttctga cctggctgca cacatgcctg | 100 |
| gcccaccatg acccctccct caggggggcac ccccacagtc acggtacccc | 150 |
| acactgctac tcggctgagg aactgcccct cggccaggcc cccccacacc | 200 |
| tgctggctcg aggtgccaag tgggggcagg ctttgcctgt agccctggtg | 250 |
| tccagcctgg aggcagcaag ccacaggggg aggcacgaga ggccctcagc | 300 |
| tacgacccag tgcccggtgc tgcggccgga ggaggtgttg gaggcagaca | 350 |

```
cccaccagcg ctccatctca ccctggagat accgtgtgga cacggatgag        400
gaccgctatc cacagaagct ggccttcgcc gagtgcctgt gcagaggctg        450
tatcgatgca cggacgggcc gcgagacagc tgcgctcaac tccgtgcggc        500
tgctccagag cctgctggtg ctgcgccgcc ggccctgctc ccgcgacggc        550
tcggggctcc ccacacctgg ggcctttgcc ttccacaccg agttcatcca        600
cgtccccgtc ggctgcacct gcgtgctgcc ccgttcagtg tgaccgccga        650
ggccgtgggg cccctagact ggacacgtgt gctccccaga gggcaccccc        700
tatttatgtg tatttattgt tatttatatg cctcccccaa cactacccTt        750
ggggtctggg cattccccgt gtctggagga cagcccccca ctgttctcct        800
catctccagc ctcagtagtt gggggtagaa ggagctcagc acctcttcca        850
gcccttaaag ctgcagaaaa ggtgtcacac ggctgcctgt accttggctc        900
cctgtcctgc tcccggcttc ccttacccta tcactggcct caggcccgc         950
aggctgcctc ttcccaacct ccttggaagt acccctgttt cttaaacaat       1000
tatttaagtg tacgtgtatt attaaactga tgaacacatc cccaaaa         1047
```

<210> SEQ ID NO 11
<211> LENGTH: 197
<212> TYPE: PRT
<213> ORGANISM: Homo Sapien

<400> SEQUENCE: 11

```
Met Thr Leu Leu Pro Gly Leu Leu Phe Leu Thr Trp Leu His Thr
 1               5                  10                  15

Cys Leu Ala His His Asp Pro Ser Leu Arg Gly His Pro His Ser
                20                  25                  30

His Gly Thr Pro His Cys Tyr Ser Ala Glu Glu Leu Pro Leu Gly
                35                  40                  45

Gln Ala Pro Pro His Leu Leu Ala Arg Gly Ala Lys Trp Gly Gln
                50                  55                  60

Ala Leu Pro Val Ala Leu Val Ser Ser Leu Glu Ala Ala Ser His
                65                  70                  75

Arg Gly Arg His Glu Arg Pro Ser Ala Thr Thr Gln Cys Pro Val
                80                  85                  90

Leu Arg Pro Glu Glu Val Leu Glu Ala Asp Thr His Gln Arg Ser
                95                 100                 105

Ile Ser Pro Trp Arg Tyr Arg Val Asp Thr Glu Asp Arg Tyr
               110                 115                 120

Pro Gln Lys Leu Ala Phe Ala Glu Cys Leu Cys Arg Gly Cys Ile
               125                 130                 135

Asp Ala Arg Thr Gly Arg Glu Thr Ala Ala Leu Asn Ser Val Arg
               140                 145                 150

Leu Leu Gln Ser Leu Leu Val Leu Arg Arg Pro Cys Ser Arg
               155                 160                 165

Asp Gly Ser Gly Leu Pro Thr Pro Gly Ala Phe Ala Phe His Thr
               170                 175                 180

Glu Phe Ile His Val Pro Val Gly Cys Thr Cys Val Leu Pro Arg
               185                 190                 195

Ser Val
```

<210> SEQ ID NO 12

```
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 12
atccacagaa gctggccttc gccg                                          24

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 13
gggacgtgga tgaactcggt gtgg                                          24

<210> SEQ ID NO 14
<211> LENGTH: 40
<212> TYPE: DNA
<213> ORGANISM: Artificial Sequence
<220> FEATURE:
<223> OTHER INFORMATION: Synthetic oligonucleotide probe

<400> SEQUENCE: 14
tatccacaga agctggcctt cgccgagtgc ctgtgcagag                         40

<210> SEQ ID NO 15
<211> LENGTH: 660
<212> TYPE: DNA
<213> ORGANISM: Homo Sapien

<400> SEQUENCE: 15
cggccagggc gccgacagcc cgacctcacc aggagaacat gcagctcggc              50
actgggctcc tgctggccgc cgtcctgagc ctgcagctgg ctgcagccga             100
agccatatgg tgtcaccagt gcacgggctt cggagggtgc tcccatggat             150
ccagatgcct gagggactcc acccactgtg tcaccactgc cacccgggtc             200
ctcagcaaca ccgaggattt gcctctggtc accaagatgt gccacatagg             250
ctgccccgat atccccagcc tgggcctggg cccctacgta tccatcgctt             300
gctgccagac cagcctctgc aaccatgact gacggctgcc ctcctccagg             350
cccccggacg ctcagccccc acagcccccca cagcctggcg ccagggctca            400
cggccgcccc tccctcgaga ctggccagcc cacctctccc ggcctctgca             450
gccaccgtcc agcaccgctt gtcctaggga agtcctgcgt ggagtcttgc             500
ctcaatctgc tgccgtccaa gcctggggcc catcgtgcct gccgccccctt            550 caggtcccga cctccccaca ataaaatgtg attggatcgt gtggtacaaa             600
aaaaaaaaaa aaaaaaaaaa aaaaaaaaaa aaaaaaaaaa aaaaaaaaaa             650
aaaaaaaaaa                                                         660

<210> SEQ ID NO 16
<211> LENGTH: 97
<212> TYPE: PRT
<213> ORGANISM: Homo Sapien

<400> SEQUENCE: 16

Met Gln Leu Gly Thr Gly Leu Leu Leu Ala Ala Val Leu Ser Leu
```

```
          1               5               10              15
        Gln Leu Ala Ala Ala Glu Ala Ile Trp Cys His Gln Cys Thr Gly
                        20                  25                  30
        Phe Gly Gly Cys Ser His Gly Ser Arg Cys Leu Arg Asp Ser Thr
                        35                  40                  45
        His Cys Val Thr Thr Ala Thr Arg Val Leu Ser Asn Thr Glu Asp
                        50                  55                  60
        Leu Pro Leu Val Thr Lys Met Cys His Ile Gly Cys Pro Asp Ile
                        65                  70                  75
        Pro Ser Leu Gly Leu Gly Pro Tyr Val Ser Ile Ala Cys Cys Gln
                        80                  85                  90
        Thr Ser Leu Cys Asn His Asp
                        95
```

<210> SEQ ID NO 17
<211> LENGTH: 2570
<212> TYPE: DNA
<213> ORGANISM: Homo Sapien

<400> SEQUENCE: 17

| | |
|---|---:|
| ccaggaccag ggcgcaccgg ctcagcctct cacttgtcag aggccgggga | 50 |
| agagaagcaa agcgcaacgg tgtggtccaa gccggggctt ctgcttcgcc | 100 |
| tctaggacat acacgggacc ccctaacttc agtcccccaa acgcgcaccc | 150 |
| tcgaagtctt gaactccagc cccgcacatc acgcgcggc acaggcgcgg | 200 |
| caggcggcag gtcccggccg aaggcgatgc gcgcagggg tcgggcagct | 250 |
| gggctcgggc ggcgggagta gggcccggca gggaggcagg gaggctgcat | 300 |
| attcagagtc gcgggctgcg ccctgggcag aggccgccct cgctccacgc | 350 |
| aacacctgct gctgccaccg cgccgcgatg agccgcgtgg tctcgctgct | 400 |
| gctgggcgcc gcgctgctct gcggccacgg agccttctgc cgccgcgtgg | 450 |
| tcagcggcca aaaggtgtgt tttgctgact tcaagcatcc ctgctacaaa | 500 |
| atggcctact ccatgaact gtccagccga gtgagctttc aggaggcacg | 550 |
| cctggcttgt gagagtgagg gaggagtcct cctcagcctt gagaatgaag | 600 |
| cagaacagaa gttaatagag agcatgttgc aaaacctgac aaaacccggg | 650 |
| acagggattt ctgatggtga tttctggata gggctttgga ggaatggaga | 700 |
| tgggcaaaca tctggtgcct gcccagatct ctaccagtgg tctgatggaa | 750 |
| gcaattccca gtaccgaaac tggtacacag atgaaccttc ctgcggaagt | 800 |
| gaaaagtgtg ttgtgatgta tcaccaacca actgccaatc ctggccttgg | 850 |
| gggtccctac ctttaccagt ggaatgatga caggtgtaac atgaagcaca | 900 |
| attatatttg caagtatgaa ccagagatta tccaacagc ccctgtagaa | 950 |
| aagccttatc ttacaaatca accaggagac accatcaga atgtggttgt | 1000 |
| tactgaagca ggtataattc ccaatctaat ttatgttgtt ataccaacaa | 1050 |
| taccccctgct cttactgata ctggttgctt ttggaacctg ttgtttccag | 1100 |
| atgctgcata aaagtaaagg aagaacaaaa actagtccaa accagtctac | 1150 |
| actgtggatt tcaaagagta ccagaaaaga agtggcatg aagtataat | 1200 |
| aactcattga cttggttcca gaattttgta attctggatc tgtataagga | 1250 |
| atggcatcag aacaatagct tggaatggct tgaaatcaca aaggatctgc | 1300 |

```
aagatgaact gtaagctccc ccttgaggca aatattaaag taattttat      1350 atgtctatta tttcatttaa agaatatgct gtgctaataa tggagtgaga      1400
catgcttatt ttgctaaagg atgcacccaa acttcaaact tcaagcaaat      1450
gaaatggaca atgcagataa agttgttatc aacacgtcgg gagtatgtgt      1500
gttagaagca attcctttta tttctttcac ctttcataag ttgttatcta      1550
gtcaatgtaa tgtatattgt attgaaattt acagtgtgca aaagtatttt      1600
acctttgcat aagtgtttga taaaaatgaa ctgttctaat atttatttt       1650 atggcatctc attttcaat acatgctctt ttgattaaag aaacttatta       1700
ctgttgtcaa ctgaattcac acacacacaa atatagtacc atagaaaaag      1750
tttgttttct cgaaataatt catctttcag cttctctgct tttggtcaat      1800
gtctaggaaa tctcttcaga aataagaagc tatttcatta agtgtgatat      1850
aaacctcctc aaacatttta cttagaggca aggattgtct aatttcaatt      1900
gtgcaagaca tgtgccttat aattattttt agcttaaaat taaacagatt      1950
ttgtaataat gtaactttgt taataggtgc ataaacacta atgcagtcaa      2000
tttgaacaaa agaagtgaca tacacaatat aaatcatatg tcttcacacg      2050
ttgcctatat aatgagaagc agctctctga gggttctgaa atcaatgtgg      2100
tccctctctt gcccactaaa caaagatggt tgttcggggt ttgggattga      2150
cactggaggc agatagttgc aaagttagtc taaggtttcc ctagctgtat      2200
ttagcctctg actatattag tatacaaaga ggtcatgtgg ttgagaccag      2250
gtgaatagtc actatcagtg tggagacaag cacagcacac agacatttta      2300
ggaaggaaag gaactacgaa atcgtgtgaa aatgggttgg aacccatcag      2350
tgatcgcata ttcattgatg agggtttgct tgagatagaa aatggtggct      2400
cctttctgtc ttatctccta gtttcttcaa tgcttacgcc ttgttcttct      2450
caagagaaag ttgtaactct ctggtcttca tatgtccctg tgctccttt       2500 aaccaaataa agagttcttg tttctggggg aaaaaaaaaa aaaaaaaaa       2550 aaaaaaaaaa aaaaaaaaaa                                      2570
```

<210> SEQ ID NO 18
<211> LENGTH: 273
<212> TYPE: PRT
<213> ORGANISM: Homo Sapien

<400> SEQUENCE: 18

```
Met Ser Arg Val Val Ser Leu Leu Leu Gly Ala Ala Leu Leu Cys
 1               5                  10                  15

Gly His Gly Ala Phe Cys Arg Arg Val Val Ser Gly Gln Lys Val
                20                  25                  30

Cys Phe Ala Asp Phe Lys His Pro Cys Tyr Lys Met Ala Tyr Phe
                35                  40                  45

His Glu Leu Ser Ser Arg Val Ser Phe Gln Glu Ala Arg Leu Ala
                50                  55                  60

Cys Glu Ser Glu Gly Gly Val Leu Leu Ser Leu Glu Asn Glu Ala
                65                  70                  75

Glu Gln Lys Leu Ile Glu Ser Met Leu Gln Asn Leu Thr Lys Pro
                80                  85                  90
```

```
Gly Thr Gly Ile Ser Asp Gly Asp Phe Trp Ile Gly Leu Trp Arg
                95                 100                 105

Asn Gly Asp Gly Gln Thr Ser Gly Ala Cys Pro Asp Leu Tyr Gln
            110                 115                 120

Trp Ser Asp Gly Ser Asn Ser Gln Tyr Arg Asn Trp Tyr Thr Asp
            125                 130                 135

Glu Pro Ser Cys Gly Ser Glu Lys Cys Val Val Met Tyr His Gln
            140                 145                 150

Pro Thr Ala Asn Pro Gly Leu Gly Gly Pro Tyr Leu Tyr Gln Trp
            155                 160                 165

Asn Asp Asp Arg Cys Asn Met Lys His Asn Tyr Ile Cys Lys Tyr
            170                 175                 180

Glu Pro Glu Ile Asn Pro Thr Ala Pro Val Glu Lys Pro Tyr Leu
            185                 190                 195

Thr Asn Gln Pro Gly Asp Thr His Gln Asn Val Val Val Thr Glu
            200                 205                 210

Ala Gly Ile Ile Pro Asn Leu Ile Tyr Val Val Ile Pro Thr Ile
            215                 220                 225

Pro Leu Leu Leu Leu Ile Leu Val Ala Phe Gly Thr Cys Cys Phe
            230                 235                 240

Gln Met Leu His Lys Ser Lys Gly Arg Thr Lys Thr Ser Pro Asn
            245                 250                 255

Gln Ser Thr Leu Trp Ile Ser Lys Ser Thr Arg Lys Glu Ser Gly
            260                 265                 270

Met Glu Val

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 19
caccaaccaa ctgccaatcc tggc                                           24

<210> SEQ ID NO 20
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 20
accacattct gatgggtgtc tcctgg                                         26

<210> SEQ ID NO 21
<211> LENGTH: 49
<212> TYPE: DNA
<213> ORGANISM: Artificial Sequence
<220> FEATURE:
<223> OTHER INFORMATION: Synthetic oligonucleotide probe

<400> SEQUENCE: 21
gggtccctac ctttaccagt ggaatgatga caggtgtaac atgaagcac               49

<210> SEQ ID NO 22
<211> LENGTH: 3824
<212> TYPE: DNA
<213> ORGANISM: Homo Sapien
```

<400> SEQUENCE: 22

```
ggagaatgga gagagcagtg agagtggagt ccggggtcct ggtcgggtg        50
gtctgtctgc tcctggcatg ccctgccaca gccactgggc ccgaagttgc       100
tcagcctgaa gtagacacca ccctgggtcg tgtgcgaggc cggcaggtgg       150
gcgtgaaggg cacagaccgc cttgtgaatg tctttctggg cattccattt       200
gcccagccgc cactgggccc tgaccggttc tcagccccac acccagcaca       250
gccctgggag ggtgtgcggg atgccagcac tgcgccccca atgtgcctac       300
aagacgtgga gagcatgaac agcagcagat ttgtcctcaa cggaaaacag       350
cagatcttct ccgtttcaga ggactgcctg gtcctcaacg tctatagccc       400
agctgaggtc cccgcagggt ccggtaggcc ggtcatggta tgggtccatg       450
gaggcgctct gataactggc gctgccacct cctacgatgg atcagctctg       500
gctgcctatg gggatgtggt cgtggttaca gtccagtacc gccttggggt       550
ccttggcttc ttcagcactg agatgagca tgcacctggc aaccagggct        600
tcctagatgt ggtagctgct tgcgctgggt gcaagaaaa catcgccccc        650
ttcgggggtg acctcaactg tgtcactgtc tttggtggat ctgccggtgg       700
gagcatcatc tctggcctgg tcctgtcccc agtggctgca gggctgttcc       750
acagagccat cacacagagt ggggtcatca ccaccccagg gatcatcgac       800
tctcacctt ggcccctagc tcagaaaatc gcaaacacct tggcctgcag        850
ctccagctcc ccggctgaga tggtgcagtg ccttcagcag aaagaaggag       900
aagagctggt ccttagcaag aagctgaaaa atactatcta tcctctcacc       950
gttgatggca ctgtcttccc caaaagcccc aaggaactcc tgaaggagaa      1000
gcccttccac tctgtgccct tcctcatggg tgtcaacaac catgagttca      1050
gctggctcat ccccagggc tggggtctcc tggatacaat ggagcagatg       1100
agccgggagg acatgctggc catctcaaca cccgtcttga ccagtctgga      1150
tgtgcccct gagatgatgc ccaccgtcat agatgaatac ctaggaagca       1200
actcggacgc acaagccaaa tgccaggcgt tccaggaatt catgggtgac      1250
gtattcatca atgttcccac cgtcagtttt tcaagatacc ttcgagattc      1300
tggaagccct gtctttttct atgagttcca gcatcgaccc agttcttttg      1350
cgaagatcaa acctgcctgg gtgaaggctg atcatggggc cgagggtgct      1400
tttgtgttcg gaggtcccctt cctcatggac gagagctccc gcctggcctt     1450
tccagaggcc acagaggagg agaagcagct aagcctcacc atgatggccc      1500
agtggaccca ctttgcccgg acaggggacc ccaatagcaa ggctctgcct      1550
ccttggcccc aattcaacca ggcggaacaa tatctggaga tcaacccagt      1600
gccacgggcc ggacagaagt tcaggagggc ctggatgcag ttctggtcag      1650
agacgctccc cagcaagata caacagtggc accagaagca gaagaacagg      1700
aaggcccagg aggacctctg aggccaggcc tgaaccttct tggctggggc      1750
aaaccactct tcaagtggtg gcagagtccc agcacggcag cccgcctctc      1800
cccctgctga gactttaatc tccaccagcc cttaaagtgt cggccgctct      1850
gtgactggag ttatgctctt ttgaaatgtc acaaggccgc ctcccacctc      1900
```

```
tggggcattg tacaagttct tccctctccc tgaagtgcct ttcctgcttt         1950
cttcgtggta ggttctagca cattcctcta gcttcctgga ggactcactc         2000
cccaggaagc cttccctgcc ttctctgggc tgtgcggccc cgagtctgcg         2050
tccattagag cacagtccac ccgaggctag caccgtgtct gtgtctgtct         2100 cccccctcaga ggagctctct caaaatgggg attagcctaa ccccactctg        2150
tcacccacac caggatcggg tgggacctgg agctaggggg tgtttgctga         2200
gtgagtgagt gaaacacaga atatgggaat ggcagctgct gaacttgaac         2250
ccagagcctt caggtgccaa agccatactc aggcccccac cgacattgtc         2300
caccctggcc agaagggtgc atgccaatgg cagagacctg ggatgggaga         2350
agtcctgggg cgccagggga tccagcctag agcagacctt agcccctgac         2400
taaggcctca gactagggcg ggagggggtct cctcctctct gctgcccagt        2450
cctggcccct gcacaagaca acagaatcca tcagggccat gagtgtcacc         2500
cagacctgac cctcaccaat tccagcccct gaccctcagg acgctggatg         2550
ccagctccca gccccagtgc cgggtcctcc ctcccttcct ggcttgggga         2600
gaccagtttc tggggagctt ccaagagcac ccaccaagac acagcaggac         2650
aggccagggg agggcatctg gaccagggca tccgtcgggc tattgtcaca         2700
gagaaaagaa gagacccacc cactcgggct gcaaaaggtg aaaagcacca         2750
agaggttttc agatggaagt gagaggtgac agtgtgctgg cagccctcac         2800
agccctcgct tgctctccct gccgcctctg cctgggctcc cactttggca         2850
gcacttgagg agcccttcaa cccgccgctg cactgtagga gccccttttct        2900 gggctggcca aggccggagc cagctccctc agcttgcggg gaggtgcgga         2950
gggagagggg cgggcaggaa ccggggctgc gcgcagcgct tgcgggccag         3000
agtgagttcc gggtgggcgt gggctcggcg gggccccact cagagcagct         3050
ggccggcccc aggcagtgag ggccttagca cctgggccag cagctgctgt         3100
gctcgatttc tcgctgggcc ttagctgcct ccccgcgggg cagggctcgg         3150
gacctgcagc cctccatgcc tgaccctccc cccaccccccc gtgggctcct        3200 gtgcggccgg agcctcccca aggagcgccg ccccctgctc cacagcgccc         3250
agtcccatcg accacccaag ggctgaggag tgcgggtgca cagcgcggga         3300
ctggcaggca gctccacctg ctgccccagt gctggatcca ctgggtgaag         3350
ccagctgggc tcctgagtct ggtgggggact tggagaacct ttatgtctag        3400
ctaagggatt gtaaatacac cgatgggcac tctgtatcta gctcaaggtt         3450
tgtaaacaca ccaatcagca ccctgtgtct agctcagtgt ttgtgaatgc         3500
accaatccac actctgtatc tggctactct ggtggggact tggagaacct         3550
ttgtgtccac actctgtatc tagctaatct agtggggatg tggagaacct         3600
ttgtgtctag ctcagggatc gtaaacgcac caatcagcac cctgtcaaaa         3650
cagaccactt gactctctgt aaaatggacc aatcagcagg atgtgggtgg         3700
ggcgagacaa gagaataaaa gcaggctgcc tgagccagca gtgacaaccc         3750
ccctcgggtc cctcccacg ccgtggaagc tttgttcttt cgctctttgc          3800
aataaatctt gctactgccc aaaa                                      3824
```

<210> SEQ ID NO 23
<211> LENGTH: 571
<212> TYPE: PRT
<213> ORGANISM: Homo Sapien

<400> SEQUENCE: 23

```
Met Glu Arg Ala Val Arg Val Glu Ser Gly Val Leu Val Gly Val
  1               5                  10                  15

Val Cys Leu Leu Leu Ala Cys Pro Ala Thr Ala Thr Gly Pro Glu
                 20                  25                  30

Val Ala Gln Pro Glu Val Asp Thr Thr Leu Gly Arg Val Arg Gly
                 35                  40                  45

Arg Gln Val Gly Val Lys Gly Thr Asp Arg Leu Val Asn Val Phe
                 50                  55                  60

Leu Gly Ile Pro Phe Ala Gln Pro Pro Leu Gly Pro Asp Arg Phe
                 65                  70                  75

Ser Ala Pro His Pro Ala Gln Pro Trp Glu Gly Val Arg Asp Ala
                 80                  85                  90

Ser Thr Ala Pro Pro Met Cys Leu Gln Asp Val Glu Ser Met Asn
                 95                 100                 105

Ser Ser Arg Phe Val Leu Asn Gly Lys Gln Gln Ile Phe Ser Val
                110                 115                 120

Ser Glu Asp Cys Leu Val Leu Asn Val Tyr Ser Pro Ala Glu Val
                125                 130                 135

Pro Ala Gly Ser Gly Arg Pro Val Met Val Trp Val His Gly Gly
                140                 145                 150

Ala Leu Ile Thr Gly Ala Ala Thr Ser Tyr Asp Gly Ser Ala Leu
                155                 160                 165

Ala Ala Tyr Gly Asp Val Val Val Thr Val Gln Tyr Arg Leu
                170                 175                 180

Gly Val Leu Gly Phe Phe Ser Thr Gly Asp Glu His Ala Pro Gly
                185                 190                 195

Asn Gln Gly Phe Leu Asp Val Val Ala Ala Leu Arg Trp Val Gln
                200                 205                 210

Glu Asn Ile Ala Pro Phe Gly Gly Asp Leu Asn Cys Val Thr Val
                215                 220                 225

Phe Gly Gly Ser Ala Gly Gly Ser Ile Ile Ser Gly Leu Val Leu
                230                 235                 240

Ser Pro Val Ala Ala Gly Leu Phe His Arg Ala Ile Thr Gln Ser
                245                 250                 255

Gly Val Ile Thr Thr Pro Gly Ile Ile Asp Ser His Pro Trp Pro
                260                 265                 270

Leu Ala Gln Lys Ile Ala Asn Thr Leu Ala Cys Ser Ser Ser
                275                 280                 285

Pro Ala Glu Met Val Gln Cys Leu Gln Gln Lys Glu Gly Glu
                290                 295                 300

Leu Val Leu Ser Lys Lys Leu Lys Asn Thr Ile Tyr Pro Leu Thr
                305                 310                 315

Val Asp Gly Thr Val Phe Pro Lys Ser Pro Lys Glu Leu Leu Lys
                320                 325                 330

Glu Lys Pro Phe His Ser Val Pro Phe Leu Met Gly Val Asn Asn
                335                 340                 345

His Glu Phe Ser Trp Leu Ile Pro Arg Gly Trp Gly Leu Leu Asp
                350                 355                 360
```

```
Thr Met Glu Gln Met Ser Arg Glu Asp Met Leu Ala Ile Ser Thr
            365                 370                 375
Pro Val Leu Thr Ser Leu Asp Val Pro Glu Met Met Pro Thr
            380                 385                 390
Val Ile Asp Glu Tyr Leu Gly Ser Asn Ser Asp Ala Gln Ala Lys
            395                 400                 405
Cys Gln Ala Phe Gln Glu Phe Met Gly Asp Val Phe Ile Asn Val
            410                 415                 420
Pro Thr Val Ser Phe Ser Arg Tyr Leu Arg Asp Ser Gly Ser Pro
            425                 430                 435
Val Phe Phe Tyr Glu Phe Gln His Arg Pro Ser Ser Phe Ala Lys
            440                 445                 450
Ile Lys Pro Ala Trp Val Lys Ala Asp His Gly Ala Glu Gly Ala
            455                 460                 465
Phe Val Phe Gly Gly Pro Phe Leu Met Asp Glu Ser Ser Arg Leu
            470                 475                 480
Ala Phe Pro Glu Ala Thr Glu Glu Lys Gln Leu Ser Leu Thr
            485                 490                 495
Met Met Ala Gln Trp Thr His Phe Ala Arg Thr Gly Asp Pro Asn
            500                 505                 510
Ser Lys Ala Leu Pro Pro Trp Pro Gln Phe Asn Gln Ala Glu Gln
            515                 520                 525
Tyr Leu Glu Ile Asn Pro Val Pro Arg Ala Gly Gln Lys Phe Arg
            530                 535                 540
Glu Ala Trp Met Gln Phe Trp Ser Glu Thr Leu Pro Ser Lys Ile
            545                 550                 555
Gln Gln Trp His Gln Lys Gln Lys Asn Arg Lys Ala Gln Glu Asp
            560                 565                 570
Leu
```

```
<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 24
gcaaagctct gcctccttgg cc                                          22

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 25
gggtggactg tgctctaatg gacgc                                       25

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 26
cgtggcactg ggttgatc                                               18
```

<210> SEQ ID NO 27
<211> LENGTH: 45
<212> TYPE: DNA
<213> ORGANISM: Artificial Sequence
<220> FEATURE:
<223> OTHER INFORMATION: Synthetic oligonucleotide probe

<400> SEQUENCE: 27

| gatgcagttc tggtcagaga cgctccccag caagatacaa cagtg | 45 |
|---|---|

<210> SEQ ID NO 28
<211> LENGTH: 1342
<212> TYPE: DNA
<213> ORGANISM: Homo Sapien

<400> SEQUENCE: 28

| catggagcct cttgcagctt acccgctaaa atgttccggg cccagagcaa | 50 |
|---|---|
| aggtatttgc agttttgctg tctatagttc tatgcacagt aacgctattt | 100 |
| cttctacaac taaaattcct caaacctaaa atcaacagct tttatgcctt | 150 |
| tgaagtgaag gatgcaaaag gaagaactgt ttctctggaa aagtataaag | 200 |
| gcaaagtttc actagttgta aacgtggcca gtgactgcca actcacagac | 250 |
| agaaattact tagggctgaa ggaactgcac aaagagtttg gaccatccca | 300 |
| cttcagcgtg ttggcttttc cctgcaatca gtttggagaa tcggagcccc | 350 |
| gcccaagcaa ggaagtagaa tcttttgcaa gaaaaaacta cggagtaact | 400 |
| ttccccatct tccacaagat taagattcta ggatctgaag gagaacctgc | 450 |
| atttagattt cttgttgatt cttcaaagaa ggaaccaagg tggaattttt | 500 |
| ggaagtatct tgtcaaccct gagggtcaag ttgtgaagtt ctggaggcca | 550 |
| gaggagccca ttgaagtcat caggcctgac atagcagctc tggttagaca | 600 |
| agtgatcata aaaagaaag aggatctatg agaatgccat tgcgtttcta | 650 |
| atagaacaga gaaatgtctc catgagggtt tggtctcatt ttaaacattt | 700 |
| ttttttttgga gacagtgtct cactctgtca cccaggctgg agtgcagtag | 750 |
| tgcgttctca gctcattgca acctctgcct ttttaaacat gctattaaat | 800 |
| gtggcaatga aggattttt tttaatgtta tcttgctatt aagtggtaat | 850 |
| gaatgttccc aggatgagga tgttacccaa agcaaaaatc aagagtagcc | 900 |
| aaagaatcaa catgaaatat attaactact tcctctgacc atactaaaga | 950 |
| attcagaata cacagtgacc aatgtgcctc aatatcttat tgttcaactt | 1000 |
| gacattttct aggactgtac ttgatgaaaa tgccaacaca ctagaccact | 1050 |
| ctttggattc aagagcactg tgtatgactg aaatttctgg aataactgta | 1100 |
| aatggttatg ttaatggaat aaaacacaaa tgttgaaaaa tgtaaaatat | 1150 |
| atatacatag attcaaatcc ttatatatgt atgcttgttt tgtgtacagg | 1200 |
| attttgtttt ttcttttaa gtacaggttc ctagtgtttt actataactg | 1250 |
| tcactatgta tgtaactgac atatataaat agtcatttat aaatgaccgt | 1300 |
| attataacat ttgaaaaagt cttcatcaaa aaaaaaaaaa aa | 1342 |

<210> SEQ ID NO 29
<211> LENGTH: 209
<212> TYPE: PRT

<213> ORGANISM: Homo Sapien

<400> SEQUENCE: 29

| Met | Glu | Pro | Leu | Ala | Ala | Tyr | Pro | Leu | Lys | Cys | Ser | Gly | Pro | Arg |
| 1 | | | | 5 | | | | | 10 | | | | | 15 |

| Ala | Lys | Val | Phe | Ala | Val | Leu | Leu | Ser | Ile | Val | Leu | Cys | Thr | Val |
| | | | | 20 | | | | | 25 | | | | | 30 |

| Thr | Leu | Phe | Leu | Leu | Gln | Leu | Lys | Phe | Leu | Lys | Pro | Lys | Ile | Asn |
| | | | | 35 | | | | | 40 | | | | | 45 |

| Ser | Phe | Tyr | Ala | Phe | Glu | Val | Lys | Asp | Ala | Lys | Gly | Arg | Thr | Val |
| | | | | 50 | | | | | 55 | | | | | 60 |

| Ser | Leu | Glu | Lys | Tyr | Lys | Gly | Lys | Val | Ser | Leu | Val | Val | Asn | Val |
| 65 | | | | | | | | 70 | | | | | | 75 |

| Ala | Ser | Asp | Cys | Gln | Leu | Thr | Asp | Arg | Asn | Tyr | Leu | Gly | Leu | Lys |
| | | | | 80 | | | | | 85 | | | | | 90 |

| Glu | Leu | His | Lys | Glu | Phe | Gly | Pro | Ser | His | Phe | Ser | Val | Leu | Ala |
| | | | | 95 | | | | | 100 | | | | | 105 |

| Phe | Pro | Cys | Asn | Gln | Phe | Gly | Glu | Ser | Glu | Pro | Arg | Pro | Ser | Lys |
| | | | | 110 | | | | | 115 | | | | | 120 |

| Glu | Val | Glu | Ser | Phe | Ala | Arg | Lys | Asn | Tyr | Gly | Val | Thr | Phe | Pro |
| | | | | 125 | | | | | 130 | | | | | 135 |

| Ile | Phe | His | Lys | Ile | Lys | Ile | Leu | Gly | Ser | Glu | Gly | Glu | Pro | Ala |
| | | | | 140 | | | | | 145 | | | | | 150 |

| Phe | Arg | Phe | Leu | Val | Asp | Ser | Ser | Lys | Lys | Glu | Pro | Arg | Trp | Asn |
| | | | | 155 | | | | | 160 | | | | | 165 |

| Phe | Trp | Lys | Tyr | Leu | Val | Asn | Pro | Glu | Gly | Gln | Val | Val | Lys | Phe |
| | | | | 170 | | | | | 175 | | | | | 180 |

| Trp | Arg | Pro | Glu | Glu | Pro | Ile | Glu | Val | Ile | Arg | Pro | Asp | Ile | Ala |
| | | | | 185 | | | | | 190 | | | | | 195 |

| Ala | Leu | Val | Arg | Gln | Val | Ile | Ile | Lys | Lys | Lys | Glu | Asp | Leu |
| | | | | 200 | | | | | 205 | | | | |

<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 30
atcctccaac atggagcctc ttgc    24

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 31
gtatcttgtc aaccctgagg    20

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 32

| | |
|---|---|
| taaccagagc tgctatgtca ggcc | 24 |

<210> SEQ ID NO 33
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 33

| | |
|---|---|
| aggcaaagtt tcactagttg taaacgtggc cagtgactgc caactcacag | 50 |

<210> SEQ ID NO 34
<211> LENGTH: 3721
<212> TYPE: DNA
<213> ORGANISM: Homo Sapien

<400> SEQUENCE: 34

| | |
|---|---|
| tgtcgcctgg ccctcgccat gcagacccccg cgagcgtccc ctccccgccc | 50 |
| ggccctcctg cttctgctgc tgctactggg gggcgcccac ggcctctttc | 100 |
| ctgaggagcc gccgccgctt agcgtggccc ccagggacta cctgaaccac | 150 |
| tatcccgtgt ttgtgggcag cgggcccgga cgcctgaccc ccgcagaagg | 200 |
| tgctgacgac ctcaacatcc agcgagtcct gcgggtcaac aggacgctgt | 250 |
| tcattgggga cagggacaac ctctaccgcg tagagctgga gccccccacg | 300 |
| tccacggagc tgcggtacca gaggaagctg acctggagat ctaaccccag | 350 |
| cgacataaac gtgtgtcgga tgaagggcaa acaggagggc gagtgtcgaa | 400 |
| acttcgtaaa ggtgctgctc cttcgggacg agtccacgct ctttgtgtgc | 450 |
| ggttccaacg ccttcaaccc ggtgtgcgcc aactacagca tagacaccct | 500 |
| gcagcccgtc ggagacaaca tcagcggtat ggcccgctgc ccgtacgacc | 550 |
| ccaagcacgc caatgttgcc ctcttctctg acgggatgct cttcacagct | 600 |
| actgttaccg acttcctagc cattgatgct gtcatctacc gcagcctcgg | 650 |
| ggacaggccc accctgcgca ccgtgaaaca tgactccaag tggttcaaag | 700 |
| agccttactt tgtccatgcg gtggagtggg gcagccatgt ctacttcttc | 750 |
| ttccgggaga ttgcgatgga gtttaactac ctggagaagg tggtggtgtc | 800 |
| ccgcgtggcc cgagtgtgca agaacgacgt gggaggctcc ccccgcgtgc | 850 |
| tggagaagca gtggacgtcc ttcctgaagg cgcggctcaa ctgctctgta | 900 |
| cccgagact cccatttcta cttcaacgtg ctgcaggctg tcacgggcgt | 950 |
| ggtcagcctc gggggccggc ccgtggtcct ggccgttttt tccacgccca | 1000 |
| gcaacagcat ccctggctcg gctgtctgcg cctttgacct gacacaggtg | 1050 |
| gcagctgtgt ttgaaggccg cttccgagag cagaagtccc ccgagtccat | 1100 |
| ctggacgccg gtgccggagg atcaggtgcc tcgaccccgg cccgggtgct | 1150 |
| gcgcagcccc cgggatgcag tacaatgcct ccagcgcctt gccggatgac | 1200 |
| atcctcaact tgtcaagac ccacccctctg atggacgagg cggtgccctc | 1250 |
| gctgggccat gcgccctgga tcctgcggac cctgatgagg caccagctga | 1300 |
| ctcgagtggc tgtggacgtg ggagccggcc cctggggcaa ccagaccgtt | 1350 |
| gtcttcctgg gttctgaggc ggggacggtc ctcaagttcc tcgtccggcc | 1400 |

```
caatgccagc acctcaggga cgtctgggct cagtgtcttc ctggaggagt      1450
ttgagaccta ccggccggac aggtgtggac ggcccggcgg tggcgagaca      1500
gggcagcggc tgctgagctt ggagctggac gcagcttcgg ggggcctgct      1550
ggctgccttc ccccgctgcg tggtccgagt gcctgtggct cgctgccagc      1600
agtactcggg gtgtatgaag aactgtatcg gcagtcagga cccctactgc      1650
gggtgggccc ccgacggctc ctgcatcttc ctcagcccgg gcaccagagc      1700
cgcctttgag caggacgtgt ccggggccag cacctcaggc ttaggggact      1750
gcacaggact cctgcgggcc agcctctccg aggaccgcgc ggggctggtg      1800
tcggtgaacc tgctggtaac gtcgtcggtg gcggccttcg tggtgggagc      1850
cgtggtgtcc ggcttcagcg tgggctggtt cgtgggcctc cgtgagcggc      1900
gggagctggc ccggcgcaag gacaaggagg ccatcctggc gcacgggcg      1950
ggcgaggcgg tgctgagcgt cagccgcctg gcgagcgca gggcgcaggg      2000
tcccgggggc cggggcggag gcggtggcgg tggcgccggg gttcccccgg      2050
aggccctgct ggcgcccctg atgcagaacg gctgggccaa ggccacgctg      2100
ctgcagggcg ggccccacga cctggactcg ggctgctgc ccacgcccga      2150
gcagacgccc ctgccgcaga agcgcctgcc cactccgcac ccgcaccccc      2200
acgccctggg ccccgcgcc tgggaccacg gccaccccct gctcccggcc      2250
tccgcttcat cctccctcct gctgctggcg cccgccggg cccccgagca      2300
gcccccgcg cctggggagc cgaccccga cggccgcctc tatgctgccc       2350
ggcccggccg cgcctcccac ggcgacttcc cgctcacccc ccacgccagc      2400
ccggaccgcc ggcgggtggt gtccgcgccc acgggcccct ggacccagc      2450
ctcagccgcc gatggcctcc cgcggccctg gagcccgccc ccgacgggca      2500
gcctgaggag gccactgggc ccccacgccc ctccggccgc caccctgcgc      2550
cgcacccaca cgttcaacag cggcgaggcc cggcctgggg accgccaccg      2600
cggctgccac gcccggccgg gcacagactt ggcccacctc ctcccctatg      2650
gggggggcgga caggactgcg ccccccgtgc cctaggccgg ggccccccg      2700
atgccttggc agtgccagcc acgggaacca ggagcgagag acggtgccag      2750
aacgccgggg cccggggcaa ctccgagtgg gtgctcaagt ccccccgcg      2800
acccacccgc ggagtggggg gccccctccg ccacaaggaa gcacaaccag      2850
ctcgccctcc ccctacccgg ggccgcagga cgctgagacg gtttgggggt      2900
gggtgggcgg gaggactttg ctatggattt gaggttgacc ttatgcgcgt      2950
aggttttggt ttttttttgc agttttggtt tcttttgcgg ttttctaacc      3000
aattgcacaa ctccgttctc ggggtggcgg caggcagggg aggcttggac      3050
gccggtgggg aatggggggc cacagctgca gacctaagcc ctccccacc      3100
cctgaaaagg tccctcccca acccaggccc ctggcgtgtg tgggtgtgcg      3150
tgcgtgtgcg tgccgtgttc gtgtgcaagg ggccgggag tgggcgtgt       3200
gtgtgcgtgc cagcgaaggc tgctgtgggc gtgtgtgtca agtgggccac      3250
gcgtgcaggg tgtgtgtcca cgagcgacga tcgtggtggc cccagcggcc      3300
tgggcgttgg ctgagccgac gctgggcctt ccagaaggcc cggggtctc      3350
cgaggtgccg gttaggagtt tgaaccccc ccactctgca gagggaagcg      3400
```

-continued

```
gggacaatgc cggggtttca ggcaggagac acgaggaggg cctgcccgga        3450
agtcacatcg gcagcagctg tctaaagggc ttgggggcct ggggggcggc        3500
gaaggtgggt ggggcccctc tgtaaatacg gccccagggt ggtgagagag        3550
tcccatgcca cccgtcccct tgtgacctcc ccctatgac ctccagctga         3600 ccatgcatgc cacgtggctg gctgggtcct ctgccctctt tggagtttgc        3650
ctcccccagc ccctcccca tcaataaaac tctgtttaca accaaaaaaa         3700
aaaaaaaaaa aaaaaaaaaa a                                       3721
```

<210> SEQ ID NO 35
<211> LENGTH: 888
<212> TYPE: PRT
<213> ORGANISM: Homo Sapien

<400> SEQUENCE: 35

```
Met Gln Thr Pro Arg Ala Ser Pro Pro Arg Pro Ala Leu Leu Leu
 1               5                  10                  15

Leu Leu Leu Leu Leu Gly Gly Ala His Gly Leu Phe Pro Glu Glu
                20                  25                  30

Pro Pro Pro Leu Ser Val Ala Pro Arg Asp Tyr Leu Asn His Tyr
                35                  40                  45

Pro Val Phe Val Gly Ser Gly Pro Gly Arg Leu Thr Pro Ala Glu
                50                  55                  60

Gly Ala Asp Asp Leu Asn Ile Gln Arg Val Leu Arg Val Asn Arg
                65                  70                  75

Thr Leu Phe Ile Gly Asp Arg Asp Asn Leu Tyr Arg Val Glu Leu
                80                  85                  90

Glu Pro Pro Thr Ser Thr Glu Leu Arg Tyr Gln Arg Lys Leu Thr
                95                 100                 105

Trp Arg Ser Asn Pro Ser Asp Ile Asn Val Cys Arg Met Lys Gly
               110                 115                 120

Lys Gln Glu Gly Glu Cys Arg Asn Phe Val Lys Val Leu Leu Leu
               125                 130                 135

Arg Asp Glu Ser Thr Leu Phe Val Cys Gly Ser Asn Ala Phe Asn
               140                 145                 150

Pro Val Cys Ala Asn Tyr Ser Ile Asp Thr Leu Gln Pro Val Gly
               155                 160                 165

Asp Asn Ile Ser Gly Met Ala Arg Cys Pro Tyr Asp Pro Lys His
               170                 175                 180

Ala Asn Val Ala Leu Phe Ser Asp Gly Met Leu Phe Thr Ala Thr
               185                 190                 195

Val Thr Asp Phe Leu Ala Ile Asp Ala Val Ile Tyr Arg Ser Leu
               200                 205                 210

Gly Asp Arg Pro Thr Leu Arg Thr Val Lys His Asp Ser Lys Trp
               215                 220                 225

Phe Lys Glu Pro Tyr Phe Val His Ala Val Glu Trp Gly Ser His
               230                 235                 240

Val Tyr Phe Phe Arg Glu Ile Ala Met Glu Phe Asn Tyr Leu
               245                 250                 255

Glu Lys Val Val Val Ser Arg Val Ala Arg Val Cys Lys Asn Asp
               260                 265                 270

Val Gly Gly Ser Pro Arg Val Leu Glu Lys Gln Trp Thr Ser Phe
               275                 280                 285
```

```
Leu Lys Ala Arg Leu Asn Cys Ser Val Pro Gly Asp Ser His Phe
            290                 295                 300

Tyr Phe Asn Val Leu Gln Ala Val Thr Gly Val Val Ser Leu Gly
            305                 310                 315

Gly Arg Pro Val Leu Ala Val Phe Ser Thr Pro Ser Asn Ser
            320                 325                 330

Ile Pro Gly Ser Ala Val Cys Ala Phe Asp Leu Thr Gln Val Ala
            335                 340                 345

Ala Val Phe Glu Gly Arg Phe Arg Glu Gln Lys Ser Pro Glu Ser
            350                 355                 360

Ile Trp Thr Pro Val Pro Glu Asp Gln Val Pro Arg Pro Arg Pro
            365                 370                 375

Gly Cys Cys Ala Ala Pro Gly Met Gln Tyr Asn Ala Ser Ser Ala
            380                 385                 390

Leu Pro Asp Asp Ile Leu Asn Phe Val Lys Thr His Pro Leu Met
            395                 400                 405

Asp Glu Ala Val Pro Ser Leu Gly His Ala Pro Trp Ile Leu Arg
            410                 415                 420

Thr Leu Met Arg His Gln Leu Thr Arg Val Ala Val Asp Val Gly
            425                 430                 435

Ala Gly Pro Trp Gly Asn Gln Thr Val Val Phe Leu Gly Ser Glu
            440                 445                 450

Ala Gly Thr Val Leu Lys Phe Leu Val Arg Pro Asn Ala Ser Thr
            455                 460                 465

Ser Gly Thr Ser Gly Leu Ser Val Phe Leu Glu Glu Phe Glu Thr
            470                 475                 480

Tyr Arg Pro Asp Arg Cys Gly Arg Pro Gly Gly Glu Thr Gly
            485                 490                 495

Gln Arg Leu Leu Ser Leu Glu Leu Asp Ala Ala Ser Gly Gly Leu
            500                 505                 510

Leu Ala Ala Phe Pro Arg Cys Val Val Arg Val Pro Val Ala Arg
            515                 520                 525

Cys Gln Gln Tyr Ser Gly Cys Met Lys Asn Cys Ile Gly Ser Gln
            530                 535                 540

Asp Pro Tyr Cys Gly Trp Ala Pro Asp Gly Ser Cys Ile Phe Leu
            545                 550                 555

Ser Pro Gly Thr Arg Ala Ala Phe Glu Gln Asp Val Ser Gly Ala
            560                 565                 570

Ser Thr Ser Gly Leu Gly Asp Cys Thr Gly Leu Leu Arg Ala Ser
            575                 580                 585

Leu Ser Glu Asp Arg Ala Gly Leu Val Ser Val Asn Leu Leu Val
            590                 595                 600

Thr Ser Ser Val Ala Ala Phe Val Gly Ala Val Val Ser Gly
            605                 610                 615

Phe Ser Val Gly Trp Phe Val Gly Leu Arg Glu Arg Glu Leu
            620                 625                 630

Ala Arg Arg Lys Asp Lys Glu Ala Ile Leu Ala His Gly Ala Gly
            635                 640                 645

Glu Ala Val Leu Ser Val Ser Arg Leu Gly Glu Arg Ala Gln
            650                 655                 660

Gly Pro Gly Gly Arg Gly Gly Gly Gly Gly Ala Gly Val
            665                 670                 675
```

-continued

```
Pro Pro Glu Ala Leu Leu Ala Pro Leu Met Gln Asn Gly Trp Ala
            680                 685                 690

Lys Ala Thr Leu Leu Gln Gly Gly Pro His Asp Leu Asp Ser Gly
            695                 700                 705

Leu Leu Pro Thr Pro Glu Gln Thr Pro Leu Pro Gln Lys Arg Leu
            710                 715                 720

Pro Thr Pro His Pro His Pro His Ala Leu Gly Pro Arg Ala Trp
            725                 730                 735

Asp His Gly His Pro Leu Leu Pro Ala Ser Ala Ser Ser Ser Leu
            740                 745                 750

Leu Leu Leu Ala Pro Ala Arg Ala Pro Glu Gln Pro Pro Ala Pro
            755                 760                 765

Gly Glu Pro Thr Pro Asp Gly Arg Leu Tyr Ala Ala Arg Pro Gly
            770                 775                 780

Arg Ala Ser His Gly Asp Phe Pro Leu Thr Pro His Ala Ser Pro
            785                 790                 795

Asp Arg Arg Arg Val Val Ser Ala Pro Thr Gly Pro Leu Asp Pro
            800                 805                 810

Ala Ser Ala Ala Asp Gly Leu Pro Arg Pro Trp Ser Pro Pro Pro
            815                 820                 825

Thr Gly Ser Leu Arg Arg Pro Leu Gly Pro His Ala Pro Pro Ala
            830                 835                 840

Ala Thr Leu Arg Arg Thr His Thr Phe Asn Ser Gly Glu Ala Arg
            845                 850                 855

Pro Gly Asp Arg His Arg Gly Cys His Ala Arg Pro Gly Thr Asp
            860                 865                 870

Leu Ala His Leu Leu Pro Tyr Gly Gly Ala Asp Arg Thr Ala Pro
            875                 880                 885

Pro Val Pro

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 36
gaggacctac cggccggaca g                                              21

<210> SEQ ID NO 37
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 37
atacaccccg agtactgctg gcag                                           24

<210> SEQ ID NO 38
<211> LENGTH: 42
<212> TYPE: DNA
<213> ORGANISM: Artificial Sequence
<220> FEATURE:
<223> OTHER INFORMATION: Synthetic oligonucleotide probe

<400> SEQUENCE: 38
agacagggca gcggctgctg agcttggagc tggacgcagc tt                       42
```

<210> SEQ ID NO 39
<211> LENGTH: 2014
<212> TYPE: DNA
<213> ORGANISM: Homo Sapien

<400> SEQUENCE: 39

| | | |
|---|---|---|
| agcaactcaa gttcatcatt gtcctgagag agaggagcag cgcggttctc | 50 | |
| ggccgggaca gcagaacgcc aggggaccct cacctgggcg cgccggggca | 100 | |
| cgggctttga ttgtcctggg gtcgcggaga cccgcgcgcc tgccctgcac | 150 | |
| gccggccggc aacctttgca gtcgcgttgg ctgctgcgat cggccggcgg | 200 | |
| gtccctgccg aaggctcggc tgcttctgtc cacctcttac acttcttcat | 250 | |
| ttatcggtgg atcatttcga gagtccgtct tgtaaatgtt tggcactttg | 300 | |
| ctactttatt gcttctttct ggcgacagtt ccagcactcg ccagaccgg | 350 | |
| cggagaaagg cagctgagcc ggagaagag cgaaatatgg ggacccgggc | 400 | |
| taaaagcaga cgtcgtcctt cccgcccgct atttctatat tcaggcagtg | 450 | |
| gatacatcag ggaataaatt cacatcttct ccaggcgaaa aggtcttcca | 500 | |
| ggtgaaagtc tcagcaccag aggagcaatt cactagagtt ggagtccagg | 550 | |
| ttttagaccg aaaagatggg tccttcatag taagatacag aatgtatgca | 600 | |
| agctacaaaa atctgaaggt ggaaattaaa ttccaagggc aacatgtggc | 650 | |
| caaatcccca tatattttaa aagggccggt ttaccatgag aactgtgact | 700 | |
| gtcctctgca agatagtgca gcctggctac gggagatgaa ctgccctgaa | 750 | |
| accattgctc agattcagag agatctggca catttccctg ctgtggatcc | 800 | |
| agaaaagatt gcagtagaaa tcccaaaaag atttggacag aggcagagcc | 850 | |
| tatgtcacta caccttaaag gataacaagg tttatatcaa gactcatggt | 900 | |
| gaacatgtag gttttagaat tttcatggat gccatactac tttctttgac | 950 | |
| tagaaaggtg aagatgccag atgtggagct ctttgttaat ttgggagact | 1000 | |
| ggccttttga aaaaagaaa tccaattcaa acatccatcc gatcttttcc | 1050 | |
| tggtgtggct ccacagattc caaggatatc gtgatgccta cgtacgattt | 1100 | |
| gactgattct gttctggaaa ccatgggccg ggtaagtctg gatatgatgt | 1150 | |
| ccgtgcaagc taacacgggt cctccctggg aaagcaaaaa ttccactgcc | 1200 | |
| gtctggagag ggcgagacag ccgcaaagag agactcgagc tggttaaact | 1250 | |
| cagtagaaaa cacccagaac tcatagacgc tgctttcacc aactttttct | 1300 | |
| tctttaaaca cgatgaaaac ctgtatggtc ccattgtgaa acatatttca | 1350 | |
| tttttttgatt tcttcaagca taagtatcaa ataaatatcg atggcactgt | 1400 | |
| agcagcttat cgcctgccat atttgctagt tggtgacagt gttgtgctga | 1450 | |
| agcaggattc catctactat gaacattttt acaatgagct gcagccctgg | 1500 | |
| aaacactaca ttccagttaa gagcaacctg agcgatctgc tagaaaaact | 1550 | |
| taaatgggcg aaagatcacg atgaagaggc caaaagata gcaaaagcag | 1600 | |
| gacaagaatt tgcaagaaat aatctcatgg gcgatgacat attctgttat | 1650 | |
| tatttcaaac ttttccagga atatgccaat ttacaagtga gtgagcccca | 1700 | |
| aatccgagag ggcatgaaaa gggtagaacc acagactgag gacgacctct | 1750 | |

-continued

```
tcccttgtac ttgccatagg aaaaagacca aagatgaact ctgatatgca          1800
aaataacttc tattagaata atggtgctct gaagactctt cttaactaaa          1850
aagaagaatt ttttaagta ttaattccat ggacaatata aaatctgtgt           1900
gattgtttgc agtatgaaga cacatttcta cttatgcagt attctcatga          1950
ctgtacttta aagtacattt ttagaatttt ataataaaac caccttttatt         2000 ttaaaggaaa aaaa                                                 2014
```

<210> SEQ ID NO 40
<211> LENGTH: 502
<212> TYPE: PRT
<213> ORGANISM: Homo Sapien

<400> SEQUENCE: 40

```
Met Phe Gly Thr Leu Leu Leu Tyr Cys Phe Phe Leu Ala Thr Val
 1               5                  10                  15

Pro Ala Leu Ala Glu Thr Gly Gly Glu Arg Gln Leu Ser Pro Glu
                20                  25                  30

Lys Ser Glu Ile Trp Gly Pro Gly Leu Lys Ala Asp Val Val Leu
                35                  40                  45

Pro Ala Arg Tyr Phe Tyr Ile Gln Ala Val Asp Thr Ser Gly Asn
                50                  55                  60

Lys Phe Thr Ser Ser Pro Gly Glu Lys Val Phe Gln Val Lys Val
                65                  70                  75

Ser Ala Pro Glu Glu Gln Phe Thr Arg Val Gly Val Gln Val Leu
                80                  85                  90

Asp Arg Lys Asp Gly Ser Phe Ile Val Arg Tyr Arg Met Tyr Ala
                95                  100                 105

Ser Tyr Lys Asn Leu Lys Val Glu Ile Lys Phe Gln Gly Gln His
                110                 115                 120

Val Ala Lys Ser Pro Tyr Ile Leu Lys Gly Pro Val Tyr His Glu
                125                 130                 135

Asn Cys Asp Cys Pro Leu Gln Asp Ser Ala Ala Trp Leu Arg Glu
                140                 145                 150

Met Asn Cys Pro Glu Thr Ile Ala Gln Ile Gln Arg Asp Leu Ala
                155                 160                 165

His Phe Pro Ala Val Asp Pro Glu Lys Ile Ala Val Glu Ile Pro
                170                 175                 180

Lys Arg Phe Gly Gln Arg Gln Ser Leu Cys His Tyr Thr Leu Lys
                185                 190                 195

Asp Asn Lys Val Tyr Ile Lys Thr His Gly Glu His Val Gly Phe
                200                 205                 210

Arg Ile Phe Met Asp Ala Ile Leu Leu Ser Leu Thr Arg Lys Val
                215                 220                 225

Lys Met Pro Asp Val Glu Leu Phe Val Asn Leu Gly Asp Trp Pro
                230                 235                 240

Leu Glu Lys Lys Lys Ser Asn Ser Asn Ile His Pro Ile Phe Ser
                245                 250                 255

Trp Cys Gly Ser Thr Asp Ser Lys Asp Ile Val Met Pro Thr Tyr
                260                 265                 270

Asp Leu Thr Asp Ser Val Leu Glu Thr Met Gly Arg Val Ser Leu
                275                 280                 285

Asp Met Met Ser Val Gln Ala Asn Thr Gly Pro Pro Trp Glu Ser
```

```
                    290                 295                 300
Lys Asn Ser Thr Ala Val Trp Arg Gly Arg Asp Ser Arg Lys Glu
                305                 310                 315
Arg Leu Glu Leu Val Lys Leu Ser Arg Lys His Pro Glu Leu Ile
                320                 325                 330
Asp Ala Ala Phe Thr Asn Phe Phe Phe Lys His Asp Glu Asn
                335                 340                 345
Leu Tyr Gly Pro Ile Val Lys His Ile Ser Phe Asp Phe Phe
                350                 355                 360
Lys His Lys Tyr Gln Ile Asn Ile Asp Gly Thr Val Ala Ala Tyr
                365                 370                 375
Arg Leu Pro Tyr Leu Leu Val Gly Asp Ser Val Val Leu Lys Gln
                380                 385                 390
Asp Ser Ile Tyr Tyr Glu His Phe Tyr Asn Glu Leu Gln Pro Trp
                395                 400                 405
Lys His Tyr Ile Pro Val Lys Ser Asn Leu Ser Asp Leu Leu Glu
                410                 415                 420
Lys Leu Lys Trp Ala Lys Asp His Asp Glu Glu Ala Lys Lys Ile
                425                 430                 435
Ala Lys Ala Gly Gln Glu Phe Ala Arg Asn Asn Leu Met Gly Asp
                440                 445                 450
Asp Ile Phe Cys Tyr Tyr Phe Lys Leu Phe Gln Glu Tyr Ala Asn
                455                 460                 465
Leu Gln Val Ser Glu Pro Gln Ile Arg Glu Gly Met Lys Arg Val
                470                 475                 480
Glu Pro Gln Thr Glu Asp Asp Leu Phe Pro Cys Thr Cys His Arg
                485                 490                 495
Lys Lys Thr Lys Asp Glu Leu
                500

<210> SEQ ID NO 41
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 41
gaaggtggaa attaaattcc aagggc                                          26

<210> SEQ ID NO 42
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 42
cgataagctg ctacagtgcc atcg                                            24

<210> SEQ ID NO 43
<211> LENGTH: 40
<212> TYPE: DNA
<213> ORGANISM: Artificial Sequence
<220> FEATURE:
<223> OTHER INFORMATION: Synthetic oligonucleotide probe

<400> SEQUENCE: 43
gtgactgtcc tctgcaagat agtgcagcct ggctacggga                           40
```

<210> SEQ ID NO 44
<211> LENGTH: 2395
<212> TYPE: DNA
<213> ORGANISM: Homo Sapien

<400> SEQUENCE: 44

| | |
|---|---|
| cctggagccg gaagcgcggc tgcagcaggg cgaggctcca ggtggggtcg | 50 |
| gttccgcatc cagcctagcg tgtccacgat gcggctgggc tccgggactt | 100 |
| tcgctacctg ttgcgtagcg atcgaggtgc tagggatcgc ggtcttcctt | 150 |
| cggggattct tcccggctcc cgttcgttcc tctgccagag cggaacacgg | 200 |
| agcggagccc ccagcgcccg aaccctcggc tggagccagt tctaactgga | 250 |
| ccacgctgcc accacctctc ttcagtaaag ttgttattgt tctgatagat | 300 |
| gccttgagag atgattttgt gtttgggtca aagggtgtga aatttatgcc | 350 |
| ctacacaact taccttgtgg aaaaaggagc atctcacagt tttgtggctg | 400 |
| aagcaaagcc acctcagtt actatgcctc gaatcaaggc attgatgacg | 450 |
| gggagccttc ctggctttgt cgacgtcatc aggaacctca attctcctgc | 500 |
| actgctggaa gacagtgtga taagacaagc aaaagcagct ggaaaaagaa | 550 |
| tagtcttta tggagatgaa acctgggtta aattattccc aaagcatttt | 600 |
| gtggaatatg atggaacaac ctcattttc gtgtcagatt acacagaggt | 650 |
| ggataataat gtcacgaggc atttggataa agtattaaaa agaggagatt | 700 |
| gggacatatt aatcctccac tacctggggc tggaccacat tggccacatt | 750 |
| tcagggccca acagccccct gattgggcag aagctgagcg agatggacag | 800 |
| cgtgctgatg aagatccaca cctcactgca gtcgaaggag agagagacgc | 850 |
| ctttacccaa tttgctggtt ctttgtggtg accatggcat gtctgaaaca | 900 |
| ggaagtcacg gggcctcctc caccgaggag gtgaatacac ctctgatttt | 950 |
| aatcagttct gcgtttgaaa ggaaacccgg tgatatccga catccaaagc | 1000 |
| acgtccaata gacggatgtg gctgcgacac tggcgatagc acttggctta | 1050 |
| ccgattccaa aagacagtgt agggagcctc ctattcccag ttgtggaagg | 1100 |
| aagaccaatg agagagcagt tgagattttt acatttgaat acagtgcagc | 1150 |
| ttagtaaact gttgcaagag aatgtgccgt catatgaaaa agatcctggg | 1200 |
| tttgagcagt ttaaaatgtc agaaagattg catgggaact ggatcagact | 1250 |
| gtacttggag gaaaagcatt cagaagtcct attcaacctg gctccaaggg | 1300 |
| ttctcaggca gtacctggat gctctgaaga cgctgagctt gtccctgagt | 1350 |
| gcacaagtgg cccagttctc accctgctcc tgctcagcgt cccacaggca | 1400 |
| ctgcacagaa aggctgagct ggaagtccca ctgtcatctc ctgggttttc | 1450 |
| tctgctcttt tatttggtga tcctggttct ttcggccgtt cacgtcattg | 1500 |
| tgtgcaccctc agctgaaagt tcgtgctact tctgtggcct ctcgtggctg | 1550 |
| gcggcaggct gcctttcgtt taccagactc tggttgaaca cctggtgtgt | 1600 |
| gccaagtgct ggcagtgccc tggacagggg gcctcaggga aggacgtgga | 1650 |
| gcagccttat cccaggcctc tgggtgtccc gacacaggtg ttcacatctg | 1700 |
| tgctgtcagg tcagatgcct cagttcttgg aaagctaggt tcctgcgact | 1750 |

| | |
|---|---|
| gttaccaagg tgattgtaaa gagctggcgg tcacagagga acaagccccc | 1800 |
| cagctgaggg ggtgtgtgaa tcggacagcc tcccagcaga ggtgtgggag | 1850 |
| ctgcagctga gggaagaaga gacaatcggc ctggacactc aggagggtca | 1900 |
| aaaggagact tggtcgcacc actcatcctg ccacccccag aatgcatcct | 1950 |
| gcctcatcag gtccagattt ctttccaagg cggacgtttt ctgttggaat | 2000 |
| tcttagtcct tggcctcgga caccttcatt cgttagctgg ggagtggtgg | 2050 |
| tgaggcagtg aagaagaggc ggatggtcac actcagatcc acagagccca | 2100 |
| ggatcaaggg acccactgca gtggcagcag gactgttggg cccccacccc | 2150 |
| aaccctgcac agccctcatc ccctcttggc ttgagccgtc agaggccctg | 2200 |
| tgctgagtgt ctgaccgaga cactcacagc tttgtcatca gggcacaggc | 2250 |
| ttcctcggag ccaggatgat ctgtgccacg cttgcacctc gggcccatct | 2300 |
| gggctcatgc tctctctcct gctattgaat tagtacctag ctgcacacag | 2350 |
| tatgtagtta ccaaaagaat aaacggcaat aattgagaaa aaaaa | 2395 |

<210> SEQ ID NO 45
<211> LENGTH: 310
<212> TYPE: PRT
<213> ORGANISM: Homo Sapien

<400> SEQUENCE: 45

Met Arg Leu Gly Ser Gly Thr Phe Ala Thr Cys Cys Val Ala Ile
1               5                   10                  15

Glu Val Leu Gly Ile Ala Val Phe Leu Arg Gly Phe Phe Pro Ala
                20                  25                  30

Pro Val Arg Ser Ser Ala Arg Ala Glu His Gly Ala Glu Pro Pro
                35                  40                  45

Ala Pro Glu Pro Ser Ala Gly Ala Ser Ser Asn Trp Thr Thr Leu
                50                  55                  60

Pro Pro Pro Leu Phe Ser Lys Val Val Ile Val Leu Ile Asp Ala
                65                  70                  75

Leu Arg Asp Asp Phe Val Phe Gly Ser Lys Gly Val Lys Phe Met
                80                  85                  90

Pro Tyr Thr Thr Tyr Leu Val Glu Lys Gly Ala Ser His Ser Phe
                95                  100                 105

Val Ala Glu Ala Lys Pro Pro Thr Val Thr Met Pro Arg Ile Lys
                110                 115                 120

Ala Leu Met Thr Gly Ser Leu Pro Gly Phe Val Asp Val Ile Arg
                125                 130                 135

Asn Leu Asn Ser Pro Ala Leu Leu Glu Asp Ser Val Ile Arg Gln
                140                 145                 150

Ala Lys Ala Ala Gly Lys Arg Ile Val Phe Tyr Gly Asp Glu Thr
                155                 160                 165

Trp Val Lys Leu Phe Pro Lys His Phe Val Glu Tyr Asp Gly Thr
                170                 175                 180

Thr Ser Phe Phe Val Ser Asp Tyr Thr Glu Val Asp Asn Asn Val
                185                 190                 195

Thr Arg His Leu Asp Lys Val Leu Lys Arg Gly Asp Trp Asp Ile
                200                 205                 210

Leu Ile Leu His Tyr Leu Gly Leu Asp His Ile Gly His Ile Ser
                215                 220                 225

```
Gly Pro Asn Ser Pro Leu Ile Gly Gln Lys Leu Ser Glu Met Asp
                230                 235                 240

Ser Val Leu Met Lys Ile His Thr Ser Leu Gln Ser Lys Glu Arg
            245                 250                 255

Glu Thr Pro Leu Pro Asn Leu Leu Val Leu Cys Gly Asp His Gly
            260                 265                 270

Met Ser Glu Thr Gly Ser His Gly Ala Ser Ser Thr Glu Glu Val
        275                 280                 285

Asn Thr Pro Leu Ile Leu Ile Ser Ser Ala Phe Glu Arg Lys Pro
            290                 295                 300

Gly Asp Ile Arg His Pro Lys His Val Gln
        305                 310
```

<210> SEQ ID NO 46
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 46
cgggactttc gctacctgtt gc                                           22

<210> SEQ ID NO 47
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 47
catcatattc cacaaaatgc tttggg                                       26

<210> SEQ ID NO 48
<211> LENGTH: 38
<212> TYPE: DNA
<213> ORGANISM: Artificial Sequence
<220> FEATURE:
<223> OTHER INFORMATION: Synthetic oligonucleotide probe

<400> SEQUENCE: 48
ccttcgggga ttcttcccgg ctcccgttcg ttcctctg                          38

<210> SEQ ID NO 49
<211> LENGTH: 918
<212> TYPE: DNA
<213> ORGANISM: Homo Sapien

<400> SEQUENCE: 49
agccaggcag cacatcacag cgggaggagc tgtcccaggt ggcccagctc             50
agcaatggca atggggtcc ccagagtcat tctgctctgc ctctttgggg             100
ctgcgctctg cctgacaggg tcccaagccc tgcagtgcta cagctttgag            150
cacacctact ttggccccctt tgacctcagg gccatgaagc tgcccagcat           200
ctcctgtcct catgagtgct tgaggctat cctgtctctg gacaccgggt             250
atcgcgcgcc ggtgaccctg gtgcggaagg gctgctggac cgggcctcct            300
gcgggccaga cgcaatcgaa cccggacgcg ctgccgccag actactcggt            350
ggtgcgcggc tgcacaactg acaaatgcaa cgcccacctc atgactcatg            400
acgccctccc caacctgagc caagcacccg acccgccgac gctcagcggc            450

```
gccgagtgct acgcctgtat cggggtccac caggatgact gcgctatcgg          500
caggtcccga cgagtccagt gtcaccagga ccagaccgcc tgcttccagg          550
gcagtggcag aatgacagtt ggcaatttct cagtccctgt gtacatcaga          600
acctgccacc ggccctcctg caccaccgag ggcaccacca gcccctggac          650
agccatcgac ctccagggct cctgctgtga ggggtacctc tgcaacagga          700
aatccatgac ccagcccttc accagtgctt cagccaccac ccctccccga          750
gcactacagg tcctggccct gctcctccca gtcctcctgc tggtggggct          800
ctcagcatag accgcccctc caggatgctg gggacagggc tcacacacct          850
cattcttgct gcttcagccc ctatcacata gctcactgga aaatgatgtt          900
aaagtaagaa ttgcaaaa                                              918
```

<210> SEQ ID NO 50
<211> LENGTH: 251
<212> TYPE: PRT
<213> ORGANISM: Homo Sapien

<400> SEQUENCE: 50

```
Met Ala Met Gly Val Pro Arg Val Ile Leu Leu Cys Leu Phe Gly
 1               5                  10                  15

Ala Ala Leu Cys Leu Thr Gly Ser Gln Ala Leu Gln Cys Tyr Ser
                20                  25                  30

Phe Glu His Thr Tyr Phe Gly Pro Phe Asp Leu Arg Ala Met Lys
                35                  40                  45

Leu Pro Ser Ile Ser Cys Pro His Glu Cys Phe Glu Ala Ile Leu
                50                  55                  60

Ser Leu Asp Thr Gly Tyr Arg Ala Pro Val Thr Leu Val Arg Lys
                65                  70                  75

Gly Cys Trp Thr Gly Pro Pro Ala Gly Gln Thr Gln Ser Asn Pro
                80                  85                  90

Asp Ala Leu Pro Pro Asp Tyr Ser Val Val Arg Gly Cys Thr Thr
                95                 100                 105

Asp Lys Cys Asn Ala His Leu Met Thr His Asp Ala Leu Pro Asn
               110                 115                 120

Leu Ser Gln Ala Pro Asp Pro Pro Thr Leu Ser Gly Ala Glu Cys
               125                 130                 135

Tyr Ala Cys Ile Gly Val His Gln Asp Asp Cys Ala Ile Gly Arg
               140                 145                 150

Ser Arg Arg Val Gln Cys His Gln Asp Gln Thr Ala Cys Phe Gln
               155                 160                 165

Gly Ser Gly Arg Met Thr Val Gly Asn Phe Ser Val Pro Val Tyr
               170                 175                 180

Ile Arg Thr Cys His Arg Pro Ser Cys Thr Thr Glu Gly Thr Thr
               185                 190                 195

Ser Pro Trp Thr Ala Ile Asp Leu Gln Gly Ser Cys Cys Glu Gly
               200                 205                 210

Tyr Leu Cys Asn Arg Lys Ser Met Thr Gln Pro Phe Thr Ser Ala
               215                 220                 225

Ser Ala Thr Thr Pro Pro Arg Ala Leu Gln Val Leu Ala Leu Leu
               230                 235                 240

Leu Pro Val Leu Leu Leu Val Gly Leu Ser Ala
               245                 250
```

<210> SEQ ID NO 51
<211> LENGTH: 3288
<212> TYPE: DNA
<213> ORGANISM: Homo Sapien

<400> SEQUENCE: 51

| | | |
|---|---|---|
| cccacgcgtc cgggacagat gaacttaaaa gagaagcttt agctgccaaa | 50 |
| gattgggaaa gggaaaggac aaaaaagacc cctgggctac acggcgtagg | 100 |
| tgcaggtttt cctactgctg ttcttttatg ctgggagctg tggctgtaac | 150 |
| caactaggaa ataacgtatg cagcagctat ggctgtcaga gagttgtgct | 200 |
| tcccaagaca aaggcaagtc ctgtttcttt ttctttttg gggagtgtcc | 250 |
| ttggcaggtt ctgggtttgg acgttattcg gtgactgagg aaacagagaa | 300 |
| aggatccttt gtggtcaatc tggcaaagga tctgggacta gcagagggg | 350 |
| agctggctgc aaggggaacc agggtggttt ccgatgataa caaacaatac | 400 |
| ctgctcctgg attcacatac cgggaatttg ctcacaaatg agaaactgga | 450 |
| ccgagagaag ctgtgtggcc ctaaagagcc ctgtatgctg tatttccaaa | 500 |
| ttttaatgga tgatcccttt cagatttacc gggctgagct gagagtcagg | 550 |
| gatataaatg atcacgcgcc agtatttcag gacaaagaaa cagtcttaaa | 600 |
| aatatcagaa aatacagctg aagggacagc atttagacta gaaagagcac | 650 |
| aggatccaga tggaggactt aacggtatcc aaaactacac gatcagcccc | 700 |
| aactcttttt tccatattaa cattagtggc ggtgatgaag gcatgatata | 750 |
| tccagagcta gtgttggaca aagcactgga tcggggaggag cagggagagc | 800 |
| tcagcttaac cctcacagcg ctggatggtg ggtctccatc caggtctggg | 850 |
| acctctactg tacgcatcgt tgtcttggac gtcaatgaca atgccccaca | 900 |
| gtttgcccag gctctgtatg agacccaggc tccagaaaac agccccattg | 950 |
| ggttccttat tgttaaggta tgggcagaag atgtagactc tggagtcaac | 1000 |
| gcggaagtat cctattcatt ttttgatgcc tcagaaaata ttcgaacgac | 1050 |
| cttcaaatc aatcctttt ctggggaaat ctttctcaga gaattgcttg | 1100 |
| attatgagtt agtaaattct tacaaaataa atatacaggc aatggacggt | 1150 |
| ggaggccttt ctgcaagatg tagggtttta gtggaagtat tggacaccaa | 1200 |
| tgacaatccc cctgaactga tcgtatcatc atttttccaac tctgttgctg | 1250 |
| agaattctcc tgagacgccg ctggctgttt ttaagattaa tgacagagac | 1300 |
| tctggagaaa atggaaagat ggtttgctac attcaagaga atctgccatt | 1350 |
| cctactaaaa ccttctgtgg agaatttta catcctaatt acagaaggcg | 1400 |
| cgctggacag agagatcaga gccgagtaca acatcactat caccgtcact | 1450 |
| gacttgggga cacccaggct gaaaaccgag cacaacataa cggtcctggt | 1500 |
| ctccgacgtc aatgacaacg ccccgccctt cacccaaacc tcctacaccc | 1550 |
| tgttcgtccg cgagaacaac agcccgccc tgcacatcgg cagcgtcagc | 1600 |
| gccacagaca gagactcggg caccaacgcc caggtcacct actcgctgct | 1650 |
| gccgccccaa gacccgcacc tgcccctcgc ctccctggtc tccatcaacg | 1700 |
| cggacaacgg ccacctgttc gccctcaggt cgctggacta cgaggccctg | 1750 |

-continued

| | |
|---|---|
| caggctttcg agttccgcgt gggcgccaca gaccgcggct cccccgcgct | 1800 |
| gagcagagag gcgctggtgc gcgtgctggt gctggacgcc aacgacaact | 1850 |
| cgcccttcgt gctgtacccg ctgcagaacg gctccgcgcc ctgcaccgag | 1900 |
| ctggtgcccc gggcggccga gccgggctac ctggtgacca aggtggtggc | 1950 |
| ggtggacggc gactcgggcc agaacgcctg gctgtcgtac cagctgctca | 2000 |
| aggccacgga gcccggctg ttcggtgtgt gggcgcacaa tggggaggtg | 2050 |
| cgcaccgcca ggctgctgag cgagcgcgac gcagccaagc acaggctcgt | 2100 |
| ggtgcttgtc aaggacaatg gcgagcctcc tcgctcggcc accgccacgc | 2150 |
| tgcacttgct cctggtggac ggcttctccc agccctacct gcctctcccg | 2200 |
| gaggcggccc cggcccaggc ccaggccgag gccgacttgc tcaccgtcta | 2250 |
| cctggtggtg gcgttggcct cggtgtcttc gctcttcctc ctctcggtgc | 2300 |
| tcctgttcgt ggcggtgcgg ctgtgcagga ggagcagggc ggcctcggtg | 2350 |
| ggtcgctgct cggtgcccga gggtcctttt ccagggcatc tggtggacgt | 2400 |
| gaggggcgct gagaccctgt cccagagcta ccagtatgag gtgtgtctga | 2450 |
| cgggaggccc cgggaccagt gagttcaagt tcttgaaacc agttatttcg | 2500 |
| gatattcagg cacagggccc tgggaggaag ggtgaagaaa attccacctt | 2550 |
| ccgaaatagc tttggattta atattcagta aagtctgttt ttagtttcat | 2600 |
| atacttttgg tgtgttacat agccatgttt ctattagttt acttttaaat | 2650 |
| ctcaaattta agttattatg caacttcaag cattattttc aagtagtata | 2700 |
| ccctgtggt tttacaatgt ttcatcattt ttttgcatta ataacaactg | 2750 |
| ggtttaattt aatgagtatt ttttctaaa tgatagtgtt aaggttttaa | 2800 |
| ttctttccaa ctgcccaagg aattaattac tattatatct cattacagaa | 2850 |
| atctgaggtt ttgattcatt tcagagcttg catctcatga ttctaatcac | 2900 |
| ttctgtctat agtgtacttg ctctatttaa gaaggcatat ctacatttcc | 2950 |
| aaactcattc taacattcta tatattcgtg tttgaaaacc atgtcattta | 3000 |
| tttctacatc atgtatttaa aaagaaatat ttctctacta ctatgctcat | 3050 |
| gacaaaatga aacaaagcat attgtgagca atactgaaca tcaataatac | 3100 |
| ccttagtttta tacttatt attttatctt taagcatgct acttttactt | 3150 |
| ggccaatatt ttcttatgtt aacttttgct gatgtataaa acagactatg | 3200 |
| ccttataatt gaaataaaat tataatctgc ctgaaaatga ataaaaataa | 3250 |
| aacatttga aatgtgaaaa aaaaaaaaaa aaaaaaa | 3288 |

<210> SEQ ID NO 52
<211> LENGTH: 800
<212> TYPE: PRT
<213> ORGANISM: Homo Sapien

<400> SEQUENCE: 52

Met Ala Val Arg Glu Leu Cys Phe Pro Arg Gln Arg Gln Val Leu
1               5                   10                  15

Phe Leu Phe Leu Phe Trp Gly Val Ser Leu Ala Gly Ser Gly Phe
                20                  25                  30

Gly Arg Tyr Ser Val Thr Glu Glu Thr Glu Lys Gly Ser Phe Val
                35                  40                  45

-continued

```
Val Asn Leu Ala Lys Asp Leu Gly Leu Ala Glu Gly Glu Leu Ala
             50                  55                  60

Ala Arg Gly Thr Arg Val Val Ser Asp Asn Lys Gln Tyr Leu
             65                  70                  75

Leu Leu Asp Ser His Thr Gly Asn Leu Thr Asn Glu Lys Leu
             80                  85                  90

Asp Arg Glu Lys Leu Cys Gly Pro Lys Glu Pro Cys Met Leu Tyr
             95                 100                 105

Phe Gln Ile Leu Met Asp Asp Pro Phe Gln Ile Tyr Arg Ala Glu
            110                 115                 120

Leu Arg Val Arg Asp Ile Asn Asp His Ala Pro Val Phe Gln Asp
            125                 130                 135

Lys Glu Thr Val Leu Lys Ile Ser Glu Asn Thr Ala Glu Gly Thr
            140                 145                 150

Ala Phe Arg Leu Glu Arg Ala Gln Asp Pro Asp Gly Gly Leu Asn
            155                 160                 165

Gly Ile Gln Asn Tyr Thr Ile Ser Pro Asn Ser Phe Phe His Ile
            170                 175                 180

Asn Ile Ser Gly Gly Asp Glu Gly Met Ile Tyr Pro Glu Leu Val
            185                 190                 195

Leu Asp Lys Ala Leu Asp Arg Glu Glu Gln Gly Glu Leu Ser Leu
            200                 205                 210

Thr Leu Thr Ala Leu Asp Gly Gly Ser Pro Ser Arg Ser Gly Thr
            215                 220                 225

Ser Thr Val Arg Ile Val Val Leu Asp Val Asn Asp Asn Ala Pro
            230                 235                 240

Gln Phe Ala Gln Ala Leu Tyr Glu Thr Gln Ala Pro Glu Asn Ser
            245                 250                 255

Pro Ile Gly Phe Leu Ile Val Lys Val Trp Ala Glu Asp Val Asp
            260                 265                 270

Ser Gly Val Asn Ala Glu Val Ser Tyr Ser Phe Phe Asp Ala Ser
            275                 280                 285

Glu Asn Ile Arg Thr Thr Phe Gln Ile Asn Pro Phe Ser Gly Glu
            290                 295                 300

Ile Phe Leu Arg Glu Leu Leu Asp Tyr Glu Leu Val Asn Ser Tyr
            305                 310                 315

Lys Ile Asn Ile Gln Ala Met Asp Gly Gly Gly Leu Ser Ala Arg
            320                 325                 330

Cys Arg Val Leu Val Glu Val Leu Asp Thr Asn Asp Asn Pro Pro
            335                 340                 345

Glu Leu Ile Val Ser Ser Phe Ser Asn Ser Val Ala Glu Asn Ser
            350                 355                 360

Pro Glu Thr Pro Leu Ala Val Phe Lys Ile Asn Asp Arg Asp Ser
            365                 370                 375

Gly Glu Asn Gly Lys Met Val Cys Tyr Ile Gln Glu Asn Leu Pro
            380                 385                 390

Phe Leu Leu Lys Pro Ser Val Glu Asn Phe Tyr Ile Leu Ile Thr
            395                 400                 405

Glu Gly Ala Leu Asp Arg Glu Ile Arg Ala Glu Tyr Asn Ile Thr
            410                 415                 420

Ile Thr Val Thr Asp Leu Gly Thr Pro Arg Leu Lys Thr Glu His
            425                 430                 435

Asn Ile Thr Val Leu Val Ser Asp Val Asn Asp Asn Ala Pro Ala
```

-continued

```
            440                 445                 450
Phe Thr Gln Thr Ser Tyr Thr Leu Phe Val Arg Glu Asn Asn Ser
            455                 460                 465
Pro Ala Leu His Ile Gly Ser Val Ser Ala Thr Asp Arg Asp Ser
            470                 475                 480
Gly Thr Asn Ala Gln Val Thr Tyr Ser Leu Leu Pro Pro Gln Asp
            485                 490                 495
Pro His Leu Pro Leu Ala Ser Leu Val Ser Ile Asn Ala Asp Asn
            500                 505                 510
Gly His Leu Phe Ala Leu Arg Ser Leu Asp Tyr Glu Ala Leu Gln
            515                 520                 525
Ala Phe Glu Phe Arg Val Gly Ala Thr Asp Arg Gly Ser Pro Ala
            530                 535                 540
Leu Ser Arg Glu Ala Leu Val Arg Val Leu Leu Asp Ala Asn
            545                 550                 555
Asp Asn Ser Pro Phe Val Leu Tyr Pro Leu Gln Asn Gly Ser Ala
            560                 565                 570
Pro Cys Thr Glu Leu Val Pro Arg Ala Ala Glu Pro Gly Tyr Leu
            575                 580                 585
Val Thr Lys Val Val Ala Val Asp Gly Asp Ser Gly Gln Asn Ala
            590                 595                 600
Trp Leu Ser Tyr Gln Leu Leu Lys Ala Thr Glu Pro Gly Leu Phe
            605                 610                 615
Gly Val Trp Ala His Asn Gly Glu Val Arg Thr Ala Arg Leu Leu
            620                 625                 630
Ser Glu Arg Asp Ala Ala Lys His Arg Leu Val Val Leu Val Lys
            635                 640                 645
Asp Asn Gly Glu Pro Pro Arg Ser Ala Thr Ala Thr Leu His Leu
            650                 655                 660
Leu Leu Val Asp Gly Phe Ser Gln Pro Tyr Leu Pro Leu Pro Glu
            665                 670                 675
Ala Ala Pro Ala Gln Ala Gln Ala Glu Ala Asp Leu Leu Thr Val
            680                 685                 690
Tyr Leu Val Val Ala Leu Ala Ser Val Ser Ser Leu Phe Leu Leu
            695                 700                 705
Ser Val Leu Leu Phe Val Ala Val Arg Leu Cys Arg Arg Ser Arg
            710                 715                 720
Ala Ala Ser Val Gly Arg Cys Ser Val Pro Glu Gly Pro Phe Pro
            725                 730                 735
Gly His Leu Val Asp Val Arg Gly Ala Glu Thr Leu Ser Gln Ser
            740                 745                 750
Tyr Gln Tyr Glu Val Cys Leu Thr Gly Pro Gly Thr Ser Glu
            755                 760                 765
Phe Lys Phe Leu Lys Pro Val Ile Ser Asp Ile Gln Ala Gln Gly
            770                 775                 780
Pro Gly Arg Lys Gly Glu Glu Asn Ser Thr Phe Arg Asn Ser Phe
            785                 790                 795
Gly Phe Asn Ile Gln
            800

<210> SEQ ID NO 53
<211> LENGTH: 24
<212> TYPE: DNA
<213> ORGANISM: Artificial Sequence
```

```
<220> FEATURE:
<223> OTHER INFORMATION: Synthetic oligonucleotide probe

<400> SEQUENCE: 53
ctggggagtg tccttggcag gttc                                              24

<210> SEQ ID NO 54
<211> LENGTH: 27
<212> TYPE: DNA
<213> ORGANISM: Artificial Sequence
<220> FEATURE:
<223> OTHER INFORMATION: Synthetic oligonucleotide probe

<400> SEQUENCE: 54
cagcatacag ggctctttag ggcacac                                           27

<210> SEQ ID NO 55
<211> LENGTH: 46
<212> TYPE: DNA
<213> ORGANISM: Artificial Sequence
<220> FEATURE:
<223> OTHER INFORMATION: Synthetic oligonucleotide probe

<400> SEQUENCE: 55
cggtgactga ggaaacagag aaaggatcct ttgtggtcaa tctggc                      46

<210> SEQ ID NO 56
<211> LENGTH: 2242
<212> TYPE: DNA
<213> ORGANISM: Homo Sapien
<220> FEATURE:
<221> NAME/KEY: unsure
<222> LOCATION: 2181
<223> OTHER INFORMATION: unknown base

<400> SEQUENCE: 56
gaatgaatac ctccgaagcc gctttgttct ccagatgtga atagctccac                  50
tataccagcc tcgtcttcct tccgggggac aacgtgggtc agggcacaga                 100
gagatattta atgtcaccct cttggggctt tcatgggact ccctctgcca                 150
cattttttgg aggttgggaa agttgctaga ggcttcagaa ctccagccta                 200
atggatccca aactcgggag aatggctgcg tccctgctgg ctgtgctgct                 250
gctgctgctg gagcgcggca tgttctcctc accctccccg ccccggcgc                  300 tgttagagaa agtcttccag tacattgacc tccatcagga tgaatttgtg                 350
cagacgctga aggagtgggt ggccatcgag agcgactctg tccagcctgt                 400
gcctcgcttc agacaagagc tcttcagaat gatggccgtg gctgcggaca                 450
cgctgcagcg cctgggggcc cgtgtggcct cggtggacat gggtcctcag                 500
cagctgcccg atggtcagag tcttccaata cctcccgtca tcctggccga                 550
actggggagc gatcccacga aaggcaccgt gtgcttctac ggccacttgg                 600
acgtgcagcc tgctgaccgg ggcgatgggt ggctcacgga cccctatgtg                 650
ctgacggagg tagacgggaa actttatgga cgaggagcga ccgacaacaa                 700
aggccctgtc ttggcttgga tcaatgctgt gagcgcctt c agagccctgg                750 agcaagatct tcctgtgaat atcaaattca tcattgaggg gatggaagag                 800
gctggctctg ttgccctgga ggaacttgtg gaaaagaaa aggaccgatt                  850 cttctctggt gtggactaca ttgtaatttc agataacctg tggatcagcc                 900
```

-continued

| | |
|---|---|
| aaaggaagcc agcaatcact tatggaaccc gggggaacag ctacttcatg | 950 |
| gtggaggtga aatgcagaga ccaggatttt cactcaggaa cctttggtgg | 1000 |
| catccttcat gaaccaatgg ctgatctggt tgctcttctc ggtagcctgg | 1050 |
| tagactcgtc tggtcatatc ctggtccctg aatctatga tgaagtggtt | 1100 |
| cctcttacag aagaggaaat aaatacatac aaagccatcc atctagacct | 1150 |
| agaagaatac cggaatagca gccgggttga gaaatttctg ttcgatacta | 1200 |
| aggaggagat tctaatgcac ctctggaggt acccatctct ttctattcat | 1250 |
| gggatcgagg gcgcgtttga tgagcctgga actaaaacag tcatacctgg | 1300 |
| ccgagttata ggaaaatttt caatccgtct agtccctcac atgaatgtgt | 1350 |
| ctgcggtgga aaaacaggtg acacgacatc ttgaagatgt gttctccaaa | 1400 |
| agaaatagtt ccaacaagat ggttgtttcc atgactctag actacaccc | 1450 |
| gtggattgca aatattgatg acacccagta tctcgcagca aaaagagcga | 1500 |
| tcagaacagt gtttggaaca gaaccagata tgatccggga tggatccacc | 1550 |
| attccaattg ccaaaatgtt ccaggagatc gtccacaaga gcgtggtgct | 1600 |
| aattccgctg ggagctgttg atgatggaga acattcgcag aatgagaaaa | 1650 |
| tcaacaggtg gaactacata gagggaacca aattatttgc tgccttttc | 1700 |
| ttagagatgg cccagctcca ttaatcacaa gaaccttcta gtctgatctg | 1750 |
| atccactgac agattcacct cccccacatc cctagacagg gatggaatgt | 1800 |
| aaatatccag agaatttggg tctagtatag tacattttcc cttccattta | 1850 |
| aaatgtcttg ggatatctgg atcagtaata aaatatttca aaggcacaga | 1900 |
| tgttggaaat ggtttaaggt cccccactgc acaccttcct caagtcatag | 1950 |
| ctgcttgcag caacttgatt tccccaagtc ctgtgcaata gccccaggat | 2000 |
| tggattcctt ccaacctttt agcatatctc caaccttgca atttgattgg | 2050 |
| cataatcact ccggtttgct ttctaggtcc tcaagtgctc gtgacacata | 2100 |
| atcattccat ccaatgatcg cctttgcttt accactcttt cctttatct | 2150 |
| tattaataaa aatgttggtc tccaccactg nctcccaaaa aaaaaaaaa | 2200 |
| aaaaaaaaaa aaaaaaaaaa aaaaaaaaaa aaaaaaaaa aa | 2242 |

<210> SEQ ID NO 57
<211> LENGTH: 507
<212> TYPE: PRT
<213> ORGANISM: Homo Sapien

<400> SEQUENCE: 57

```
Met Asp Pro Lys Leu Gly Arg Met Ala Ala Ser Leu Leu Ala Val
 1               5                  10                  15

Leu Leu Leu Leu Glu Arg Gly Met Phe Ser Ser Pro Ser Pro
                20                  25                  30

Pro Pro Ala Leu Leu Glu Lys Val Phe Gln Tyr Ile Asp Leu His
                35                  40                  45

Gln Asp Glu Phe Val Gln Thr Leu Lys Glu Trp Val Ala Ile Glu
                50                  55                  60

Ser Asp Ser Val Gln Pro Val Pro Arg Phe Arg Gln Glu Leu Phe
                65                  70                  75

Arg Met Met Ala Val Ala Ala Asp Thr Leu Gln Arg Leu Gly Ala
                80                  85                  90
```

-continued

```
Arg Val Ala Ser Val Asp Met Gly Pro Gln Gln Leu Pro Asp Gly
             95                 100                 105
Gln Ser Leu Pro Ile Pro Pro Val Ile Leu Ala Glu Leu Gly Ser
            110                 115                 120
Asp Pro Thr Lys Gly Thr Val Cys Phe Tyr Gly His Leu Asp Val
            125                 130                 135
Gln Pro Ala Asp Arg Gly Asp Gly Trp Leu Thr Asp Pro Tyr Val
            140                 145                 150
Leu Thr Glu Val Asp Gly Lys Leu Tyr Gly Arg Gly Ala Thr Asp
            155                 160                 165
Asn Lys Gly Pro Val Leu Ala Trp Ile Asn Ala Val Ser Ala Phe
            170                 175                 180
Arg Ala Leu Glu Gln Asp Leu Pro Val Asn Ile Lys Phe Ile Ile
            185                 190                 195
Glu Gly Met Glu Glu Ala Gly Ser Val Ala Leu Glu Glu Leu Val
            200                 205                 210
Glu Lys Glu Lys Asp Arg Phe Phe Ser Gly Val Asp Tyr Ile Val
            215                 220                 225
Ile Ser Asp Asn Leu Trp Ile Ser Gln Arg Lys Pro Ala Ile Thr
            230                 235                 240
Tyr Gly Thr Arg Gly Asn Ser Tyr Phe Met Val Glu Val Lys Cys
            245                 250                 255
Arg Asp Gln Asp Phe His Ser Gly Thr Phe Gly Gly Ile Leu His
            260                 265                 270
Glu Pro Met Ala Asp Leu Val Ala Leu Leu Gly Ser Leu Val Asp
            275                 280                 285
Ser Ser Gly His Ile Leu Val Pro Gly Ile Tyr Asp Glu Val Val
            290                 295                 300
Pro Leu Thr Glu Glu Ile Asn Thr Tyr Lys Ala Ile His Leu
            305                 310                 315
Asp Leu Glu Glu Tyr Arg Asn Ser Ser Arg Val Glu Lys Phe Leu
            320                 325                 330
Phe Asp Thr Lys Glu Glu Ile Leu Met His Leu Trp Arg Tyr Pro
            335                 340                 345
Ser Leu Ser Ile His Gly Ile Glu Gly Ala Phe Asp Glu Pro Gly
            350                 355                 360
Thr Lys Thr Val Ile Pro Gly Arg Val Ile Gly Lys Phe Ser Ile
            365                 370                 375
Arg Leu Val Pro His Met Asn Val Ser Ala Val Glu Lys Gln Val
            380                 385                 390
Thr Arg His Leu Glu Asp Val Phe Ser Lys Arg Asn Ser Ser Asn
            395                 400                 405
Lys Met Val Val Ser Met Thr Leu Gly Leu His Pro Trp Ile Ala
            410                 415                 420
Asn Ile Asp Asp Thr Gln Tyr Leu Ala Ala Lys Arg Ala Ile Arg
            425                 430                 435
Thr Val Phe Gly Thr Glu Pro Asp Met Ile Arg Asp Gly Ser Thr
            440                 445                 450
Ile Pro Ile Ala Lys Met Phe Gln Glu Ile Val His Lys Ser Val
            455                 460                 465
Val Leu Ile Pro Leu Gly Ala Val Asp Asp Gly Glu His Ser Gln
            470                 475                 480
```

```
Asn Glu Lys Ile Asn Arg Trp Asn Tyr Ile Glu Gly Thr Lys Leu
            485                 490                 495
Phe Ala Ala Phe Phe Leu Glu Met Ala Gln Leu His
            500                 505

<210> SEQ ID NO 58
<211> LENGTH: 1470
<212> TYPE: DNA
<213> ORGANISM: Homo Sapien

<400> SEQUENCE: 58
```

| | | | |
|---|---|---|---|
| ctcggctgga tttaaggttg ccgctagccg cctgggaatt taagggaccc | 50 |
| acactacctt cccgaagttg aaggcaagcg gtgattgttt gtagacggcg | 100 |
| cttttgtcatg ggacctgtgc ggttgggaat attgcttttc ctttttttgg | 150 |
| ccgtgcacga ggcttgggct gggatgttga aggaggagga cgatgacaca | 200 |
| gaacgcttgc ccagcaaatg cgaagtgtgt aagctgctga gcacagagct | 250 |
| acaggcggaa ctgagtcgca ccggtcgatc tcgagaggtg ctggagctgg | 300 |
| ggcaggtgct ggatacaggc aagaggaaga gacacgtgcc ttacagcgtt | 350 |
| tcagagacaa ggctggaaga ggccttagag aatttatgtg agcggatcct | 400 |
| ggactatagt gttcacgctg agcgcaaggg ctcactgaga tatgccaagg | 450 |
| gtcagagtca gaccatggca acactgaaag gcctagtgca aagggggtg | 500 |
| aaggtggatc tggggatccc tctggagctt tgggatgagc ccagcgtgga | 550 |
| ggtcacatac ctcaagaagc agtgtgagac catgttggag gagtttgaag | 600 |
| acattgtggg agactggtac ttccaccatc aggagcagcc cctacaaaat | 650 |
| tttctctgtg aaggtcatgt gctcccagct gctgaaactg catgtctaca | 700 |
| ggaaacttgg actggaaagg agatcacaga tggggaagga aaaacagaag | 750 |
| gggaggaaga gcaggaggag gaggaggaag aggaggaaga ggaaggggga | 800 |
| gacaagatga ccaagacagg aagccacccc aaacttgacc gagaagatct | 850 |
| ttgacccttg cctttgagcc cccaggaggg gaagggatca tggagagccc | 900 |
| tctaaagcct gcactctccc tgctccacag ctttcagggt gtgtttatga | 950 |
| gtgactccac ccaagcttgt agctgttctc tcccatctaa cctcaggcaa | 1000 |
| gatcctggtg aaacagcatg acatggcttc tggggtggag ggtgggggtg | 1050 |
| gaggtcctgc tcctagagat gaactctatc cagcccctta attggcaggt | 1100 |
| gtatgtgctg acagtactga aagctttcct ctttaactga tcccaccccc | 1150 |
| acccaaaagt cagcagtggc actggagctg tgggctttgg ggaagtcact | 1200 |
| tagctcctta aggtctgttt ttagacccct ccaaggaaga ggccagaacg | 1250 |
| gacattctct gcgatctata tacattgcct gtatccagga ggctacacac | 1300 |
| cagcaaaccg tgaaggagaa tgggacactg ggtcatggcc tggagttgct | 1350 |
| gataatttag gtgggataga tacttggtct acttaagctc aatgtaaccc | 1400 |
| agagcccacc atatagtttt ataggtgctc aactttctat atcgctatta | 1450 |
| aacttttttc ttttttttcta | 1470 |

```
<210> SEQ ID NO 59
<211> LENGTH: 248
<212> TYPE: PRT
<213> ORGANISM: Homo Sapien
```

-continued

<400> SEQUENCE: 59

```
Met Gly Pro Val Arg Leu Gly Ile Leu Leu Phe Leu Phe Leu Ala
 1               5                  10                  15

Val His Glu Ala Trp Ala Gly Met Leu Lys Glu Glu Asp Asp Asp
             20                  25                  30

Thr Glu Arg Leu Pro Ser Lys Cys Glu Val Cys Lys Leu Leu Ser
         35                  40                  45

Thr Glu Leu Gln Ala Glu Leu Ser Arg Thr Gly Arg Ser Arg Glu
     50                  55                  60

Val Leu Glu Leu Gly Gln Val Leu Asp Thr Gly Lys Arg Lys Arg
 65                  70                  75

His Val Pro Tyr Ser Val Ser Glu Thr Arg Leu Glu Glu Ala Leu
             80                  85                  90

Glu Asn Leu Cys Glu Arg Ile Leu Asp Tyr Ser Val His Ala Glu
         95                 100                 105

Arg Lys Gly Ser Leu Arg Tyr Ala Lys Gly Gln Ser Gln Thr Met
    110                 115                 120

Ala Thr Leu Lys Gly Leu Val Gln Lys Gly Val Lys Val Asp Leu
    125                 130                 135

Gly Ile Pro Leu Glu Leu Trp Asp Pro Ser Val Glu Val Thr
    140                 145                 150

Tyr Leu Lys Lys Gln Cys Glu Thr Met Leu Glu Glu Phe Glu Asp
            155                 160                 165

Ile Val Gly Asp Trp Tyr Phe His His Gln Glu Pro Leu Gln
        170                 175                 180

Asn Phe Leu Cys Glu Gly His Val Leu Pro Ala Ala Glu Thr Ala
    185                 190                 195

Cys Leu Gln Glu Thr Trp Thr Gly Lys Glu Ile Thr Asp Gly Glu
        200                 205                 210

Glu Lys Thr Glu Gly Glu Glu Glu Gln Glu Glu Glu Glu Glu Glu
        215                 220                 225

Glu Glu Glu Glu Gly Gly Asp Lys Met Thr Lys Thr Gly Ser His
        230                 235                 240

Pro Lys Leu Asp Arg Glu Asp Leu
                245
```

<210> SEQ ID NO 60
<211> LENGTH: 890
<212> TYPE: DNA
<213> ORGANISM: Homo Sapien

<400> SEQUENCE: 60

| | | |
|---|---|---|
| aagtacttgt gtccgggtgg tggactggat tagctgcgga gccctggaag | 50 |
| ctgcctgtcc ttctccctgt gcttaaccag aggtgcccat gggttggaca | 100 |
| atgaggctgg tcacagcagc actgttactg ggtctcatga tggtggtcac | 150 |
| tggagacgag gatgagaaca gcccgtgtgc ccatgaggcc ctcttggacg | 200 |
| aggacaccct cttttgccag ggccttgaag ttttctaccc agagttgggg | 250 |
| aacattggct gcaaggttgt tcctgattgt aacaactaca gacagaagat | 300 |
| cacctcctgg atggagccga tagtcaagtt cccgggggcc gtggacggcg | 350 |
| caacctatat cctggtgatg gtggatccag atgcccctag cagagcagaa | 400 |
| cccagacaga gattctggag acattggctg gtaacagata tcaagggcgc | 450 |

```
cgacctgaag aaagggaaga ttcagggcca ggagttatca gcctaccagg          500
ctccctcccc accggcacac agtggcttcc atcgctacca gttctttgtc          550
tatcttcagg aaggaaaagt catctctctc cttcccaagg aaaacaaaac          600
tcgaggctct tggaaaatgg acagatttct gaaccgcttc cacctgggcg          650
aacctgaagc aagcacccag ttcatgaccc agaactacca ggactcacca          700
accctccagg ctcccagagg aagggccagc gagcccaagc acaaaaccag          750
gcagagatag ctgcctgcta gatagccggc tttgccatcc gggcatgtgg          800
ccacactgct caccaccgac gatgtgggta tggaaccccc tctggataca          850 gaacccttc ttttccaaat taaaaaaaaa aatcatcaaa                      890
```

<210> SEQ ID NO 61
<211> LENGTH: 223
<212> TYPE: PRT
<213> ORGANISM: Homo Sapien

<400> SEQUENCE: 61

```
Met Gly Trp Thr Met Arg Leu Val Thr Ala Ala Leu Leu Leu Gly
 1               5                  10                  15

Leu Met Met Val Val Thr Gly Asp Glu Asp Glu Asn Ser Pro Cys
                20                  25                  30

Ala His Glu Ala Leu Leu Asp Glu Asp Thr Leu Phe Cys Gln Gly
                35                  40                  45

Leu Glu Val Phe Tyr Pro Glu Leu Gly Asn Ile Gly Cys Lys Val
                50                  55                  60

Val Pro Asp Cys Asn Asn Tyr Arg Gln Lys Ile Thr Ser Trp Met
            65                  70                  75

Glu Pro Ile Val Lys Phe Pro Gly Ala Val Asp Gly Ala Thr Tyr
                80                  85                  90

Ile Leu Val Met Val Asp Pro Asp Ala Pro Ser Arg Ala Glu Pro
                95                 100                 105

Arg Gln Arg Phe Trp Arg His Trp Leu Val Thr Asp Ile Lys Gly
               110                 115                 120

Ala Asp Leu Lys Lys Gly Lys Ile Gln Gly Gln Glu Leu Ser Ala
               125                 130                 135

Tyr Gln Ala Pro Ser Pro Pro Ala His Ser Gly Phe His Arg Tyr
               140                 145                 150

Gln Phe Phe Val Tyr Leu Gln Glu Gly Lys Val Ile Ser Leu Leu
               155                 160                 165

Pro Lys Glu Asn Lys Thr Arg Gly Ser Trp Lys Met Asp Arg Phe
               170                 175                 180

Leu Asn Arg Phe His Leu Gly Glu Pro Glu Ala Ser Thr Gln Phe
               185                 190                 195

Met Thr Gln Asn Tyr Gln Asp Ser Pro Thr Leu Gln Ala Pro Arg
               200                 205                 210

Gly Arg Ala Ser Glu Pro Lys His Lys Thr Arg Gln Arg
               215                 220
```

<210> SEQ ID NO 62
<211> LENGTH: 1321
<212> TYPE: DNA
<213> ORGANISM: Homo Sapien

<400> SEQUENCE: 62

-continued

```
gtcgacccac gcgtccgaag ctgctggagc cacgattcag tcccctggac        50
tgtagataaa gacccttct tgccaggtgc tgagacaacc acactatgag        100
aggcactcca ggagacgctg atggtggagg aagggccgtc tatcaatcaa        150
tcactgttgc tgttatcaca tgcaagtatc cagaggctct tgagcaaggc        200 agagggatc ccatttattt gggaatccag aatccagaaa tgtgtttgta         250
ttgtgagaag gttggagaac agcccacatt gcagctaaaa gagcagaaga        300
tcatggatct gtatggccaa cccgagcccg tgaaacccct ccttttctac        350
cgtgccaaga ctggtaggac ctccacccct gagtctgtgg ccttcccgga        400
ctggttcatt gcctcctcca agagagacca gcccatcatt ctgacttcag        450
aacttgggaa gtcatacaac actgcctttg aattaaatat aaatgactga        500
actcagccta gaggtggcag cttggtcttt gtcttaaagt ttctggttcc        550
caatgtgttt tcgtctacat tttcttagtg tcattttcac gctggtgctg        600
agacaggagc aaggctgctg ttatcatctc attttataat gaagaagaag        650
caattacttc atagcaactg aagaacagga tgtggcctca gaagcaggag        700
agctgggtgg tataaggctg tcctctcaag ctggtgctgt gtaggccaca        750
aggcatctgc atgagtgact ttaagactca agaccaaac actgagcttt         800 cttctagggg tgggtatgaa gatgcttcag agctcatgcg cgttacccac        850
gatggcatga ctagcacaga gctgatctct gtttctgttt tgctttattc        900
cctcttggga tgatatcatc cagtctttat atgttgccaa tatacctcat        950
tgtgtgtaat agaaccttct tagcattaag accttgtaaa caaaaataat        1000
tcttggggtg ggtatgaaga tgcttcagag ctcatgcgcg ttacccacga        1050
tggcatgact agcacagagc tgatctctgt ttctgttttg ctttattccc        1100
tcttgggatg atatcatcca gtctttatat gttgccaata tacctcattg        1150
tgtgtaatag aaccttctta gcattaagac cttgtaaaca aaaataattc        1200
ttgtgttaag ttaaatcatt tttgtcctaa ttgtaatgtg taatcttaaa        1250
gttaaataaa ctttgtgtat ttatataata ataaagctaa aactgatata        1300
aaataaagaa agagtaaact g                                       1321
```

<210> SEQ ID NO 63
<211> LENGTH: 134
<212> TYPE: PRT
<213> ORGANISM: Homo Sapien

<400> SEQUENCE: 63

```
Met Arg Gly Thr Pro Gly Asp Ala Asp Gly Gly Gly Arg Ala Val
  1               5                  10                 15

Tyr Gln Ser Ile Thr Val Ala Val Ile Thr Cys Lys Tyr Pro Glu
                 20                  25                 30

Ala Leu Glu Gln Gly Arg Gly Asp Pro Ile Tyr Leu Gly Ile Gln
                 35                  40                 45

Asn Pro Glu Met Cys Leu Tyr Cys Glu Lys Val Gly Glu Gln Pro
                 50                  55                 60

Thr Leu Gln Leu Lys Glu Gln Lys Ile Met Asp Leu Tyr Gly Gln
                 65                  70                 75

Pro Glu Pro Val Lys Pro Phe Leu Phe Tyr Arg Ala Lys Thr Gly
```

```
                80                  85                  90
Arg Thr Ser Thr Leu Glu Ser Val Ala Phe Pro Asp Trp Phe Ile
                95                 100                 105

Ala Ser Ser Lys Arg Asp Gln Pro Ile Ile Leu Thr Ser Glu Leu
               110                 115                 120

Gly Lys Ser Tyr Asn Thr Ala Phe Glu Leu Asn Ile Asn Asp
               125                 130

<210> SEQ ID NO 64
<211> LENGTH: 999
<212> TYPE: DNA
<213> ORGANISM: Homo Sapien

<400> SEQUENCE: 64
gcgaggctgc accagcgcct ggcaccatga ggacgcctgg gcctctgccc         50
gtgctgctgc tgctcctggc gggagccccc gccgcgcggc ccactccccc        100
gacctgctac tcccgcatgc gggccctgag ccaggagatc acccgcgact        150
tcaacctcct gcaggtctcg gagccctcgg agccatgtgt gagataccta        200
cccaggctgt acctggacat acacaattac tgtgtgctgg acaagctgcg        250
ggactttgtg gcctcgcccc cgtgttggaa agtggcccag gtagattcct        300
tgaaggacaa agcacggaag ctgtacacca tcatgaactc gttctgcagg        350
agagatttgg tattcctgtt ggatgactgc aatgccttgg aatacccaat        400
cccagtgact acggtcctgc cagatcgtca gcgctaaggg aactgagacc        450
agagaaagaa cccaagagaa ctaaagttat gtcagctacc cagacttaat        500
gggccagagc catgaccctc acaggtcttg tgttagttgt atctgaaact        550
gttatgtatc tctctacctt ctggaaaaca gggctggtat tcctacccag        600
gaacctcctt tgagcataga gttagcaacc atgcttctca ttcccttgac        650
tcatgtcttg ccaggatggt tagatacaca gcatgttgat ttggtcacta        700
aaaagaagaa aaggactaac aagcttcact tttatgaaca actattttga        750
gaacatgcac aatagtatgt ttttattact ggtttaatgg agtaatggta        800
cttttattct ttcttgatag aaacctgctt acatttaacc aagcttctat        850
tatgcctttt tctaacacag actttcttca ctgtctttca tttaaaaga         900 aattaatgct cttaagatat atattttacg tagtgctgac aggacccact        950
ctttcattga aggtgatga aaatcaaata aagaatctct tcacatgga          999

<210> SEQ ID NO 65
<211> LENGTH: 136
<212> TYPE: PRT
<213> ORGANISM: Homo Sapien

<400> SEQUENCE: 65

Met Arg Thr Pro Gly Pro Leu Pro Val Leu Leu Leu Leu Leu Ala
  1               5                  10                  15

Gly Ala Pro Ala Ala Arg Pro Thr Pro Thr Cys Tyr Ser Arg
                 20                  25                  30

Met Arg Ala Leu Ser Gln Glu Ile Thr Arg Asp Phe Asn Leu Leu
                 35                  40                  45

Gln Val Ser Glu Pro Ser Glu Pro Cys Val Arg Tyr Leu Pro Arg
                 50                  55                  60
```

Leu Tyr Leu Asp Ile His Asn Tyr Cys Val Leu Asp Lys Leu Arg
              65                  70                  75

Asp Phe Val Ala Ser Pro Pro Cys Trp Lys Val Ala Gln Val Asp
          80                  85                  90

Ser Leu Lys Asp Lys Ala Arg Lys Leu Tyr Thr Ile Met Asn Ser
      95                 100                 105

Phe Cys Arg Arg Asp Leu Val Phe Leu Leu Asp Asp Cys Asn Ala
         110                 115                 120

Leu Glu Tyr Pro Ile Pro Val Thr Thr Val Leu Pro Asp Arg Gln
         125                 130                 135

Arg

<210> SEQ ID NO 66
<211> LENGTH: 1893
<212> TYPE: DNA
<213> ORGANISM: Homo Sapien

<400> SEQUENCE: 66

| gtctccgcgt cacaggaact tcagcaccca cagggcggac agcgctcccc | 50 |
| tctacctgga gacttgactc ccgcgcgccc caaccctgct tatcccttga | 100 |
| ccgtcgagtg tcagagatcc tgcagccgcc cagtcccggc ccctctcccg | 150 |
| ccccacaccc accctcctgg ctcttcctgt ttttactcct ccttttcatt | 200 |
| cataacaaaa gctacagctc caggagccca gcgccgggct gtgacccaag | 250 |
| ccgagcgtgg aagaatgggg ttcctcggga ccggcacttg gattctggtg | 300 |
| ttagtgctcc cgattcaagc tttccccaaa cctggaggaa gccaagacaa | 350 |
| atctctacat aatagagaat taagtgcaga agacctttg aatgaacaga | 400 |
| ttgctgaagc agaagaagac aagattaaaa aaacatatcc tccagaaaac | 450 |
| aagccaggtc agagcaacta ttcttttgtt gataacttga acctgctaaa | 500 |
| ggcaataaca gaaaaggaaa aaattgagaa agaaagacaa tctataagaa | 550 |
| gctccccact tgataataag ttgaatgtgg aagatgttga ttcaaccaag | 600 |
| aatcgaaaac tgatcgatga ttatgactct actaagagtg gattggatca | 650 |
| taaatttcaa gatgatccag atggtcttca tcaactagac gggactcctt | 700 |
| taaccgctga agacattgtc cataaaatcg ctgccaggat ttatgaagaa | 750 |
| aatgacagag ccgtgtttga caagattgtt tctaaactac ttaatctcgg | 800 |
| ccttatcaca gaaagccaag cacatacact ggaagatgaa gtagcagagg | 850 |
| ttttacaaaa attaatctca aaggaagcca acaattatga ggaggatccc | 900 |
| aataagccca caagctggac tgagaatcag gctggaaaaa taccagagaa | 950 |
| agtgactcca atggcagcaa ttcaagatgg tcttgctaag ggagaaaacg | 1000 |
| atgaaacagt atctaacaca ttaaccttga caaatggctt ggaaaggaga | 1050 |
| actaaaacct acagtgaaga caactttgag gaactccaat atttcccaaa | 1100 |
| tttctatgcg ctactgaaaa gtattgattc agaaaaagaa gcaaagaga | 1150 |
| aagaaacact gattactatc atgaaaacac tgattgactt tgtgaagatg | 1200 |
| atggtgaaat atggaacaat atctccagaa gaaggtgttt cctaccttga | 1250 |
| aaacttggat gaaatgattg ctcttcagac caaaaacaag ctagaaaaaa | 1300 |
| atgctactga caatataagc aagcttttcc cagcaccatc agagaagagt | 1350 |

| | |
|---|---:|
| catgaagaaa cagacagtac caaggaagaa gcagctaaga tggaaaagga | 1400 |
| atatggaagc ttgaaggatt ccacaaaaga tgataactcc aacccaggag | 1450 |
| gaaagacaga tgaacccaaa ggaaaaacag aagcctattt ggaagccatc | 1500 |
| agaaaaaata ttgaatggtt gaagaaacat gacaaaaagg gaaataaaga | 1550 |
| agattatgac ctttcaaaga tgagagactt catcaataaa caagctgatg | 1600 |
| cttatgtgga gaaaggcatc cttgacaagg aagaagccga ggccatcaag | 1650 |
| cgcatttata gcagcctgta aaatggcaa aagatccagg agtctttcaa | 1700 |
| ctgtttcaga aaacataata tagcttaaaa cacttctaat tctgtgatta | 1750 |
| aaattttttg acccaagggt tattagaaag tgctgaattt acagtagtta | 1800 |
| accttttaca agtggttaaa acatagcttt cttcccgtaa aaactatctg | 1850 |
| aaagtaaagt tgtatgtaag ctgaaaaaaa aaaaaaaaa aaa | 1893 |

<210> SEQ ID NO 67
<211> LENGTH: 468
<212> TYPE: PRT
<213> ORGANISM: Homo Sapien

<400> SEQUENCE: 67

```
Met Gly Phe Leu Gly Thr Gly Thr Trp Ile Leu Val Leu Val Leu
 1               5                  10                  15

Pro Ile Gln Ala Phe Pro Lys Pro Gly Gly Ser Gln Asp Lys Ser
                20                  25                  30

Leu His Asn Arg Glu Leu Ser Ala Glu Arg Pro Leu Asn Glu Gln
                35                  40                  45

Ile Ala Glu Ala Glu Glu Asp Lys Ile Lys Lys Thr Tyr Pro Pro
                50                  55                  60

Glu Asn Lys Pro Gly Gln Ser Asn Tyr Ser Phe Val Asp Asn Leu
                65                  70                  75

Asn Leu Leu Lys Ala Ile Thr Glu Lys Glu Lys Ile Glu Lys Glu
                80                  85                  90

Arg Gln Ser Ile Arg Ser Ser Pro Leu Asp Asn Lys Leu Asn Val
                95                 100                 105

Glu Asp Val Asp Ser Thr Lys Asn Arg Lys Leu Ile Asp Asp Tyr
               110                 115                 120

Asp Ser Thr Lys Ser Gly Leu Asp His Lys Phe Gln Asp Asp Pro
               125                 130                 135

Asp Gly Leu His Gln Leu Asp Gly Thr Pro Leu Thr Ala Glu Asp
               140                 145                 150

Ile Val His Lys Ile Ala Ala Arg Ile Tyr Glu Glu Asn Asp Arg
               155                 160                 165

Ala Val Phe Asp Lys Ile Val Ser Lys Leu Leu Asn Leu Gly Leu
               170                 175                 180

Ile Thr Glu Ser Gln Ala His Thr Leu Glu Asp Glu Val Ala Glu
               185                 190                 195

Val Leu Gln Lys Leu Ile Ser Lys Glu Ala Asn Asn Tyr Glu Glu
               200                 205                 210

Asp Pro Asn Lys Pro Thr Ser Trp Thr Glu Asn Gln Ala Gly Lys
               215                 220                 225

Ile Pro Glu Lys Val Thr Pro Met Ala Ala Ile Gln Asp Gly Leu
               230                 235                 240

Ala Lys Gly Glu Asn Asp Glu Thr Val Ser Asn Thr Leu Thr Leu
```

```
                    245                 250                 255
Thr Asn Gly Leu Glu Arg Arg Thr Lys Thr Tyr Ser Glu Asp Asn
            260                 265                 270
Phe Glu Glu Leu Gln Tyr Phe Pro Asn Phe Tyr Ala Leu Leu Lys
            275                 280                 285
Ser Ile Asp Ser Glu Lys Glu Ala Lys Glu Lys Glu Thr Leu Ile
            290                 295                 300
Thr Ile Met Lys Thr Leu Ile Asp Phe Val Lys Met Met Val Lys
            305                 310                 315
Tyr Gly Thr Ile Ser Pro Glu Glu Gly Val Ser Tyr Leu Glu Asn
            320                 325                 330
Leu Asp Glu Met Ile Ala Leu Gln Thr Lys Asn Lys Leu Glu Lys
            335                 340                 345
Asn Ala Thr Asp Asn Ile Ser Lys Leu Phe Pro Ala Pro Ser Glu
            350                 355                 360
Lys Ser His Glu Glu Thr Asp Ser Thr Lys Glu Glu Ala Ala Lys
            365                 370                 375
Met Glu Lys Glu Tyr Gly Ser Leu Lys Asp Ser Thr Lys Asp Asp
            380                 385                 390
Asn Ser Asn Pro Gly Gly Lys Thr Asp Glu Pro Lys Gly Lys Thr
            395                 400                 405
Glu Ala Tyr Leu Glu Ala Ile Arg Lys Asn Ile Glu Trp Leu Lys
            410                 415                 420
Lys His Asp Lys Lys Gly Asn Lys Glu Asp Tyr Asp Leu Ser Lys
            425                 430                 435
Met Arg Asp Phe Ile Asn Lys Gln Ala Asp Ala Tyr Val Glu Lys
            440                 445                 450
Gly Ile Leu Asp Lys Glu Glu Ala Glu Ala Ile Lys Arg Ile Tyr
            455                 460                 465
Ser Ser Leu

<210> SEQ ID NO 68
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 68
cgtcacagga acttcagcac cc                                             22

<210> SEQ ID NO 69
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 69
gtcttggctt cctccaggtt tgg                                            23

<210> SEQ ID NO 70
<211> LENGTH: 38
<212> TYPE: DNA
<213> ORGANISM: Artificial Sequence
<220> FEATURE:
<223> OTHER INFORMATION: Synthetic oligonucleotide probe

<400> SEQUENCE: 70
```

```
ggacagcgct cccctctacc tggagacttg actcccgc                      38

<210> SEQ ID NO 71
<211> LENGTH: 2379
<212> TYPE: DNA
<213> ORGANISM: Homo Sapien

<400> SEQUENCE: 71
gttgctccgg cggcgctcgg ggagggagcc agcagcctag ggcctaggcc          50
cgggccacca tggcgctgcc tccaggccca gccgccctcc ggcacacact         100
gctgctcctg ccagcccttc tgagctcagg ttgggggag ttggagccac          150 aaatagatgg tcagacctgg gctgagcggg cacttcggga gaatgaacgc         200
cacgccttca cctgccgggt ggcaggggg cctggcaccc ccagattggc          250
ctggtatctg gatggacagc tgcaggaggc cagcaccctca agactgctga        300 gcgtgggagg ggaggccttc tctggaggca ccagcacctt cactgtcact         350
gcccatcggg cccagcatga gctcaactgc tctctgcagg accccagaag         400
tggccgatca gccaacgcct ctgtcatcct taatgtgcaa ttcaagccag         450
agattgccca gtcggcgcc aagtaccagg aagctcaggg cccaggcctc          500
ctggttgtcc tgtttgccct ggtgcgtgcc aacccgccgg ccaatgtcac         550
ctggatcgac caggatgggc cagtgactgt caacacctct gacttcctgg         600
tgctggatgc gcagaactac ccctggctca ccaaccacac ggtgcagctg         650
cagctccgca gcctggcaca caacctctcg gtggtggcca ccaatgacgt         700
gggtgtcacc agtgcgtcgc ttccagcccc aggcccctcc cggcacccat         750
ctctgatatc aagtgactcc aacaacctaa aactcaacaa cgtgcgcctg         800
ccacgggaga acatgtccct cccgtccaac cttcagctca atgacctcac         850
tccagattcc agagcagtga accagcaga ccggcagatg gctcagaaca          900
acagccggcc agagcttctg gacccggagc ccggcggcct cctcaccagc         950
caaggtttca tccgcctccc agtgctgggc tatatctatc gagtgtccag        1000
cgtgagcagt gatgagatct ggctctgagc cgagggcgag acaggagtat        1050
tctcttggcc tctggacacc ctcccattcc tccaaggcat cctctaccta        1100
gctaggtcac caacgtgaag aagttatgcc actgccactt ttgcttgccc        1150
tcctggctgg ggtgccctcc atgtcatgca cgtgatgcat tcactgggc         1200 tgtaacccgc agggcacag gtatctttgg caaggctacc agttggacgt         1250
aagcccctca tgctgactca gggtgggccc tgcatgtgat gactgggccc        1300
ttccagaggg agctctttgg ccaggggtgt tcagatgtca tccagcatcc        1350
aagtgtggca tggcctgctg tatacccccac cccagtactc cacagcacct      1400
tgtacagtag gcatggggc gtgcctgtgt gggggacagg gagggccctg        1450
catggatttt cctccttcct atgctatgta gccttgttcc ctcaggtaaa        1500
atttaggacc ctgctagctg tgcagaaccc aattgccctt tgcacagaaa       1550 ccaaccctg acccagcggt accggccaag cacaaacgtc ctttttgctg         1600
cacacgtctc tgcccttcac ttcttctctt ctgtccccac ctcctcttgg       1650
gaattctagg ttacacgttg gaccttctct actacttcac tgggcactag       1700
```

-continued

```
actttctat tggcctgtgc catcgcccag tattagcaca agttagggag        1750
gaagaggcag gcgatgagtc tagtagcacc caggacggct tgtagctatg        1800
catcattttc ctacggcgtt agcactttaa gcacatcccc taggggaggg        1850
ggtgagtgag gggcccagag ccctctttgt ggcttcccca cgtttggcct        1900
tctgggattc actgtgagtg tcctgagctc tcggggttga tggttttct         1950 ctcagcatgt ctcctccacc acgggacccc agccctgacc aacccatggt        2000
tgcctcatca gcaggaaggt gcccttcctg gaggatggtc gccacaggca        2050
cataattcaa cagtgtggaa gctttagggg aacatggaga agaaggaga         2100 ccacataccc caaagtgacc taagaacact ttaaaaagca acatgtaaat        2150
gattggaaat taatatagta cagaatatat ttttcccttg ttgagatctt        2200
cttttgtaat gttttcatg ttactgccta gggcggtgct gagcacacag         2250
caagtttaat aaacttgact gaattcattt aaaaaaaaaa aaaaaaaaa         2300 aaaaaaaaaa aaaaaaaaaa aaaaaaaaaa aaaaaaaaa  aaaaaaaaaa        2350 aaaaaaaaaa aaaaaaaaaa aaaaaaaaa                                2379
```

<210> SEQ ID NO 72
<211> LENGTH: 322
<212> TYPE: PRT
<213> ORGANISM: Homo Sapien

<400> SEQUENCE: 72

```
Met Ala Leu Pro Pro Gly Pro Ala Ala Leu Arg His Thr Leu Leu
  1               5                  10                  15

Leu Leu Pro Ala Leu Ser Ser Gly Trp Gly Glu Leu Glu Pro
                 20                  25                  30

Gln Ile Asp Gly Gln Thr Trp Ala Glu Arg Ala Leu Arg Glu Asn
                 35                  40                  45

Glu Arg His Ala Phe Thr Cys Arg Val Ala Gly Gly Pro Gly Thr
                 50                  55                  60

Pro Arg Leu Ala Trp Tyr Leu Asp Gly Gln Leu Gln Glu Ala Ser
                 65                  70                  75

Thr Ser Arg Leu Leu Ser Val Gly Gly Glu Ala Phe Ser Gly Gly
                 80                  85                  90

Thr Ser Thr Phe Thr Val Thr Ala His Arg Ala Gln His Glu Leu
                 95                 100                 105

Asn Cys Ser Leu Gln Asp Pro Arg Ser Gly Arg Ser Ala Asn Ala
                110                 115                 120

Ser Val Ile Leu Asn Val Gln Phe Lys Pro Glu Ile Ala Gln Val
                125                 130                 135

Gly Ala Lys Tyr Gln Glu Ala Gln Gly Pro Gly Leu Leu Val Val
                140                 145                 150

Leu Phe Ala Leu Val Arg Ala Asn Pro Pro Ala Asn Val Thr Trp
                155                 160                 165

Ile Asp Gln Asp Gly Pro Val Thr Val Asn Thr Ser Asp Phe Leu
                170                 175                 180

Val Leu Asp Ala Gln Asn Tyr Pro Trp Leu Thr Asn His Thr Val
                185                 190                 195

Gln Leu Gln Leu Arg Ser Leu Ala His Asn Leu Ser Val Val Ala
                200                 205                 210

Thr Asn Asp Val Gly Val Thr Ser Ala Ser Leu Pro Ala Pro Gly
```

```
                          215                 220                 225

Pro Ser Arg His Pro Ser Leu Ile Ser Ser Asp Ser Asn Asn Leu
                230                 235                 240

Lys Leu Asn Asn Val Arg Leu Pro Arg Glu Asn Met Ser Leu Pro
                245                 250                 255

Ser Asn Leu Gln Leu Asn Asp Leu Thr Pro Asp Ser Arg Ala Val
                260                 265                 270

Lys Pro Ala Asp Arg Gln Met Ala Gln Asn Asn Ser Arg Pro Glu
                275                 280                 285

Leu Leu Asp Pro Glu Pro Gly Gly Leu Leu Thr Ser Gln Gly Phe
                290                 295                 300

Ile Arg Leu Pro Val Leu Gly Tyr Ile Tyr Arg Val Ser Ser Val
                305                 310                 315

Ser Ser Asp Glu Ile Trp Leu
                320
```

```
<210> SEQ ID NO 73
<211> LENGTH: 843
<212> TYPE: DNA
<213> ORGANISM: Homo Sapien

<400> SEQUENCE: 73
cggggacgga agcggcccct gggcccgagg ggctggagcc gggccggggc              50
gatgtggagc gcgggccgcg gcggggctgc ctggccggtg ctgttggggc             100
tgctgctggc gctgttagtg ccgggcggtg gtgccgccaa gaccggtgcg             150
gagctcgtga cctgcgggtc ggtgctgaag ctgctcaata cgcaccaccg             200
cgtgcggctg cactcgcacg acatcaaata cggatccggc agcggccagc             250
aatcggtgac cggcgtagag gcgtcggacg acgccaatag ctactggcgg             300
atccgcggcg gctcggaggg cgggtgcccg cgcgggtccc cggtgcgctg             350
cgggcaggcg gtgaggctca cgcatgtgct tacgggcaag aacctgcaca             400
cgcaccactt cccgtcgccg ctgtccaaca accaggaggt gagtgccttt             450
ggggaagacg gcgagggcga cgacctggac ctatggacag tgcgctgctc             500
tggacagcac tgggagcgtg aggctgctgt gcgcttccag catgtgggca             550
cctctgtgtt cctgtcagtc acgggtgagc agtatggaag ccccatccgt             600
gggcagcatg aggtccacgg catgcccagt gccaacacgc acaatacgtg             650
gaaggccatg gaaggcatct tcatcaagcc tagtgtggag ccctctgcag             700
gtcacgatga actctgagtg tgtggatgga tgggtggatg gagggtggca             750
ggtggggcgt ctgcagggcc actcttggca gagactttgg gtttgtaggg             800
gtcctcaagt gcctttgtga ttaaagaatg ttggtctatg aaa                   843
```

```
<210> SEQ ID NO 74
<211> LENGTH: 221
<212> TYPE: PRT
<213> ORGANISM: Homo Sapien

<400> SEQUENCE: 74

Met Trp Ser Ala Gly Arg Gly Gly Ala Ala Trp Pro Val Leu Leu
  1               5                  10                  15

Gly Leu Leu Leu Ala Leu Leu Val Pro Gly Gly Gly Ala Ala Lys
                20                  25                  30
```

-continued

| | | | | | | | | | | | |
|---|---|---|---|---|---|---|---|---|---|---|---|
|Thr|Gly|Ala|Glu|Leu|Val|Thr|Cys|Gly|Ser|Val|Leu|Lys|Leu|Leu|
| | |35| | | | |40| | | | |45|

Asn Thr His His Arg Val Arg Leu His Ser His Asp Ile Lys Tyr
              50                      55                      60

Gly Ser Gly Ser Gly Gln Gln Ser Val Thr Gly Val Glu Ala Ser
              65                      70                      75

Asp Asp Ala Asn Ser Tyr Trp Arg Ile Arg Gly Gly Ser Glu Gly
              80                      85                      90

Gly Cys Pro Arg Gly Ser Pro Val Arg Cys Gly Gln Ala Val Arg
              95                     100                     105

Leu Thr His Val Leu Thr Gly Lys Asn Leu His Thr His His Phe
             110                     115                     120

Pro Ser Pro Leu Ser Asn Asn Gln Glu Val Ser Ala Phe Gly Glu
             125                     130                     135

Asp Gly Glu Gly Asp Asp Leu Asp Leu Trp Thr Val Arg Cys Ser
             140                     145                     150

Gly Gln His Trp Glu Arg Glu Ala Ala Val Arg Phe Gln His Val
             155                     160                     165

Gly Thr Ser Val Phe Leu Ser Val Thr Gly Glu Gln Tyr Gly Ser
             170                     175                     180

Pro Ile Arg Gly Gln His Glu Val His Gly Met Pro Ser Ala Asn
             185                     190                     195

Thr His Asn Thr Trp Lys Ala Met Glu Gly Ile Phe Ile Lys Pro
             200                     205                     210

Ser Val Glu Pro Ser Ala Gly His Asp Glu Leu
             215                     220

<210> SEQ ID NO 75
<211> LENGTH: 1049
<212> TYPE: DNA
<213> ORGANISM: Homo Sapien

<400> SEQUENCE: 75

| | |
|---|---|
|gttgctatgt tgcccaggct ggtcttgaag tgccttgacc tcctaaagtg|50|
|ttggaaccac agacgtgagc cactccaccc agcctaaaac ttcatcttct|100|
|ttggatgaga tgaacacttt taacaagaga acaggactct atataaatcg|150|
|ctgtgggctc accacctcta aggaggagca ctgactgaag acagaaaaat|200|
|tgatgaactg aagaagacat ggtccattat gccttacaaa cttacacagt|250|
|gctttgggaa ttccaaagta ctcagtggag agaggtgttt caggagccgt|300|
|agagccagat cgtcatcatg tctgcattgt ggctgctgct gggcctcctt|350|
|gccctgatgg acttgtctga aagcagcaac tggggatgct atggaaacat|400|
|ccaaagcctg acaccctg gagcatcttg tgggattgga agacgtcacg|450|
|gcctgaacta ctgtggagtt cgtgcttctg aaaggctggc tgaaatagac|500|
|atgccatacc tcctgaaata tcaacccatg atgcaaacca ttggccaaaa|550|
|gtactgcatg gatcctgccg tgatcgctgg tgtcttgtcc aggaagtctc|600|
|ccggtgacaa aattctggtc aacatgggcg ataggactag catggtgcag|650|
|gaccctggct ctcaagctcc cacatcctgg attagtgagt ctcaggtttc|700|
|ccagacaact gaagttctga ctactagaat caaagaaatc cagaggaggt|750|
|ttccaacctg gaccctgac cagtacctga gaggtggact ctgtgcctac|800|

```
agtgggggtg ctggctatgt ccgaagcagc caggacctga gctgtgactt          850
ctgcaatgat gtccttgcac gagccaagta cctcaagaga catggcttct          900
aacatctcag atgaaaccca agaccatgat cacatatgca gcctcaaatg          950
ttacacagat aaaactagcc aagggcacct gtaactggga atctgagttt         1000
gacctaaaag tcattaaaat aacatgaatc ccattaaaaa aaaaaaaa           1049
```

<210> SEQ ID NO 76
<211> LENGTH: 194
<212> TYPE: PRT
<213> ORGANISM: Homo Sapien

<400> SEQUENCE: 76

```
Met Ser Ala Leu Trp Leu Leu Gly Leu Leu Ala Leu Met Asp
 1               5                  10                  15

Leu Ser Glu Ser Ser Asn Trp Gly Cys Tyr Gly Asn Ile Gln Ser
            20                  25                  30

Leu Asp Thr Pro Gly Ala Ser Cys Gly Ile Gly Arg Arg His Gly
            35                  40                  45

Leu Asn Tyr Cys Gly Val Arg Ala Ser Glu Arg Leu Ala Glu Ile
            50                  55                  60

Asp Met Pro Tyr Leu Leu Lys Tyr Gln Pro Met Met Gln Thr Ile
            65                  70                  75

Gly Gln Lys Tyr Cys Met Asp Pro Ala Val Ile Ala Gly Val Leu
            80                  85                  90

Ser Arg Lys Ser Pro Gly Asp Lys Ile Leu Val Asn Met Gly Asp
            95                 100                 105

Arg Thr Ser Met Val Gln Asp Pro Gly Ser Gln Ala Pro Thr Ser
           110                 115                 120

Trp Ile Ser Glu Ser Gln Val Ser Gln Thr Thr Glu Val Leu Thr
           125                 130                 135

Thr Arg Ile Lys Glu Ile Gln Arg Arg Phe Pro Thr Trp Thr Pro
           140                 145                 150

Asp Gln Tyr Leu Arg Gly Gly Leu Cys Ala Tyr Ser Gly Gly Ala
           155                 160                 165

Gly Tyr Val Arg Ser Ser Gln Asp Leu Ser Cys Asp Phe Cys Asn
           170                 175                 180

Asp Val Leu Ala Arg Ala Lys Tyr Leu Lys Arg His Gly Phe
           185                 190
```

<210> SEQ ID NO 77
<211> LENGTH: 899
<212> TYPE: DNA
<213> ORGANISM: Homo Sapien

<400> SEQUENCE: 77

```
ttgaaaatct actctatcag ctgctgtggt tgccaccatt ctcaggaccc            50
tcgccatgaa agcccttatg ctgctcaccc tgtctgttct gctctgctgg           100
gtctcagctg acattcgctg tcactcctgc tacaaggtcc ctgtgctggg           150
ctgtgtggac cggcagtcct gccgcctgga gccaggacag caatgcctga          200
caacacatgc ataccttggt aagatgtggg ttttctccaa tctgcgctgt          250
ggcacaccag aagagccctg tcaggaggcc ttcaaccaaa ccaaccgcaa          300
gctgggtctg acatataaca ccacctgctg caacaaggac aactgcaaca          350
```

-continued

| | |
|---|---|
| gcgcaggacc ccggcccact ccagccctgg gccttgtctt ccttacctcc | 400 |
| ttggctggcc ttggcctctg gctgctgcac tgagactcat tccattggct | 450 |
| gcccctcctc ccacctgcct tggcctgagc ctctctccct gtgtctctgt | 500 |
| atcccctggc tttacagaat cgtctctccc tagctcccat ttctttaatt | 550 |
| aaacactgtt ccgagtggtc tcctcatcca tccttcccac ctcacaccct | 600 |
| tcactctcct ttttctgggt cccttcccac ttccttccag gacctccatt | 650 |
| ggctcctaga agggctcccc actttgcttc ctatactctg ctgtccccta | 700 |
| cttgaggagg gattgggatc tgggcctgaa atggggcttc tgtgttgtcc | 750 |
| ccagtgaagg ctcccacaag gacctgatga cctcactgta cagagctgac | 800 |
| tccccaaacc caggctccca tatgtacccc atccccata ctcacctctt | 850 |
| tccattttga gtaataaatg tctgagtctg gaaaaaaaaa aaaaaaaa | 899 |

<210> SEQ ID NO 78
<211> LENGTH: 125
<212> TYPE: PRT
<213> ORGANISM: Homo Sapien

<400> SEQUENCE: 78

Met Lys Ala Leu Met Leu Leu Thr Leu Ser Val Leu Leu Cys Trp
 1               5                   10                  15

Val Ser Ala Asp Ile Arg Cys His Ser Cys Tyr Lys Val Pro Val
                20                  25                  30

Leu Gly Cys Val Asp Arg Gln Ser Cys Arg Leu Glu Pro Gly Gln
                35                  40                  45

Gln Cys Leu Thr Thr His Ala Tyr Leu Gly Lys Met Trp Val Phe
                50                  55                  60

Ser Asn Leu Arg Cys Gly Thr Pro Glu Glu Pro Cys Gln Glu Ala
                65                  70                  75

Phe Asn Gln Thr Asn Arg Lys Leu Gly Leu Thr Tyr Asn Thr Thr
                80                  85                  90

Cys Cys Asn Lys Asp Asn Cys Asn Ser Ala Gly Pro Arg Pro Thr
                95                  100                 105

Pro Ala Leu Gly Leu Val Phe Leu Thr Ser Leu Ala Gly Leu Gly
                110                 115                 120

Leu Trp Leu Leu His
                125

<210> SEQ ID NO 79
<211> LENGTH: 1977
<212> TYPE: DNA
<213> ORGANISM: Homo Sapien

<400> SEQUENCE: 79

| | |
|---|---|
| acgggccgca gcggcagtga cgtagggttg gcgcacggat ccgttgcggc | 50 |
| tgcagctctg cagtcgggcc gttccttcgc cgccgccagg ggtagcggtg | 100 |
| tagctgcgca gcgtcgcgcg cgctaccgca cccaggttcg gcccgtaggc | 150 |
| gtctggcagc ccggcgccat cttcatcgag cgccatggcc gcagcctgcg | 200 |
| ggccgggagc ggccgggtac tgcttgctcc tcggcttgca tttgtttctg | 250 |
| ctgaccgcgg gccctgccct gggctggaac gaccctgaca gaatgttgct | 300 |
| gcgggatgta aaagctctta ccctccacta tgaccgctat accacctccc | 350 |

-continued

| | |
|---|---|
| gcaggctgga tcccatccca cagttgaaat gtgttggagg cacagctggt | 400 |
| tgtgattctt atacccccaaa agtcatacag tgtcagaaca aaggctggga | 450 |
| tgggtatgat gtacagtggg aatgtaagac ggacttagat attgcataca | 500 |
| aatttggaaa aactgtggtg agctgtgaag gctatgagtc ctctgaagac | 550 |
| cagtatgtac taagaggttc ttgtggcttg gagtataatt tagattatac | 600 |
| agaacttggc ctgcagaaac tgaaggagtc tggaaagcag cacggctttg | 650 |
| cctctttctc tgattattat tataagtggt cctcggcgga ttcctgtaac | 700 |
| atgagtggat tgattaccat cgtggtactc cttgggatcg cctttgtagt | 750 |
| ctataagctg ttcctgagtg acgggcagta ttctcctcca ccgtactctg | 800 |
| agtatcctcc attttcccac cgttaccaga gattcaccaa ctcagcagga | 850 |
| cctcctcccc caggctttaa gtctgagttc acaggaccac agaatactgg | 900 |
| ccatggtgca acttctggtt ttggcagtgc ttttacagga caacaaggat | 950 |
| atgaaaattc aggaccaggg ttctggacag gcttgggaac tggtggaata | 1000 |
| ctaggatatt tgtttggcag caatagagcg gcaacaccct tctcagactc | 1050 |
| gtggtactac ccgtcctatc ctccctccta ccctggcacg tggaataggg | 1100 |
| cttactcacc ccttcatgga ggctcgggca gctattcggt atgttcaaac | 1150 |
| tcagacacga aaccagaact gcatcagga tatggtggta ccaggagacg | 1200 |
| ataaagtaga agttggagt caaacactgg atgcagaaat tttggatttt | 1250 |
| tcatcacttt ctctttagaa aaaaagtact acctgttaac aattgggaaa | 1300 |
| aggggatatt caaaagttct gtggtgttat gtccagtgta gcttttttgta | 1350 |
| ttctattatt tgaggctaaa agttgatgtg tgacaaaata cttatgtgtt | 1400 |
| gtatgtcagt gtaacatgca gatgtatatt gcagtttttg aaagtgatca | 1450 |
| ttactgtgga atgctaaaaa tacattaatt tctaaaacct gtgatgccct | 1500 |
| aagaagcatt aagaatgaag gtgttgtact aatagaaact aagtacagaa | 1550 |
| aatttcagtt ttaggtggtt gtagctgatg agttattacc tcatagagac | 1600 |
| tataatattc tatttggtat tatattattt gatgtttgct gttcttcaaa | 1650 |
| catttaaatc aagctttgga ctaattatgc taatttgtga gttctgatca | 1700 |
| cttttgagct ctgaagcttt gaatcattca gtggtggaga tggccttctg | 1750 |
| gtaactgaat attaccttct gtaggaaaag gtggaaaata agcatctaga | 1800 |
| aggttgttgt gaatgactct gtgctggcaa aaatgcttga aacctctata | 1850 |
| tttctttcgt tcataagagg taaaggtcaa atttttcaac aaaagtcttt | 1900 |
| taataacaaa agcatgcagt tctctgtgaa atctcaaata ttgttgtaat | 1950 |
| agtctgtttc aatcttaaaa agaatca | 1977 |

<210> SEQ ID NO 80
<211> LENGTH: 339
<212> TYPE: PRT
<213> ORGANISM: Homo Sapien

<400> SEQUENCE: 80

Met Ala Ala Ala Cys Gly Pro Gly Ala Ala Gly Tyr Cys Leu Leu
1               5                   10                  15

Leu Gly Leu His Leu Phe Leu Leu Thr Ala Gly Pro Ala Leu Gly
            20                  25                  30

-continued

```
Trp Asn Asp Pro Asp Arg Met Leu Leu Arg Asp Val Lys Ala Leu
            35                  40                  45
Thr Leu His Tyr Asp Arg Tyr Thr Thr Ser Arg Arg Leu Asp Pro
            50                  55                  60
Ile Pro Gln Leu Lys Cys Val Gly Gly Thr Ala Gly Cys Asp Ser
            65                  70                  75
Tyr Thr Pro Lys Val Ile Gln Cys Gln Asn Lys Gly Trp Asp Gly
            80                  85                  90
Tyr Asp Val Gln Trp Glu Cys Lys Thr Asp Leu Asp Ile Ala Tyr
            95                 100                 105
Lys Phe Gly Lys Thr Val Val Ser Cys Glu Gly Tyr Glu Ser Ser
           110                 115                 120
Glu Asp Gln Tyr Val Leu Arg Gly Ser Cys Gly Leu Glu Tyr Asn
           125                 130                 135
Leu Asp Tyr Thr Glu Leu Gly Leu Gln Lys Leu Lys Glu Ser Gly
           140                 145                 150
Lys Gln His Gly Phe Ala Ser Phe Ser Asp Tyr Tyr Lys Trp
           155                 160                 165
Ser Ser Ala Asp Ser Cys Asn Met Ser Gly Leu Ile Thr Ile Val
           170                 175                 180
Val Leu Leu Gly Ile Ala Phe Val Val Tyr Lys Leu Phe Leu Ser
           185                 190                 195
Asp Gly Gln Tyr Ser Pro Pro Tyr Ser Glu Tyr Pro Pro Phe
           200                 205                 210
Ser His Arg Tyr Gln Arg Phe Thr Asn Ser Ala Gly Pro Pro Pro
           215                 220                 225
Pro Gly Phe Lys Ser Glu Phe Thr Gly Pro Gln Asn Thr Gly His
           230                 235                 240
Gly Ala Thr Ser Gly Phe Gly Ser Ala Phe Thr Gly Gln Gln Gly
           245                 250                 255
Tyr Glu Asn Ser Gly Pro Gly Phe Trp Thr Gly Leu Gly Thr Gly
           260                 265                 270
Gly Ile Leu Gly Tyr Leu Phe Gly Ser Asn Arg Ala Ala Thr Pro
           275                 280                 285
Phe Ser Asp Ser Trp Tyr Tyr Pro Ser Tyr Pro Pro Ser Tyr Pro
           290                 295                 300
Gly Thr Trp Asn Arg Ala Tyr Ser Pro Leu His Gly Gly Ser Gly
           305                 310                 315
Ser Tyr Ser Val Cys Ser Asn Ser Asp Thr Lys Thr Arg Thr Ala
           320                 325                 330
Ser Gly Tyr Gly Gly Thr Arg Arg Arg
           335
```

US 7,241,862 B2

POLYPEPTIDES THAT INDUCE CELL PROLIFERATION OR INDUCE FETAL HEMOGLOBIN

This application is a continuation of, and claims priority under 35 USC §120 to, U.S. application Ser. No. 09/931836 filed Aug. 16, 2001, which is a continuation of, and claims priority under 35 USC §120 to, PCT Application PCT/US00/05601 filed Mar. 1, 2000, which claims priority under 35 USC §119 to U.S. Provisional Application 60/131270 filed Apr. 27, 1999.

FIELD OF THE INVENTION

The present invention relates generally to the identification and isolation of novel DNA and to the recombinant production of novel polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., Proc. Natl. Acad. Sci. 93:7108–7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

1. PRO1484

Adipose differentiation is accompanied by changes in cellular morphology, a dramatic accumulation of intracellular lipid and activation of a specific program of gene expression (Liang et al., J. Biol. Chem. 271:10697–10703 (1996)). Adipose complement-related protein is a protein whose expression is highly induced during adipocyte differentiation and which shares significant homology with subunits of complement factor C1q, collagen alpha 1(x) and the brain-specific facto cerebellin (Scherer et al., J. Biol. Chem. 270:26746–26749 (1995)). While the function of adipocyte complement-related protein is presently unknown, the tissue-specific expression thereof suggests that this protein functions as a novel signaling molecule for adipose tissue. As such, there is significant interest in identifying and characterizing novel polypeptides having homology to adipocyte complement-related protein. We herein describe the identification and characterization of novel polypeptides having homology to adipocyte complement-related protein, designated herein as PRO1484 polypeptides.

2. PRO4334

Plasma cell membrane glycoprotein PC-1 is of interest. The cloning of PC-1 is described in the art, i.e., see Buckley, et al., J. Biol. Chem., 265(29):17506–11 (1990) and WO9519570-A. WO9519570-A describes the human insulin receptor tyrosine kinase inhibitor PC-1. It is reported that PC-1 is useful in the diagnosis and treatment of diseases involving inappropriate insulin receptor tyrosine kinase inhibitor expression such as non-insulin dependent mellitus. Thus, proteins having homology to PC-1 are of interest.

3. PRO1122

It has been reported that the cytokine interleukin 17 (IL-17) stimulates epithelial, endothelial, and fibroblastic cells to secrete cytokines such as IL-6, IL-8, and granulocyte-colony-stimulating factor, as well as prostaglandin E2. Moreover, it has been shown that when cultured in the presence of IL-17, fibroblasts could sustain proliferation of CD34+preferential maturation into neutrophils. Thus it has been suggested that IL-17 constitutes an early initiator of the T celldependent inflammatory reaction and/or an element of the cytokine network that bridges the immune system to hematopoiesis. See, Yao, et al., J. Immunol., 155(12):5483–5486 (1995); Fossiez, et al., J. Exp. Med., 183(6):2593–2603 (1996); Kennedy, et al., J. Interferon Cytoki Res., 16(8):611–617 (1996). Thus, proteins related to IL-17, including CTLA-8, which has been mistaken for IL-17 (see Kennedy, *supra*) are of interest.

4. PRO1889

E48 antigen protein is a cysteine-rich GPI-anchored membrane protein that belongs to the LY-6 family of human proteins (see, e.g., WO 96/35808). The E48 antigen serves as a marker for squamous cells, exhibits biological activity of cell-cell/cell-matrix adhesion and is a target for antibody-based immunotherapy. The amino acid sequence of the E48 antigen protein has previously been deduced from a cDNA clone which was obtained from a squamous cell carcinoma of the head and neck. As such, the E48 antigen serves as a potential target for the treatment of squamous cell cancer.

We herein describe the identification and characterization of novel polypeptides having homology to E48 antigen protein, designated herein as PRO1889 polypeptides.

5. PRO1890

The recognition of carbohydrates by lectins has been found to play an important role in various aspects of eukaryotic physiology. A number of different animal and plant lectin families exist, but it is the calcium dependent, or type C, lectins that have recently garnered the most attention. For example, the recognition of carbohydrate residues on either endothelial cells or leukocytes by the selectin family of calcium dependent lectins has been found to be of profound importance to the trafficking of leukocytes to inflammatory sites. Lasky, L., *Ann. Rev. Biochem.*, 64 113–139 (1995). The biophysical analysis of these adhesive interactions has suggested that lectin-carbohydrate binding evolved in this case to allow for the adhesion between leukocytes and the endothelium under the high shear conditions of the vasculature. Thus, the rapid on rates of carbohydrate recognition by such lectins allows for a hasty acquisition of ligand, a necessity under the high shear of the vascular flow. The physiological use of type C lectins in this case is also supported by the relatively low affinities of these interactions, a requirement for the leukocyte rolling phenomenon that has been observed to occur at sites of acute inflammation. The crystal structures of the mannose binding protein (Weis et al., *Science* 254, 1608–1615 [1991]; Weis et al., *Nature* 360 127–134 [1992]) and E-selectin (Graves et al., *Nature* 367(6463), 532–538 [1994]), together with various mutagenesis analyses (Erbe et al., *J. Cell. Biol.* 119(1), 215–227 [1992]; Drickamer, *Nature* 360, 183–186 [1992]; Iobst et al., *J. Biol. Chem.* 169(22), 15505–15511 [1994]; Kogan et al., *J. Biol. Chem.* 270(23), 14047–14055 [1995]), is consistent with the supposition that the type C lectins are in general, involved with the rapid recognition of clustered carbohydrates. Together, these data suggest that type C lectins perform a number of critical physiological phenomena through the rapid, relatively low affinity recognition of carbohydrates.

Given the obvious importance of the lectin proteins in numerous biological processes, efforts are currently being made to identify novel lectin proteins or proteins having sequence homology to lectin proteins. We herein describe the identification and characterization of novel polypeptides having homology to a lectin protein, designated herein as PRO1890 polypeptides.

6. PRO1887

Enzymatic proteins play important roles in the chemical reactions involved in the digestion of foods, the biosynthesis of macromolecules, the controlled release and utilization of chemical energy, and other processes necessary to sustain life. Enzymes have also been shown to play important roles in combating various diseases and disorders. For example, liver carboxylesterases have been reported to assist in sensitizing human tumor cells to the cancer prodrugs. Danks et al., report that stable expression of the cDNA encoding a carboxylesterase in Rh30 human rhabdomyosarcoma cells increased the sensitivity of the cells to the CPT-11 cancer prodrug 8.1-fold. Cancer Res. (1998) 58(1):20–22. The authors propose that this prodrug/enzyme combination could be exploited therapeutically in a manner analogous to approaches currently under investigation with the combinations of ganciclovir/herpes simplex virus thymidine kinase and 5-fluorocytosine/cytosine deaminase. van Pelt et al. demonstrated that a 55 kD human liver carboxylesterase inhibits the invasion of Plasmodium falciparum malaria sporozoites into primary human hepatocytes in culture. J Hepatol (1997) 27(4):688–698.

Carboxylesterases have also been found to be of importance in the detoxification of drugs, pesticides and other xenobiotics. Purified human liver carboxylesterases have been shown to be involved in the metabolism of various drugs including cocaine and heroin. Prindel et al. describe the purification and cloning of a broad substrate specificity human liver carboxylesterase which catalyzes the hydrolysis of cocaine and heroin and which may play an important role in the degradation of these drugs in human tissues. *J. Biol. Chem.* (1997) 6:272(23):14769–14775. Brzenzinski et al. describe a spectrophotometric competitive inhibition assay used to identify drug or environmental esters that are metabolized by carboxylesterases. Drug Metab Dispos (1997) 25(9):1089–1096.

As additional background information on carboxylesterases, Kroetz et al. (Biochemistry, (1993) 32(43): 11606–17) reported the cDNA cloning and characterization of human liver carboxylesterases. Aida et al. (Biochim Biophys Acta (1993) 1174(1):72–4) reported the cDNA cloning and characterization of a male-predominant carboxylesterase in mouse liver carboxylesterases.

In light of the important physiological roles played by carboxylesterases, efforts are being undertaken by both industry and academia to identify new, native carboxylesterase homologs. We herein describe the identification and characterization of a novel polypeptide having homology to carboxylesterase.

7. PRO1785

Antioxidant enzymes are thought to play a crucial role in the survival of the parasite, Schistosoma mansoni, during its migration through the tissues of a definitive host. Recently, one such enzyme, glutathione peroxidase was cloned. Roche, et al., Gene, 138:149–152 (1994), accession number GSHC_SCHMA. Glutathione perxodiases are further described in FR2689906-A. Thus, glutathione peroxidases, and the nucleic acids which encode them are useful as diagnostic reagents, vaccines and in assays to find modulators of antioxidant enzymes.

8. PRO4353

Semaphorins comprise a large family of proteins implicated in axonal guidance during development. Semaphorin Y may be used to inhibit peripheral nerve growth. Semaphorin Z is useful as a central nerve extension inhibitor. Semaphorin Z inhibitors can be used as promoters of central nerve regeneration. Thus semaphorins and regulators of semaphorins are of great interest. Kikuchi, et al., Brain Res Mol Brain Res., 51(1–2):229–37 (1997); Shoji, et al., Development, 125(7):1275–83 (1998).

9. PRO4357

Efforts are being undertaken by both industry and academia to identify new, native secreted proteins. Many of these efforts are focused on the screening of mammalian recombinant DNA libraries to identify the coding sequences for novel secreted proteins. We herein describe the identification and characterization of novel secreted polypeptides, designated herein as PRO4357 polypeptides.

10. PRO4405

Efforts are being undertaken by both industry and academia to identify new, native transmembrane receptor proteins. Many efforts are focused on the screening of mammalian recombinant DNA libraries to identify the coding sequences for novel transmembrane receptor proteins. We herein describe the identification and characterization of novel transmembrane polypeptides, designated herein as PRO4405 polypeptides.

11. PRO4356

Glycosylphosphatidylinositol (GPI) anchored proteoglycans are generally localized to the cell surface and are thus known to be involved in the regulation of responses of cells to numerous growth factors, cell adhesion molecules and extracellular matrix components. The metastasis-associated GPI-anchored protein (MAGPIAP) is one of these cell surface proteins which appears to be involved in metastasis. Metastasis is the form of cancer wherein the transformed or malignant cells are traveling and spreading the cancer from one site to another. Therefore, identifying the polypeptides related to metastasis and MAGPIAP is of interest.

12. PRO4352

Cadherins are a large family of transmembrane proteins. Cadherins comprise a family of calcium-dependent glycoproteins that function in mediating cell-cell adhesion in virtually all solid tissues of multicellular organisms. At least cadherins 1–13 as well as types B, E, EP, M, N, P and R have been characterized. Among the functions cadherins are known for, with some exceptions, cadherins participate in cell aggregation and are associated with cell-cell adhesion sites. Recently, it has been reported that while all cadherins share multiple repeats of a cadherin specific motif believed to correspond to folding of extracellular domains, members of the cadherin superfamily have divergent structures and, possibly, functions. In particular it has been reported that members of the cadherin superfamily are involved in signal transduction. See, Suzuki, *J. Cell Biochem.,* 61(4):531–542 (1996). Cadherins are further described in Tanihara, et al., *J. Cell Sci.,* 107(6):1697–1704 (1994), Aberle, et al., *J. Cell Biochem.,* 61(4):514–523 (1996), Obata, et al., *Cell Adhes. Commun.,* 6(4):323–33 (1998) and Tanihara, et al., *Cell Adhes. Commun.,* 2(l):15–26 (1994).

Protocadherins are members of the cadherin superfamily which are highly expressed in the brain. In some studies, protocadherins have shown cell adhesion activity. See, Sano, et al., *EMBO J.,* 12(6):2249–2256 (1993). However, studies have also shown that some protocadherins, such as protocadherin 3 (also referred to as Pcdh3 or pc3), do not show strong calcium dependent cell aggregation activity. See, Sago, et al., *Genomics,* 29(3):631–640 (1995) for this study and further characteristics of Pcdh3. Molecules related to pc3 are thus of great interest. Also of great interest is the subtype of desmosomal cadherin described in Koch, et al., *Differentiation,* 47(1):29–36 (1991).

Of particular interest are proteins having a sequence with homology to that described in Amagai, et al., *Cell,* 67(5): 869–77 (1991). This study describes antibodies against a novel epithelial cadherin in pemphigus vulgaris, a disease of cell adhesion. Also of interest are full-length cadherins. Additionally, proteins having homology to the fat tumor suppressor gene which are novel cadherins are of interest.

13. PRO4380

Efforts are being undertaken by both industry and academia to identify new, native secreted proteins. Many of these efforts are focused on the screening of mammalian recombinant DNA libraries to identify the coding sequences for novel secreted proteins. We herein describe the identification and characterization of novel secreted polypeptides, designated herein as PRO4380 polypeptides.

14. PRO4354

Efforts are being undertaken by both industry and academia to identify new, native secreted proteins. Many of these efforts are focused on the screening of mammalian recombinant DNA libraries to identify the coding sequences for novel secreted proteins. We herein describe the identification and characterization of novel secreted polypeptides, designated herein as PRO4354 polypeptides.

15. PRO4408

Efforts are being undertaken by both industry and academia to identify new, native secreted proteins. Many of these efforts are focused on the screening of mammalian recombinant DNA libraries to identify the coding sequences for novel secreted proteins. We herein describe the identification and characterization of novel secreted polypeptides, designated herein as PRO4408 polypeptides.

16. PRO5737

Interleukin-1 refers to two proteins (IL-1α and IL-1β) which play a key role early in the inflammatory response (for a review, see Dinarello, *Blood*, 87: 2095–2147 (1996) and references therein). Both proteins are made as intracellular precursor proteins which are cleaved upon secretion to yield mature carboxy-terminal 17 kDa fragments which are biologically active. In the case of IL-1β, this cleavage involves an intracellular cysteine protease, known as ICE, which is required to release the active fragment from the inactive precursor. The precursor of IL-1α is active.

These two proteins act by binding to cell surface receptors found on almost all cell types and triggering a range of responses either alone or in concert with other secreted factors. These range from effects on proliferation (e.g. fibroblasts, T cells) apoptosis (e.g. A375 melanoma cells), cytokine induction (e.g. of TNF, IL-I, IL-8), receptor activation (e.g. E-selectin), eicosanoid production (e.g. PGE2) and the secretion of degradative enzymes (e.g. collagenase). To achieve these effects, IL-1 activates transcription factors such as NF-KB and AP-1. Several of the activities of IL-1 action on target cells are believed to be mediated through activation of kinase cascades that have also been associated with cellular stresses, such as the stress activated MAP kinase JNK/SAPK and p38.

A third member of the IL-1 family was subsequently discovered which acts as a natural antagonist of IL-1α and IL-1β by binding to the IL-1 receptor but not transducing an intracellular signal or a biological response. The protein is called IL-1Ra (for IL-1 receptor antagonist) or IRAP (for IL-1 receptor antagonist protein). At least three alternatively spliced forms of IL-1Ra exist: one encodes secreted protein, and the other two encode intracellular proteins. IL-1α, IL-1β and IL-1Ra exhibit approximately 25–30% sequence identity with each other and share a similar three dimensional structure consisting of twelve β-strands folded into a β-barrel, with an internal thrice repeated structural motif.

There are three known IL-1 receptor subunits. The active receptor complex consists of the type I receptor and IL-1 accessory protein (IL-1RAcP). The type I receptor is responsible for binding of the IL-1α, IL-1β and IL-1Ra ligands, and is able to do so in the absence of the IL-1RAcP. However, signal transduction requires the interaction of IL-1α or IL-1β with the IL-1RAcP. IL-1Ra does not interact with the IL-1RAcP and hence cannot induce signal transduction. A third receptor subunit, the type II receptor, binds IL-1α and IL-1β but cannot transduce signal due its lack of an intracellular domain. Instead, the type II receptor either acts as a decoy in its membrane bound form or as an IL-1 antagonist in its processed, secreted form, and hence inhibits IL-1 activity. The type II receptor weakly binds to IL-1Ra.

Many studies using IL-1Ra, soluble IL-1R derived from the extracellular domain of the type I IL-1 receptor, antibodies to IL-1α or IL-1β, and transgenic knockout mice for these genes have shown that IL-1 plays a role in a number of pathophysiologies (for a review, see Dinarello, Blood, 87: 2095-2147 (1996)). For example, IL-1Ra has been shown to be effective in animal models of septic shock, rheumatoid arthritis, graft-versus-host disease (GVHD), stroke, cardiac ischemia, psoriasis, inflammatory bowel disease, and asthma. In addition, IL-1Ra has demonstrated efficacy in clinical trials for rheumatoid arthritis and GVHD, and is also in clinical trials for inflammatory bowel disease, asthma and psoriasis.

More recently, interleukin-18 (IL-18) was placed in the IL-I family (for a review, see Dinarello et al, J. Leukocyte Biol., 63: 658–664 (1998)). IL-18 shares the β-pleated, barrel-like form of IL-1α and IL-1β. In addition, IL-18 is the natural ligand for the IL-1 receptor family member formerly known as IL-1R-related protein (IL-1Rrp) (now known as the IL-18 receptor (IL-18R)). IL-18 has been shown to initiate the inflammatory cytokine cascade in a mixed population of peripheral blood mononuclear cells (PBMCs) by triggering the constitutive IL-18 receptors on lymphocytes and NK cells, inducing TNF production in the activated cells. TNF, in turn, stimulates IL-1 and IL-8 production in CD14+ cells. Because of its ability to induce TNF, IL-1, and both C—C and C—X—C chemokines, and because IL-18 induces Fas ligand as well as nuclear translocation of nuclear factor 6B (NF-6B), IL-18 ranks with other pro-inflammatory cytokines as a likely contributor to systemic and local inflammation.

17. PRO4425

Efforts are being undertaken by both industry and academia to identify new, native secreted proteins. Many of these efforts are focused on the screening of mammalian recombinant DNA libraries to identify the coding sequences for novel secreted proteins. We herein describe the identification and characterization of novel secreted polypeptides, designated herein as PRO4425 polypeptides.

18. PRO5990

The secretogranin proteins (e.g. secretogranin I and II) are found in secretory granules in a variety of endocrine cells and neurons. Schimmel, A. et al., *FEBS Lett.* 314(3):375–80 (1992); Gerdes, H. H. et al., *J. Biol. Chem.* 264(20): 12009–15. A possible function of the secretogranin proteins is the packaging of secretory products, including regulatory peptides. Chanat, E. et al., *FEBS Lett.* 351(2):225–30 (1994); Rosa, P. et al., *J. Cell. Biol.* 101(5):1999–2011 (1985); Gorr, S. U. et al., *Am. J. Physiol.* 257(2):E247–54 (1989). Secretogranins have been successfully used as biological markers in a number of contexts. For example, secretogranin II has gained importance as an immunohistochemical marker for endocrine neoplasms. See Fischer-Colbrie, R. et al., *J. Biol. Chem.* 265(16):9208–13 (1990). Eder et al. found that the ratio of secretogranin II to chroinogranins was remarkably constant within patient populations, and suggest that the ratio may be used as a parameter to standardize CSF levels of other peptides, such as neuropeptides. Eder, U., et al., *J. Neural Transm.*, 105 (1):39–51 (1998).

We herein describe the identification and characterization of novel polypeptides having sequence similarity to secretogranin, designated herein as PRO5990 polypeptides.

19. PRO6030

Efforts are being undertaken by both industry and academia to identify new, native transmembrane receptor proteins. Many efforts are focused on the screening of mammalian recombinant DNA libraries to identify the coding sequences for novel transmembrane receptor proteins. We herein describe the identification and characterization of novel transmembrane polypeptides, designated herein as PRO6030 polypeptides.

20. PRO4424

Efforts are being undertaken by both industry and academia to identify new, native secreted proteins. Many of these efforts are focused on the screening of mammalian recombinant DNA libraries to identify the coding sequences for novel secreted proteins. We herein describe the identification and characterization of novel secreted polypeptides, designated herein as PRO4424 polypeptides.

21. PRO4422

Lysozyme is a protein which is widely distributed in several human tissues and secretions including milk, tears and saliva. It has been demonstrated to hydrolyze linkages between N-acetylglucosamines. It has been demonstrated to be an inhibitor of chemotaxis and of the production of toxic oxygen free radicals and may also have some role in the calcification process. As such, there is substantial interest in identifying novel polypeptides having homology to lysozyme. Nakano and Graf, Biochim. Biophys Acta, 1090 (2):273–6 (1991).

22. PRO4430

Efforts are being undertaken by both industry and academia to identify new, native secreted proteins. Many of these efforts are focused on the screening of mammalian recombinant DNA libraries to identify the coding sequences for novel secreted proteins. We herein describe the identification and characterization of novel secreted polypeptides, designated herein as PRO4430 polypeptides.

23. PRO4499

Efforts are being undertaken by both industry and academia to identify new, native transmembrane receptor proteins. Many efforts are focused on the screening of mammalian recombinant DNA libraries to identify the coding sequences for novel transmembrane receptor proteins. We herein describe the identification and characterization of novel transmembrane polypeptides, designated herein as PRO4499 polypeptides.

SUMMARY OF THE INVENTION

1. PRO1484

A cDNA clone (DNA44686-1653) has been identified, having homology to nucleic acid encoding adipocyte complement-related protein that encodes a novel polypeptide, designated in the present application as "PRO1484".

In one embodiment, the invention provides an isolated nucleic acid molecule comprising DNA encoding a PRO1484 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO1484 polypeptide having the sequence of amino acid residues from about 1 or about 23 to about 246, inclusive of FIG. 2 (SEQ ID NO:2), or (b) the complement of the DNA molecule of (a).

In another aspect, the invention concerns an isolated nucleic acid molecule encoding a PRO1484 polypeptide comprising DNA hybridizing to the complement of the nucleic acid between about nucleotides 77 or about 143 and about 814, inclusive, of FIG. 1 (SEQ ID NO:1). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203581 (DNA44686-1653) or (b) the complement of the nucleic acid molecule of (a). In a preferred embodiment, the nucleic acid comprises a DNA encoding the same mature polypeptide encoded by the human protein cDNA in ATCC Deposit No. 203581 (DNA44686-1653).

In still a further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues 1 or about 23 to about 246, inclusive of FIG. 2 (SEQ ID NO:2), or (b) the complement of the DNA of (a).

In a further aspect, the invention concerns an isolated nucleic acid molecule having at least 600 nucleotides and produced by hybridizing a test DNA molecule under stringent conditions with (a) a DNA molecule encoding a PRO1484 polypeptide having the sequence of amino acid residues from 1 or about 23 to about 246, inclusive of FIG. 2 (SEQ ID NO:2), or (b) the complement of the DNA molecule of (a), and, if the DNA molecule has at least about an 80% sequence identity, prefereably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO1484 polypeptide, with or without the N-terminal signal sequence and/or the initiating methionine, or is complementary to such encoding nucleic acid molecule. The signal peptide has been tentatively identified as extending from about amino acid position 1 to about amino acid position 22 in the sequence of FIG. 2 (SEQ ID NO:2).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 or about 23 to about 246, inclusive of FIG. 2 (SEQ ID NO:2), or (b) the complement of the DNA of (a).

Another embodiment is directed to fragments of a PRO1484 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length and most preferably from about 20 to about 40 nucleotides in length and may be derived from the nucleotide sequence shown in FIG. 1 (SEQ ID NO:1).

In another embodiment, the invention provides isolated PRO1484 polypeptide encoded by any of the isolated nucleic acid sequences hereinabove identified.

In a specific aspect, the invention provides isolated native sequence PRO1484 polypeptide, which in certain embodiments, includes an amino acid sequence comprising residues 1 or about 23 to about 246 of FIG. 2 (SEQ ID NO:2).

In another aspect, the invention concerns an isolated PRO1484 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 or about 23 to about 246, inclusive of FIG. 2 (SEQ ID NO:2).

In a further aspect, the invention concerns an isolated PRO1484 polypeptide, comprising an amino acid sequence scoring at least about 80% positives, preferably at least about 85% positives, more preferably at least about 90% positives, most preferably at least about 95% positives when compared with the amino acid sequence of residues 1 or about 23 to about 246, inclusive of FIG. 2 (SEQ ID NO:2).

In yet another aspect, the invention concerns an isolated PRO1484 polypeptide, comprising the sequence of amino acid residues 1 or about 23 to about 246, inclusive of FIG. 2 (SEQ ID NO:2), or a fragment thereof sufficient to provide a binding site for an anti-PRO1484 antibody. Preferably, the PRO1484 fragment retains a qualitative biological activity of a native PRO1484 polypeptide.

In a still further aspect, the invention provides a polypeptide produced by (i) hybridizing a test DNA molecule under stringent conditions with (a) a DNA molecule encoding a PRO1484 polypeptide having the sequence of amino acid residues from about 1 or about 23 to about 246, inclusive of FIG. 2 (SEQ ID NO: 3), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

2. PRO4334

A cDNA clone (DNA59608-2577) has been identified that encodes a novel polypeptide having homology to PC-1 and designated in the present application as "PRO4334".

In one embodiment, the invention provides an isolated nucleic acid molecule comprising DNA encoding a PRO4334 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4334 polypeptide having the sequence of amino acid residues from 1 or about 23 to about 440, inclusive of FIG. 4 (SEQ ID NO:9), or (b) the complement of the DNA molecule of (a).

In another aspect, the invention concerns an isolated nucleic acid molecule encoding a PRO4334 polypeptide comprising DNA hybridizing to the complement of the nucleic acid between about residues 150 and about 1403, inclusive, of FIG. 3 (SEQ ID NO:8). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203870 (DNA59608-2577), or (b) the complement of the DNA molecule of (a). In a preferred embodiment, the nucleic acid comprises a DNA encoding the same mature polypeptide encoded by the human protein cDNA in ATCC Deposit No. 203870 (DNA59608-2577).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 23 to about 440, inclusive of FIG. 4 (SEQ ID NO:9), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4334 polypeptide having the sequence of amino acid residues from about 23 to about 440, inclusive of FIG. 4 (SEQ ID NO:9), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 23 to about 440, inclusive of FIG. 4 (SEQ ID NO:9), or (b) the complement of the DNA of (a).

Another embodiment is directed to fragments of a PRO4334 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4334 polypeptide encoded by any of the isolated nucleic acid sequences hereinabove defined.

In a specific aspect, the invention provides isolated native sequence PRO4334 polypeptide, which in one embodiment, includes an amino acid sequence comprising residues 23 through 440 of FIG. 4 (SEQ ID NO:9).

In another aspect, the invention concerns an isolated PRO4334 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 23 to about 440, inclusive of FIG. 4 (SEQ ID NO:9).

In a further aspect, the invention concerns an isolated PRO4334 polypeptide, comprising an amino acid sequence scoring at least about 80% positives, preferably at least about 85% positives, more preferably at least about 90% positives, most preferably at least about 95% positives when compared with the amino acid sequence of residues 23 through 440 of FIG. 4 (SEQ ID NO:9).

In yet another aspect, the invention concerns an isolated PRO4334 polypeptide, comprising the sequence of amino acid residues 23 to about 440, inclusive of FIG. 4 (SEQ ID NO:9), or a fragment thereof sufficient to provide a binding site for an anti-PRO4334 antibody. Preferably, the PRO4334 fragment retains a qualitative biological activity of a native PRO4334 polypeptide.

In a still further aspect, the invention provides a polypeptide produced by (i) hybridizing a test DNA molecule under stringent conditions with (a) a DNA molecule encoding a PRO4334 polypeptide having the sequence of amino acid residues from about 23 to about 440, inclusive of FIG. 4 (SEQ ID NO:9), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

3. PRO1122

A cDNA clone (DNA62377-1381) has been identified, having sequence identity with CTLA-8 that encodes a novel polypeptide, designated in the present application as "PRO1122."

In one embodiment, the invention provides an isolated nucleic acid molecule comprising DNA encoding a PRO1122 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO1122 polypeptide having the sequence of amino acid residues from 1 or about 19 to about 197, inclusive of FIG. 6 (SEQ ID NO:11), or (b) the complement of the DNA molecule of (a).

In another aspect, the invention concerns an isolated nucleic acid molecule encoding a PRO1122 polypeptide comprising DNA hybridizing to the complement of the nucleic acid between about residues 104 and about 640, inclusive, of FIG. 5 (SEQ ID NO:10). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203552 (DNA62377-1381), or (b) the complement of the DNA molecule of (a). In a preferred embodiment, the nucleic acid comprises a DNA encoding the same mature polypeptide encoded by the human protein cDNA in ATCC Deposit No. 203552 (DNA62377-1381).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 19 to about 197, inclusive of FIG. 6 (SEQ ID NO:11), or the complement of the DNA of (a).

In a further aspect, the invention concerns an isolated nucleic acid molecule produced by hybridizing a test DNA molecule under stringent conditions with (a) a DNA molecule encoding a PRO1122 polypeptide having the sequence of amino acid residues from about 19 to about 197, inclusive of FIG. 6 (SEQ ID NO:11), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 19 to about 197, inclusive of FIG. 6 (SEQ ID NO:11), or (b) the complement of the DNA of (a).

In another embodiment, the invention provides isolated PRO1122 polypeptide encoded by any of the isolated nucleic acid sequences hereinabove defined.

In a specific aspect, the invention provides isolated native sequence PRO1122 polypeptide, which in one embodiment, includes an amino acid sequence comprising residues 19 through 197 of FIG. 6 (SEQ ID NO:11).

In another aspect, the invention concerns an isolated PRO1122 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 19 to about 197, inclusive of FIG. 6 (SEQ ID NO:11).

In a further aspect, the invention concerns an isolated PRO1122 polypeptide, comprising an amino acid sequence scoring at least about 80% positives, preferably at least about 85% positives, more preferably at least about 90% positives, most preferably at least about 95% positives when compared with the amino acid sequence of residues 19 through 197 of FIG. 6 (SEQ ID NO:11).

In a still further aspect, the invention provides a polypeptide produced by (i) hybridizing a test DNA molecule under stringent conditions with (a) a DNA molecule encoding a PRO1122 polypeptide having the sequence of amino acid residues from about 19 to about 197, inclusive of FIG. 6 (SEQ ID NO:1), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

4. PRO1889

A cDNA clone (DNA77623-2524) has been identified, having homology to nucleic acid encoding E48 antigen protein, that encodes a novel polypeptide, designated in the present application as "PRO1889".

In one embodiment, the invention provides an isolated nucleic acid molecule comprising DNA encoding a PRO1889 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO1889 polypeptide having the sequence of amino acid residues from about 1 or about 21 to about 97, inclusive of FIG. 8 (SEQ ID NO:16), or (b) the complement of the DNA molecule of (a).

In another aspect, the invention concerns an isolated nucleic acid molecule encoding a PRO1889 polypeptide comprising DNA hybridizing to the complement of the nucleic acid between about nucleotides 39 or about 99 and about: 329, inclusive, of FIG. 7 (SEQ ID NO:15). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203546 (DNA77623-2524) or (b) the complement of the nucleic acid molecule of (a). In a preferred embodiment, the nucleic acid comprises a DNA encoding the same mature polypeptide encoded by the human protein cDNA in ATCC Deposit No. 203546 (DNA77623-2524).

In still a further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues 1 or about 21 to about 97, inclusive of FIG. 8 (SEQ ID NO:16), or (b) the complement of the DNA of (a).

In a further aspect, the invention concerns an isolated nucleic acid molecule having at least 315 nucleotides and produced by hybridizing a test DNA molecule under stringent conditions with (a) a DNA molecule encoding a PRO1889 polypeptide having the sequence of amino acid residues from 1 or about 21 to about 97, inclusive of FIG. 8 (SEQ ID NO:16), or (b) the complement of the DNA molecule of (a), and, if the DNA molecule has at least about an 80% sequence identity, prefereably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO1889 polypeptide, with or without the N-terminal signal sequence and/or the initiating methionine, or is complementary to such encoding nucleic acid molecule. The signal peptide has been tentatively identified as extending from about amino acid position 1 to about amino acid position 20 in the sequence of FIG. 8 (SEQ ID NO:16).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 or about 21 to about 97, inclusive of FIG. 8 (SEQ ID NO:16), or (b) the complement of the DNA of (a).

Another embodiment is directed to fragments of a PRO1889 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length and most preferably from about 20 to about 40 nucleotides in length and may be derived from the nucleotide sequence shown in FIG. 7 (SEQ ID NO:15).

In another embodiment, the invention provides isolated PRO1889 polypeptide encoded by any of the isolated nucleic acid sequences hereinabove identified.

In a specific aspect, the invention provides isolated native sequence PRO1889 polypeptide, which in certain embodiments, includes an amino acid sequence comprising residues 1 or about 21 to about 97 of FIG. 8 (SEQ ID NO:16).

In another aspect, the invention concerns an isolated PRO1889 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 or about 21 to about 97, inclusive of FIG. 8 (SEQ ID NO:16).

In a further aspect, the invention concerns an isolated PRO1889 polypeptide, comprising an amino acid sequence scoring at least about 80% positives, preferably at least about 85% positives, more preferably at least about 90% positives, most preferably at least about 95% positives when compared with the amino acid sequence of residues 1 or about 21 to about 97, inclusive of FIG. 8 (SEQ ID NO:16).

In yet another aspect, the invention concerns an isolated PRO1889 polypeptide, comprising the sequence of amino acid residues 0.1 or about 21 to about 97, inclusive of FIG. 8 (SEQ ID NO:16), or a fragment thereof sufficient to provide a binding site for an anti-PRO1889 antibody. Preferably, the PRO1889 fragment retains a qualitative biological activity of a native PRO1889 polypeptide.

In a still further aspect, the invention provides a polypeptide produced by (i) hybridizing a test DNA molecule under stringent conditions with (a) a DNA molecule encoding a PRO1889 polypeptide having the sequence of amino acid residues from about 1 or about 21 to about 97, inclusive of FIG. 8 (SEQ ID NO:16), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In another embodiment, the invention concerns a method for determining the presence of a PRO1889 polypeptide comprising exposing a cell suspected of containing the polypeptide to an anti-PRO1889 antibody and determining binding of the antibody to the cell.

In yet another embodiment, the present invention relates to a method of diagnosing the presence of a cancerous cell in a mammal, comprising detecting the level of expression of a gene encoding a PRO1889 polypeptide (a) in a test sample of tissue cells obtained from the mammal, and (b) in a control sample of known normal tissue cells of the same cell type, wherein a higher expression level in the test sample indicates the presence of a cancerous cell, particularly a cancerous squamous cell, in the mammal.

A further embodiment is a method for identifying a compound capable of inhibiting the expression and/or activity of a PRO1889 polypeptide by contacting a candidate compound with a PRO1889 polypeptide under conditions and for time sufficient to allow these two compounds to interact. In a specific aspect, either the candidate compound or the PRO1889 polypeptide is immobilized on a solid support. In another aspect, the non-immobilized component carries a detectable label.

In a further embodiment, the present invention provides a method of diagnosing tumor in a mammal, comprising detecting the level of expression of a gene encoding a PRO1889 polypeptide (a) in a test sample of tissue cells obtained from the mammal, and (b) in a control sample of known normal tissue cells of the same cell type, wherein a higher expression level in the test sample indicates the presence of tumor in the mammal from which the test tissue cells were obtained.

In another embodiment, the present invention provides a method of diagnosing tumor in a mammal, comprising (a) contacting an anti-PRO1889 antibody with a test sample of the tissue cells obtained from the mammal, and (b) detecting the formation of a complex between the anti-PRO1889 and the PRO1889 polypeptide in the test sample. The detection may be qualitative or quantitative, and may be performed in comparison with monitoring the complex formation in a control sample of known normal tissue cells of the same cell type. A larger quantity of complexes formed in the test sample indicates the presence of tumor in the mammal from which the test tissue cells were obtained. The antibody preferably carries a detectable label. Complex formation can be monitored, for example, by light microscopy, flow cytometry, fluorimetry, or other techniques known in the art. Preferably, the test sample is obtained from an individual mammal suspected to have neoplastic cell growth or proliferation (e.g., cancerous cells).

In another embodiment, the present invention provides a cancer diagnostic kit, comprising an anti-PRO1889 antibody and a carrier (e.g. a buffer) in suitable packaging. The kit preferably contains instructions for using the antibody to detect the PRO1889 polypeptide.

In yet another embodiment, the invention provides a method for inhibiting the growth of tumor cells comprising exposing a cell which overexpresses a PRO1889 polypeptide to an effective amount of an agent inhibiting the expression and/or activity of the PRO1889 polypeptide. The agent preferably is an anti-PRO1889 polypeptide, a small organic and inorganic peptide, phosphopeptide, antisense or ribozyme molecule, or a triple helix molecule. In a specific aspect, the agent, e.g., anti-PRO1889 antibody induces cell death. In a further aspect, the tumor cells are further exposed to radiation treatment and/or a cytotoxic or chemotherapeutic agent.

In a further embodiment, the invention concerns an article of manufacture, comprising:
a container;
a label on the container, and
a composition comprising an active agent contained within the container; wherein the composition is effective for inhibiting the growth of tumor cells, the label on the container indicates that the composition can be used for treating conditions characterized by overexpression of a PRO1889 polypeptide, and the active agent in the composition is an agent inhibiting the expression and/or activity of the PRO1889 polypeptide. In a preferred aspect, the active agent is an anti-PRO1889 antibody.

5. PRO1890

A cDNA clone (DNA79230-2525) has been identified, having homology to nucleic acid encoding a lectin protein that encodes a novel polypeptide, designated in the present application as "PRO1890".

In one embodiment, the invention provides an isolated nucleic acid molecule comprising DNA encoding a PRO1890 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO1890 polypeptide having the sequence of amino acid residues from about 1 or about 22 to about 273, inclusive of FIG. 10 (SEQ ID NO:18), or (b) the complement of the DNA molecule of (a).

In another aspect, the invention concerns an isolated nucleic acid molecule encoding a PRO1890 polypeptide comprising DNA hybridizing to the complement of the nucleic acid between about nucleotides 378 or about 441 and about 1196, inclusive, of FIG. 9 (SEQ ID NO:17). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203549 (DNA79230-2525) or (b) the complement of the nucleic acid molecule of (a). In a preferred embodiment, the nucleic acid comprises a DNA encoding the same mature polypeptide encoded by the human protein cDNA in ATCC Deposit No. 203549 (DNA79230-2525).

In still a further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues 1 or about 22 to about 273, inclusive of FIG. 10 (SEQ ID NO:18), or (b) the complement of the DNA of (a).

In a further aspect, the invention concerns an isolated nucleic acid molecule having at least 475 nucleotides and produced by hybridizing a test DNA molecule under stringent conditions with (a) a DNA molecule encoding a PRO1890 polypeptide having the sequence of amino acid residues from 1 or about 22 to about 273, inclusive of FIG. 10 (SEQ ID NO:18), or (b) the complement of the DNA molecule of (a), and, if the DNA molecule has at least about an 80% sequence identity, prefereably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO1890 polypeptide, with or without the N-terminal signal sequence and/or the initiating methionine, and its soluble, i.e., transmembrane domain deleted or inactivated variants, or is complementary to such encoding nucleic acid molecule. The signal peptide has been tentatively identified as extending from about amino acid position 1 to about amino acid position 21 in the sequence of FIG. 10 (SEQ ID NO:18). The transmembrane domain has been tentatively identified as extending from about amino acid position 214 to about amino acid position 235 in the PRO1890 amino acid sequence (FIG. 10, SEQ ID NO:18).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 or about 22 to about 273, inclusive of FIG. 10 (SEQ ID NO:18), or (b) the complement of the DNA of (a).

Another embodiment is directed to fragments of a PRO1890 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length and most preferably from about 20 to about 40 nucleotides in length and may be derived from the nucleotide sequence shown in FIG. 9 (SEQ ID NO:17).

In another embodiment, the invention provides isolated PRO1890 polypeptide encoded by any of the isolated nucleic acid sequences hereinabove identified.

In a specific aspect, the invention provides isolated native sequence PRO1890 polypeptide, which in certain embodiments, includes an amino acid sequence comprising residues 1 or about 22 to about 273 of FIG. 10 (SEQ ID NO:18).

In another aspect, the invention concerns an isolated PRO1890 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 or about 22 to about 273, inclusive of FIG. 10 (SEQ ID NO:18).

In a further aspect, the invention concerns an isolated PRO1890 polypeptide, comprising an amino acid sequence scoring at least about 80% positives, preferably at least about 85% positives, more preferably at least about 90% positives, most preferably at least about 95% positives when compared with the amino acid sequence of residues 1 or about 22 to about 273, inclusive of FIG. 10 (SEQ ID NO:18).

In yet another aspect, the invention concerns an isolated PRO1890 polypeptide, comprising the sequence of amino acid residues 1 or about 22 to about 273, inclusive of FIG. 10 (SEQ ID NO:18), or a fragment thereof sufficient to provide a binding site for an anti-PRO1890 antibody. Preferably, the PRO1890 fragment retains a qualitative biological activity of a native PRO1890 polypeptide.

In a still further aspect, the invention provides a polypeptide produced by (i) hybridizing a test DNA molecule under stringent conditions with (a) a DNA molecule encoding a PRO1890 polypeptide having the sequence of amino acid residues from about 1 or about 22 to about 273, inclusive of FIG. 10 (SEQ ID NO:18), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

6. PRO1887

A cDNA clone (DNA79862-2522) has been identified that encodes a novel polypeptide having homology to carboxylesterases and designated in the present application as "PRO1887".

In one embodiment, the invention provides an isolated nucleic acid molecule comprising DNA encoding a PRO1887 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO1887 polypeptide having the sequence of amino acid residues from 1 or about 28 to about 571, inclusive of FIG. 12 (SEQ ID NO:23), or (b) the complement of the DNA molecule of (a).

In another aspect, the invention concerns an isolated nucleic acid molecule encoding a PRO1887 polypeptide comprising DNA hybridizing to the complement of the nucleic acid between about residues 87 and about 1718, inclusive, of FIG. 11 (SEQ ID NO:22). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203550 (DNA79862-2522), or (b) the complement of the DNA molecule of (a). In a preferred embodiment, the nucleic acid comprises a DNA encoding the same mature polypeptide encoded by the human protein cDNA in ATCC Deposit No. 203550 (DNA79862-2522).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 28 to about 571, inclusive of FIG. 12 (SEQ ID NO:23), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO1887 polypeptide having the sequence of amino acid residues from about 28 to about 571, inclusive of FIG. 12 (SEQ ID NO:23), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO1887 polypeptide, with or without the N-terminal signal sequence and/or the initiating methionine, and its soluble variants (i.e. transmembrane domain deleted or inactivated), or is complementary to such encoding nucleic acid molecule. The signal peptide has been tentatively identified as extending from amino acid position 1 through about amino acid position 27 in the sequence of FIG. 12 (SEQ ID NO:23). The transmembrane domain has been tentatively identified as extending from about amino acid position 226 to about amino acid position 245 in the PRO01887 amino acid sequence (FIG. 12, SEQ ID NO:23).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 28 to about 571, inclusive of FIG. 12 (SEQ ID NO:23), or (b) the complement of the DNA of (a).

Another embodiment is directed to fragments of a PRO1887 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length, and most preferably from about 20 to about 40 nucleotides in length.

In another embodiment, the invention provides isolated PRO1887 polypeptide encoded by any of the isolated nucleic acid sequences hereinabove defined.

In a specific aspect, the invention provides isolated native sequence PRO1887 polypeptide, which in one embodiment, includes an amino acid sequence comprising residues 28 to 571 of FIG. 12 (SEQ ID NO:23).

In another aspect, the invention concerns an isolated PRO1887 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 28 to about 571, inclusive of FIG. 12 (SEQ ID NO:23).

In a further aspect, the invention concerns an isolated PRO1887 polypeptide, comprising an amino acid sequence scoring at least about 80% positives, preferably at least about 85% positives, more preferably at least about 90% positives, most preferably at least about 95% positives when compared with the amino acid sequence of residues 28 to 571 of FIG. 12 (SEQ ID NO:23).

In yet another aspect, the invention concerns an isolated PRO1887 polypeptide, comprising the sequence of amino acid residues 28 to about 571, inclusive of FIG. 12 (SEQ ID NO:23), or a fragment thereof sufficient to provide a binding site for an anti-PRO1887 antibody. Preferably, the PRO1887 fragment retains a qualitative biological activity of a native PRO1887 polypeptide.

In a still further aspect, the invention provides a polypeptide produced by (i) hybridizing a test DNA molecule under stringent conditions with (a) a DNA molecule encoding a PRO1887 polypeptide having the sequence of amino acid residues from about 28 to about 571, inclusive of FIG. 12 (SEQ ID NO:23), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

7. PRO1785

A cDNA clone (DNA80136-2503) has been identified that encodes a novel polypeptide having sequence identity with peroxidases and designated in the present application as "PRO1785."

In one embodiment, the invention provides an isolated nucleic acid molecule comprising DNA encoding a PRO1785 polypeptide.

In one aspect, the isolated nucleic acid comprises DNA having at least about 80% sequence identity, preferably at least about 85% sequence identity, more preferably at least about 90% sequence identity, most preferably at least abo at 95% sequence identity to (a) a DNA molecule encoding a PRO1785 polypeptide having the sequence of amino acid residues from 1 or about 32 to about 209, inclusive of FIG. 14 (SEQ ID NO:29), or (b) the complement of the DNA molecule of (a).

In another aspect, the invention concerns an isolated nucleic acid molecule encoding a PRO1785 polypeptide comprising DNA hybridizing to the complement of the nucleic acid between about residues 95 and about 628, inclusive., of FIG. 13 (SEQ ID NO:28). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203541 (DNA80136-2503), or (b) the complement of the DNA molecule of (a). In a preferred embodiment, the nucleic acid comprises a DNA encoding the same mature polypeptide encoded by the human protein cDNA in ATCC Deposit No. 203541 (DNA80136-2503).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 32 to about 209, inclusive of FIG. 14 (SEQ ID NO:29), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO1785 polypeptide having the sequence of amino acid residues from about 32 to about 209, inclusive of FIG. 14 (SEQ ID NO:29), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO1785 polypeptide, with or without the N-terminal signal sequence and/or the initiating methionine, and its soluble, i.e. transmembrane domain deleted or inactivated variants, or is complementary to such encoding nucleic acid molecule. The signal peptide has been tentatively identified as extending from amino acid position 1 through about amino acid position 31 in the sequence of FIG. 14 (SEQ ID NO:29). The transmembrane domain has been tentatively identified as extending from about amino acid position 18 through about amino acid position 37 in the PRO1785 amino acid sequence (FIG. 14, SEQ ID NO:29).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 32 to about 209, inclusive of FIG. 14 (SEQ ID NO:29), or (b) the complement of the DNA of (a).

Another embodiment is directed to fragments of a PRO1785 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length, and most preferably from about 20 to about 40 nucleotides in length.

In another embodiment, the invention provides isolated PRO1785 polypeptide encoded by any of the isolated nucleic acid sequences hereinabove defined.

In a specific aspect, the invention provides isolated native sequence PRO1785 polypeptide, which in one embodiment, includes an amino acid sequence comprising residues 32 through 209 of FIG. 14 (SEQ ID NO:29).

In another aspect, the invention concerns an isolated PRO1785 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 32 to about 209, inclusive of FIG. 14 (SEQ ID NO:29).

In a further aspect, the invention concerns an isolated PRO1785 polypeptide, comprising an amino acid sequence scoring at least about 80% positives, preferably at least about 85% positives, more preferably at least about 90% positives, most preferably at least about 95% positives when compared with the amino acid sequence of residues 32 through 209 of FIG. 14 (SEQ ID NO:29).

In yet another aspect, the invention concerns an isolated PRO1785 polypeptide, comprising the sequence of amino acid residues 32 to about 209, inclusive of FIG. 14 (SEQ ID NO:29), or a fragment thereof sufficient to provide a binding site for an anti-PRO1785 antibody. Preferably, the PRO1785 fragment retains a qualitative biological activity of a native PRO1785 polypeptide.

In a still further aspect, the invention provides a polypeptide produced by (i) hybridizing a test DNA molecule under stringent conditions with (a) a DNA molecule encoding a PRO1785 polypeptide having the sequence of amino acid residues from about 32 to about 209, inclusive of FIG. 14 (SEQ ID NO:29), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

8. PRO4353

A cDNA clone (DNA80145-2594) has been identified that encodes a novel polypeptide having homology to semaphorin Z and designated in the present application as "PRO4353".

In one embodiment, the invention provides an isolated nucleic acid molecule comprising DNA encoding a PRO4353 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4353 polypeptide having the sequence of amino acid residues from 1 or about 26 to about 888, inclusive of FIG. 16 (SEQ ID NO:35), or (b) the complement of the DNA molecule of (a).

In another aspect, the invention concerns an isolated nucleic acid molecule encoding a PRO4353 polypeptide comprising DNA hybridizing to the complement of the nucleic acid between about residues 94 and about 2682, inclusive, of FIG. 15 (SEQ ID NO:34). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 204-PTA (DNA80145-2594), or (b) the complement of the DNA molecule of (a). In a preferred embodiment, the nucleic acid comprises a DNA encoding the same mature polypeptide encoded by the human protein cDNA in ATCC Deposit No. 204-PTA (DNA80145-2594).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 26 to about 888, inclusive of FIG. 16 (SEQ ID NO:35), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4353 polypeptide having the sequence of amino acid residues from about 26 to about 888, inclusive of FIG. 16 (SEQ ID NO:35), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO4353 polypeptide, with or without the N-terminal signal sequence and/or the initiating methionine, and its soluble variants (i.e. transmembrane domain deleted or inactivated), or is complementary to such encoding nucleic acid molecule. The signal peptide has been tentatively identified as extending from amino acid position 1 through about amino acid position 25 in the sequence of FIG. 16 (SEQ ID NO:35). The transmembrane domains have been tentatively identified as extending from about amino acid positions 318–339 and 598–617 (FIG. 16, SEQ ID NO:35).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 26 to about 888, inclusive of FIG. 16 (SEQ ID NO:35), or (b) the complement of the DNA of (a).

Another embodiment is directed to fragments of a PRO4353 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4353 polypeptide encoded by any of the isolated nucleic acid sequences hereinabove defined.

In a specific aspect, the invention provides isolated native sequence PRO4353 polypeptide, which in one embodiment, includes an amino acid sequence comprising residues 26 through 888 of FIG. 16 (SEQ ID NO:35).

In another aspect, the invention concerns an isolated PRO4353 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 26 to about 888, inclusive of FIG. 16 (SEQ ID NO:35).

In a further aspect, the invention concerns an isolated PRO4353 polypeptide, comprising an amino acid sequence scoring at least about 80% positives, preferably at least about 85% positives, more preferably at least about 90% positives, most preferably at least about 95% positives when compared with the amino acid sequence of residues 26 through 888 of FIG. 16 (SEQ ID NO:35).

In yet another aspect, the invention concerns an isolated PRO4353 polypeptide, comprising the sequence of amino acid residues 26 to about 888, inclusive of FIG. 16 (SEQ ID NO:35), or a fragment thereof sufficient to provide a binding site for an anti-PRO4353 antibody. Preferably, the PRO4353 fragment retains a qualitative biological activity of a native PRO4353 polypeptide.

In a still further aspect, the invention provides a polypeptide produced by (i) hybridizing a test DNA molecule under stringent conditions with (a) a DNA molecule encoding a PRO4353 polypeptide having the sequence of amino acid residues from about 26 to about 888, inclusive of FIG. 16 (SEQ ID NO:35), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

9. PRO4357

A cDNA clone (DNA84917-2597) has been identified that encodes a novel polypeptide having homology to "BK158_1" and designated in the present application as "PRO4357".

In one embodiment, the invention provides an isolated nucleic acid molecule comprising DNA encoding a PRO4357 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4357 polypeptide having the sequence of amino acid residues from 1 or about 18 to about 502, inclusive of FIG. 18 (SEQ ID NO:40), or (b) the complement of the DNA molecule of (a).

In another aspect, the invention concerns an isolated nucleic acid molecule encoding a PRO4357 polypeptide comprising DNA hybridizing to the complement of the nucleic acid between about residues 337 and about 1791, inclusive, of FIG. 17 (SEQ ID NO:39). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203863 (DNA84917-2597), or (b) the complement of the DNA molecule of (a). In a preferred embodiment, the nucleic acid comprises a DNA encoding the same mature protein encoded by the human protein cDNA in ATCC Deposit No. 203863 (DNA84917-2597).

In a still further aspect, the invention concerns an isolated nucleic acid molecule comprising (a) DNA encoding a polypeptice having at least about 80% sequence identity, preferably at least about 85% sequence identity, more preferably at least about 90% sequence identity, most preferably at least about 95% sequence identity to the sequence of amino acid residues from about 18 to about 502, inclusive of FIG. 18 (SEQ ID NO:40), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4357 polypeptide having the sequence of amino acid residues from about 18 to about 502, inclusive of FIG. 18 (SEQ ID NO:40), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 18 to about 502, inclusive of FIG. 18 (SEQ ID NO:40), or (b) the complement of the DNA of (a).

Another embodiment is directed to fragments of a PRO4357 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4357 polypeptide encoded by any of the isolated nucleic acid sequences hereinabove defined.

In a specific aspect, the invention provides isolated native sequence PRO4357 polypeptide, which in one embodiment, includes an amino acid sequence comprising residues 18 through 502 of FIG. 18 (SEQ ID NO:40).

In another aspect, the invention concerns an isolated PRO4357 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 18 to about 502, inclusive of FIG. 18 (SEQ ID NO:40).

In a further aspect, the invention concerns an isolated PRO4357 polypeptide, comprising an amino acid sequence scoring at least about 80% positives, preferably at least about 85% positives, more preferably at least about 90% positives, most preferably at least about 95% positives when compared with the amino acid sequence of residues 18 through 502 of FIG. 18 (SEQ ID NO:40).

In yet another aspect, the invention concerns an isolated PRO4357 polypeptide, comprising the sequence of amino acid residues 18 to about 502, inclusive of FIG. 18 (SEQ ID NO:40), or a fragment thereof sufficient to provide a binding site for an anti-PRO4357 antibody. Preferably, the PRO4357 fragment retains a qualitative biological activity of a native PRO4357 polypeptide.

In a still further aspect, the invention provides a polypeptide produced by (i) hybridizing a test DNA molecule under stringent conditions with (a) a DNA molecule encoding a PRO4357 polypeptide having the sequence of amino acid residues from about 18 to about 502, inclusive of FIG. 18 (SEQ ID NO:40), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

10. PRO4405

A cDNA clone (DNA84920-2614) has been identified that encodes a novel polypeptide designated in the present application as "PRO4405".

In one embodiment, the invention provides an isolated nucleic acid molecule comprising DNA encoding a PRO4405 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4405 polypeptide having the sequence of amino acid residues from 1 or about 35 to about 310, inclusive of FIG. 20 (SEQ ID NO:45), or (b) the complement of the DNA molecule of (a).

In another aspect, the invention concerns an isolated nucleic acid molecule encoding a PRO4405 polypeptide comprising DNA hybridizing to the complement of the nucleic acid between about residues 181 and about 1008, inclusive, of FIG. 19 (SEQ ID NO:44). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203966 (DNA84920-2614), or (b) the complement of the DNA molecule of (a). In a preferred embodiment, the nucleic acid comprises a DNA encoding the same mature polypeptide encoded by the human protein cDNA in ATCC Deposit No. 203966 (DNA84920-2614).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 35 to about 310, inclusive of FIG. 20 (SEQ ID NO:45), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4405 polypeptide having the sequence of amino acid residues from about 35 to about 310, inclusive of FIG. 20 (SEQ ID NO:45), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO4405 polypeptide, with or without the N-terminal signal sequence and/or the initiating methionine, and its soluble variants (i.e. transmembrane domain deleted or inactivated), or is complementary to such encoding nucleic acid molecule. The signal peptide has been tentatively identified as extending from amino acid position 1 through about amino acid position 34 in the sequence of FIG. 20 (SEQ ID NO:45). The transmembrane domain has been tentatively identified as extending from about amino acid position 58 through about amino acid position 76 in the PRO4405 amino acid sequence (FIG. 20, SEQ ID NO:45) and may be a type II transmembrane domain.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 35 to about 310, inclusive of FIG. 20 (SEQ ID NO:45), or (b) the complement of the DNA of (a).

Another embodiment is directed to fragments of a PRO4405 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4405 polypeptide encoded by any of the isolated nucleic acid sequences hereinabove defined.

In a specific aspect, the invention provides isolated native sequence PRO4405 polypeptide, which in one embodiment, includes an amino acid sequence comprising residues 35 through 310 of FIG. 20 (SEQ ID NO:45).

In another aspect, the invention concerns an isolated PRO4405 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 35 to about 310, inclusive of FIG. 20 (SEQ ID NO:45).

In a further aspect, the invention concerns an isolated PRO4405 polypeptide, comprising an amino acid sequence scoring at least about 80% positives, preferably at least about 85% positives, more preferably at least about 90% positives, most preferably at least about 95% positives when compared with the amino acid sequence of residues 35 through 310 of FIG. 20 (SEQ ID NO:45).

In yet another aspect, the invention concerns an isolated PRO4405 polypeptide, comprising the sequence of amino acid residues 35 to about 310, inclusive of FIG. 20 (SEQ ID NO:45), or a fragment thereof sufficient to provide a binding site for an anti-PRO4405 antibody. Preferably, the PRO4405 fragment retains a qualitative biological activity of a native PRO4405 polypeptide.

In a still further aspect, the invention provides a polypeptide produced by (i) hybridizing a test DNA molecule under stringent conditions with (a) a DNA molecule encoding a PRO4405 polypeptide having the sequence of amino acid residues from about 35 to about 310, inclusive of FIG. 20 (SEQ ID NO:45), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

11. PRO4356

A cDNA clone (DNA86576-2595) has been identified that encodes a novel polypeptide having homology to MAG-PIAP and designated in the present application as "PRO4356".

In one embodiment, the invention provides an isolated nucleic acid molecule comprising DNA encoding a PRO4356 polypeptide.

In one aspect, the isolated nucleic acid comprises DNA having at least about 80% sequence identity, preferably at least about 85% sequence identity, more preferably at least about 90% sequence identity, most preferably at least about at 95% sequence identity to (a) a DNA molecule encoding a PRO4356 polypeptide having the sequence of amino acid residues from 1 or about 20 to about 251, inclusive of FIG. 22 (SEQ ID NO:50), or (b) the complement of the DNA molecule of (a).

In another aspect, the invention concerns an isolated nucleic acid molecule encoding a PRO4356 polypeptide comprising DNA hybridizing to the complement of the nucleic acid between about residues 112 and about 807, inclusive, of FIG. 21 (SEQ ID NO:49). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203868 (DNA86576-2595), or (b) the complement of the DNA molecule of (a). In a preferred embodiment, the nucleic acid comprises a DNA encoding the same mature polypeptide encoded by the human protein cDNA in ATCC Deposit No. 203868 (DNA86576-2595).

In a still further aspect, the invention concerns an isolated nucleic acid molecule comprising (a) DNA encoding a polypepticle having at least about 80% sequence identity, preferably at least about 85% sequence identity, more preferably at least about 90% sequence identity, most preferably at least about 95% sequence identity to the sequence of amino acid residues from about 20 to about 251, inclusive of FIG. 22 (SEQ ID NO:50), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4356 polypeptide having the sequence of amino acid residues from about 20 to about 251, inclusive of FIG. 22 (SEQ ID NO:50), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO4356 polypeptide, with or without the N-terminal signal sequence and/or the initiating methionine, and its soluble variants (i.e. transmembrane domain deleted or inactivated), or is complementary to such encoding nucleic acid molecule. The signal peptide has been tentatively identified as extending from amino acid position 1 through about amino acid position 19 in the sequence of FIG. 22 (SEQ ID NO:50). The transmembrane domain has been tentatively identified as extending from about amino acid position 233 through about amino acid position 251 in the PRO4356 amino acid sequence (FIG. 22, SEQ ID NO:50).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 20 to about 251, inclusive of FIG. 22 (SEQ ID NO:50), or (b) the complement of the DNA of (a).

Another embodiment is directed to fragments of a PRO4356 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4356 polypeptide encoded by any of the isolated nucleic acid sequences hereinabove defined.

In a specific aspect, the invention provides isolated native sequence PRO4356 polypeptide, which in one embodiment, includes an amino acid sequence comprising residues 20 through 251 of FIG. 22 (SEQ ID NO:50).

In another aspect, the invention concerns an isolated PRO4356 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 20 to about 251, inclusive of FIG. 22 (SEQ ID NO:50).

In a further aspect, the invention concerns an isolated PRO4356 polypeptide, comprising an amino acid sequence scoring at least about 80% positives, preferably at least about 85% positives, more preferably at least about 90% positives, most preferably at least about 95% positives when compared with the amino acid sequence of residues 20 through 251 of FIG. 22 (SEQ ID NO:50).

In yet another aspect, the invention concerns an isolated PRO4356 polypeptide, comprising the sequence of amino acid residues 20 to about 251, inclusive of FIG. 22 (SEQ ID NO:50), or a fragment thereof sufficient to provide a binding site for an anti-PRO4356 antibody. Preferably, the PRO4356 fragment retains a qualitative biological activity of a native PRO4356 polypeptide.

In a still further aspect, the invention provides a polypeptide produced by (i) hybridizing a test DNA molecule under stringent conditions with (a) a DNA molecule encoding a PRO4356 polypeptide having the sequence of amino acid residues from about 20 to about 251, inclusive of FIG. 22 (SEQ ID NO:50), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

12. PRO4352

A cDNA clone (DNA87976-2593) has been identified that encodes a novel polypeptide having homology to protocadherin pc3 designated in the present application as "PRO4352".

In one embodiment, the invention provides an isolated nucleic acid molecule comprising DNA encoding a PRO4352 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4352 polypeptide having the sequence of amino acid residues from 1 or about 27 to about 800, inclusive of FIG. 24 (SEQ ID NO:52), or (b) the complement of the DNA molecule of (a).

In another aspect, the invention concerns an isolated nucleic acid molecule encoding a PRO4352 polypeptide comprising DNA hybridizing to the complement of the nucleic acid between about residues 257 and about 2578, inclusive, of FIG. 23 (SEQ ID NO:51). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203888 (DNA87976-2593), or (b) the complement of the DNA molecule of (a). In a preferred embodiment, the nucleic acid comprises a DNA encoding the same mature polypeptide encoded by the human protein cDNA in ATCC Deposit No. 203888 (DNA87976-2593).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 27 to about 800, inclusive of FIG. 24 (SEQ ID NO:52), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4352 polypeptide having the sequence of amino acid residues from about 27 to about 800, inclusive of FIG. 24 (SEQ ID NO:52), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO4352 polypeptide, with or without the N-terminal signal sequence and/or the initiating methionine, and its soluble variants (i.e. transmembrane domain deleted or inactivated), or is complementary to such encoding nucleic acid molecule, The signal peptide has been tentatively identified as extending from amino acid position 1 through about amino acid position 26 in the sequence of FIG. 24 (SEQ ID NO:52). The transmembrane domain has been tentatively identified as extending from about amino acid position 687 through about amino acid position 711 in the PRO4352 amino acid sequence (FIG. 24, SEQ ID NO:52).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 27 to about 800, inclusive of FIG. 24 (SEQ ID NO:52), or (b) the complement of the DNA of (a).

Another embodiment is directed to fragments of a PRO4352 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4352 polypeptide encoded by any of the isolated nucleic acid sequences hereinabove defined.

In a specific aspect, the invention provides isolated native sequence PRO4352 polypeptide, which in one embodiment, includes an amino acid sequence comprising residues 27 through 800 of FIG. 24 (SEQ ID NO:52).

In another aspect, the invention concerns an isolated PRO4352 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 27 to about 800, inclusive of FIG. 24 (SEQ ID NO:52).

In a further aspect, the invention concerns an isolated PRO4352 polypeptide, comprising an amino acid sequence scoring at least about 80% positives, preferably at least about 85% positives, more preferably at least about 90% positives, most preferably at least about 95% positives when compared with the amino acid sequence of residues 27 through 800 of FIG. 24 (SEQ ID NO:52).

In yet another aspect, the invention concerns an isolated PRO4352 polypeptide, comprising the sequence of amino acid residues 27 to about 800, inclusive of FIG. 24 (SEQ ID NO:52), or a fragment thereof sufficient to provide a binding site for an anti-PRO4352 antibody. Preferably, the PRO4352 fragment retains a qualitative biological activity of a native PRO4352 polypeptide.

In a still further aspect, the invention provides a polypeptide produced by (i) hybridizing a test DNA molecule under stringent conditions with (a) a DNA molecule encoding a PRO4352 polypeptide having the sequence of amino acid residues from about 27 to about 800, inclusive of FIG. 24 (SEQ ID NO:52), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

13. PRO4380

A cDNA clone (DNA92234-2602) has been identified that encodes a novel polypeptide designated in the present application as "PRO4380".

In one embodiment, the invention provides an isolated nucleic acid molecule comprising DNA encoding a PRO4380 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4380 polypeptide having the sequence of amino acid residues from 1 or about 27 to about 507, inclusive of FIG. 26 (SEQ ID NO:57), or (b) the complement of the DNA molecule of (a).

In another aspect, the invention concerns an isolated nucleic acid molecule encoding a PRO4380 polypeptide comprising DNA hybridizing to the complement of the nucleic acid between about residues 279 and about 1721, inclusive, of FIG. 25 (SEQ ID NO:56). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203948 (DNA92234-2602), or (b) the complement of the DNA molecule of (a). In a preferred embodiment, the nucleic acid comprises a DNA encoding the same mature polypeptide encoded by the human protein cDNA in ATCC Deposit No. 203948 (DNA92234-2602).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 27 to about 507, inclusive of FIG. 26 (SEQ ID NO:57), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4380 polypeptide having the sequence of amino acid residues from about 27 to about 507, inclusive of FIG. 26 (SEQ ID NO:57), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO4380 polypeptide, with or without the N-terminal signal sequence and/or the initiating methionine, and its soluble variants (i.e. transmembrane domain deleted or inactivated), or is complementary to such encoding nucleic acid molecule. The signal peptide has been tentatively identified as extending from amino acid position 1 through about amino acid position 26 in the sequence of FIG. 26 (SEQ ID NO:57). The transmembrane domain has been tentatively identified as extending from about amino acid position 273 through about amino acid position 292 in the PRO4380 amino acid sequence (FIG. 26, SEQ ID NO:57).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 27 to about 507, inclusive of FIG. 26 (SEQ ID NO:57), or (b) the complement of the DNA of (a).

Another embodiment is directed to fragments of a PRO4380 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4380 polypeptide encoded by any of the isolated nucleic acid sequences hereinabove defined.

In a specific aspect, the invention provides isolated native sequence PRO4380 polypeptide, which in one embodiment, includes an amino acid sequence comprising residues 27 through 507 of FIG. 26 (SEQ ID NO:57).

In another aspect, the invention concerns an isolated PRO4380 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 27 to about 507, inclusive of FIG. 26 (SEQ ID NO:57).

In a further aspect, the invention concerns an isolated PRO4380 polypeptide, comprising an amino acid sequence scoring at least about 80% positives, preferably at least about 85% positives, more preferably at least about 90% positives, most preferably at least about 95% positives when compared with the amino acid sequence of residues 27 through 507 of FIG. 26 (SEQ ID NO:57).

In yet another aspect, the invention concerns an isolated PRO4380 polypeptide, comprising the sequence of amino acid residues 27 to about 507, inclusive of FIG. 26 (SEQ ID NO:57), or a fragment thereof sufficient to provide a binding site for an anti-PRO4380 antibody. Preferably, the PRO4380 fragment retains a qualitative biological activity of a native PRO4380 polypeptide.

In a still further aspect, the invention provides a polypeptide produced by (i) hybridizing a test DNA molecule under stringent conditions with (a) a DNA molecule encoding a PRO4380 polypeptide having the sequence of amino acid residues from about 27 to about 507, inclusive of FIG. 26 (SEQ ID NO:57), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

14. PRO4354

A cDNA clone (DNA92256-2596) has been identified that encodes a novel polypeptide designated in the present application as "PRO4354".

In one embodiment, the invention provides an isolated nucleic acid molecule comprising DNA encoding a PRO4354 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4354 polypeptide having the sequence of amino acid residues from about 22 to about 248, inclusive of FIG. 28 (SEQ ID NO:59), or (b) the complement of the DNA molecule of (a).

In another aspect, the invention concerns an isolated nucleic acid molecule encoding a PRO4354 polypeptide comprising DNA hybridizing to the complement of the nucleic acid between about residues 171 and about 851, inclusive, of FIG. 27 (SEQ ID NO:58). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203891 (DNA92256-2596), or (b) the complement of the DNA molecule of (a). In a preferred embodiment, the nucleic acid comprises a DNA encoding the same mature polypeptide encoded by the human protein cDNA in ATCC Deposit No. 203891 (DNA92256-2596).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 22 to about 248, inclusive of FIG. 28 (SEQ ID NO:59), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4354 polypeptide having the sequence of amino acid residues from about 22 to about 248, inclusive of FIG. 28 (SEQ ID NO:59), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 22 to about 248, inclusive of FIG. 28 (SEQ ID NO:59), or (b) the complement of the DNA of (a).

Another embodiment is directed to fragments of a PRO4354 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4354 polypeptide encoded by any of the isolated nucleic acid sequences hereinabove defined.

In a specific aspect, the invention provides isolated native sequence PRO4354 polypeptide, which in one embodiment, includes an amino acid sequence comprising residues 22 through 248 of FIG. 28 (SEQ ID NO:59).

In another aspect, the invention concerns an isolated PRO4354 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 22 to about 248, inclusive of FIG. 28 (SEQ ID NO:59).

In a further aspect, the invention concerns an isolated PRO4354 polypeptide, comprising an amino acid sequence scoring at least about 80% positives, preferably at least about 85% positives, more preferably at least about 90% positives, most preferably at least about 95% positives when compared with the amino acid sequence of residues 22 through 248 of FIG. 28 (SEQ ID NO:59).

In yet another aspect, the invention concerns an isolated PRO4354 polypeptide, comprising the sequence of amino acid residues 22 to about 248, inclusive of FIG. 28 (SEQ ID NO:59), or a fragment thereof sufficient to provide a binding site for an anti-PRO4354 antibody. Preferably, the PRO4354 fragment retains a qualitative biological activity of a native PRO4354 polypeptide.

In a still further aspect, the invention provides a polypeptide produced by (i) hybridizing a test DNA molecule under stringent conditions with (a) a DNA molecule encoding a PRO4354 polypeptide having the sequence of amino acid residues from about 22 to about 248, inclusive of FIG. 28 (SEQ ID NO:59), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

15. PRO4408

A cDNA clone (DNA92274-2617) has been identified that encodes a novel polypeptide designated in the present application as "PRO4408".

In one embodiment, the invention provides an isolated nucleic acid molecule comprising DNA encoding a PRO4408 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4408 polypeptide having the sequence of amino acid residues from about 23 to about 223, inclusive of FIG. 30 (SEQ ID NO:61), or (b) the complement of the DNA molecule of (a).

In another aspect, the invention concerns an isolated nucleic acid molecule encoding a PRO4408 polypeptide comprising DNA hybridizing to the complement of the nucleic acid between about residues 155 and about 757, inclusive, of FIG. 29 (SEQ ID NO:60). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203971 (DNA92274-2617), or (b) the complement of the DNA molecule of (a). In a preferred embodiment, the nucleic acid comprises a DNAK encoding the same mature polypeptide encoded by the human protein cDNA in ATCC Deposit No. 203971 (DNA92274-2617).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 23 to about 223, inclusive of FIG. 30 (SEQ ID NO:61), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4408 polypeptide having the sequence of amino acid residues from about 23 to about 223, inclusive of FIG. 30 (SEQ ID NO:61), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 23 to about 223, inclusive of FIG. 30 (SEQ ID NO:61), or (b) the complement of the DNA of (a).

Another embodiment is directed to fragments of a PRO4408 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4408 polypeptide encoded by any of the isolated nucleic acid sequences hereinabove defined.

In a specific aspect, the invention provides isolated native sequence PRO4408 polypeptide, which in one embodiment, includes an amino acid sequence comprising residues 23 through 223 of FIG. 30 (SEQ ID NO:61).

In another aspect, the invention concerns an isolated PRO4408 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 23 to about 223, inclusive of FIG. 30 (SEQ ID NO:61).

In a further aspect, the invention concerns an isolated PRO4408 polypeptide, comprising an amino acid sequence scoring at least about 80% positives, preferably at least about 85% positives, more preferably at least about 90% positives, most preferably at least about 95% positives when compared with the amino acid sequence of residues 23 through 223 of FIG. 30 (SEQ ID NO:61).

In yet another aspect, the invention concerns an isolated PRO4408 polypeptide, comprising the sequence of amino acid residues 23 to about 223, inclusive of FIG. 30 (SEQ ID NO:61), or a fragment thereof sufficient to provide a binding site for an anti-PRO4408 antibody. Preferably, the PRO4408 fragment retains a qualitative biological activity of a native PRO4408 polypeptide.

In a still further aspect, the invention provides a polypeptide produced by (i) hybridizing a test DNA molecule under stringent conditions with (a) a DNA molecule encoding a PRO4408 polypeptide having the sequence of amino acid residues from about 23 to about 223, inclusive of FIG. 30 (SEQ ID NO:61), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

16. PRO5737

A cDNA clone (DNA92929-2534) has been identified that encodes a novel polypeptide having homology to IL-1 and is designated in the present application as "PRO5737".

In one embodiment, the invention provides an isolated nucleic acid molecule comprising DNA encoding a PRO5737 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO5737 polypeptide having the sequence of amino acid residues from 1 or about 18 to about 134, inclusive of FIG. 32 (SEQ ID NO:63), or (b) the complement of the DNA molecule of (a).

In another aspect, the invention concerns an isolated nucleic acid molecule encoding a PRO5737 polypeptide comprising DNA hybridizing to the complement of the nucleic acid between about residues 96 or about 147 and about 497, inclusive, of FIG. 31 (SEQ ID NO:62). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203586 (DNA92929-2534), or (b) the complement of the DNA molecule of (a). In a preferred embodiment, the nucleic acid comprises a DNA encoding the same mature polypeptide encoded by the human protein cDNA in ATCC Deposit No. 203586 (DNA92929-2534).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 18 to about 134, inclusive of FIG. 32 (SEQ ID NO:63), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO5737 polypeptide having the sequence of amino acid residues from about 18 to about 134, inclusive of FIG. 32 (SEQ ID NO:63), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 18 to about 134, inclusive of FIG. 32 (SEQ ID NO:63), or (1)) the complement of the DNA of (a).

Another embodiment is directed to fragments of a PRO5737 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO5737 polypeptide encoded by any of the isolated nucleic acid sequences hereinabove defined.

In a specific aspect, the invention provides isolated native sequence PRO5737 polypeptide, which in one embodiment, includes an amino acid sequence comprising residues 18 through 134 of FIG. 32 (SEQ ID NO:63).

In another aspect, the invention concerns an isolated PRO5737 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 18 to about 134, inclusive of FIG. 32 (SEQ ID NO:63).

In a further aspect, the invention concerns an isolated PRO5737 polypeptide, comprising an amino acid sequence scoring at least about 80% positives, preferably at least about 85% positives, more preferably at least about 90% positives, most preferably at least about 95% positives when compared with the amino acid sequence of residues 18 throught 134 of FIG. 32 (SEQ ID NO:63).

In yet another aspect, the invention concerns an isolated PRO5737 polypeptide, comprising the sequence of amino acid residues 18 to about 134, inclusive of FIG. 32 (SEQ ID NO:63), or a fragment thereof sufficient to provide a binding site for an anti-PRO5737 antibody. Preferably, the PRO5737 fragment retains a qualitative biological activity of a native PRO5737 polypeptide.

In a still further aspect, the invention provides a polypeptide produced by (i) hybridizing a test DNA molecule under stringent conditions with (a) a DNA molecule encoding a PRO5737 polypeptide having the sequence of amino acid residues from about 18 to about 134, inclusive of FIG. 32 (SEQ ID NO:63), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

17. PRO4425

A cDNA clore (DNA93011-2637) has been identified that encodes a novel polypeptide having homology to a protein in GenBank, accession number HGS_RE295, and designated in the present application as "PRO4425".

In one embodiment, the invention provides an isolated nucleic acid molecule comprising DNA encoding a PRO4425 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4425 polypeptide having the sequence of amino acid residues from 1 OR about 20 to about 136, inclusive of FIG. 34 (SEQ ID NO:65), or (b) the complement of the DNA molecule of (a).

In another aspect, the invention concerns an isolated nucleic acid molecule encoding a PRO4425 polypeptide comprising DNA hybridizing to the complement of the nucleic acid between about residues 84 and about 434, inclusive, of FIG. 33 (SEQ ID NO:64). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein CDNA in ATCC Deposit No. 20-PTA (DNA93011-2637), or (b) the complement of the DNA molecule of (a). In a preferred embodiment, the nucleic acid comprises a DNA encoding the same mature polypeptide encoded by the human protein cDNA in ATCC Deposit No. 20-PTA (DNA93011-2637).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 20 to about 136, inclusive of FIG. 34 (SEQ ID NO:65), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4425 polypeptide having the sequence of amino acid residues from about 20 to about 136, inclusive of FIG. 34 (SEQ ID NO:65), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 20 to about 136, inclusive of FIG. 34 (SEQ ID NO:65), or (b) the complement of the DNA of (a).

Another embodiment is directed to fragments of a PRO4425 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4425 polypeptide encoded by any of the isolated nucleic acid sequences hereinabove defined.

In a specific aspect, the invention provides isolated native sequence PRO4425 polypeptide, which in one embodiment, includes an amino acid sequence comprising residues 20 through 136 of FIG. 34 (SEQ ID NO:65).

In another aspect, the invention concerns an isolated PRO4425 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 20 to about 136, inclusive of FIG. 34 (SEQ ID NO:65).

In a further aspect, the invention concerns an isolated PRO4425 polypeptide, comprising an amino acid sequence scoring at least about 80% positives, preferably at least about 85% positives, more preferably at least about 90% positives, most preferably at least about 95% positives when compared with the amino acid sequence of residues 20 through 136 of FIG. 34 (SEQ ID NO:65).

In yet another aspect, the invention concerns an isolated PRO4425 polypeptide, comprising the sequence of amino acid residues 20 to about 136, inclusive of FIG. 34 (SEQ ID NO:65), or a fragment thereof sufficient to provide a binding site for an anti-PRO4425 antibody. Preferably, the PRO4425 fragment retains a qualitative biological activity of a native PRO4425 polypeptide.

In a still further aspect, the invention provides a polypeptide produced by (i) hybridizing a test DNA molecule under stringent conditions with (a) a DNA molecule encoding a PRO4425 polypeptide having the sequence of amino acid residues from about 20 to about 136, inclusive of FIG. 34 (SEQ ID NO:65), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

18. PRO5990

A cDNA clone (designated herein as DNA96042-2682) has been identified that has homology to nucleic acid encoding secretogranin and that encodes a novel polypeptide, designated in the present application as "PRO5990".

In one embodiment, the invention provides an isolated nucleic acid molecule comprising a nucleotide sequence that encodes a PRO5990 polypeptide.

In one aspect, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule encoding a PRO5990 polypeptide having the sequence of amino acid residues from about 1 or about 22 to about 468, inclusive, of FIG. 36 (SEQ ID NO:67), or (b) the complement of the DNA molecule of (a).

In another aspect, the isolated nucleic acid molecule comprises (a) a nucleotide sequence encoding a PRO5990 polypeptide having the sequence of amino acid residues from about 1 or about 22 to about 468, inclusive, of FIG. 36 (SEQ ID NO:67), or (b) the complement of the nucleotide sequence of (a).

In other aspects, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule having the sequence of nucleotides from about 265 or about 328 to about 1668, inclusive, of FIG. 35 (SEQ ID NO:66), or (b) the complement of the DNA molecule of (a).

In another aspect, the isolated nucleic acid molecule comprises (a) the nucleotide sequence of from about 265 or about 328 to about 1668, inclusive, of FIG. 35 (SEQ ID NO:66), or (b) the complement of the nucleotide sequence of (a).

In a further aspect, the invention concerns an isolated nucleic acid molecule comprising a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule that encodes the same mature polypeptide encoded by the human protein cDNA deposited with the ATCC on Jul. 20, 1999 under ATCC Deposit No. 382-PTA (DNA96042-2682) or (b) the complement of the DNA molecule of (a). In a preferred embodiment, the isolated nucleic acid molecule comprises (a) a nucleotide sequence encoding the same mature polypeptide encoded by the human protein cDNA deposited with the ATCC on Jul. 20, 1999 under ATCC Deposit No. 382-PTA (DNA96042-2682) or (b) the complement of the nucleotide sequence of (a).

In another aspect, the invention concerns an isolated nucleic acid molecule comprising a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequ ence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) the full-length polypeptide coding sequence of the human protein cDNA deposited with the ATCC on Jul. 20, 1999 under ATCC Deposit No. 382-PTA (DNA96042-2682) or (b) the complement of the nucleotide sequence of (a). In a preferred embodiment, the isolated nucleic acid molecule comprises (a) the full-length polypeptide coding sequence of the DNA deposited with the ATCC on Jul. 20, 1999 under ATCC Deposit No. 382-PTA (DNA96042-2682) or (b) the complement of the nucleotide sequence of (a).

In another aspect, the invention concerns an isolated nucleic acid molecule which encodes an active PRO5990 polypeptide as defined below comprising a nucleotide sequence that hybridizes to the complement of a nucleic acid sequence that encodes amino acids 1 or about 22 to about 468, inclusive, of FIG. 36 (SEQ ID NO:67). Preferably, hybridization occurs under stringent hybridization and wash conditions.

In yet another aspect, the invention concerns an isolated nucleic acid molecule which encodes an active PRO5990 polypeptide as defined below comprising a nucleotide sequence that hybridizes to the complement of the nucleic acid sequence between about nucleotides 265 or about 328 and about 1668, inclusive, of FIG. 35 (SEQ ID NO:66). Preferably, hybridization occurs under stringent hybridization and wash conditions.

In a further aspect, the invention concerns an isolated nucleic acid molecule having at least about 1301 nucleotides and which is produced by hybridizing a test DNA molecule under stringent conditions with (a) a DNA molecule encoding a PRO5990 polypeptide having the sequence of amino acid residues from about 1 or about 22 to about 468, inclusive, of FIG. 36 (SEQ ID NO:67), or (b) the complement of the DNA molecule of (a), and, if the test DNA molecule has at least about an 80% sequence identity, preferably at least about an 81% sequence identity, more preferably at least about an 82% sequence identity, yet more preferably at least about an 83% sequence identity, yet more preferably at least about an 84% sequence identity, yet more preferably at least about an 85% sequence identity, yet more preferably at least about an 86% sequence identity, yet more preferably at least about an 87% sequence identity, yet more preferably at least about an 88% sequence identity, yet more preferably at least about an 89% sequence identity, yet more preferably at least about a 90% sequence identity, yet more preferably at least about a 91% sequence identity, yet more preferably at least about a 92% sequence identity, yet more preferably at least about a 93% sequence identity, yet more preferably at least a bout a 94% sequence identity, yet more preferably at least about a 95% sequence identity, yet more preferably at least about a 96% sequence identity, yet more preferably at least about a 97% sequence identity, yet more prefera bly at least about a 98% sequence identity and yet more preferably at least about a 99% sequence identity to (a) or (b), and isolating the test DNA molecule.

In another aspect, the invention concerns an isolated nucleic acid molecule comprising (a) a nucleotide sequence encoding a polypeptide scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of residues about 1 or about 22 to 468, inclusive, of FIG. 36 (SEQ ID NO:67), or (b) the complement of the nucleotide sequence of (a).

In a specific aspect, the invention provides an isolated nucleic acid molecule comprising DNA encoding a PRO5990 polypeptide without the N-terminal signal sequence and/or the initiating methionine, or is complementary to such encoding nucleic acid molecule. The signal peptide has been tentatively identified as extending from about amino acid position 1 to about amino acid position 21 in the sequence of FIG. 36 (SEQ ID NO:67). It is noted, however, that the C-terminal boundary of the signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Enz.* 10:1–6 (1997) and von Heinje et al., *Nucl. Acids. Res.* 14:4683–4690 (1986)). Moreover, it is also recognized that, in some cases, cleavage of a signal sequence from a secreted polypeptide is not entirely uniform, resulting in more than one secreted species. These polypeptides, and the polynucleotides encoding them, are contemplated by the present invention. As such, for purposes of the present application, the signal peptide of the PRO5990 polypeptide shown in FIG. 36 (SEQ ID NO:67) extends from amino acids 1 to X of FIG. 36 (SEQ ID NO:67), wherein X is any amino acid from 16 to 26 of FIG. 36 (SEQ ID NO:67). Therefore, mature forms of the PRO5990 polypeptide which are encompassed by the present invention include those comprising amino acids X to 468 of FIG. 36 (SEQ ID NO:67), wherein X is any amino acid from 16 to 26 of FIG. 36 (SEQ ID NO:67) and variants thereof as described below. Isolated nucleic acid molecules encoding these polypeptides are also contemplated.

Another embodiment is directed to fragments of a PRO5990 polypeptide coding sequence that may find use as, for example, hybridization probes or for encoding fragments of a PRO5990 polypeptide that may optionally encode a polypeptide comprising a binding site for an anti-PRO5990 antibody. Such nucleic acid fragments are usually at least about 20 nucleotides in length, preferably at least about 30 nucleotides in length, more preferably at least about 40 nucleotides in length, yet more preferably at least about 50 nucleotides in length, yet more preferably at least about 60 nucleotides in length, yet more preferably at least about 70 nucleotides in length, yet more preferably at least about 80 nucleotides in length, yet more preferably at least about 90 nucleotides in length, yet more preferably at least about 100 nucleotides in length, yet more preferably at least about 110 nucleotides in length, yet more preferably at least about 120 nucleotides in length, yet more preferably at least about 130 nucleotides in length, yet more preferably at least about 140 nucleotides in length, yet more preferably at least about 150 nucleotides in length, yet more preferably at least about 160 nucleotides in length, yet more preferably at least about 170 nucleotides in length, yet more preferably at least about 180 nucleotides in length, yet more preferably at least about 190 nucleotides in length, yet more preferably at least about 200 nucleotides in length, yet more preferably at least about 250 nucleotides in length, yet more preferably at least about 300 nucleotides in length, yet more preferably at least about 350 nucleotides in length, yet more preferably at least about 400 nucleotides in length, yet more preferably at least about 450 nucleotides in length, yet more preferably at least about 500 nucleotides in length, yet more preferably at least about 600 nucleotides in length, yet more preferably at least about 700 nucleotides in length, yet more preferably at least about 800 nucleotides in length, yet more preferably at least about 900 nucleotides in length and yet more preferably at least about 1000 nucleotides in length, wherein in this context the term "about" means the referenced nucleotide sequence length plus or minus 10% of that referenced length. In a preferred embodiment, the nucleotide sequence fragment is derived from any coding region of the nucleotide sequence shown in FIG. 35 (SEQ ID NO:66). It is noted that novel fragments of a PRO5990 polypeptide-encoding nucleotide sequence may be determined in a routine manner by aligning the PRO5990 polypeptide-encoding nucleotide sequence with other known nucleotide sequences using any of a number of well known sequence alignment programs and determining which PRO5990 polypeptide-encoding nucleotide sequence fragment(s) are novel. All of such PRO5990 polypeptide-encoding nucleotide sequences are contemplated herein and can be determined without undue experimentation. Also contemplated are the PRO5990 polypeptide fragments encoded by these nucleotide molecule fragments, preferably those PRO5990 polypeptide fragments that comprise a binding site for an anti-PRO5990 antibody.

In another embodiment, the invention provides isolated PRO5990 polypeptide encoded by any of the isolated nucleic acid sequences hereinabove identified.

In a specific aspect, the invention provides isolated native sequence PRO5990 polypeptide, which in certain embodiments, includes an amino acid sequence comprising residues from about 1 or about 22 to about 468 of FIG. 36 (SEQ ID NO:67).

In another aspect, the invention concerns an isolated PRO5990 polypeptide, comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to the sequence of amino acid residues from about 1 or about 22 to about 468, inclusive, of FIG. 36 (SEQ ID NO:67).

In a further aspect, the invention concerns an isolated PRO5990 polypeptide comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequences identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to an amino acid sequence encoded by the human protein CDNA deposited with the ATCC on Jul. 20, 1999 under ATCC Deposit No. 382-PTA (DNA96042-2682). In a preferred embodiment, the isolated PRO5990 polypeptide comprises an amino acid sequence encoded by the human protein cDNA deposited with the ATCC on Jul. 20, 1999 under ATCC Deposit No. 382-PTA (DNA96042-2682).

In a further aspect, the invention concerns an isolated PRO5990 polypeptide comprising an amino acid sequence scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of residues from about 1 or about 22 to about 468, inclusive, of FIG. 36 (SEQ ID NO:67).

In a specific aspect, the invention provides an isolated PRO5990 polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO5990 polypeptide and recovering the PRO5990 polypeptide from the cell culture.

In yet another aspect, the invention concerns an isolated PRO5990 polypeptide, comprising the sequence of amino acid residues from about 1 or about 22 to about 468, inclusive, of FIG. 36 (SEQ ID NO:67), or a fragment thereof which is biologically active or sufficient to provide a binding site for an anti-PRO5990 antibody, wherein the identification of PRO5990 polypeptide fragments that possess biological activity or provide a binding site for an anti-PRO5990 antibody may be accomplished in a routine manner using techniques which are well known in the art. Preferably, the PRO5990 fragment retains a qualitative biological activity of a native PRO5990 polypeptide.

In a still further aspect, the invention provides a polypeptide produced by (i) hybridizing a test DNA molecule under stringent conditions with (a) a DNA molecule encoding a PRO5990 polypeptide having the sequence of amino acid residues from about 1 or about 22 to about 468, inclusive, of FIG. 36 (SEQ ID NO:67), or (b) the complement of the DNA molecule of (a), and if the test DNA molecule has at least about an 80% sequence identity, preferably at least about an 81% sequence identity, more preferably at least about an 82% sequence identity, yet more preferably at least about an 83% sequence identity, yet more preferably at least about an 84% sequence identity, yet more preferably at least about an 85% sequence identity, yet more preferably at least about an 86% sequence identity, yet more preferably at least about an 87% sequence identity, yet more preferably at least about an 88% sequence identity, yet more preferably at least about an 89% sequence identity, yet more preferably at least about a 90% sequence identity, yet more preferably at least about a 91% sequence identity, yet more preferably at least about a 92% sequence identity, yet more preferably at least about a 93% sequence identity, yet more preferably at least about a 94% sequence identity, yet more preferably at least about a 95% sequence identity, yet more preferably at least about a 96% sequence identity, yet more preferably at least about a 97% sequence identity, yet more preferably at least about a 98% sequence identity and yet more preferably at least about a 99% sequence identity to (a) or (b), (ii) culturing a host cell comprising the test DNA molecule under conditions suitable for expression of the polypeptide, and (iii) recovering the polypeptide from the cell culture.

Another embodiment of the present invention is directed to the use of a PRO5990 polypeptide, or an agonist or antagonist thereof as herein described, or an anti-PRO5990 antibody, for the preparation of a medicament useful in the treatment of a condition which is responsive to the PRO5990 polypeptide, an agonist or antagonist thereof or an anti-PRO5990 antibody.

19. PRO6030

A cDNA clone (designated herein as DNA96850-2705) has been identified that encodes a novel polypeptide, designated in the present application as "PRO6030".

In one embodiment, the invention provides an isolated nucleic acid molecule comprising a nucleotide sequence that encodes a PRO6030 polypeptide.

In one aspect, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule encoding a PRO6030 polypeptide having the sequence of amino acid residues from about 1 or about 27 to about 322, inclusive, of FIG. 38 (SEQ ID NO:72), or (b) the complement of the DNA molecule of (a).

In another aspect, the isolated nucleic acid molecule comprises (a) a nucleotide sequence encoding a PRO6030 polypeptide having the sequence of amino acid residues from about 1 or about 27 to about 322, inclusive, of FIG. 38 (SEQ ID NO:72), or (b) the complement of the nucleotide sequence of (a).

In other aspects, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule having the sequence of nucleotides from about 60 or about 138 to about 1025, inclusive, of FIG. 37 (SEQ ID NO:71), or (b) the complement of the DNA molecule of (a).

In another aspect, the isolated nucleic acid molecule comprises (a) the nucleotide sequence of from about 60 or about 138 to about 1025, inclusive, of FIG. 37 (SEQ ID NO:71), or (b) the complement of the nucleotide sequence of (a).

In a further aspect, the invention concerns an isolated nucleic acid molecule comprising a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule that encodes the same mature polypeptide encoded by the human protein cDNA deposited with the ATCC on Aug. 3, 1999 under ATCC Deposit No. 479-PTA (DNA96850-2705) or (b) the complement of the DNA molecule of (a). In a preferred embodiment, the isolated nucleic acid molecule comprises (a) a nucleotide sequence encoding the same mature polypeptide encoded by the human protein cDNA deposited with the ATCC on Aug. 3, 1999 under ATCC Deposit No. 479-PTA (DNA96850-2705) or (b) the complement of the nucleotide sequence of (a).

In another aspect, the invention concerns an isolated nucleic acid molecule comprising a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) the full-length polypeptide coding sequence of the human protein cDNA deposited with the ATCC on Aug. 3, 1999 under ATCC Deposit No. 479-PTA (DNA96850-2705) or (b) the complement of the nucleotide sequence of (a). In a preferred embodiment, the isolated nucleic acid molecule comprises (a) the full-length polypeptide coding sequence of the DNA deposited with the ATCC on Aug. 3, 1999 under ATCC Deposit No. 479-PTA (DNA96850-2705) or (b) the complement of the nucleotide sequence of (a).

In another aspect, the invention concerns an isolated nucleic acid molecule which encodes an active PRO6030 polypeptide as defined below comprising a nucleotide sequence that hybridizes to the complement of a nucleic acid sequence that encodes amino acids 1 or about 27 to about 322, inclusive, of FIG. 38 (SEQ ID NO:72). Preferably, hybridization occurs under stringent hybridization and wash conditions.

In yet another aspect, the invention concerns an isolated nucleic acid molecule which encodes an active PRO6030 polypeptide as defined below comprising a nucleotide sequence that hybridizes to the complement of the nucleic acid sequence between about nucleotides 60 or about 138 and about 1025, inclusive, of FIG. 37 (SEQ ID NO:71). Preferably, hybridization occurs under stringent hybridization and wash conditions.

In a further aspect, the invention concerns an isolated nucleic acid molecule having at least about 528 nucleotides and which is produced by hybridizing a test DNA molecule under stringent conditions with (a) a DNA molecule encoding a PRO6030 polypeptide having the sequence of amino acid residues from about 1 or about 27 to about 322, inclusive, of FIG. 38 (SEQ ID NO:72), or (b) the complement of the DNA molecule of (a), and, if the test DNA molecule has at least about an 80% sequence identity, preferably at least about an 81% sequence identity, more preferably at least about an 82% sequence identity, yet more preferably at least about an 83% sequence identity, yet more preferably at least about an 84% sequence identity, yet more preferably at least about an 85% sequence identity, yet more preferably at least about an 86% sequence identity, yet more preferably at least about an 87% sequence identity, yet more preferably at least about an 88% sequence identity, yet more preferably at least about an 89% sequence identity, yet more preferably at least about a 90% sequence identity, yet more preferably at least about a 91% sequence identity, yet more preferably at least about a 92% sequence identity, yet more preferably at least about a 93% sequence identity, yet more preferably at least about a 94% sequence identity, yet more preferably at least about a 95% sequence identity, yet more preferably at least about a 96% sequence identity, yet more preferably at least about a 97% sequence identity, yet more preferably at least about a 98% sequence identity and yet more preferably at least about a 99% sequence identity to (a) or (b), and isolating the test DNA molecule.

In another aspect, the invention concerns an isolated nucleic acid molecule comprising (a) a nucleotide sequence encoding a polypeptide scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably it least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of residues about 1 or about 27 to 322, inclusive, of FIG. 38 (SEQ ID NO:72), or (b) the complement of the nucleotide sequence of (a).

In a specific aspect, the invention provides an isolated nucleic acid molecule comprising DNA encoding a PRO6030 polypeptide without the N-terminal signal sequence and/or the initiating methionine, or is complementary to such encoding nucleic acid molecule. The signal peptide has been tentatively identified as extending from about amino acid position 1 to about amino acid position 26 in the sequence of FIG. 38 (SEQ ID NO:72). It is noted, however, that the C-terminal boundary of the signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1–6 (1997) and von Heinje et al., *Nucl. Acids. Res.* 14:4683–4690 (1986)). Moreover, it is also recognized that, in some cases, cleavage of a signal sequence from a secreted polypeptide is not entirely uniform, resulting in more than one secreted species. These polypeptides, and the polynucleotides encoding them, are contemplated by the present invention. As such, for purposes of the present application, the signal peptide of the PRO6030 polypeptide shown in FIG. 38 (SEQ ID NO:72) extends from amino acids 1 to X of FIG. 38 (SEQ ID NO:72), wherein X is any amino acid from 21 to 31 of FIG. 38 (SEQ ID NO:72). Therefore, mature forms of the PRO6030 polypeptide which are encompassed by the present invention include those comprising amino acids X to 322 of FIG. 38 (SEQ ID NO:72), wherein X is any amino acid from 21 to 31 of FIG. 38 (SEQ ID NO:72) and variants thereof as described below. Isolated nucleic acid molecules encoding these polypeptides are also contemplated.

Another aspect the invention provides an isolated nucleic acid molecule comprising a nucleotide sequence encoding a PRO6030 polypeptide which is either transmembrane domain-deleted or transmembrane domain-inactivated, or is complementary to such encoding nucleotide sequence, wherein the transmembrane domain has been tentatively identified as extending from about amino acid position 142 to about amino acid position 158 in the sequence of FIG. 38 (SEQ ID NO:72). Therefore, soluble extracellular domains of the herein described PRO6030 polypeptides are contemplated.

In this regard, another aspect of the present invention is directed to an isolated nucleic acid molecule which comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule encoding amino acids 1 to X of FIG. 38 (SEQ ID NO:72), where X is any amino acid from 137 to 147 of FIG. 38 (SEQ ID NO:72), or (b) the complement of the DNA molecule of (a). In a specific aspect, the isolated nucleic acid molecule comprises a nucleotide sequence which (a) encodes amino acids 1 to X of FIG. 38 (SEQ ID NO:72), where X is any amino acid from 137 to 147 of FIG. 38 (SEQ ID NO:72), or (b) is the complement of the DNA molecule of (a).

In yet another aspect of the present invention, the isolated nucleic acid molecule (a) encodes a polypeptide scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of residues about 1 to X of FIG. 38 (SEQ ID NO:72), where X is any amino acid from 137 to 147 of FIG. 38 (SEQ ID NO:72), or (b) is the complement of the DNA molecule of (a).

Another embodiment is directed to fragments of a PRO6030 polypeptide coding sequence that may find use as, for example, hybridization probes or for encoding fragments of a PRO6030 polypeptide that may optionally encode a polypeptide comprising a binding site for an anti-PRO6030 antibody. Such nucleic acid fragments are usually at least about 20 nucleotides in length, preferably at least about 30 nucleotides in length, more preferably at least about 40 nucleotides in length, yet more preferably at least about 50 nucleotides in length, yet more preferably at least about 60 nucleotides in length, yet more preferably at least about 70 nucleotides in length, yet more preferably at least about 80 nucleotides in length, yet more preferably at least about 90 nucleotides in length, yet more preferably at least about 100 nucleotides in length, yet more preferably at least about 110 nucleotides in length, yet more preferably at least about 120 nucleotides in length, yet more preferably at least about 130 nucleotides in length, yet more preferably at least about 140 nucleotides in length, yet more preferably at least about 150 nucleotides in length, yet more preferably at least about 160 nucleotides in length, yet more preferably at least about 170 nucleotides in length, yet more preferably at least about 180 nucleotides in length, yet more preferably at least about 190 nucleotides in length, yet more preferably at least about 200 nucleotides in length, yet more preferably at least about 250 nucleotides in length, yet more preferably at least about 300 nucleotides in length, yet more preferably at least about 350 nucleotides in length, yet more preferably at least about 400 nucleotides in length, yet more preferably at least about 450 nucleotides in length, yet more preferably at least about 500 nucleotides in length, yet more preferably at least about 600 nucleotides in length, yet more preferably at least about 700 nucleotides in length, yet more preferably at least about 800 nucleotides in length, yet more preferably at least about 900 nucleotides in length and yet more preferably at least about 1000 nucleotides in length, wherein in this context the term "about" means the referenced nucleotide sequence length plus or minus 10% of that referenced length. In a preferred embodiment, the nucleotide sequence fragment is derived from any coding region of the nucleotide sequence shown in FIG. 37 (SEQ ID NO:71). It is noted that novel fragments of a PRO6030 polypeptide-encoding nucleotide sequence may be determined in a routine manner by aligning the PRO6030 polypeptide-encoding nucleotide sequence with other known nucleotide sequences using any of a number of well known sequence alignment programs and determining which PRO6030 polypeptide-encoding nucleotide sequence fragment(s) are novel. All of such PRO6030 polypeptide-encoding nucleotide sequences are contemplated herein and can be determined without undue experimentation. Also contemplated are the PRO6030 polypeptide fragments encoded by these nucleotide molecule fragments, preferably those PRO6030 polypeptide fragments that comprise a binding site for an anti-PRO6030 antibody.

In another embodiment, the invention provides isolated PRO6030 polypeptide encoded by any of the isolated nucleic acid sequences hereinabove identified.

In a specific aspect, the invention provides isolated native sequence PRO6030 polypeptide, which in certain embodiments, includes an amino acid sequence comprising residues from about 1 or about 27 to about 322 of FIG. 38 (SEQ ID NO:72).

In another aspect, the invention concerns an isolated PRO6030 polypeptide, comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to the sequence of amino acid residues from about 1 or about 27 to about 322, inclusive, of FIG. 38 (SEQ ID NO:72).

In a further aspect, the invention concerns an isolated PRO6030 polypeptide comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to an amino acid sequence encoded by the human protein cDNA deposited with the ATCC on Aug. 3, 1999 under ATCC Deposit No. 479-PTA (DNA96850-2705). In a preferred embodiment, the isolated PRO6030 polypeptide comprises an amino acid sequence encoded by the human protein cDNA deposited with the ATCC on Aug. 3, 1999 under ATCC Deposit No. 479-PTA (DNA96850-2705).

In a further aspect, the invention concerns an isolated PRO6030 polypeptide comprising an amino acid sequence scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of residues from about 1 or about 27 to about 322, inclusive, of FIG. 38 (SEQ ID NO:72).

In a specific aspect, the invention provides an isolated PRO6030 polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO6030 polypeptide and recovering the PRO6030 polypeptide from the cell culture.

Another aspect the invention provides an isolated PRO6030 polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO6030 polypeptide and recovering the PRO6030 polypeptide from the cell culture.

As such, one aspect of the present invention is directed to an isolated soluble PRO6030 polypeptide which comprises an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to amino acids 1 to X of FIG. 38 (SEQ ID NO:72), where X is any amino acid from 137 to 147 of FIG. 38 (SEQ ID NO:72). In a preferred aspect, the isolated soluble PRO6030 polypeptide comprises amino acids 1 to X of FIG. 38 (SEQ ID NO:72), where X is any amino acid from 137 to 147 of FIG. 38 (SEQ ID NO:72).

In yet another aspect of the present invention, the isolated soluble PRO6030 polypeptide comprises an amino acid sequence which scores at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of residues about 1 to X of FIG. 38 (SEQ ID NO:72), where X is any amino acid from 137 to 147 of FIG. 38 (SEQ ID NO:72).

In yet another aspect, the invention concerns an isolated PRO6030 polypeptide, comprising the sequence of amino acid residues from about 1 or about 27 to about 322, inclusive, of FIG. 38 (SEQ ID NO:72), or a fragment thereof which is biologically active or sufficient to provide a binding site for an anti-PRO6030 antibody, wherein the identification of PRO6030 polypeptide fragments that possess biological activity or provide a binding site for an anti-PRO6030 antibody may be accomplished in a routine manner using techniques which are well known in the art. Preferably, the PRO6030 fragment retains a qualitative biological activity of a native PRO6030 polypeptide.

In a still further aspect, the invention provides a polypeptide produced by (i) hybridizing a test DNA molecule under stringent conditions with (a) a DNA molecule encoding a PRO6030 polypeptide having the sequence of amino acid residues from about 1 or about 27 to about 322, inclusive, of FIG. 38 (SEQ ID NO:72), or (b) the complement of the DNA molecule of (a), and if the test DNA molecule has at least about an 80% sequence identity, preferably at least about an 81% sequence identity, more preferably at least about an 82% sequence identity, yet more preferably at least about an 83% sequence identity, yet more preferably at least about an 84% sequence identity, yet more preferably at least about an 85% sequence identity, yet more preferably at least about an 86% sequence identity, yet more preferably at least about an 87% sequence identity, yet more preferably at least about an 88% sequence identity, yet more preferably at least about an 89% sequence identity, yet more preferably at least about a 90% sequence identity, yet more preferably at least about a 91% sequence identity, yet more preferably at least about a 92% sequence identity, yet more preferably at least about a 93% sequence identity, yet more preferably at least about a 94% sequence identity, yet more preferably at least about a 95% sequence identity, yet more preferably at least about a 96% sequence identity, yet more preferably at least about a 97% sequence identity, yet more preferably at least about a 98% sequence identity and yet more preferably at least about a 99% sequence identity to (a) or (b), (ii) culturing a host cell comprising the test DNA molecule under conditions suitable for expression of the polypeptide, and (iii) recovering the polypeptide from the cell culture.

In a still further embodiment, the invention concerns a composition of matter comprising a PRO6030 polypeptide, or an agonist or antagonist of a PRO6030 polypeptide as herein described, or an anti-PRO6030 antibody, in combination with a carrier. Optionally, the carrier is a pharmaceutically acceptable carrier.

Another embodiment of the present invention is directed to the use of a PRO6030 polypeptide, or an agonist or antagonist thereof as herein described, or an anti-PRO6030 antibody, for the preparation of a medicament useful in the treatment of a condition which is responsive to the PRO6030 polypeptide, an agonist or antagonist thereof or an anti-PRO6030 antibody.

20. PRO4424

A cDNA clone (DNA96857-2636) has been identified that encodes a novel polypeptide having homology to a protein in GenBank, accession number HGS_A135 and designated in the present application as "PRO4424".

In one embodiment, the invention provides an isolated nucleic acid molecule comprising DNA encoding a PRO4424 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4424 polypeptide having the sequence of amino acid residues from 1 or about 29 to about 221, inclusive of FIG. 40 (SEQ ID NO:74), or (b) the complement of the DNA molecule of (a).

In another aspect, the invention concerns an isolated nucleic acid molecule encoding a PRO4424 polypeptide comprising DNA hybridizing to the complement of the nucleic acid between about residues 136 and about 714, inclusive, of FIG. 39 (SEQ ID NO:73). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 17-PTA (DNA96857-2636), or (b) the complement of the DNA molecule of (a). In a preferred embodiment, the nucleic acid comprises a DNA encoding the same mature polypeptide encoded by the human protein cDNA in ATCC Deposit No. 17-PTA (DNA96857-2636).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 29 to about 221, inclusive of FIG. 40 (SEQ ID NO:74), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4424 polypeptide having the sequence of amino acid residues from about 29 to about 221, inclusive of FIG. 40 (SEQ ID NO:74), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 29 to about 221, inclusive of FIG. 40 (SEQ ID NO:74), or (b) the complement of the DNA of (a).

Another embodiment is directed to fragments of a PRO4424 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4424 polypeptide encoded by any of the isolated nucleic acid sequences hereinabove defined.

In a specific aspect, the invention provides isolated native sequence PRO4424 polypeptide, which in one embodiment, includes an amino acid sequence comprising residues 29 through 221 of FIG. 40 (SEQ ID NO:74).

In another aspect, the invention concerns an isolated PRO4424 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 29 to about 221, inclusive of FIG. 40 (SEQ ID NO:74).

In a further aspect, the invention concerns an isolated PRO4424 polypeptide, comprising an amino acid sequence scoring at least about 80% positives, preferably at least about 85% positives, more preferably at least about 90% positives, most preferably at least about 95% positives when compared with the amino acid sequence of residues 29 through 221 of FIG. 40 (SEQ ID NO:74).

In yet another aspect, the invention concerns an isolated PRO4424 polypeptide, comprising the sequence of amino acid residues 29 to about 221, inclusive of FIG. 40 (SEQ ID NO:74), or a fragment thereof sufficient to provide a binding site for an anti-PRO4424 antibody. Preferably, the PRO4424 fragment retains a qualitative biological activity of a native PRO4424 polypeptide.

In a still further aspect, the invention provides a polypeptide produced by (i) hybridizing a test DNA molecule under stringent conditions with (a) a DNA molecule encoding a PRO4424 polypeptide having the sequence of amino acid residues from about 29 to about 221, inclusive of FIG. 40 (SEQ ID NO:74), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

21. PRO4422

A cDNA clone (DNA96867-2620) has been identified that encodes a novel polypeptide having homology to lysozyme g and designated in the present application as "PRO4422".

In one embodiment, the invention provides an isolated nucleic acid molecule comprising DNA encoding a PRO4422 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4422 polypeptide having the sequence of amino acid residues from 1 or about 20 to about 194, inclusive of FIG. 42 (SEQ ID NO:76), or (b) the complement of the DNA molecule of (a).

In another aspect, the invention concerns an isolated nucleic acid molecule encoding a PRO4422 polypeptide comprising DNA hybridizing to the complement of the nucleic acid between about residues 375 and about 899, inclusive, of FIG. 41 (SEQ ID NO:75). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203972 (DNA96867-2620), or (b) the complement of the DNA molecule of (a). In a preferred embodiment, the nucleic acid comprises a DNA encoding the same mature polypeptide encoded by the human protein cDNA in ATCC Deposit No. 203972 (DNA96867-2620).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 20 to about 194, inclusive of FIG. 42 (SEQ ID NO:76), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4422 polypeptide having the sequence of amino acid residues from about 20 to about 194, inclusive of FIG. 42 (SEQ ID NO:76), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 20 to about 194, inclusive of FIG. 42 (SEQ ID NO:76), or (b) the complement of the DNA of (a).

Another embodiment is directed to fragments of a PRO4422 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4422 polypeptide encoded by any of the isolated nucleic acid sequences hereinabove defined.

In a specific aspect, the invention provides isolated native sequence PRO4422 polypeptide, which in one embodiment, includes an amino acid sequence comprising residues 20 through 194 of FIG. 42 (SEQ ID NO:76).

In another aspect, the invention concerns an isolated PRO4422 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 20 to about 194, inclusive of FIG. 42 (SEQ ID NO:76).

In a further aspect, the invention concerns an isolated PRO4422 polypeptide, comprising an amino acid sequence scoring at least about 80% positives, preferably at least about 85% positives, more preferably at least about 90% positives, most preferably at least about 95% positives when compared with the amino acid sequence of residues 20 through 194 of FIG. 42 (SEQ ID NO:76).

In yet another aspect, the invention concerns an isolated PRO4422 polypeptide, comprising the sequence of amino acid residues 20 to about 194, inclusive of FIG. 42 (SEQ ID NO:76), or a fragment thereof sufficient to provide a binding site for an anti-PRO4422 antibody. Preferably, the PRO4422 fragment retains a qualitative biological activity of a native PRO4422 polypeptide.

In a still further aspect, the invention provides a polypeptide produced by (i) hybridizing a test DNA molecule under stringent conditions with (a) a DNA molecule encoding a PRO4422 polypeptide having the sequence of amino acid residues from about 20 to about 194, inclusive of FIG. 42 (SEQ ID NO:76), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

22. PRO4430

A cDNA clone (DNA96878-2626) has been identified that encodes a novel polypeptide having homology to a protein in GenBank, accession number MMHC213L3_9, and designated in the present application as "PRO4430".

In one embodiment, the invention provides an isolated nucleic acid molecule comprising DNA encoding a PRO4430 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4430 polypeptide having the sequence of amino acid residues from 1 or about 19 to about 125, inclusive of FIG. 44 (SEQ ID NO:78), or (b) the complement of the DNA molecule of (a).

In another aspect, the invention concerns an isolated nucleic acid molecule encoding a PRO4430 polypeptide comprising DNA hybridizing to the complement of the nucleic acid between about residues 110 and about 430, inclusive, of FIG. 43 (SEQ ID NO:77). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 23-PTA (DNA96878-2626), or (b) the complement of the DNA molecule of (a). In a preferred embodiment, the nucleic acid comprises a DNA encoding the same mature polypeptide encoded by the human protein cDNA in ATCC Deposit No. 23-PTA (DNA96878-2626).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 19 to about 125, inclusive of FIG. 44 (SEQ ID NO:78), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4430 polypeptide having the sequence of amino acid residues from about 19 to about 125, inclusive of FIG. 44 (SEQ ID NO:78), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 19 to about 125, inclusive of FIG. 44 (SEQ ID NO:78), or (b) the complement of the DNA of (a).

Another embodiment is directed to fragments of a PRO4430 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4430 polypeptide encoded by any of the isolated nucleic acid sequences hereinabove defined.

In a specific aspect, the invention provides isolated native sequence PRO4430 polypeptide, which in one embodiment, includes an amino acid sequence comprising residues 19 through 125 of FIG. 44 (SEQ ID NO:78).

In another aspect, the invention concerns an isolated PRO4430 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 19 to about 125, inclusive of FIG. 44 (SEQ ID NO:78).

In a further aspect, the invention concerns an isolated PRO4430 polypeptide, comprising an amino acid sequence scoring at least about 80% positives, preferably at least about 85% positives, more preferably at least about 90% positives, most preferably at least about 95% positives when compared with the amino acid sequence of residues 19 through 125 of FIG. 44 (SEQ ID NO:78).

In yet another aspect, the invention concerns an isolated PRO4430 polypeptide, comprising the sequence of amino acid residues 19 to about 125, inclusive of FIG. 44 (SEQ ID NO:78), or a fragment thereof sufficient to provide a binding site for an anti-PRO4430 antibody. Preferably, the PRO4430 fragment retains a qualitative biological activity of a native PRO4430 polypeptide.

In a still further aspect, the invention provides a polypeptide produced by (i) hybridizing a test DNA molecule under stringent conditions with (a) a DNA molecule encoding a PRO4430 polypeptide having the sequence of amino acid residues from about 19 to about 125, inclusive of FIG. 44 (SEQ ID NO:78), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

23. PRO4499

A cDNA clone (DNA96889-2641) has been identified that encodes a novel polypeptide and designated in the present application as "PRO4499".

In one embodiment, the invention provides an isolated nucleic acid molecule comprising DNA encoding a PRO4499 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO4499 polypeptide having the sequence of amino acid residues from 1 or about 31 to about 339, inclusive of FIG. 46 (SEQ ID NO:80), or (b) the complement of the DNA molecule of (a).

In another aspect, the invention concerns an isolated nucleic acid molecule encoding a PRO4499 polypeptide comprising DNA hybridizing to the complement of the nucleic acid between about residues 275 and about 1201, inclusive, of FIG. 45 (SEQ ID NO:79). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 119-PTA (DNA96889-2641), or (b) the complement of the DNA molecule of (a). In a preferred embodiment, the nucleic acid comprises a DNA encoding the same mature polypeptide encoded by the human protein cDNA in ATCC Deposit No. 119-PTA (DNA96889-2641).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 31 to about 339, inclusive of FIG. 46 (SEQ ID NO:80), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO4499 polypeptide having the sequence of amino acid residues from about 31 to about 339, inclusive of FIG. 46 (SEQ ID NO:80), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO4499 polypeptide, with or without the N-terminal signal sequence and/or the initiating methionine, and its soluble variants (i.e. transmembrane domain deleted or inactivated), or is complementary to such encoding nucleic acid molecule. The signal peptide has been tentatively identified as extending from amino acid position 1 through about amino acid position 30 in the sequence of FIG. 46 (SEQ ID NO:80). The transmembrane domain has been tentatively identified as extending from about amino acid position 171 through about amino acid position 190 in the PRO4499 amino acid sequence (FIG. 46, SEQ ID NO:80).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 31 to about 339, inclusive of FIG. 46 (SEQ ID NO:80), or (b) the complement of the DNA of (a).

Another embodiment is directed to fragments of a PRO4499 polypeptide coding sequence that may find use as hybridization probes. Such nucleic acid fragments are from about 20 through about 80 nucleotides in length, preferably from about 20 through about 60 nucleotides in length, more preferably from about 20 through about 50 nucleotides in length, and most preferably from about 20 through about 40 nucleotides in length.

In another embodiment, the invention provides isolated PRO4499 polypeptide encoded by any of the isolated nucleic acid sequences hereinabove defined.

In a specific aspect, the invention provides isolated native sequence PRO4499 polypeptide, which in one embodiment, includes an amino acid sequence comprising residues 31 through 339 of FIG. 46 (SEQ ID NO:80).

In another aspect, the invention concerns an isolated PRO4499 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 31 to about 339, inclusive of FIG. 46 (SEQ ID NO:80).

In a further aspect, the invention concerns an isolated PRO4499 polypeptide, comprising an amino acid sequence scoring at least about 80% positives, preferably at least about 85% positives, more preferably at least about 90% positives, most preferably at least about 95% positives when compared with the amino acid sequence of residues 31 through 339 of FIG. 46 (SEQ ID NO:80).

In yet another aspect, the invention concerns an isolated PRO4499 polypeptide, comprising the sequence of amino acid residues 31 to about 339, inclusive of FIG. 46 (SEQ ID NO:80), or a fragment thereof sufficient to provide a binding site for an anti-PRO4499 antibody. Preferably, the PRO4499 fragment retains a qualitative biological activity of a native PRO4499 polypeptide.

In a still further aspect, the invention provides a polypeptide produced by (i) hybridizing a test DNA molecule under stringent conditions with (a) a DNA molecule encoding a PRO4499 polypeptide having the sequence of amino acid residues from about 31 to about 339, inclusive of FIG. 46 (SEQ ID NO:80), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

24. Additional Embodiments

In other embodiments of the present invention, the invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

In other embodiments, the invention provides an isolated nucleic acid molecule comprising a nucleotide sequence that encodes a PRO polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In a further aspect, the invention concerns an isolated PRO polypeptide comprising an amino acid sequence scoring at least about 80% positives, alternatively at least about 81% positives, alternatively at least about 82% positives, alternatively at least about 83% positives, alternatively at least about 84% positives, alternatively at least about 85% positives, alternatively at least about 86% positives, alternatively at least about 87% positives, alternatively at least about 88% positives, alternatively at least about 89% positives, alternatively at least about 90% positives, alternatively at least about 91% positives, alternatively at least about 92% positives, alternatively at least about 93% positives, alternatively at least about 94% positives, alternatively at least about 95% positives, alternatively at least about 96% positives, alternatively at least about 97% positives, alternatively at least about 98% positives and alternatively at least about 99% positives when compared with the amino acid sequence of a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting tile PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

BRIEF DESCRIPTION OF THE DRAWINGS

FIG. 1 shows a nucleotide sequence (SEQ ID NO:1) of a native sequence PRO1484 cDNA, wherein SEQ ID NO:1 is a clone designated herein as "DNA44686-1653".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:8) of a native sequence PRO4334 cDNA, wherein SEQ ID NO:8 is a clone designated herein as "DNA59608-2577".

FIG. 4 shows the amino acid sequence (SEQ ID NO:9) derived from the coding sequence of SEQ ID NO:8 shown in FIG. 3.

FIG. 5 shows a nucleotide sequence (SEQ ID NO:10) of a native sequence PRO1122 cDNA, wherein SEQ ID NO:10 is a clone designated herein as "DNA62377-1381".

FIG. 6 shows the amino acid sequence (SEQ ID NO:11) derived from the coding sequence of SEQ ID NO:10 shown in FIG. 5.

FIG. 7 shows a nucleotide sequence (SEQ ID NO:15) of a native sequence PRO1889 cDNA, wherein SEQ ID NO:15 is a clone designated herein as "DNA77623-2524".

FIG. 8 shows the amino acid sequence (SEQ ID NO:16) derived from the coding sequence of SEQ ID NO:15 shown in FIG. 7.

FIG. 9 shows a nucleotide sequence (SEQ ID NO:17) of a native sequence PRO1890 cDNA, wherein SEQ ID NO:17 is a clone designated herein as "DNA79230-2525".

FIG. 10 shows the amino acid sequence (SEQ ID NO:18) derived from the coding sequence of SEQ ID NO:17 shown in FIG. 9.

FIG. 11 shows a nucleotide sequence (SEQ ID NO:22) of a native sequence PRO1887 cDNA, wherein SEQ ID NO:22 is a clone designated herein as "DNA79862-2522".

FIG. 12 shows the amino acid sequence (SEQ ID NO:23) derived from the coding sequence of SEQ ID NO:22 shown in FIG. 11.

FIG. 13 shows a nucleotide sequence (SEQ ID NO:28) of a native sequence PRO1785 cDNA, wherein SEQ ID NO:28 is a clone designated herein as "DNA80136-2503".

FIG. 14 shows the amino acid sequence (SEQ ID NO:29) derived from the coding sequence of SEQ ID NO:28 shown in FIG. 13.

FIG. 15 shows a nucleotide sequence (SEQ ID NO:34) of a native sequence PRO4353 cDNA, wherein SEQ ID NO:34 is a clone designated herein as "DNA80145-2594".

FIG. 16 shows the amino acid sequence (SEQ ID NO:35) derived from the coding sequence of SEQ ID NO:34 shown in FIG. 15.

FIG. 17 shows a nucleotide sequence (SEQ ID NO:39) of a native sequence PRO4357 cDNA, wherein SEQ ID NO:39 is a clone designated herein as "DNA84917-2597".

FIG. 18 shows the amino acid sequence (SEQ ID NO:40) derived from the coding sequence of SEQ ID NO:39 shown in FIG. 17.

FIG. 19 shows a nucleotide sequence (SEQ ID NO:44) of a native sequence PRO4405 cDNA, wherein SEQ ID NO:44 is a clone designated herein as "DNA84920-2614".

FIG. 20 shows the amino acid sequence (SEQ ID NO:45) derived from the coding sequence of SEQ ID NO:44 shown in FIG. 19.

FIG. 21 shows a nucleotide sequence (SEQ ID NO:49) of a native sequence PRO4356 cDNA, wherein SEQ ID NO:49 is a clone designated herein as "DNA86576-2595".

FIG. 22 shows the amino acid sequence (SEQ ID NO:50) derived from the coding sequence of SEQ ID NO:49 shown in FIG. 21.

FIG. 23 shows a nucleotide sequence (SEQ ID NO:51) of a native sequence PRO4352 cDNA, wherein SEQ ID NO:51 is a clone designated herein as "DNA87976-2593".

FIG. 24 shows the amino acid sequence (SEQ ID NO:52) derived from the coding sequence of SEQ ID NO:51 shown in FIG. 23.

FIG. 25 shows a nucleotide sequence (SEQ ID NO:56) of a native sequence PRO4380 cDNA, wherein SEQ ID NO:56 is a clone designated herein as "DNA92234-2602".

FIG. 26 shows the amino acid sequence (SEQ ID NO:57) derived from the coding sequence of SEQ ID NO:56 shown in FIG. 25.

FIG. 27 shows a nucleotide sequence (SEQ ID NO:58) of a native sequence PRO4354 cDNA, wherein SEQ ID NO:58 is a clone designated herein as "DNA92256-2596".

FIG. 28 shows the amino acid sequence (SEQ ID NO:59) derived from the coding sequence of SEQ ID NO:58 shown in FIG. 27.

FIG. 29 shows a nucleotide sequence (SEQ ID NO:60) of a native sequence PRO4408 cDNA, wherein SEQ ID NO:60 is a clone designated herein as "DNA92274-2617".

FIG. 30 shows the amino acid sequence (SEQ ID NO:61) derived from the coding sequence of SEQ ID NO:60 shown in FIG. 29.

FIG. 31 shows a nucleotide sequence (SEQ ID NO:62) of a native sequence PRO5737 cDNA, wherein SEQ ID NO:62 is a clone designated herein as "DNA92929-2534".

FIG. 32 shows the amino acid sequence (SEQ ID NO:63) derived from the coding sequence of SEQ ID NO:62 shown in FIG. 31.

FIG. 33 shows a nucleotide sequence (SEQ ID NO:64) of a native sequence PRO4425 cDNA, wherein SEQ ID NO:64 is a clone designated herein as "DNA93011-2637".

FIG. 34 shows the amino acid sequence (SEQ ID NO:65) derived from the coding sequence of SEQ ID NO:64 shown in FIG. 33.

FIG. 35 shows a nucleotide sequence (SEQ ID NO:66) of a native sequence PRO5990 cDNA, wherein SEQ ID NO:66 is a clone designated herein as "DNA96042-2682".

FIG. 36 shows the amino acid sequence (SEQ ID NO:67) derived from the coding sequence of SEQ ID NO:66 shown in FIG. 35.

FIG. 37 shows a nucleotide sequence (SEQ ID NO:71) of a native sequence PRO6030 cDNA, wherein SEQ ID NO:71 is a clone designated herein as "DNA96850-2705".

FIG. 38 shows the amino acid sequence (SEQ ID NO:72) derived from the coding sequence of SEQ ID NO:71 shown in FIG. 37.

FIG. 39 shows a nucleotide sequence (SEQ ID NO:73) of a native sequence PRO4424 cDNA, wherein SEQ ID NO:73 is a clone designated herein as "DNA96857-2636".

FIG. 40 shows the amino acid sequence (SEQ ID NO:74) derived from the coding sequence of SEQ ID NO:73 shown in FIG. 39.

FIG. 41 shows a nucleotide sequence (SEQ ID NO:75) of a native sequence PRO4422 cDNA, wherein SEQ ID NO:75 is a clone designated herein as "DNA96867-2620".

FIG. 42 shows the amino acid sequence (SEQ ID NO:76) derived from the coding sequence of SEQ ID NO:75 shown in FIG. 41.

FIG. 43 shows a nucleotide sequence (SEQ ID NO:77) of a native sequence PRO4430 cDNA, wherein SEQ ID NO:77 is a clone designated herein as "DNA96878-2626".

FIG. 44 shows the amino acid sequence (SEQ ID NO:78) derived from the coding sequence of SEQ ID NO:77 shown in FIG. 43.

FIG. 45 shows a nucleotide sequence (SEQ ID NO:79) of a native sequence PRO4499 cDNA, wherein SEQ ID NO:79 is a clone designated herein as "DNA96889-2641".

FIG. 46 shows the amino acid sequence (SEQ ID NO:80) derived from the coding sequence of SEQ ID NO:79 shown in FIG. 45.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1–6 (1997) and von Heinje et al., *Nucl. Acids. Res.* 14:4683–4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alter natively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered inder U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X, Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., Nucleic Acids Res. 25:3389–3402 (1997)). The NCBI-BLAST2 sequence comparison program may be downloaded from the National Institutes of Health website or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO polypeptide sequence as disclosed herein, a fill-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designaled "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., Methods in Enzymology 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypepticle-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., Nucleic Acids Res. 25:3389–3402 (1997)). The NCBI-BLAST2 sequence comparison program may be downloaded from the National Institutes of Health website or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

The term "positives", in the context of sequence comparison performed as described above, includes residues in the sequences compared that are not identical but have similar properties (e.g. as a result of conservative substitutions, see Table 6 below). For purposes herein, the % value of positives is determined by dividing (a) the number of amino acid residues scoring a positive value between the PRO polypeptide amino acid sequence of interest having a sequence derived from the native PRO polypeptide sequence and the comparison amino acid sequence of interest (i.e., the amino acid sequence against which the PRO polypeptide sequence is being compared) as determined in the BLOSUM62 matrix of WU-BLAST-2 by (b) the total number of amino acid residues of the PRO polypeptide of interest.

Unless specifically stated otherwise, the % value of positives is calculated as described in the immediately preceding paragraph. However, in the context of the amino acid sequence identity comparisons performed as described for ALIGN-2 and NCBI-BLAST-2 above, includes amino acid residues in the sequences compared that are not only identical, but also those that have similar properties. Amino acid residues that score a positive value to an amino acid residue of interest are those that are either identical to the amino acid residue of interest or are a preferred substitution (as defined in Table 6 below) of the amino acid residue of interest.

For amino acid sequence comparisons using ALIGN-2 or NCBI-BLAST2, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 or NCBI-BLAST2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substanially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5× SSC (0.75 M NaCl, 0.075 M sodium citrate), 50 mM sodium phosphate (pH 6.8), 0.1% sodium pyrophosphate, 5× Derhardt's solution, sonicated salmon sperm DNA (50 µg/ml), 0.1% SDS, and 10% dextran sulfate at 42° C., with washes at 42° C. in 0.2× SSC (sodium chloride/sodium citrate) and 50% formamide at 55° C., followed by a high-stringency wash consisting of 0.1× SSC containing EDTA at 55° C.

"Moderately stringent conditions" may be identified as described by Sambrook et al., *Molecular Cloning: A Laboratoiy Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5× SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1× SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10): 1057–1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and binding site. This region consists of a dimer of one heavy and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthum in *The Pharmacology of Monoclonal Antibodies*, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

Table 1

```
/*
 *
 * C-C increased from 12 to 15
 * Z is average of EQ
 * B is average of ND
 * match with stop is _M; stop-stop = 0; J (joker) match = 0
 */
define  _M     -8          /* value of a match with a stop */ int     _day[26][26] = {
/*      A  B  C  D  E  F  G  H  I  J  K  L  M  N  O  P  Q  R  S  T  U  V  W  X  Y  Z */
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0,-1,-7, 0,-5, 0},
/* H */ {-1, 1,-3, 1, 1,-2,-2, 6,-2, 0, 0,-2,-2, 2,_M, 0, 3, 2,-1,-1, 0,-2,-3, 0, 0, 2},
/* I */ {-1,-2,-2,-2,-2, 1,-3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0,_M, 0, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0,-2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M, 0,_M,_M,_M,_M,_M,_M,_M,_M,_M,_M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1,-5, 2, 2,-5,-1, 3,-2, 0, 1,-2,-1, 1,_M, 0, 4, 1,-1,-1, 0,-2,-5, 0,-4, 3},
/* R */ {-2, 0,-4,-1,-1,-4,-3, 2,-2, 0, 3,-3, 0, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0,-4,-4, 7,-5, 0,-1, 0,-4,-1,-2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};
```

Page 1 of day.h

Table 1 (cont')

```
/*
*/
#include <stdio.h>
include <ctype.h> define  MAXJMP   16      /* max jumps in a diag */
define  MAXGAP   24      /* don't continue to penalize gaps larger than this */
#define  JMPS     1024    /* max jmps in an path */
define  MX       4       /* save if there's at least MX-1 bases since last jmp */ define  DMAT     3       /* value of matching bases */
define  DMIS     0       /* penalty for mismatched bases */
#define  DINS0    8       /* penalty for a gap */
#define  DINS1    1       /* penalty per base */
#define  PINS0    8       /* penalty for a gap */
define  PINS1    4       /* penalty per residue */ struct jmp {
    short          n[MAXJMP];       /* size of jmp (neg for dely) */
    unsigned short x[MAXJMP];       /* base no. of jmp in seq x */
};                                  /* limits seq to 2^16 -1 */ struct diag {
    int       score;                /* score at last jmp */
    long      offset;               /* offset of prev block */
    short     ijmp;                 /* current jmp index */
    struct jmp jp;                  /* list of jmps */
};

struct path {
    int       spc;                  /* number of leading spaces */
    short     n[JMPS];              /* size of jmp (gap) */
    int       x[JMPS];              /* loc of jmp (last elem before gap) */
};

char      *ofile;                   /* output file name */
char      *namex[2];                /* seq names: getseqs() */
char      *prog;                    /* prog name for err msgs */
char      *seqx[2];                 /* seqs: getseqs() */
int       dmax;                     /* best diag: nw() */
int       dmax0;                    /* final diag */
int       dna;                      /* set if dna: main() */
int       endgaps;                  /* set if penalizing end gaps */
int       gapx, gapy;               /* total gaps in seqs */
int       len0, len1;               /* seq lens */
int       ngapx, ngapy;             /* total size of gaps */
int       smax;                     /* max score: nw() */
int       *xbm;                     /* bitmap for matching */
long      offset;                   /* current offset in jmp file */
struct diag *dx;                    /* holds diagonals */
struct path pp[2];                  /* holds path for seqs */ char      *calloc(), *malloc(), *index(), *strcpy();
char      *getseq(), *g_calloc();
```

Page 1 of nw.h

Table 1 (cont')

```
/* Needleman-Wunsch alignment program
 *
 * usage: progs file1 file2
 * where file1 and file2 are two dna or two protein sequences.
 * The sequences can be in upper- or lower-case an may contain ambiguity
 * Any lines beginning with ';', '>' or '<' are ignored
 * Max file length is 65535 (limited by unsigned short x in the jmp struct)
 * A sequence with 1/3 or more of its elements ACGTU is assumed to be DNA
 * Output is in the file "align.out"
 *
 * The program may create a tmp file in /tmp to hold info about traceback.
 * Original version developed under BSD 4.3 on a vax 8650
 */
include "nw.h"
#include "day.h"

static    _dbval[26] = {
          1,14,2,13,0,0,0,4,11,0,0,12,0,3,15,0,0,0,5,6,8,8,7,9,0,10,0
};

static    _pbval[26] = {
          1, 2|(1<<('D'-'A'))|(1<<('N'-'A')), 4, 8, 16, 32, 64,
          128, 256, 0xFFFFFFF, 1<<10, 1<<11, 1<<12, 1<<13, 1<<14,
          1<<15, 1<<16, 1<<17, 1<<18, 1<<19, 1<<20, 1<<21, 1<<22,
          1<<23, 1<<24, 1<<25|(1<<('E'-'A'))|(1<<('Q'-'A'))
};

main(ac, av)                                                                    main
         int     ac;
         char    *av[];
{
         prog = av[0];
         if (ac != 3) {
                  fprintf(stderr,"usage: %s file1 file2\n", prog);
                  fprintf(stderr,"where file1 and file2 are two dna or two protein sequences.\n");
                  fprintf(stderr,"The sequences can be in upper- or lower-case\n");
                  fprintf(stderr,"Any lines beginning with ';' or '<' are ignored\n");
                  fprintf(stderr,"Output is in the file \"align.out\"\n");
                  exit(1);
         }
         namex[0] = av[1];
         namex[1] = av[2];
         seqx[0] = getseq(namex[0], &len0);
         seqx[1] = getseq(namex[1], &len1);
         xbm = (dna)? _dbval : _pbval;

endgaps = 0;              /* 1 to penalize endgaps */
         ofile = "align.out";      /* output file */ nw();                     /* fill in the matrix, get the possible jmps */
         readjmps();               /* get the actual jmps */
         print();                  /* print stats, alignment */ cleanup(0);               /* unlink any tmp files */
}
```

Page 1 of nw.c

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()
{
        char       *px, *py;            /* seqs and ptrs */
        int        *ndely, *dely;       /* keep track of dely */
        int        ndelx, delx;         /* keep track of delx */
        int        *tmp;                /* for swapping row0, row1 */
        int        mis;                 /* score for each type */
        int        ins0, ins1;          /* insertion penalties */
        register   id;                  /* diagonal index */
        register   ij;                  /* jmp index */
        register   *col0, *col1;        /* score for curr, last row */
        register   xx, yy;              /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely", len1+1, sizeof(int));
        col0  = (int *)g_calloc("to get col0", len1+1, sizeof(int));
        col1  = (int *)g_calloc("to get col1", len1+1, sizeof(int));
        ins0 = (dna)? DINS0 : PINS0;
        ins1 = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;            /* Waterman Bull Math Biol 84 */
        }
        else
                for (yy = 1; yy <= len1; yy++)
                        dely[yy] = -ins0;

/* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Page 2 of nw.c

Table 1 (cont')

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

Page 3 of nw.c

Table 1 (cont')

...nw

```
                id = xx - yy + len1 - 1;
                if (mis > = delx && mis > = dely[yy])
                        col1[yy] = mis;
                else if (delx > = dely[yy]) {
                        col1[yy] = delx;
                        ij = dx[id].ijmp;
                        if (dx[id].jp.n[0] && (!dna || (ndelx > = MAXJMP
                           && xx > dx[id].jp.x[ij]+MX) || mis > dx[id].score+DINS0)) {
                                dx[id].ijmp++;
                                if (++ij > = MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;
                        if (dx[id].jp.n[0] && (!dna || (ndely[yy] > = MAXJMP
                           && xx > dx[id].jp.x[ij]+MX) || mis > dx[id].score+DINS0)) {
                                dx[id].ijmp++;
                                if (++ij > = MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = -ndely[yy];
                        dx[id].jp.x[ij] = xx;
                        dx[id].score = dely[yy];
                }
                if (xx == len0 && yy < len1) {
                        /* last col
                        */
                        if (endgaps)
                                col1[yy] -= ins0+ins1*(len1-yy);
                        if (col1[yy] > smax) {
                                smax = col1[yy];
                                dmax = id;
                        }
                }
        }
        if (endgaps && xx < len0)
                col1[yy-1] -= ins0+ins1*(len0-xx);
        if (col1[yy-1] > smax) {
                smax = col1[yy-1];
                dmax = id;
        }
        tmp = col0; col0 = col1; col1 = tmp;
    }
    (void) free((char *)ndely);
    (void) free((char *)dely);
    (void) free((char *)col0);
    (void) free((char *)col1);
}
```

Page 4 of nw.c

Table 1 (cont')

```
/*
 *
 * print() -- only routine visible outside this module
 *
 * static:
 * getmat() -- trace back best path, count matches: print()
 * pr_align() -- print alignment of described in array p[]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */ include "nw.h"

define SPC     3
#define P_LINE  256     /* maximum output line */
define P_SPC   3       /* space between name or num and seq */ extern  _day[26][26];
int     olen;           /* set output line length */
FILE    *fx;            /* output file */ print()                                                         print
{
        int     lx, ly, firstgap, lastgap;      /* overlap */ if ((fx = fopen(ofile, "w")) == 0) {
                fprintf(stderr,"%s: can't write %s\n", prog, ofile);
                cleanup(1);
        }
        fprintf(fx, " <first sequence: %s (length = %d)\n", namex[0], len0);
        fprintf(fx, " <second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) {         /* trailing gap in x */
                lastgap = len0 - dmax0 -1;
                lx -= lastgap;
        }
        else if (dmax0 > len0 - 1) {    /* trailing gap in y */
                lastgap = dmax0 - (len0 - 1);
                ly -= lastgap;
        }
        getmat(lx, ly, firstgap, lastgap);
        pr_align();
}
```

Page 1 of nwprint.c

Table 1 (cont')

```
/*
 * trace back the best path, count matches
 */
static
getmat(lx, ly, firstgap, lastgap)
        int     lx, ly;                 /* "core" (minus endgaps) */
        int     firstgap, lastgap;      /* leading trailing overlap */
{
        int     nm, i0, i1, siz0, siz1;
        char    outx[32];
        double  pct;
        register n0, n1;
        register char *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, " <%d match%s in an overlap of %d: %.2f percent similarity\n",
                nm, (nm == 1)? "" : "es", lx, pct);
``` getmat

Page 2 of nwprint.c

Table 1 (cont')

...getmat

```
        fprintf(fx, "<gaps in first sequence: %d", gapx);
        if (gapx) {
                (void) sprintf(outx, " (%d %s%s)",
                        ngapx, (dna)? "base":"residue", (ngapx == 1)? "":"s");
                fprintf(fx,"%s", outx);
        } fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
} static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars() */

/*
* print alignment of described in struct path pp[]
*/
static
pr_align()
{
        int             nn;     /* char count */
        int             more;
        register        i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
                ps[i] = seqx[i];
                po[i] = out[i];
        }
``` pr_align

Page 3 of nwprint.c

Table 1 (cont')

```
                for (nn = nm = 0, more = 1; more; ) {                        ...pr_align
                    for (i = more = 0; i < 2; i++) {
                        /*
                         * do we have more of this sequence?
                         */
                        if (!*ps[i])
                            continue;
                        more++;

if (pp[i].spc) {        /* leading space */
                            *po[i]++ = ' ';
                            pp[i].spc--;
                        }
                        else if (siz[i]) {      /* in a gap */
                            *po[i]++ = '-';
                            siz[i]--;
                        }
                        else {                  /* we're putting a seq element
                                                 */
                            *po[i] = *ps[i];
                            if (islower(*ps[i]))
                                *ps[i] = toupper(*ps[i]);
                            po[i]++;
                            ps[i]++;

/*
                             * are we at next gap for this seq?
                             */
                            if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                    siz[i] += pp[i].n[ij[i]++];
                            }
                            ni[i]++;
                        }
                    }
                    if (++nn == olen || !more && nn) {
                        dumpblock();
                        for (i = 0; i < 2; i++)
                            po[i] = out[i];
                        nn = 0;
                    }
                }
            }
            /*
             * dump a block of lines, including numbers, stars: pr_align()
             */
            static                                                           dumpblock
            dumpblock()
            {
                register i;

for (i = 0; i < 2; i++)
                    *po[i]-- = '\0';
```

Page 4 of nwprint.c

Table 1 (cont')

...dumpblock

```
            (void) putc('\n', fx);
            for (i = 0; i < 2; i++) {
 5                  if (*out[i] && (*out[i] != ' ' || *(po[i]) != ' ')) {
                        if (i == 0)
                            nums(i);
                        if (i == 0 && *out[1])
                            stars();
10                      putline(i);
                        if (i == 0 && *out[1])
                            fprintf(fx, star);
                        if (i == 1)
                            nums(i);
15                  }
            }
      }

/*
20     * put out a number line: dumpblock()
       */
      static
      nums(ix)                                              nums
            int     ix;      /* index in out[] holding seq line */
25    {
            char            nline[P_LINE];
            register        i, j;
            register char   *pn, *px, *py;

30          for (pn = nline, i = 0; i < lmax+P_SPC; i++, pn++)
                  *pn = ' ';
            for (i = nc[ix], py = out[ix]; *py; py++, pn++) {
                  if (*py == ' ' || *py == '-')
                        *pn = ' ';
35                else {
                        if (i%10 == 0 || (i == 1 && nc[ix] != 1)) {
                            j = (i < 0)? -i : i;
                            for (px = pn; j; j /= 10, px--)
                                *px = j%10 + '0';
40                          if (i < 0)
                                *px = '-';
                        }
                        else
                            *pn = ' ';
45                      i++;
                  }
            }
            *pn = '\0';
            nc[ix] = i;
50          for (pn = nline; *pn; pn++)
                  (void) putc(*pn, fx);
            (void) putc('\n', fx);
      }

55    /*
       * put out a line (name, [num], seq, [num]): dumpblock()
       */
      static
      putline(ix)                                           putline
60          int     ix;
      {
```

Page 5 of nwprint.c

Table 1 (cont')

...putline

```
        int         i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()                                                                 stars
{
        int         i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

Page 6 of nwprint.c

Table 1 (cont')

```
/*
 * strip path or prefix from pn, return len: pr_align()
 */
static
stripname(pn)                                                    stripname
    char      *pn;      /* file name (may be path) */
{
    register char    *px, *py;

py = 0;
    for (px = pn; *px; px++)
        if (*px == '/')
            py = px + 1;
    if (py)
        (void) strcpy(pn, py);
    return(strlen(pn));

}
```

Page 7 of nwprint.c

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char     *jname = "/tmp/homgXXXXXX";       /* tmp file for jmps */
FILE     *fj;

int      cleanup();                        /* cleanup tmp file */
long     lseek();

/*
 * remove any tmp file if we blow
 */
cleanup(i)                                                           cleanup
         int     i;
{
         if (fj)
                 (void) unlink(jname);
         exit(i);
}

/*
 * read, return ptr to seq, set dna, len, maxlen
 * skip lines starting with ';', '<', or '>'
 * seq in upper or lower case
 */
char    *
getseq(file, len)                                                    getseq
         char    *file;    /* file name */
         int     *len;     /* seq len */
{
         char           line[1024], *pseq;
         register char  *px, *py;
         int            natgc, tlen;
         FILE           *fp;

if ((fp = fopen(file,"r")) == 0) {
                 fprintf(stderr," %s: can't read %s\n", prog, file);
                 exit(1);
         }
         tlen = natgc = 0;
         while (fgets(line, 1024, fp)) {
                 if (*line == ';' || *line == '<' || *line == '>')
                         continue;
                 for (px = line; *px != '\n'; px++)
                         if (isupper(*px) || islower(*px))
                                 tlen++;
         }
         if ((pseq = malloc((unsigned)(tlen+6))) == 0) {
                 fprintf(stderr," %s: malloc() failed to get %d bytes for %s\n", prog, tlen+6, file);
                 exit(1);
         }
         pseq[0] = pseq[1] = pseq[2] = pseq[3] = '\0';
```

Page 1 of nwsubr.c

Table 1 (cont')

...getseq

```
                py = pseq + 4;
                *len = tlen;
                rewind(fp);
                while (fgets(line, 1024, fp)) {
                        if (*line == ';' || *line == '<' || *line == '>')
                                continue;
                        for (px = line; *px != '\n'; px++) {
                                if (isupper(*px))
                                        *py++ = *px;
                                else if (islower(*px))
                                        *py++ = toupper(*px);
                                if (index("ATGCU",*(py-1)))
                                        natgc++;
                        }
                }
                *py++ = '\0';
                *py = '\0';
                (void) fclose(fp);
                dna = natgc > (tlen/3);
                return(pseq+4);
        }
        char    *
        g_calloc(msg, nx, sz)                                           g_calloc
                char    *msg;           /* program, calling routine */
                int     nx, sz;         /* number and size of elements */
        {
                char    *px, *calloc();

if ((px = calloc((unsigned)nx, (unsigned)sz)) == 0) {
                        if (*msg) {
                                fprintf(stderr, "%s: g_calloc() failed %s (n=%d, sz=%d)\n", prog, msg, nx, sz);
                                exit(1);
                        }
                }
                return(px);
        }
        /*
         * get final jmps from dx[] or tmp file, set pp[], reset dmax: main()
         */
        readjmps()                                                      readjmps
        {
                int     fd = -1;
                int     siz, i0, i1;
                register i, j, xx;

if (fj) {
                        (void) fclose(fj);
                        if ((fd = open(jname, O_RDONLY, 0)) < 0) {
                                fprintf(stderr, "%s: can't open() %s\n", prog, jname);
                                cleanup(1);
                        }
                }
                for (i = i0 = i1 = 0, dmax0 = dmax, xx = len0; ; i++) {
                        while (1) {
                                for (j = dx[dmax].ijmp; j >= 0 && dx[dmax].jp.x[j] >= xx; j--)
                                        ;
```

Page 2 of nwsubr.c

Table 1 (cont')

...readjmps

```
                if (j < 0 && dx[dmax].offset && fj) {
                        (void) lseek(fd, dx[dmax].offset, 0);
                        (void) read(fd, (char *)&dx[dmax].jp, sizeof(struct jmp));
                        (void) read(fd, (char *)&dx[dmax].offset, sizeof(dx[dmax].offset));
                        dx[dmax].ijmp = MAXJMP-1;
                }
                else
                        break;
        }
        if (i >= JMPS) {
                fprintf(stderr, "%s: too many gaps in alignment\n", prog);
                cleanup(1);
        }
        if (j >= 0) {
                siz = dx[dmax].jp.n[j];
                xx  = dx[dmax].jp.x[j];
                dmax += siz;
                if (siz < 0) {              /* gap in second seq */
                        pp[1].n[i1] = -siz;
                        xx += siz;
                        /* id = xx - yy + len1 - 1
                        */
                        pp[1].x[i1] = xx - dmax + len1 - 1;
                        gapy++;
                        ngapy -= siz;
/* ignore MAXGAP when doing endgaps */
                        siz = (-siz < MAXGAP || endgaps)? -siz : MAXGAP;
                        i1++;
                }
                else if (siz > 0) {  /* gap in first seq */
                        pp[0].n[i0] = siz;
                        pp[0].x[i0] = xx;
                        gapx++;
                        ngapx += siz;
/* ignore MAXGAP when doing endgaps */
                        siz = (siz < MAXGAP || endgaps)? siz : MAXGAP;
                        i0++;
                }
        }
        else
                break;
}

/* reverse the order of jmps
*/
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
}
if (fd >= 0)
        (void) close(fd);
if (fj) {
        (void) unlink(jname);
        fj = 0;
        offset = 0;
}
}
```

Page 3 of nwsubr.c

Table 1 (cont')

```
/*
 * write a filled jmp struct offset of the prev one (if any): nw()
 */
writejmps(ix)                                                                          writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

Page 4 of nwsubr.c

TABLE 2

| PRO | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptides sequences as determined by ALIGN-2) divided by (the total number of amino acid residues of the PRO polypeptide) = 5 divided by 15 = 33.3%

TABLE 3

| PRO | XXXXXXXXXX | (Length = 10 amino acids) |
|---|---|---|
| Comparison Protein | XXXXXYYYYYYZZYZ | (Length = 15 amino acids) |

% amino acid sequence identity = (the number of identically matching amino acid residues between the two polypeptides sequences as determined by ALIGN-2) divided by (the total number of amino acid residues of the PRO polypeptide) = 5 divided by 10 = 50%

TABLE 4

| PRO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| PRO-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

1. Full-length PRO1484 Polypeptides

Using the WU-BLAST2 sequence alignment computer program, it has been found that a full-length native sequence PRO1484 (shown in FIG. 2 and SEQ ID NO:2) has certain amino acid sequence identity with a portion of the mouse adipocyte complement related protein (ACR3_MOUSE). Accordingly, it is presently believed that PRO1484 disclosed in the present application is a newly identified adipocyte complement-related protein homolog and may possess activity typical of that protein.

2. Full-length PRO4334 Polypeptides

Using WU-BLAST2 sequence alignment computer programs, it has been found that a full-length native sequence PRO4334 (shown in FIG. 4 and SEQ ID NO:9) has certain amino acid sequence identity with PC-1. Accordingly, it is presently believed that PRO4334 disclosed in the present application is a newly identified member of the PC-1 family and shares similar mechanisms.

3. Full-length PRO1122 Polypeptides

The present invention provides newly identified and isolated nucleotide sequences encoding polypeptides referred to in the present application as PRO1122. In particular, Applicants have identified and isolated cDNA encoding a PRO1122 polypeptide, as disclosed in further detail in the Examples below. Using BLAST and FastA sequence alignment computer programs, Applicants found that the PRO1122 polypeptide has sequence identity with CTLA-8. The amino acid sequence shows a region having sequence identity with IL-17. Accordingly, it is presently believed that PRO1122 polypeptide disclosed in the present application is a novel cytokine and thus may be involved in inflammation responses.

4. Full-length PRO1889 Polyeptides

Using the WU-BLAST2 sequence alignment computer program, it has been found that a portion of the full-length native sequence PRO1889 (shown in FIG. 8 and SEQ ID NO:16) has certain amino acid sequence identity with a portion of the human E48 antigen protein (HSE48ATGN_1). Accordingly, it is presently believed that PRO1889 disclosed in the present application is a newly identified E48 homolog and may possess activity or properties typical of the E48 protein.

5. Full-length PRO1890 Polypeptides

Using the WU-BLAST2 sequence alignment computer program, it has been found that a portion of the full-length native sequence PRO1890 (shown in FIG. 10 and SEQ ID NO:18) has certain amino acid sequence identity with a portion of the layilin protein (AF093673_1).

6. Full-length PRO1887 Polypeptides

Using WU-BLAST2 sequence alignment computer programs, it has been found that a full-length native sequence PRO1887 (FIG. 12; SEQ ID NO:23) has certain amino acid sequence identity with a mouse liver carboxylesterase precursor identified on the Dayhoff database as "ESTM_MOUSE". Accordingly, it is presently believed that PRO1887 disclosed in the present application is a newly identified member of the carboxylesterase family and may possess enzymatic activity typical of carboxylesterases.

7. Full-length PRO1785 Polypeptides

Using WU-BLAST2 sequence alignment computer programs, it has been found that a full-length native sequence PRO1785 (shown in FIG. 14 and SEQ ID NO:29) has certain amino acid sequence identity with glutathione peroxidase. Accordingly, it is presently believed that PRO1785 disclosed in the present application is a newly identified member of the peroxidase family and may possess antioxidant enzyme activity. Regulation of antioxidant activity is of interest in the treatment of cancer and aging.

8. Full-length PRO4353 Polypeptides

Using WU-BLAST2 sequence alignment computer programs, it has been found that a full-length native sequence PRO4353 (shown in FIG. 16 and SEQ ID NO:35) has certain amino acid sequence identity with semaphorin Z. Accordingly, it is presently believed that PRO4353 disclosed in the present application is a newly identified member of the semaphorin Z family and is involved in inhibition of nerve growth. PRO4353 can be used in assays to identify modulators of semaphorin Z, particularly inhibitors to promote central nerve regeneration.

9. Full-length PRO4357 Polypeptides

Using WU-BLAST2 sequence alignment computer programs, it has been found that a full-length native sequence PRO4357 (shown in FIG. 18 and SEQ ID NO:40) has certain amino acid sequence identity with 289 amino acids in accession number P_W48804.However, PRO4357 has an additional 213 amino acids at the N-terminus.

10. Full-length PRO4405 Polypeptides

As far as is known, the DNA84920-2614 sequence encodes a novel factor designated herein as PRO4405; using WU-BLAST2 sequence alignment computer programs, limited sequence identities to known proteins were revealed.

11. Full-length PRO4356 Polypeptides

Using WU-BLAST2 sequence alignment computer programs, it has been found that a full-length native sequence PRO4356 (shown in FIG. 22 and SEQ ID NO:50) has certain amino acid sequence identity with metastasis associated GPI-anchored protein. Accordingly, it is presently believed that PRO4356 disclosed in the present application is a newly identified member of this family and shares similar mechanisms.

12. Full-length PRO4352 Polyleptides

Using WU-BLAST2 sequence alignment computer programs, it has been found that a full-length native sequence PRO4352 (shown in FIG. 24 and SEQ ID NO:52) has certain amino acid sequence identity with protocadherin pc3 and protocadherin pc4. Accordingly, it is believed that PRO4352 is involved in cell adhesin and can be used in treatments regarding differentiation disorders, cell adhesin, neural receptor or skin disorders. Moreover, it can be used in screens to identify agonists and antagonists to treat such disorders.

13. Full-length PRO4380 Polypeptides

As far as is known, the DNA92234-2602 sequence encodes a novel factor designated herein as PRO4380; using WU-BLAST2 sequence alignment computer programs, limited sequence identities to proteins with known functions were revealed.

14. Full-length PRO4354 Polypeptides

As far as is known, the DNA92256-2596 sequence encodes a novel factor designated herein as PRO4354; using WU-BLAST2 sequence alignment computer programs, limited sequence identities to proteins with known functions were revealed.

15. Full-length PRO4408 Polypeptides

As far as is known, the DNA92274-2617 sequence encodes a novel factor designated herein as PRO4408; using WU-BLAST2 sequence alignment computer programs, limited sequence identities to known proteins were revealed.

16. Full-length PRO5737 Polypeptides

Using WU-BLAST2 sequence alignment computer programs, it has been found that a full-length native sequence PRO5737 (shown in FIG. 32 and SEQ ID NO:63) has certain amino acid sequence identity with IL-1 and/or IL-1Ra. Accordingly, it is presently believed that PRO5737 disclosed in the present application is a newly identified member of this family and shares similar mechanisms.

17. Full-length PRO4425 Polypeptides

As far as is known, the DNA93011-2637 sequence encodes a novel factor designated herein as PRO4425; using WU-BLAST2 sequence alignment computer programs, PRO4425 showed homology to a protein in GenBank, accession number HGS_RE295, but is not identical.

18. Full-length PRO5990 Polypeptides

Using the ALIGN-2 sequence alignment computer program referenced above, it has been found that the full-length native sequence PRO5990 (shown in FIG. 36 and SEQ ID NO:67) has certain amino acid sequence identity with Secretogranin II (Dayhoff No. GEN14673). Accordingly, it is presently believed that the PRO5990 polypeptide disclosed in the present application is a newly identified member of the secretogranin protein family and may possess one or more biological and/or immunological activities or properties typical of that protein family.

19. Full-length PRO6030 Polypeptides

The DNA96850-2705 clone was isolated from a human library as described in the Examples below. As far as is known, the DNA96850-2705 nucleotide sequence encodes a novel factor designated herein as PRO6030; using the ALIGN-2 sequence alignment computer program, no significant sequence identities to any known proteins were revealed.

20. Full-length PRO4424 Polypeptides

As far as is known, the DNA96857-2636 sequence encodes a novel factor designated herein as PRO4424; using WU-BLAST2 sequence alignment computer programs, PRO4424 showed homology to a protein in GenBank, accession number HGS_A135, but is not identical thereto.

21. Full-length PRO4422 Polypeptides

Using WU-BLAST2 sequence alignment computer programs, it has been found that a full-length native sequence PRO4422 (shown in FIG. 42 and SEQ ID NO:76) has certain amino acid sequence identity with lysozyme g. Accordingly, it is presently believed that PRO4422 disclosed in the present application is a newly identified member of the lysozyme family and may have lysozyme activy.

22. Full-length PRO4430 Polypeptides

Using WU-BLAST2 sequence alignment computer programs, it has been found that a full-length native sequence PRO4430 (shown in FIG. 44 and SEQ ID NO:78) has certain amino acid sequence identity with the protein in GenBank accession number MMHC213L3__9. Accordingly, it is presently believed that PRO4430 disclosed in the present application is related to the GenBank protein and may share at least one similar mechanism.

23. Full-length PRO4499 Polypeptides

As far as is known, the DNA96889-2641 sequence encodes a novel factor designated herein as PRO4499; using WU-BLAST2 sequence alignment computer programs, limited sequence identities to known proteins were revealed.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gin, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081–1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivalization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glcosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., *Solid-Phase Peptide Synthesis*, W. H. Freeman Co., San Francisco, Calif. (1969); Merrifield, *J. Am. Chem. Soc.*, 85:2149–2154 (1963)]. *In vitro* protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO is to use PCR methodology [Sambrook et al., *supra*; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., *supra*.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., *supra*, to detect precursors and processing intermediates of mRNA that may not have been reverse-transcribed into cDNA.

2. Selection and Transformation of Host Cells

Host cells are transfected or transformed with expression or cloning vectors described herein for PRO production and cultural in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., *supra*.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., *supra*, or electroporation is generally used for prokaryotes. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology*, 52:456–457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76: 3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveronyces* hosts (U.S. Pat. No. 4,943,529; Fleer et al., *Bio/Technology*, 9:968–975 (1991)) such as, e.g.,

*K. lactis* (MW98-8C, CBS683, CBS4574; Louvencourt et al., *J. Bacteriol.*, 154(2):737–742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrislna et al., *J. Basic Microbiol.*, 28:265–278 [1988]); *Candida; Trichodenna reesia* (EP 244,234); *Neurospora crassa* (Case et al., *Proc. Natl. Acad. Sci. USA*, 76:5259–5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284–289 [1983]; Tilbum et al., *Gene*, 26:205–221 [1983]; Yelton et al., *Proc. Natl. Acad. Sci. USA*, 81: 1470–1474 [1984]) and *A. niger* (Kelly and Hynes, *EMBO J.*, 4:475–479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated PRO are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); human lung cells (W138, ATCC CCL 75); human liver cells (Hep G2,HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptilde, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces*α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub etal., *Proc. Natl. Acad. Sci. USA*, 77:4216(1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)]. Promoters for use in bacterial systems also will contain a Shine-Dalgamo (S.D.) sequence operably linked to the DNA encoding PRO.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (glolbin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., *Nature,* 293: 620–625 (1981); Mantei et al., *Nature,* 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypetide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Emnbryonic Stem Cells: A Practical Approach,* E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve *in vivo* synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes *in vivo*. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, erc. The currently preferred in vivo gene transfer techniques include transfection with viral (typically retroviral) vectors and viral coat protein-liposome mediated transfection (Dzau et al., *Trends in Biotechnology* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429–4432 (1987); and Wagner et al., *Proc. Natl. Acad. Sci. USA* 87, 3410–3414 (1990). For review of gene marking and gene therapy protocols see Anderson et al., *Science* 256, 808–813 (1992).

The PRO polypeptides described herein may also be employed as molecular weight markers for protein electrophoresis purposes and the isolated nucleic acid sequences may be used for recombinandy expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used for tissue typing, wherein the PRO polypeptides of the present invention may be differentially expressed in one tissue as compared to another. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96.

When in vivo administration of a PRO polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon-(rhIFN-), interleukin-2, and MN rgp120. Johnson et al., Nat. Med., 2:795–799 (1996); Yasuda, Biomed. Ther., 27:1221–1223 (1993); Hora et al., Bio/Technology. 8:755–758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439–462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1–41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245–246 (1989); Chien et al., Proc. Natl. Acad. Sci. USA, 88:9578–9582 (1991)) as disclosed by Chevray and Nathans, Proc. Natl. Acad. Sci. USA, 89: 5789–5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-*lacZ* reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor. In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469–471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines, on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Uses of the herein disclosed molecules may also be based upon the positive functional assay hits disclosed and described below.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., *supra*] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522–525 (1986); Riechmann et al., *Nature,* 332:323–329 (1988); and Presta, *Curr. Op. Struct. Biol.,* 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522–525 (1986); Riechmann et al., *Nature,* 332:323–327 (1988); Verhoeyen *Science,* 239:1534–15:36 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.,* 227:381 (1991); Marks et al., *J. Mol. Biol.,* 222:581 (1991)]. The techniques of Cole et al. and Boemer et al. are also available for the preparation of human monoclonal antibodies (Cole et al., *Monoclonal Antibodies and Cancer Therapy,* Alan R. Liss, p. 77 (1985) and Boerner et al., *J. Immunol.,* 147(1):86–95 (1991)]. Similarly, human antibodies can be made by introducing of human immunoglobulin loci into transgenic animals, e.g., nice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and [luszar, *Intern. Rev. Immunol.* 13 65–93 (1995).

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature,* 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.,* 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5): 1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994). Antibodies with more than two valencies are contemplated. For example, trispecific antibodies can be prepared. Tutt el al., *J. Immunol.* 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared *in vitro* using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191–1195 (1992) and Shopes, *J. Immunol.*, 148: 2918–2922 (1992). Homodimeric antibodies with enhanced anti-tumor activity may also be prepared using heterobifunctional cross-linkers as described in Wolff et al. *Cancer Research*, 53: 2560–2565 (1993). Alternatively, an antibody can be engineered that has dual Fc regions and may thereby have enhanced complement lysis and ADCC capabilities. See Stevenson et al., *Anti-Cancer Drug Design.* 3: 219–230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glularelde-hyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene tri-aminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286–288 (1982) via a disulfide-interchange reaction. A chemotherapeutic agent (such as Doxorubicin) is optionally contained within the liposome. See Gabizon et al., *J. National Cancer Inst.,* 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889–7893 (1993). The formation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences, supra.*

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO Antibodies

The anti-PRO antibodies of the invention have various utilities. For example, anti-PRO antibodies may be used in diagnostic assays for PRO, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques,* CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology* 266:460–480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100–1000 bp in length. The probe sequences are typically 40–55 bp in length. In some cases, additional oligonucleotides are synthesized when the consensus sequence is greater than about 1–1.5kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278–1280 (1991),) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI Tinkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY0.0 using reagents and protocols from Life Technologies (Super Script Plasmid System, referenced above). In this procedure the double stranded cDNA was sized to 500–1000 bp, Tinkered with blunt to NotI adaptors, cleaved with SfiI, and cloned into SfiI/NotI cleaved vector. pSST-AMY0.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37°

C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56–5A (ATCC-90785). This strain has the following genotype: MAT alpha, ura3–52, leu214 3, leu2–112, his3–11, his3–15, MAL$^+$, SUC$^+$, GAL$^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1 p–4p) or the complex formation of these proteins may also be preferably employed in combination with the amylase-expressing yeast.

Transformation was performed based on the protocol outlined by Gietz et al., *Nucl. Acid. Res.*, 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about $2\times10^6$ cells/ml (approx. $OD_{600}$=0.1) into fresh YEPD broth (500 ml) and regrown to $1\times10^7$ cells/ml (approx. $OD_{600}$=0.4–0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM Li$_2$OOCCH$_3$), and resuspended into LiAc/TE (2.5 ml).

Transformation took place by mixing the prepared cells (100 µl) with freshly denatured single stranded salmon testes DNA (Lofstrand Labs, Gaithersburg, Md.) and transforming DNA (1 µg, vol. <10 µl) in microfuge tubes. The mixture was mixed briefly by vortexing, then 40% PEG/TE (600 µl, 40% polyethylene glycol-4000, 10 mM Tris-HCl, 1 mM EDTA, 100 mM Li$_2$OOCCH$_3$, pH 7.5) was added. This mixture was gently mixed and incubated at 30° C. while agitating for 30 minutes. The cells were then heat shocked at 42° C. for 15 minutes, and the reactionvessel centrifuged in a microfuge at 12,000 rpm for 5–10 seconds, decanted and resuspended into TE (500 µl, 10 mM Tris-HCl, 1 mM EDTA pH 7.5) followed by recentrifugation. The cells were then diluted into TE (1 ml) and aliquots (200 µl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208–210 (1994). Transformants were grown at 30° C. for 2–3 days.

The detection of colonies secreting amylase was performed by including red starch in the selective growth media. Starch was coupled to the red dye (Reactive Red-120, Sigma) as per the procedure described by Biely et al., *Anal. Biochem.*, 172:176–179 (1988). The coupled starch was incorporated into the SCD-Ura agar plates at a final concentration of 0.15% (w/v), and was buffered with potassium phosphate to a pH of 7.0 (50–100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 µl) in a 96 well plate. At this time, the positive colonies were either frozen and stored for subsequent analysis or immediately amplified. An aliquot of cells (5 µl) was used as a template for the PCR reaction in a 25 µl volume containing: 0.5 µl Klentaq (Clontech, Palo Alto, Calif.); 4.0 µl 10 mM dNTP's (Perkin Elmer-Cetus); 2.5 µl Kentaq buffer (Clontech); 0.25 µl forward oligo 1; 0.25 reverse oligo 2; 12.5 µl distilled water. The sequence of the forward oligonucleotide 1 was:

(SEQ ID NO:3)
5'-TGTAAAACGACGGCCAGT<u>TAAATAGACCTGCAATTATTAATCT</u>-3'

The sequence of reverse oligonucleotide 2 was:

(SEQ ID NO:4)
5'-CAGGAAACAGCTATGACC<u>ACCTGCACACCTGCAAATCCATT</u>-3'

PCR was then performed as follows:

| a. | | Denature | 92° C., 5 minutes |
|---|---|---|---|
| b. | 3 cycles of: | Denature | 92° C., 30 seconds |
| | | Anneal | 59° C., 30 seconds |
| | | Extend | 72° C., 60 seconds |
| c. | 3 cycles of: | Denature | 92° C., 30 seconds |
| | | Anneal | 57° C., 30 seconds |
| | | Extend | 72° C., 60 seconds |
| d. | 25 cycles of: | Denature | 92° C., 30 seconds |
| | | Anneal | 55° C., 30 seconds |
| | | Extend | 72° C., 60 seconds |
| e. | | Hold | 4° C. |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused-cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., *supra*. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Example 4

Isolation of cDNA Clones Encoding Human PRO1484

A consensus DNA sequence was assembled relative to other EST sequences using phrap as described in Example 1 above. This consensus sequence is herein designated DNA39616. Based on the DNA39616 consensus sequence, oligonucleotides were synthesized: 1) to identify by PCR a cDNA library that contained the sequence of interest, and 2) for use as probes to isolate a clone of the full-length coding sequence for PRO1484.

PCR primers (forward and reverse) were synthesized:

```
forward PCR primer  (39616.f1)  5'-GCAACAATGGAGCCACTGGTCATG-3'  (SEQ ID NO:5)

reverse PCR primer  (39616.r1)  5'-GCAAAGGTGGAGAAGCGTTGGTGG-3'  (SEQ ID NO:6)
```

Additionally, a synthetic oligonucleotide hybridization probe was constructed from the consensus DNA39616 sequence which had the following nucleotide sequence

```
hybridization probe (39616.p1)
5'-CCCACTTCAGCAATCAGAACAGTGGGATTATCTTTCAGCAGTGTTTGAGACC-3'  (SEQ ID NO:7)
```

In order to screen several libraries for a source of a full-length clone, DNA from the libraries was screened by PCR amplification with the PCR primer pair identified above. A positive library was then used to isolate clones encoding the PRO1484 gene using the probe oligonucleotide and one of the PCR primers. RNA for construction of the cDNA libraries was isolated from human fetal kidney tissue.

DNA sequencing of the clones isolated as described above gave the full-length DNA sequence for PRO1484 (designated herein as DNA44686-1653 [FIG. 1, SEQ ID NO:1]; (UNQ753) and the derived protein sequence for PRO1484.

The entire nucleotide sequence of DNA44686-1653 is shown in FIG. 1 (SEQ ID NO:1). Clone DNA44686-1653 contains a single open reading frame with an apparent translational initiation site at nucleotide positions 77–79 and ending at the stop codon at nucleotide positions 815–817 (FIG. 1). The predicted polypeptide precursor is 246 amino acids long (FIG. 2). The full-length PRO1484 protein shown in FIG. 2 has an estimated molecular weight of about 26,994 daltons and a pI of about 6.43. Analysis of the full-length PRO1484 sequence shown in FIG. 2 (SEQ ID NO:2) evidences the presence of the following: a signal peptide from about amino acid 1 to about amino acid 22, a Clq domain signature sequence from about amino acid 137 to about amino acid 167 and various amino acid sequence blocks having homology to Clq domain-containing proteins as shown in FIG. 2. Clone DNA44686-1653 has been deposited with ATCC on Jan. 12, 1999 and is assigned ATCC deposit no. 203581.

An analysis of the Dayhoff database (version 35.45 SwissProt 35), using a WU-BLAST2 sequence alignment analysis of the full-length sequence shown in FIG. 2 (SEQ ID NO:2), evidenced significant homology between the PRO1484 amino acid sequence and the following Dayhoff sequences: P_WO9108, CA1A_HUMAN, C1QC_HUMAN, HUMC1QB2_1, COLE_LEPMA, MMU32107_1, CAS4_EPHMU, A57131, A41207 and CERL_RAT.

Example 5

Isolation of cDNA Clones Encoding Human PRO4334

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266: 460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56421.

In light of an observed sequence homology between the DNA56421 sequence and an EST sequence contained within the Incyte EST clone no. 3347532, the Incyte clone was purchased and the cDNA insert was obtained and sequenced. The sequence of this cDNA insert is shown in FIG. 3 and is herein designated as DNA59608-2577.

The full length clone shown in FIG. 3 contained a single open reading frame with an apparent translational initiation site at nucleotide positions 83-85 and ending at the stop codon found at nucleotide positions 1404–1406 (FIG. 3; SEQ ID NO:8). The predicted polypeptide precursor (FIG. 4, SEQ ID NO:9) is 440 amino acids long. PRO4334 has a calculated molecular weight of approximately 50,211 daltons and an estimated pI of approximately 8.29.

An analysis of the Dayhoff database (version 35.45 SwissProt 35), using a WU-BLAST2 sequence alignment analysis of the full-length sequence shown in FIG. 4 (SEQ ID NO:9), revealed homology between the PRO4334 amino acid sequence and the following Dayhoff sequences incorporated herein: AB020686_1, PC1_HUMAN, P_R79148, PC1_MOUSE, RNU78788_1, RATPDIB_1, P_W75859, AC005587_1, P_R86595 and PPD1_BOVIN.

Clone DNA5,9608-2577 was deposited with the ATCC on Mar. 23, 1999 and is assigned ATCC deposit no. 203870.

Example 6

Isolation of cDNA Clones Encoding Human PRO1122

An expressed sequence tag (EST) DNA database (LIFESEQ™, Incyte Pharmaceuticals, Palo Alto, Calif.) was searched and an EST was identified. The EST was Incyte 1347523 which is also called herein DNA49665. Based on the DNA49665 sequence, oligonucleotides were synthesized: 1) to identify by PCR a cDNA library that contained the sequence of interest, and 2) for use as probes to isolate a clone of the full-length coding sequence for PRO1122.

PCR primers (forward and reverse) were synthesized:

```
forward PCR primer  5'-ATCCACAGAAGCTGGCCTTCGCCG-3'; and   (SEQ ID NO:12)

reverse PCR primer  5'-GGGACGTGGATGAACTCGGTGTGG-3'.       (SEQ ID NO:13)
```

Additionally, a synthetic oligonucleotide hybridization probe was constructed which had the following nucleotide sequence:

```
hybridization probe                            (SEQ ID NO: 14)
5'-TATCCACAGAAGCTGGCCTTCGCCGAGTGCCTGTGCAGAG-3'
```

In order to screen several libraries for a source of a full-length clone, DNA from the libraries was screened by PCR amplification with the PCR primer pair identified above. A positive library was then used to isolate clones encoding the PRO1122 gene using the probe oligonucleotide and one of the PCR primers. RNA for construction of the cDNA libraries was isolated from human fetal kidney tissue (LIB228).

DNA sequencing of the clones isolated as described above gave the full-length DNA sequence for PRO1122 [herein designated as DNA62377-1381] (SEQ ID NO:10) and the derived protein sequence for PRO1122.

The entire nucleotide sequence of DNA62377-1381 is shown in FIG. 5 (SEQ ID NO:10). Clone DNA62377-1381 contains a single open reading frame with an apparent translational initiation site at nucleotide positions 50–52 and ending at the stop codon at nucleotide positions 641–643 of SEQ ID NO:10 (FIG. 5). The predicted polypeptide precursor is 197 amino acids long (FIG. 6). The full-length PRO1122 protein shown in FIG. 6 has an estimated molecular weight of about 21,765 daltons and a pI of about 8.53. Clone DNA62377-1381 has been deposited with ATCC on Dec. 22, 1998. It is understood that the deposited clone has the actual nucleic acid sequence and that the sequences provided herein are based on known sequencing techniques.

Analysis of the amino acid sequence of the full-length PRO1122 polypeptide suggests that it possesses similarity with CTLA-8 and IL-17, thereby indicating that PRO1122 may be a novel cytokine. More specifically, an analysis of the Dayhoff database (version 35.45 SwissProt 35) evidenced significant homology between the PRO1122 amino acid sequence and the following Dayhoff sequences, P-W13651, VG13_HSVSA and CEF25D1_1.

Example 7

Isolation of cDNA Clones Encoding Human PRO1889

A consensus DNA sequence was assembled relative to other EST sequences using phrap as described in Example 1 above. This consensus sequence is herein designated DNA49310. Based up an observed homology between the DNA49310 consensus sequence and an EST contained within the Incyte EST clone no. 2779436, Incyte EST clone no. 2779436 was purchased and its insert obtained and sequenced. The sequence of that insert is shown in FIG. 7 and is herein designated DNA77623-2524.

The entire nucleotide sequence of DNA77623-2524 is shown in FIG. 7 (SEQ ID NO:15). Clone DNA77623-2524 contains a single open reading frame with an apparent translational initiation site at nucleotide positions 39–41 and ending at the stop codon at nucleotide positions 330–332 (FIG. 7). The predicted polypeptide precursor is 97 amino acids long (FIG. 8). The full-length PRO1889 protein shown in FIG. 8 has an estimated molecular weight of about 10,160 daltons and a pI of about 6.56. Analysis of the full-length PRO1889 sequence shown in FIG. 8 (SEQ ID NO:16) evidences the presence of the following: a signal peptide from about amino acid 1 to about amino acid 20, potential N-myristolation sites from about amino acid 6 to about amino acid 11 and from about amino acid 33 to about amino acid 38 and prokaryotic membrane lipoprotein lipid attachment sites from about amino acid 24 to about amino acid 34 and from about amino acid 78 to about amino acid 88. Clone DNA77623-2524 has been deposited with ATCC on Dec. 22, 1998 and is assigned ATCC deposit no. 203546.

An analysis of the Dayhoff database (version 35.45 SwissProt 35), using a WU-BLAST2 sequence alignment analysis of the full-length sequence shown in FIG. 8 (SEQ ID NO:16), evidenced significant homology between the PRO1889 amino acid sequence and the following Dayhoff sequences: HSE48ATGN_1, P_W06292, AB012293_1, THYB_MOUSE, P_R70984, CHKSCA2A_1 , P_W61628, I48639, BMBUNGKP4_1 and UPAR_HUMAN.

Example 8

Isolation of cDNA Clones Encoding Human PRO1890

A consensus DNA sequence was assembled relative to other EST sequences using repeated cycles of BLAST and phrap as described in Example 1 above. This consensus sequence is herein designated DNA52162. Based on the DNA52162 consensus sequence, oligonucleotides were synthesized: 1) to identify by PCR a cDNA library that contained the sequence of interest, and 2) for use as probes to isolate a clone of the full-length coding sequence for PRO1890.

PCR primers (forward and reverse) were synthesized:

```
forward PCR primer (52162.f1) 5'-CACCAACCAACTGCCAATCCTGGC-3'    (SEQ ID NO:19)

reverse PCR primer (52162.r1) 5'-ACCACATTCTGATGGGTGTCTCCTGG-3'  (SEQ ID NO:20)
```

Additionally, a synthetic oligonucleotide hybridization probe was constructed from the consensus DNA52162 sequence which had the following nucleotide sequence

```
hybridization probe (5-2162.p1)
5'-GGGTCCCTACCTTTACCAGTGGAATGATGACAGGTGTAACATGAAGCAC-3'    (SEQ ID NO:21)
```

RNA for construction of the cDNA libraries was isolated from human fetal kidney tissue.

DNA sequencing of the clones isolated as described above gave the full-length DNA sequence for PRO1890 (designated herein as DNA79230-2525 [FIG. 9, SEQ ID NO:17]; (UNQ872) and the derived protein sequence for PRO1890.

The entire nucleotide sequence of DNA79230-2525 is shown in FIG. 9 (SEQ ID NO:17). Clone DNA79230-2525 contains a single open reading frame with an apparent translational initiation site at nucleotide positions 378–380 and ending at the stop codon at nucleotide positions 1197–1199 (FIG. 9). The predicted polypeptide precursor is 273 amino acids long (FIG. 10). The full-length PRO1890 protein shown in FIG. 10 has an estimated molecular weight of about 30,431 daltons and a pI of about 6.79. Analysis of the full-length PRO1890 sequence shown in FIG. 10 (SEQ ID NO:18) evidences the presence of the following: a signal peptide from about amino acid 1 to about amino acid 21, a transmembrane domain from about amino acid 214 to about amino acid 235, potential N-glycosylation sites from about amino acid 86 to about amino acid 89 and from about amino acid 255 to about amino acid 258, a cAMP- and cGMP-dependent protein kinase phosphorylation site from about amino acid 266 to about amino acid 269 and potential N-myristolation sites from about amino acid 27 to about amino acid 32, from about amino acid 66 to about amino acid 71, from about amino acid 91 to about amino acid 96, from about amino acid 93 to about amino acid 98, from about amino acid 102 to about amino acid 107, from about amino acid 109 to about amino acid 114, from about amino acid 140 to about amino acid 145 and from about amino acid 212 to about amino acid 217. Clone DNA79230-2525 has been deposited with ATCC on Dec. 22, 1998 and is assigned ATCC deposit no. 203549.

An analysis of the Dayhoff database (version 35.45 SwissProt 35), using a WU-BLAST2 sequence alignment analysis of the full-length sequence shown in FIG. 10 (SEQ ID NO:18), evidenced significant homology between the PRO1890 amino acid sequence and the following Dayhoff sequences: AF093673_1, P_W44118, AB014609_1, AC005254_1, AF026547_1, LEC2_MEGRO, PGCV_HUMAN, GEN12667, P_R06331 and CELF52E1_9.

Example 9

Isolation of cDNA Clones Encoding Human PRO1887

A consensus DNA sequence was assembled relative to other EST sequences using phrap as described in Example 1 above. This consensus sequence is designated herein "DNA43041". Based on this consensus sequence, oligonucleotides were synthesized: 1) to identify by PCR a cDNA library that contained the sequence of interest, and 2) for use as probes to isolate a clone of the full-length coding sequence for PRO1887.

PCR primers (forward and reverse) were synthesized:

```
forward PCR primer: 5'-GCAAAGCTCTGCCTCCTTGGCC-3'; and       (SEQ ID NO:24)

reverse PCR primers: 5'-GGGTGGACTGTGCTCTAATGGACGC-3',       (SEQ ID NO:25)
and

5'-CGTGGCACTGGGTTGATC-3'.                                    (SEQ ID NO:26)
```

Additionally, a synthetic oligonucleotide hybridization probe was constructed from the consensus DNA43041 sequence which had the following nucleotide sequence:

```
hybridization probe:
   5'-GATGCAGTTCTGGTCAGAGACGCTCCCCAGCAAGATACAACAGTG-3'.     (SEQ ID NO:27)
```

In order to screen several libraries for a source of a full-length clone, DNA from the libraries was screened by PCR amplification with the PCR primer pair identified above. A positive library was then used to isolate clones encoding the PRO1887 gene using the probe oligonucleotide and one of the PCR primers. RNA for construction of the cDNA libraries was isolated from human bone marrow.

DNA sequencing of the clones isolated as described above gave the full-length DNA sequence for PRO1887, designated herein as "DNA79862-2522" (FIG. 11; SEQ ID NO:22), and the derived protein sequence for PRO1887.

DNA79862-2522 is shown in FIG. 11 (SEQ ID NO:22). Clone DNA79862-2522 contains a single open reading frame with an apparent translational initiation site at nucleotide positions 6–8, and an apparent stop codon at nucleotide positions 1719–1721. The predicted polypeptide precursor is 571 amino acids long. The full-length PRO1887 protein shown in FIG. 12 has an estimated molecular weight of about 62,282 daltons and a pI of about 5.56. Additional features of the PRO1887 protein include a signal peptide at about amino acids 1–27; a transmembrane domain at about amino acids 226–245; a potential N-glycosylation site at about amino acids 105–108; N-myristoylation sites at about amino acids 10–15, 49–54, 62–67, 86–91, 150–155, 155–160, 162–167, 217–222, 227–232, 228–233, 232–237, 262–267, 257–362, and 461–466; a prokaryo membrane lipoprotein lipid attachment site at about amino acids 12–22; and a carboxylesterases type-B serine active site at about amino acids 216–231.

An analysis of the Dayhoff database (version 35.45 Swiss Prot 35), using a WU-BLAST2 sequence alignment analysis of the full-length sequence shown in FIG. 12 (SEQ ID NO:23), revealed significant homology between the PRO1887 amino acid sequence and Dayhoff sequence ESTM_ MOUSE. Homology was also found between the PRO1887 amino acid sequence and the following additional Dayhoff sequences: D50579_1, I61085, EST1_HUMAN, GEN12405, P_W39078, GEN13248, P_R58980, A31800_1, and P_R45189.

Clone DNA79862-2522 was deposited with the ATCC on Dec. 22, 1998, and is assigned ATCC deposit no. 203550.

Example 10

Isolation of cDNA clones Encoding Human PRO1785

A consensus DNA sequence was assembled relative to other EST sequences using phrap as described in Example 1 above. This consensus sequence is designated herein "DNA35718". Based on the DNA35718 consensus sequence, oligonucleotides were synthesized: 1) to identify by PCR a cDNA library that contained the sequence of interest, and 2) for use as probes to isolate a clone of the full-length coding sequence for PRO1785.

PCR primers (forward and reverse) were synthesized:

```
                                           (SEQ ID NO:30)
forward PCR primer: 5'-ATCCTCCAACATGGAGCCTCTTGC-3';

(SEQ ID NO:31)
forward PCR primer: 5'-GTATCTTGTCAACCCTGAGG-3';
and
```

Additionally, a synthetic oligonucleotide hybridization probe was constructed from the consensus DNA35718 sequence which had the following nucleotide sequence:

In order to screen several libraries for a source of a full-length clone, DNA from the libraries was screened by PCR amplification with the PCR primer pair identified above. A positive library was then used to isolate clones encoding the PRO1785 gene using the probe oligonucleotide and one of the PCR primers. RNA for construction of the cDNA libraries was isolated from human aortic endothelial cells.

DNA sequencing of the clones isolated as described above gave the full-length DNA sequence for PRO1785 (designated herein as DNA80136-2503 [FIG. 13, SEQ ID NO:28]; and the derived protein sequence for PRO1785.

The entire coding sequence of PRO1785 is shown in FIG. 13 (SEQ ID NO:28). Clone DNA80136-2503 contains a single open reading frame with an apparent translational initiation site at nucleotide positions 2-4 and an apparent stop codon at nucleotide positions 629–631 of SEQ ID NO:28. The predicted polypeptide precursor is 209 amino acids long. There is a signal peptide at about amino acids 1–31, a transmembrane domain at about amino acids 18–37 and a glutathione peroxidase signature at about amino acids 104–111 of SEQ ID NO:29. Clone DNA80136-2503 has been deposited with the ATCC and is assigned ATCC deposit no. 203541. The full-length PRO1785 protein shown in FIG. 14 has an estimated molecular weight of about 23,909 daltons and a pI of about 9.68.

An analysis of the Dayhoff database (version 35.45 SwissProt 35), using a NU-BLAST2 sequence aligment analysis of the full-length sequence shown in FIG. 14 (SEQ ID NO:29), revealed sequence identity between the PRO1785 amino acid sequence and the following Dayhoff sequences: GSHC_SCHMA, P_R44988, AB012395_1, GSHH_HUMAN, AC004151_3, BTUE_ECOLI, GSHC_HUMAN, P_R 89910, PWU88907_1 and D37916_1.

Example 11

Isolation of cDNA Clones Encoding Human PRO4353

A consensus DNA sequence was assembled relative to other EST sequences using repeated cycles of BLAST and phrap as described in Example 1 above. This consensus sequence is designated herein "DNA39482". Based on the DNA39482 consensus sequence, oligonucleotides were synthesized: 1) to identify by PCR a cDNA library that contained the sequence of interest, and 2) for use as probes to isolate a clone of the full-length coding sequence for PRO4353.

PCR primers (forward and reverse) were synthesized:

```
                                           (SEQ ID NO:36)
forward PCR primer: 5'-GAGGACCTACCGGCCGGACAG-3'
and (SEQ ID NO:37)
reverse PCR primer: 5'-ATACACCCCGAGTACTGCTGGCAG-3'.
```

Additionally, a synthetic oligonucleotide hybridization probe was constructed from the consensus DNA39482 sequence which had the following nucleotide sequence:

```
hybridization probe: 5'-AGGCAAAGTTTCACTAGTTGTAAACGTGGCCAGTGACTGCCAACTCACAG-3' (SEQ ID NO:33).
``` hybridization probe: 5'-AGACAGGGCAGCGGCTGCTGAGCTTGGAGCTGGACGCAGCTT-3' (SEQ ID NO:38).

In order to screen several libraries for a source of a full-length clone, DNA from the libraries was screened by PCR amplification with the PCR primer pair identified above. A positive library was then used to isolate clones encoding the PRO4353 gene using the probe oligonucleotide and one of the PCR primers. RNA for construction of the cDNA libraries was isolated from human aortic endothelial cells.

DNA sequencing of the clones isolated as described above gave the full-length DNA sequence for PRO4353 (designated herein as DNA80145-2594 [FIG. 15, SEQ ID NO:34]; and the derived protein sequence for PRO4353.

The entire coding sequence of PRO4353 is shown in FIG. 15 (SEQ ID NO:34). Clone DNA80145-2594 contains a single open reading frame with an apparent translational initiation site at nucleotide positions 19–21, and an apparent stop codon at nucleotide positions 2683–2685. The predicted polypeptide precursor is 888 amino acids long. Clone DNA80145-2594 has been deposited with ATCC and is assigned ATCC deposit no. 204-PTA. The full-length PRO4353 protein shown in FIG. 16 has an estimated molecular weight of about 95,285 daltons and a pI of about 8.89.

An analysis of the Dayhoff database (version 35.45 SwissProt 35), using a WU-BLAST2 sequence alignment analysis of the full-length sequence shown in FIG. 16 (SEQ ID NO:34), revealed homology between the PRO4353 amino acid sequence and the following Dayhoff sequences (sequences and related text incorporated herein): P_W19857, AB000776_1, P_W57260, JH0798, P_R71382, CEY54E 5B_1, I48747, MUSC1_1, P_R71383 and P_W63748.

Example 12

Isolation of cDNA Clones Encoding Human PRO4357

A consensus DNA sequence was assembled relative to other EST sequences using phrap as described in Example 1 above. This consensus sequence is designated herein "DNA80155". Based on the DNA80155 consensus sequence, oligonucleotides were synthesized: 1) to identify by PCR a cDNA library that contained the sequence of interest, and 2) for use as probes to isolate a clone of the full-length coding sequence for PRO4357.

PCR primers (forward and reverse) were synthesized:

In order to screen several libraries for a source of a full-length clone, DNA from the libraries was screened by PCR amplification with the PCR primer pair identified above. A positive library was then used to isolate clones encoding the PRO4357 gene using the probe oligonucleotide and one of the PCR primers. RNA for construction of the cDNA libraries was isolated from human aortic endothelial cells.

DNA sequencing of the clones isolated as described above gave the full-length DNA sequence for PRO4357; and the derived protein sequence for PRO4357.

The entire coding sequence of PRO4357 is shown in FIG. 17 (SEQ ID NO:39). Clone DNA84917-2597 contains a single open reading frame with an apparent translational initiation site at nucleotide positions 286–288, and an apparent stop codon at nucleotide positions 1792–1794. The predicted polypeptide precursor is 502 amino acids lorig. Clone DNA84917-2597 has been deposited with ATCC and is assigned ATCC deposit no. 203863. The full-length PRO4357 protein shown in FIG. 18 has an estimated molecular weight of about 58,043 daltons and a pi of about 7.94.

An analysis of the Dayhoff database (version 35.45 SwissProt 35), using a WU-BLAST2 sequence alignment analysis of the full-length sequence shown in FIG. 18 (SEQ ID NO:40), revealed homology between the PRO4357 amino acid sequence and the following Dayhoff sequences: P_W48804, AF003534_66, ATAC00466519, LPSA_BACNO, GELA_DICDI, EHU70560_1, AF089841_1, ABP2_HMAN, P_W19349 and A49551.

Example 13

Isolation of cDNA Clones Encoding Human PRO4405

A consensus DNA sequence was assembled relative to other EST sequences using repeated cycles of BLAST and phrap. This consensus sequence is designated herein "DNA80170". Based on the DNA80170 consensus sequence, oligonucleotides were synthesized: 1) to identify by PCR a cDNA library that contained the sequence of interest, and 2) for use as probes to isolate a clone of the full-length coding sequence for PRO4405.

forward PCR primer: 5'-GAAGGTGGAAATTAAATTCCAAGGGC-3' and (SEQ ID NO:41)

reverse PCR primer: 5'-CGATAAGCTGCTACAGTGCCATCG-3'.  (SEQ ID NO:42)

Additionally, a synthetic oligonucleotide hybridization probe was constructed from the consensus DNA80155 sequence which had the following nucleotide sequence:

hybridization probe: 5'-GTGACTGTCCTCTGCAAGATAGTGCAGCCTGGCTACGGGA-3' (SEQ ID NO:43).

PCR primers (forward and reverse) were synthesized:

```
forward PCR primer: 5'-CGGGACTTTCGCTACCTGTTGC-3' and      (SEQ ID NO:46)

reverse PCR primer: 5'-CATCATATTCCACAAAATGCTTTGGG-3'.     (SEQ ID NO:47)
```

Additionally, a synthetic oligonucleotide hybridization probe was constructed from the consensus sequence which had the following nucleotide sequence:

```
hybridization probe:
5'-CCTTCGGGGATTCTTCCCGGCTCCCTTCGTTCCTCTG-3'.     (SEQ ID NO:48)
```

In order to screen several libraries for a source of a full-length clone, DNA from the libraries was screened by PCR amplification with the PCR primer pair identified above. A positive library was then used to isolate clones encoding the PRO4405 gene using the probe oligonucleotide and one of the PCR primers. RNA for construction of the cDNA libraries was isolated from human fetal kidney.

DNA sequencing of the clones isolated as described above gave the full-length DNA sequence for PRO4405 (designated herein as DNA84920-2614 [FIG. 19, SEQ ID NO:44]; and the derived protein sequence for PRO4405.

The entire coding sequence of PRO4405 is shown in FIG. 19 (SEQ ID NO:44). Clone DNA84920-2614 contains a single open reading frame with an apparent translational initiation site at nucleotide positions 79–81, and an apparent stop codon at nucleotide positions 1009–1011. The predicted polypeptide precursor is 310 amino acids long. Clone DNA84920-2614 has been deposited with ATCC and is assigned ATCC deposit no. 203966. The full-length PRO4405 protein shown in FIG. 20 has an estimated molecular weight of about 33,875 daltons and a 131 of about 7.08.

An analysis of the Dayhoff database (version 35.45 SwissProt 35), using a WU-BLAST2 sequence alignment analysis of the full-length sequence shown in FIG. 20 (SEQ ID NO:45), revealed homology between the PRO4405 amino acid sequence and the following Dayhoff sequences (sequences and related text incorporated herein): YA93_SCHPO, S62432, YJG2_YEAST, AC004472_3, AB004539_7, S64782, CELC27A12_8, AF109219_1, AF086791_10, and P_W75859.

Example 14

Isolation of cDNA Clones Encoding Human PRO4356

A consensus DNA sequence was assembled relative to other EST sequences using phrap as described in Example 1 above. This consensus sequence is designated herein "DNA80200". Based upon an observed homology between the DNA80200 consensus sequence and an EST sequence contained within Merck EST clone 248287, Merck EST clone 248287 was purchased and its insert obtained and sequenced, thereby providing DNA86576-2595.

The entire coding sequence of PRO4356 is shown in FIG. 21 (SEQ ID NO:49). Clone DNA86576-2595 contains a single open reading frame with an apparent translational initiation site at nucleotide positions 55–57, and an apparent stop codon at nucleotide positions 808–810. The predicted polypeptide precursor is 251 amino acids long. Clone DNA86576-2595 has been deposited with ATCC and is assigned ATCC deposit no. 203868. The full-length PRO4356 protein shown in FIG. 22 has an estimated molecular weight of about 26,935 daltons and a pI of about 7.42.

An analysis of the Dayhoff database (version 35.45 Swiss Prot 35), using a WU-BLAST2 sequence alignment analysis of the full-length sequence shown in FIG. 22 (SEQ ID NO:50), revealed homology between the PRO4356 amino acid sequence and the following Dayhoff sequences incorporated herein: RNMAGPIAN_1, UPAR_BOVIN, S42152, AF007789_1, UPAR_RAT, UPAR_MOUSE, P_W31165, P_W31168, P_R44423 and P_W26359.

Example 15

Isolation of cDNA Clones Encoding Human PRO4352

A consensus DNA sequence was assembled relative to other EST sequences using phrap as described in Example 1 above. This consensus sequence is designated herein "DNA83397". Based on the DNA83397 consensus sequence, oligonucleotides were synthesized: 1) to identify by PCR a cDNA library that contained the sequence of interest, and 2) for use as probes to isolate a clone of the full-length coding sequence for PRO4352.

PCR primers (forward and reverse) were synthesized:

```
forward PCR primer: 5'-CTGGGGAGTGTCCTTGGCAGGTTC-3' and  (SEQ ID NO:53)

reverse PCR primer: 5'-CAGCATACAGGGCTCTTTAGGGCACAC-3'. (SEQ ID NO:54)
```

Additionally, a synthetic oligonucleotide hybridization probe was constructed from the consensus DNA83397 sequence which had the following nucleotide sequence:

```
hybridization probe:
5'-CGGTGACTGAGGAAACAGAGAAAGGATCCTTTGTGGTCAATCTGGC-3'  (SEQ ID NO:55).
```

In order to screen several libraries for a source of a full-length clone, DNA from the libraries was screened by PCR amplification with the PCR primer pair identified above. A positive library was then used to isolate clones encoding the PRO4352 gene using the probe oligonucleotide and one of the PCR primers. RNA for construction of the cDNA libraries was isolated from human fetal brain.

DNA sequencing of the clones isolated as described above gave the full-length DNA sequence for PRO4352 (designated herein as DNA87976-2593 [FIG. 23, SEQ ID NO:51]; and the derived protein sequence for PRO4352.

The entire coding sequence of PRO4352 is shown in FIG. 23 (SEQ ID NO:51). Clone DNA87976-2593 contains a single open reading frame with an apparent translational initiation site at nucleotide positions 179–181, and an apparent stop codon at nucleotide positions 2579–2581 of SEQ ID NO:51. The predicted polypeptide precursor is 800 amino acids long. Clone DNA87976-2593 has been deposited with ATCC and is assigned ATCC deposit no. 203888. The full-length PRO4352 protein shown in FIG. 24 has an estimated molecular weight of about 87,621 daltons and a pI of about 4.77.

An analysis of the Dayhoff database (version 35.45 SwissProt 35), using a WU-BLAST2 sequence alignment analysis of the full-length sequence shown in FIG. 24 (SEQ ID NO:52), revealed homology between the PRO4352 amino acid sequence and the following Dayhoff sequences: P_R86865, P_R86866, RATPCDH__1, AB011160__1, MMU88549__1, D86917__1, AB008179__1, P_R58907, HSHFATPRO__1, and AF031572__1.

Example 16

Isolation of cDNA Clones Encoding Human PRO4380

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266: 460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA79132. In light of DNA79132, DNA92234-2602 was identified.

The full length clone shown in FIG. 25 contained a single open reading frame with an apparent translational initiation site at nucleotide positions 201–203 and ending at the stop codon found at nucleotide positions 1722–1724 (FIG. 25; SEQ ID NO:56). The predicted polypeptide precursor (FIG. 26, SEQ ID NO:57) is 507 amino acids long. PRO4380 has a calculated molecular weight of approximately 56,692 daltons and an estimated pI of approximately 5.22.

An analysis of the Dayhoff database (version 35.45 SwissProt 35), using a WU-BLAST2 sequence alignment analysis of the full-length sequence shown in FIG. 26 (SEQ ID NO:57), revealed homology between the PRO4380 amino acid sequence and the following Dayhoff sequences (sequences and related text incorporated herein): CER11H6__1, S56299, D89150__1, G70870, S43914, LMO34616__5, LLU 78036__1, AF055904__2, P_W79066 and ARGE_E-COLI.

Clone DNA92234-2602 was deposited with the ATCC and is assigned ATCC deposit no. 203948.

Example 17

Isolation of cDNA Clones Encoding Human PRO4354

Use of the signal sequence algorithm described in Example 3 above allowed identification of an EST cluster (92909) sequence designated herein as DNA10195. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266: 460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated as DNA56063. In light of DNA56063, DNA92256-2596 was identified.

The full length clone shown in FIG. 27 contained a single open reading frame with an apparent translational initiation site at nucleotide positions 108–110 and ending at the stop codon found at nucleotide positions 852–854 (FIG. 27; SEQ ID NO:58). The predicted polypeptide precursor (FIG. 28, SEQ ID NO:59) is 248 amino acids long. PRO4354 has a calculated molecular weight of approximately 28,310 daltons and an estimated pI of approximately 4.63.

An analysis of the Dayhoff database (version 35.45 SwissProt 35), using a WU-BLAST2 sequence alignment analysis of the full-length sequence shown in FIG. 28 (SEQ ID NO:59), revealed homology between the PRO4354 amino acid sequence and the following Dayhoff sequences incorporated herein: HGS_RF300, CEVK04G11__2, CEC11H1__7, HSU80744__1, CEF09E8__2, RNAJ2967__1, DDICOI__1, AB020648__1, P_W33887 and A64319.

Clone DNA92256-2596 was deposited with the ATCC on Mar. 30, 1999 and is assigned ATCC deposit no.203891.

Example 18

Isolation of cDNA Clones Encoding Human PRO4408

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266: 460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA79298. In light of DNA79298, DNA92274-2617 was identified and sequenced in full.

The full length clone shown in FIG. 29 contained a single open reading frame with an apparent translational initiation site at nucleotide positions 89-91 and ending at the stop codon found at nucleotide positions 758–760 (FIG. 29; SEQ ID NO:60). The predicted polypeptide precursor (FIG. 30, SEQ ID NO:61) is 223 amino acids long. PRO4408 has a calculated molecular weight of approximately 25,402 daltons and an estimated pI of approximately 8.14.

An analysis of the Dayhoff database (version 35.45 SwissProt 35), using a WU-BLAST2 sequence alignment analysis of the full-length sequence shown in FIG. 30 (SEQ ID NO:61), revealed homology between the PRO4408 amino acid sequence and the following Dayhoff sequences: P_R27897, P_R49942, PBP_RAT, CELF40A3_3, D1ONCVO, PC4214, OV16_ONCVO, P_R27718, GEN10789, and OBA 5_DROME.

Clone DNA92274-2617 was deposited with the ATCC and is assigned ATCC deposit no. 203971.

Example 19

Isolation of cDNA Clones Encoding Human PRO5737

An expressed sequence tag (EST) DNA database (LIFESEQ®, Incyte Pharmaceuticals, Palo Alto, Calif.) was searched with a human interleukin-1 receptor antagonist (hIL-1Ra) sequence, and an EST sequence, designated herein as 1433156 was identified, which, showed homology with the hIL-1Ra known protein. EST clone 1433156 was purchased from Incyte Pharmaceuticals (Palo Alto, Calif.) and the cDNA insert was obtained and sequenced in its entirety, giving the DNA92929-2534 sequence.

The entire nucleotide sequence of DNA92929-2534 is shown in FIG. 31 (SEQ ID NO:62). Clone DNA92929-2534 contains a single open reading frame with an apparent translational initiation site at nucleotide positions 96–98 and a stop codon at nucleotide positions 498–500 (FIG. 31; SEQ ID NO:62). The predicted polypeptide precursor (hIL-1Ra2) is 134 amino acids long. The putative signal sequence extends from amino acid positions 1–17. Clone DNA92929-2534 was deposited with ATCC and was assigned ATCC deposit no. 203586. The full-length hIL-1ra2 protein shown in FIG. 32 has an estimated molecular weight of about 14,927 daltons and a pI of about 4.8.

Based on a BLAST and FastA sequence alignment analysis (using the ALIGN-2 computer program) of the full-length sequence, hIL-1Ra2 (FIG. 32, SEQ ID NO:63) shows significant amino acid sequence identity to hIL-1Rαβ protein. hIL-1Ra2 is believed to be a splice variant of hIL-1Rαβ.

databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266: 460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA81099.

In light of an observed sequence homology between the DNA81099 sequence and an EST sequence contained within the EST clone no. AA448744, the EST clone AA448744 was purchased from Merck and the cDNA insert was obtained and sequenced. The sequence of this cDNA insert is shown in FIG. 33 and is herein designated as DNA93011-2637.

The full length clone shown in FIG. 33 contained a single open reading frame with an apparent translational initiation site at nucleotide positions 27–29 and ending at the stop codon found at nucleotide positions 435–437 (FIG. 33; SEQ ID NO:64). The predicted polypeptide precursor (FIG. 34, SEQ ID NO:65) is 136 amino acids long. PRO4425 has a calculated molecular weight of approximately 15,577 daltons and an estimated pI of approximately 8.88.

An analysis of the Dayhoff database (version 35.45 SwissProt 35), using a WU-BLAST2 sequence alignment analysis of the full-length sequence shown in FIG. 34 (SEQ ID NO:65), revealed homology between the PRO4425 amino acid sequence and the following Dayhoff sequences: HGS_RE295, S44655, YOJ8_CAEEL, VBR1_CLVK, P_R39520, P_R65332, P_R39388, TGL4_HUMAN, YKAB_CAEEL, and S71105.

Clone DNA93011-2637 was deposited with the ATCC and is assigned ATCC deposit no. 20-PTA.

Example 21

Isolation of cDNA Clones Encoding Human PRO5990

A consensus DNA sequence was assembled relative to other EST sequences using phrap as described in Example 1 above. This consensus sequence is herein designated DNA86602. Based on the DNA86602 consensus sequence, oligonucleotides were synthesized: 1) to identify by PCR a cDNA library that contained the sequence of interest, and 2) for use as probes to isolate a clone of the full-length coding sequence for PRO5990.

PCR primers (forward and reverse) were synthesized:

```
forward PCR primer: 5'-CGTCACAGGAACTTCAGCACCC-3'    (SEQ ID NO:68)

reverse PCR primer: 5'-GTCTTGGCTTCCTCCAGGTTTGG-3'   (SEQ ID NO:69)
```

Example 20

Isolation of cDNA Clones Encoding Human PRO4425

Use of the signal sequence algorithm described in Example 3 above allowed identification of an EST cluster sequence from the Incyte database. This EST cluster sequence was then compared to a variety of expressed sequence tag (EST) databases which included public EST Additionally, a synthetic oligonucleotide hybridization probe was constructed from the consensus DNA86602 sequence which had the following nucleotide sequence

```
hybridization probe:                                 (SEQ ID NO:70)
5'-GGACAGCGCTCCCCTCTACCTGGAGACTTGACTCCCGC-3'
```

RNA for construction of the cDNA libraries was isolated from human fetal brain tissue.

DNA sequencing of the clones isolated as described above gave the full-length DNA sequence for a full-length PRO5990 polypeptide (designated herein as DNA96042-2682 [FIG. 35, SEQ ID NO:66]) and the derived protein sequence for that PRO5990 polypeptide.

The full length clone identified above contained a single open reading frame with an apparent translational initiation site at nucleotide positions 265–267 and a stop signal at nucleotide positions 1669–1671 (FIG. 35, SEQ ID NO:66). The predicted polypeptide precursor is 468 amino acids long, has a calculated molecular weight of approximately 53,005 daltons and an estimated pI of approximately 4.98. Analysis of the full-length PRO5990 sequence shown in FIG. 36 (SEQ ID NO:67) evidences the presence of a variety of important polypeptide domains as shown in FIG. 36, wherein the locations given for those important polypeptide domains are approximate as described above. Clone DNA96042-2682 has been deposited with ATCC on Jul. 20, 1999 and is assigned ATCC deposit no. 382-PTA.

An analysis of the Dayhoff database (version 35.45 SwissProt 35), using the ALIGN-2 sequence alignment analysis of the full-length sequence shown in FIG. 36 (SEQ ID NO:67), evidenced sequence identity between the PRO5990 amino acid sequence and the following Dayhoff sequences: SG3_MOUSE; SG3_RAT; GEN14673; ENHMHCAX__1; MYS2_DICDI; NFU43192__1; US01_YEAST; A56577; PFLSA 13__1; CELF12F3__3.

Example 22

Isolation of cDNA Clones Encoding Human PRO6030

Use of the signal sequence algorithm described in Example 3 above allowed identification of an EST cluster sequence from the LIFESEQ® (Incyte Pharmaceuticals, Palo Alto, Calif.) database, designated herein as CLU20900. This EST cluster sequence was then compared to a variety of expressed sequence tag (EST) databases which included public EST databases (e.g., Genbank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266: 460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA81229.

In light of an observed sequence homology between the DNA81229 sequence and an EST sequence encompassed within clone no. 4020130H1 from the Incyte (Incyte Pharmaceuticals, Palo Alto, Calif.) database, clone no. 4020130H1 was purchased and the cDNA insert was obtained and sequenced. It was found herein that that cDNA insert encoded a full-length protein. The sequence of this cDNA insert is shown in FIG. 37 and is herein designated as DNA96850-2705.

Clone DNA96850-2705 contains a single open reading frame with an apparent translational initiation site at nucleotide positions 60–62 and ending at the stop codon at nucleotide positions 1026–1028 (FIG. 37). The predicted polypeptide precursor is 322 amino acids long (FIG. 38). The full-length PRO6030 protein shown in FIG. 38 has an estimated molecular weight of about 34,793 daltons and a pI of about 6.34. Analysis of the full-length PRO6030 sequence shown in FIG. 38 (SEQ ID NO:72) evidences the presence of a variety of important polypeptide domains as shown in FIG. 38, wherein the locations given for those important polypeptide domains are approximate as described above. Clone DNA96850-2705 has been deposited with ATCC on Aug. 3, 1999 and is assigned ATCC Deposit No. 479-PTA.

An analysis of the Dayhoff database (version 35.45 SwissProt 35), using the ALIGN-2 sequence alignment analysis of the full-length sequence shown in FIG. 38 (SEQ ID NO:72), evidenced sequence identity between the PRO6030 amino acid sequence and the following Dayhoff sequences: AF059571__1; I38346; AF035835__1; P_W83138; P_R54714; P_R65166; P_P93995; BGP1 __$_{HUMAN;}$ $_P$_W06873; A43165__1.

Example 23

Isolation of cDNA Clones Encoding Human PRO4424

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266: 460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The extended consensus sequence obtained therefrom is designated DNA80820. In light of DNA80820, DNA96857-2636 was identified and sequenced.

The full length clone shown in FIG. 39 contained a single open reading frame with an apparent translational initiation site at nucleotide positions 52–54 and ending at the stop codon found at nucleotide positions 715–717 (FIG. 39; SEQ ID NO:73). The predicted polypeptide precursor (FIG. 40, SEQ ID NO:74) is 221 amino acids long. PRO1424 has a calculated molecular weight of approximately 23,598 daltons and an estimated pI of approximately 6.96.

An analysis of the Dayhoff database (version 35.45 SwissProt 35), using a WU-BLAST2 sequence alignment analysis of the full-length sequence shown in FIG. 40 (SEQ ID NO:74), revealed homology between the PRO4424 amino acid sequence and the following Dayhoff sequences: HGS_A135, JC5105, P_R88555, JC5106, P_R88556, CELR12E2__13, DMC34F3__8, ATG13D4__7, HGS_A204, S58331.

Clone DNA96857-2636 was deposited with the ATCC and is assigned ATCC deposit no. 17-PTA.

Example 24

Isolation of cDNA Clones Encoding Human PRO4422

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266: 460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA80134. In light of DNA80134, DNA96867-2620 was identified and sequenced in full.

The full length clone shown in FIG. 41 contained a single open reading frame with an apparent translational initiation site at nucleotide positions 318–320 and ending at the stop codon found at nucleotide positions 900–902 (FIG. 41; SEQ ID NO:75). The predicted polypeptide precursor (FIG. 42, SEQ ID NO:76) is 194 amino acids long. PRO4422 has a calculated molecular weight of approximately 21,431 daltons and an estimated pI of approximately 8.57.

An analysis of the Dayhoff database (version 35.45 SwissProt 35), using a WU-BLAST2 sequence alignment analysis of the full-length sequence shown in FIG. 42 (SEQ ID NO:76), revealed homology between the PRO4422 amino acid sequence and the following Dayhoff sequences: LYG_CHICK, LYG_CYGAT, LYG_ANSAN, LYG_STRCA, P_W69515, ATAC003680__7, ACCA_HAEIN, I64065, A 70853 and AF074611__71.

Clone DNA96867-2620 was deposited with the ATCC and is assigned ATCC deposit no. 203972.

Example 25

Isolation of cDNA Clones Encoding Human PRO4430

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266: 460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The extended consensus sequence obtained therefrom is herein designated DNA82380. In light of DNA82380, DNA96878-2626 was identified and sequenced.

The full length clone shown in FIG. 43 contained a single open reading frame with an apparent translational initiation site at nucleotide positions 56–58 and ending at the stop codon found at nucleotide positions 431–433 (FIG. 43; SEQ ID NO:77). The predicted polypeptide precursor (FIG. 44, SEQ ID NO:78) is 125 amino acids long. PRO4430 has a calculated molecular weight of approximately 13,821 daltons and an estimated pI of approximately 8.6.

An analysis of the Dayhoff database (version 35.45 SwissProt 35), using a WU-BLAST2 sequence alignment analysis of the full-length sequence shown in FIG. 44 (SEQ ID NO:78), revealed homology between the PRO4430 amino acid sequence and the following Dayhoff sequences: MMHC213L3__9, A45835, D45835, UPAR_MOUSE, AF043498__1, P_W62066, LY6C_MOUSE, LY6A_MOUSE, P_R58710, and P_R86315.

Clone DNA96878-2626 was deposited with the ATCC and is assigned ATCC deposit no. 23-PTA.

Example 26

Isolation of cDNA clones Encoding Human PRO4499

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266: 460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA81155. In light of DNA81155, DNA96889-2641 was identified and sequenced.

The full length clone shown in FIG. 45 contained a single open reading frame with an apparent translational initiation site at nucleotide positions 185–187 and ending at the stop codon found at nucleotide positions 1202–1204 (FIG. 45; SEQ ID NO:79). The predicted polypeptide precursor (FIG. 46, SEQ ID NO:80) is 339 amino acids long. PRO4499 has a calculated molecular weight of approximately 36,975 daltons and an estimated pI of approximately 7.85.

An analysis of the Dayhoff database (version 35.45 SwissProt 35), using a WU-BLAST2 sequence alignment analysis of the full-length sequence shown in FIG. 46 (SEQ ID NO:80), revealed homology between the PRO4499 amino acid sequence and the following Dayhoff sequences: CEF38B7__4, D70575, AF073993 __1, PNAPA__1, AF098967__1, AF007140__1, ROA3_HUMAN, E70969, CEY53C12B __5 and CEY53C12B__6.

Clone DNA964389-2641 was deposited with the ATCC and is assigned ATCC deposit no. 119-PTA.

Example 27

Use of PRO as a Hybridization Probe

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO can then be identified using standard techniques known in the art.

Example 28

Expression of PRO in *E. coli*

This example illustrates preparation of an unglycosylated form of PRO by recombinant expression in *E. coli*.

The DNA sequence encoding PRO is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO coding region, lambda transcriptional terminator, and an argU gene.

The ligation mixture is then used to transform a selected *E. coli* strain using the methods described in Sambrook et al., *supra*. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO may be expressed in *E. coli* in a poly-His tagged form, using the following procedure. The DNA encoding PRO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(laclq). Transformants are first grown in LB containing 50 mg/ml carbenicillin at 30° C. with shaking until an O.D.600 of 3–5 is reached. Cultures are then diluted 50–100 CRAP media (prepared by mixing 3.57 g $(NH_4)_2SO_4$, 0.71 g sodium citrate•2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20–30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6–10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3–5 volumes of metal chelate column buffer (6 M gulanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12–36 hours. The refolding reaction is quenched by the addition of TFA to a final concentration of 0.4% (pH of approximately 3). Before further purification of the protein, the solution is filtered through a 0.22 micron filter and acetonitrile is added to 2–10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO polypeptides disclosed herein were successfully expressed as described above.

Example 29

Expression of PRO in Mammalian Cells

This example illustrates preparation of a potentially glycosylated form of PRO by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., *supra*. The resulting vector is called pRK5-PRO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-PRO DNA is mixed with about 1 µg DNA encoding the VA RNA gene [Thimmappaya et al., Cell, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., Proc. Natl. Acad. Sci., 12:7575 (1981). 293 cells are grown to maximal density in a spinner flask and 700 µg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed PRO can then be concentrated and purified by any selected method, such as dialysis and/or column chromatography.

In another embodiment, PRO can be expressed in CHO cells. The pRK5-PRO can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-his tag into a Baculovirus expression vector. The poly-his tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by $Ni^{2+}$-chelate affinity chromatography.

PRO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., Nucl. Acids Res. 24:9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3\times10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1–2 days, the cells are transferred into a 250 mL spinner filled with 150 mL selective growth medium and incubated at 37° C. After another 2–3 days, 250 mL, 500 and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2\times10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 30

Expression of PRO in Yeast

The following method describes recombinant expression of PRO in yeast.

First, yeast expression vectors are constructed for intracellular production or secretion of PRO from the ADH2/GAPDH promoter. DNA encoding PRO and the promoter is inserted into suitable restriction enzyme sites in the selected plasmid to direct intracellular expression of PRO. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO can subsequently be isolated and purified by removing the yeast cells from the fermentation medium by centrifugation and then concentrating the medium using selected cartridge filters. The concentrate containing PRO may further be purified using selected column chromatography resins.

Many of the PRO polypeptides disclosed herein were successfully expressed as described above.

Example 31

Expression of PRO in Baculovirus-infected Insect Cells

The following method describes recombinant expression of PRO in Baculovirus-infected insect cells.

The sequence coding for PRO is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO can then be purified, for example, by $Ni^{2+}$-chelate affinity chromatography as follows. Extracts are prepared from recombinant virus-infected Sf9 cells as described by Rupert et al., *Nature*, 362:175–179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 32

Preparation of Antibodies that Bind PRO

This example illustrates preparation of monoclonal antibodies which can specifically bind PRO.

Techniques for producing the monoclonal antibodies are known in the art and are described, for instance, in Goding, *supra*. Immunogens that may be employed include purified PRO, fusion proteins containing PRO, and cells expressing recombinant PRO on the cell surface. Selection of the immunogen can be made by the skilled artisan without undue experimentation.

Mice, such as Balb/c, are immunized with the PRO immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic Balb/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 33

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2–3, or a high concentration of a chaotrope such as urea or thiocyanate ion), and PRO polypeptide is collected.

Example 34

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84103564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 35

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (c. f., Hodgson, *Bio/Technology*, 9: 19–21 (1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, usefull information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, *Biochemistry*. 31:7796–7801 (1992) or which act as inhibitors, agonists, or antagonists of native peptides as shown by Athauda et al., *J. Biochem.*, 113: 742–746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to x-ray crystallography.

Example 36

Chondrocyte Re-differentiation Assay (Assay 110)

This assay shows that certain polypeptides of the invention act to induce redifferentiation of chondrocytes, therefore, are expected to be useful for the treatment of various bone and/or cartilage disorders such as, for example, sports injuries and arthritis. The assay is performed as follows. Porcine chondrocytes are isolated by overnight collagenase digestion of articular cartilage of metacarpophalangeal-joints of 4–6 month old female pigs. The isolated cells are then seeded at 25,000 cells/cm$^2$ in Ham F-12 containing 10% FBS and 4 μg/ml gentamycin. The culture media is changed every third day and the cells are then seeded in 96 well plates at 5,000 cells/well in 100 μl of the same media without serum and 100 μl of the test PRO polypeptide, 5 nM staurosporin (positive control) or medium alone (negative control) is added to give a final volume of 200 μl/well. After 5 days of incubation at 37° C., a picture of each well is taken and the differentiation state of the chondrocytes is determined. A positive result in the assay occurs when the redifferentiation of the chondrocytes is determined to be more similar to the positive control than the negative control.

The following polypeptide tested positive in this assay: PRO1484, PRO1890, PRO1887, PRO4353, PRO4357, PRO4405, PRO5737 and PRO5990.

Example 37

Detection of Polypeptides That Affect Glucose or FFA Uptake in Skeletal Muscle (Assay 106)

This assay is designed to determine whether PRO polypeptides show the ability to affect glucose or FFA uptake by skeletal muscle cells. PRO polypeptides testing positive in this assay would be expected to be useful for the therapeutic treatment of disorders where either the stimulation or inhibition of glucose uptake by skeletal muscle would be beneficial including, for example, diabetes or hyper- or hypo-insulinemia.

In a 96 well format, PRO polypeptides to be assayed are added to primary rat differentiated skeletal muscle, and allowed to incubate overnight. Then fresh media with the PRO polypeptide and +/− insulin are added to the wells. The sample media is then monitored to determine glucose and FFA uptake by the skeletal muscle cells. The insulin will stimulate glucose and FFA uptake by the skeletal muscle, and insulin in media without the PRO polypeptide is used as a positive control, and a limit for scoring. As the PRO polypeptide being tested may either stimulate or inhibit glucose and FFA uptake, results are scored as positive in the assay if greater than 1.5 times or less than 0.5 times the insulin control.

The following PRO polypeptides tested positive as either stimulators or inhibitors of glucose and/or FFA uptake in this assay: ]PRO1484, PRO1122, PRO1889, PRO4357 and PRO4380.

Example 38

Detection of PRO Polypeptides That Affect Glucose or FFA Uptake by Primary Rat Adipocytes (Assay 94)

This assay is designed to determine whether PRO polypeptides show the ability to affect glucose or FFA uptake by adipocyte cells. PRO polypeptides testing positive in this assay would be expected to be useful for the therapeutic treatment of disorders where either the stimulation or inhibition of glucose uptake by adipocytes would be beneficial including, for example, obesity, diabetes or hyper- or hypo-insulinemia.

In a 96 well format, PRO polypeptides to be assayed are added to primary rat adipocytes, and allowed to incubate overnight. Samples are taken at 4 and 16 hours and assayed for glycerol, glucose and FFA uptake. After the 16 hour incubation, insulin is added to the media and allowed to incubate for 4 hours. At this time, a sample is taken and glycerol, glucose and FFA uptake is measured. Media containing insulin without the PRO polypeptide is used as a positive reference control. As the PRO polypeptide being tested may either stimulate or inhibit glucose and FFA uptake, results are scored as positive in the assay if greater than 1.5 times or less than 0.5 times the insulin control.

The following PRO polypeptides tested positive as stimulators of glucose and/or FFA uptake in this assay: PRO1890, PRO1785 and PRO4422.

The following PRO polypeptides tested positive as inhibitors of glucose and/or FFA uptake in this assay: PRO4334, PRO4425, PRO4424 and PRO4430.

Example 39

Induction of Pancreatic β-Cell Precursor Differentiation (Assay 89)

This assay shows that certain polypeptides of the invention act to induce differentiation of pancreatic β-cell precursor cells into mature pancreatic β-cells and, therefore, are useful for treating various insulin deficient states in mammals, including diabetes mellitus. The assay is performed as follows. The assay uses a primary culture of mouse fetal pancreatic cells and the primary readout is an alteration in the expression of markers that represent either β-cell precursors or mature β-cells. Marker expression is measured by real time quantitative PCR (RTQ-PCR); wherein the marker being evaluated is insulin.

The pancreata are dissected from E14 embryos (CD1 mice). The pancreata are then digested with collagenase/dispase in F12/DMEM at 37° C. for 40 to 60 minutes (collagenase/dispase, 1.37 mg/nil, Boehringer Mannheim, #1097113). The digestion is then neutralized with an equal volume of 5% BSA and the cells are washed once with RPMI1640. At day 1, the cells are seeded into 12-well tissue culture plates (pre-coated with laminin, 20 µg/ml in PBS, Boehringer Mannheim, #124317). Cells from pancreata from 1–2 embryos are distributed per well. The culture medium for this primary culture is 14F/1640. At day 2, the media is removed and the attached cells washed with RPMI/1640. Two mls of minimal media are added in addition to the protein to be tested. At day 4, the media is removed and RNA prepared from the cells and marker expression analyzed by real time quantitative RT-PCR. A protein is considered to be active in the assay if it increases the expression of the relevant β-cell marker as compared to untreated controls. 14F/1640 is RPMI1640 (Gibco) plus the following:

group A 1:1000
group B 1:1000
recombinant human insulin 10 µg/ml
Aprotinin (50 µg/ml) 1:2000 (Boehringer manheim #981532)
Bovine pituitary extract (BPE) 60 µg/ml
Gentamycin 100 ng/ml Group A: (in 10 ml PBS)
Transferrin, 100 mg (Sigma T2252)
Epidermal Growth Factor, 100 µg (BRL 100004)
Triiodothyronine, 10 µl of $5 \times 10^{-6}$ M (Sigma T5516)
Ethanolamine, 100 µl of $10^{-1}$ M (Sigma E0135)
Phosphoethalamine, 100 µl of $10^{-1}$ M (Sigma P0503)
Selenium, 4µL of $10^{-1}$ M (Aesar #12574)

Group C: (in 10 ml 100% ethanol)
Hydrocortisone, 2 µl of $5 \times 10^{-3}$ M (Sigma #H0135)
Progesterone, 100 µl of $1 \times 10^{-3}$ M (Sigma #P6149)
Forskolin, 500 µl of 20 mM (Calbiochem #44270)

Minimal media:
RPMI 1640 plus transferrin (10 µg/ml), insulin (1 µg/ml), gentamycin (100 ng/ml), aprotinin(50 µg/ml and BPE (15 µg/ml).

Defined media:
RPMI 1640 plus transferrin (10 µg/ml), insulin (1 µg/ml), gentamycin (100 ng/ml) and aprotinin (50 µg/ml).

The following polypeptides were positive in this assay: PRO4356.

Example 40

Fetal Hemoglobin Induction in an Erythroblastic Cell Line (Assay 107)

This assay is useful for screening PRO polypeptides for the ability to induce the switch from adult hemoglobin to fetal hemoglobin in an erythroblastic cell line. Molecules testing positive in this assay are expected to be useful for therapeutically treating various mammalian hemoglobin-associated disorders such as the various thalassemias. The assay is performed as follows. Erythroblastic cells are plated in standard growth medium at 1000 cells/well in a 96 well format. PRO polypeptides are added to the growth medium at a concentration of 0.2% or 2% and the cells are incubated for 5 days at 37° C. As a positive control, cells are treated with 100 µM hemin and as a negative control, the cells are untreated. After 5 days, cell lysates are prepared and analyzed for the expression of gamma globin (a fetal marker). A positive in the assay is a gamma globin level at least 2-fold above the negative control.

The following polypeptides tested positive in this assay: PRO4352, PRO4354, PRO4408, PRO6030 and PRO4499.

Example 41

Mouse Kidney Mesangial Cell Proliferation Assay (Assay 92)

This assay shows that certain polypeptides of the invention act to induce proliferation of mammalian kidney mesangial cells and, therefore, are useful for treating kidney disorders associated with decreased mesangial cell function such as Berger disease or other nephropathies associated with Schönlein-Henoch purpura, celiac disease, dermatitis herpetiformis or Crohn disease. The assay is performed as follows. On day one, mouse kidney mesangial cells are plated on a 96 well plate in growth media (3:1 mixture of Dulbecco's modified Eagle's medium and Ham's F12 medium, 95% fetal bovine serum, 5% supplemented with 14 mM HEPES) and grown overnight. On day 2, PRO polypeptides are diluted at 2 concentrations(1% and 0.1%) in serum-free medium and added to the cells. Control samples are serum-free medium alone. On day 4, 20 µl of the Cell Titer 96 Aqueous one solution reagent (Progema) was added to each well and the colormetric reaction was allowed to proceed for 2 hours. The absorbance (OD) is then measured at 490 nm. A positive in the assay is anything that gives an absorbance reading which is at least 15% above the control reading.

The following polypeptide tested positive in this assay: PRO4380, PRO4408 and PRO4425.

Deposit of Material

The following materials have been deposited with the American Type Culture Collection, 12301 Parklawn Drive, Rockville, Md., USA (ATCC):

TABLE 7

| Material | ATCC Dep. No. | Deposit Date |
| --- | --- | --- |
| DNA44686-1653 | 203581 | Jan. 12, 1999 |
| DNA59608-2577 | 203870 | Mar. 23, 1999 |
| DNA62377-1381 | 203552 | Dec. 22, 1998 |
| DNA77623-2524 | 203546 | Dec. 22, 1998 |
| DNA79230-2525 | 203549 | Dec. 22, 1998 |
| DNA79862-2522 | 203550 | Dec. 22, 1998 |
| DNA80136-2503 | 203541 | Dec. 15, 1998 |
| DNA80145-2594 | 204-PTA | Jun. 8, 1999 |
| DNA84917-2597 | 203863 | Mar. 23, 1999 |
| DNA84920-2614 | 203966 | Apr. 27, 1999 |
| DNA86576-2595 | 203868 | Mar. 23, 1999 |
| DNA87976-2593 | 203888 | Mar. 30, 1999 |
| DNA92234-2602 | 203948 | Apr. 20, 1999 |
| DNA92256-2596 | 203891 | Mar. 30, 1999 |
| DNA92274-2617 | 203971 | Apr. 27, 1999 |
| DNA92929-2534 | 203586 | Jan. 12, 1999 |
| DNA93011-2637 | 20-PTA | May 4, 1999 |
| DNA96042-2682 | 382-PTA | Jul. 20, 1999 |
| DNA96850-2705 | 479-PTA | Aug. 3, 1999 |
| DNA96857-2636 | 17-PTA | May 4, 1999 |
| DNA96867-2620 | 203972 | Apr. 27, 1999 |
| DNA96878-2626 | 23-PTA | May 4, 1999 |
| DNA96899-2641 | 119-PTA | May 25, 1999 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

APPENDIX A

I hereby claim the benefit under Title 35, United States Code, §119(e) of any United States provisional applications listed below:
1. No. 60/085579 Filed May 15, 1998
2. No. 60/112514 Filed Dec. 15, 1998
3. No. 60/113300 Filed Dec. 22, 1998
4. No. 60/113430 Filed Dec. 23, 1998
5. No. 60/113605 Filed Dec. 23, 1998
6. No. 60/113621 Filed Dec. 23, 1998
7. No. 60/114140 Filed Dec. 23, 1998
8. No. 60/115552 Filed Jan. 12, 1999
9. No. 60/116843 Filed Jan. 22, 1999
10. No. 60/125774 Filed Mar. 23, 1999
11. No. 60/125778 Filed Mar. 23, 1999
12. No. 60/125826 Filed Mar. 24, 1999
13. No. 60/127035 Filed Mar. 31, 1999
14. No. 60/127706 Filed Apr. 5, 1999
15. No. 60/129122 Filed Apr. 13, 1999
16. No. 60/130359 Filed Apr. 21, 1999
17. No. 60/131270 Filed Apr. 27, 1999
18. No. 60/131272 Filed Apr. 27, 1999
19. No. 60/131291 Filed Apr. 27, 1999
20. No. 60/132371 Filed May 4, 1999
21. No. 60/132379 Filed May 4, 1999
22. No. 60/132383 Filed May 4, 1999
23. No. 60/135750 Filed May 25, 1999
24. No. 60/138166 Filed Jun. 8, 1999
25. No. 60/144791 Filed Jul. 20, 1999
26. No. 60/146970 Filed Aug. 3, 1999
27. No. 60/162506 Filed Oct. 29, 1999

APPENDIX B

I hereby claim the benefit under Title 35, United States Code, §120 of any United States applications listed below:

US Filings
1. Ser. No. 09/311832 Filed May 14, 1999
2. Ser. No. 09/380142 Filed Aug. 25, 1999, now abandoned
3. Ser. No. 09/644848 Filed Aug. 22, 2000
4. Ser. No. 09/747259 Filed Dec. 20, 2000
5. Ser. No. 09/816744 Filed Mar. 22, 2001
6. Ser. No. 09/854208 Filed May 10, 2001
7. Ser. No. 09/854280 Filed May 10, 2001
8. Ser. No. 09/874503 Filed Jun. 5, 2001
9. Ser. No. 09/869599 Filed Jun. 29, 2001
10. Ser. No. 09/908,827 Filed Jul. 18, 2001

PCT Applications
1. PCT/US99/10733 Filed May 14, 1999
2. PCT/US99/28551 Filed Dec. 2, 1999
3. PCT/US99/30720 Filed Dec. 22, 1999
4. PCT/US00/05601 Filed Mar. 1, 2000
5. PCT/US00/05841 Filed Mar. 2, 2000
6. PCT/US00/14042 Filed May 22, 2000
7. PCT/US00/15264 Filed Jun. 2, 2000
8. PCT/US00/23522 Filed Aug. 23, 2000
9. PCT/US00/23328 Filed Aug. 24, 2000
10. PCT/US00/32678 Filed Dec. 1, 2000
11. PCT/US00/34956 Filed Dec. 20, 2000
12. PCT/US01/06520 Filed Feb. 28, 2001
13. PCT/US01/17800 Filed Jun. 1, 2001
14. PCT/US01/19692 Filed Jun. 20, 2001
15. PCT/US01/21066 Filed Jun. 29, 2001
16. PCT/US01/21735 Filed Jul. 9, 2001

What is claimed is:

1. An isolated polypeptide having at least 99% amino acid sequence identity to:

(a) the amino acid sequence of the polypeptide of SEQ ID NO:61;

(b) the amino acid sequence of the polypeptide of SEQ ID NO:61, lacking its associated signal peptide;

(c) the amino acid sequence of the polypeptide encoded by the full-length coding sequence of the cDNA deposited under ATCC accession number 203971; and wherein said isolated polypeptide has the ability to induce mesangial cell proliferation.

2. The isolated polypeptide of claim 1 having at least 99% amino acid sequence identity to the amino acid sequence of the polypeptide of SEQ ID NO:61.

3. The isolated polypeptide of claim 1 having at least 99% amino acid sequence identity to the amino acid sequence of the polypeptide of SEQ ID NO:61, lacking its associated signal peptide.

4. The isolated polypeptide of claim 1 having at least 99% amino acid sequence identity to the amino acid sequence of the polypeptide encoded by the full-length coding sequence of the cDNA deposited under ATCC accession number 203971.

5. A chimeric. polypeptide comprising a polypeptide according to claim 1 fused to a heterologous polypeptide.

6. The chimeric polypeptide of claim 5, wherein said heterologous polypeptide is a tag polypeptide or an Fc region of an immunoglobulin.

7. An isolated polypeptide comprising:
   (a) the amino acid sequence of the polypeptide of SEQ ID NO:61;
   (b) the amino acid sequence of the polypeptide of SEQ ID NO:61, lacking its associated signal peptide;
   (c) the amino acid sequence of the polypeptide encoded by the full-length coding sequence of the cDNA deposited under ATCC accession number 203971.

8. The isolated polypeptide of claim 7 comprising the amino acid sequence of the polypeptide of SEQ ID NO:61.

9. The isolated polypeptide of claim 7 comprising the amino acid sequence of the polypeptide of SEQ ID NO:61, lacking its associated signal peptide.

10. The isolated polypeptide of claim 7 comprising the amino acid sequence of the polypeptide encoded by the full-length coding sequence of the cDNA deposited under ATCC accession number 203971.

11. A chimeric polypeptide comprising a polypeptide according to claim 7 fused to a heterologous polypeptide.

12. The chimeric polypeptide of claim 11, wherein said heterologous polypeptide is a tag polypeptide or an Fc region of an immunoglobulin.

\* \* \* \* \*